United States Patent
Henkin

(10) Patent No.: US 10,598,672 B2
(45) Date of Patent: Mar. 24, 2020

(54) METHODS AND COMPOSITIONS FOR DIAGNOSING AND TREATING LOSS AND/OR DISTORTION OF TASTE OR SMELL

(71) Applicant: Cyrano Therapeutics, Inc., Washington, DC (US)

(72) Inventor: Robert I. Henkin, Bethesda, MD (US)

(73) Assignee: Cyrano Therapeutics, Inc., Washington, DC (US)

( * ) Notice: Subject to any disclaimer, the term of this patent is extended or adjusted under 35 U.S.C. 154(b) by 0 days.

(21) Appl. No.: 15/119,696

(22) PCT Filed: Feb. 18, 2015

(86) PCT No.: PCT/US2015/016381
§ 371 (c)(1),
(2) Date: Aug. 17, 2016

(87) PCT Pub. No.: WO2015/126944
PCT Pub. Date: Aug. 27, 2015

(65) Prior Publication Data
US 2017/0227548 A1     Aug. 10, 2017

Related U.S. Application Data

(60) Provisional application No. 61/941,199, filed on Feb. 18, 2014, provisional application No. 62/026,298, filed on Jul. 18, 2014, provisional application No. 62/075,337, filed on Nov. 5, 2014.

(51) Int. Cl.
| | | |
|---|---|---|
| G01N 33/68 | (2006.01) | |
| A61K 31/522 | (2006.01) | |
| A61K 9/00 | (2006.01) | |
| A61K 31/44 | (2006.01) | |
| A61K 31/4709 | (2006.01) | |

(52) U.S. Cl.
CPC ....... *G01N 33/6893* (2013.01); *A61K 9/0043* (2013.01); *A61K 31/44* (2013.01); *A61K 31/4709* (2013.01); *A61K 31/522* (2013.01)

(58) Field of Classification Search
None
See application file for complete search history.

(56) References Cited

U.S. PATENT DOCUMENTS

| | | |
|---|---|---|
| 174,915 A | 3/1876 | Lorenz |
| 4,066,405 A | 1/1978 | Henkin |
| 4,146,501 A | 3/1979 | Henkin |
| 4,444,879 A | 4/1984 | Foster et al. |
| 4,652,521 A | 3/1987 | Confer et al. |
| 4,683,195 A | 7/1987 | Mullis et al. |
| 4,683,202 A | 7/1987 | Mullis |
| 4,800,159 A | 1/1989 | Mullis et al. |
| 4,992,445 A | 2/1991 | Lawter et al. |
| 5,001,139 A | 3/1991 | Lawter et al. |
| 5,023,252 A | 6/1991 | Hseih |
| 5,079,142 A | 1/1992 | Coleman et al. |
| 5,132,324 A | 7/1992 | Meglasson |
| 5,169,849 A | 12/1992 | Kiechel et al. |
| 5,384,308 A | 1/1995 | Henkin |
| 5,525,329 A | 6/1996 | Snyder et al. |
| 5,591,645 A | 1/1997 | Rosenstein |
| 5,601,986 A | 2/1997 | Takacs |
| 5,614,627 A | 3/1997 | Takase et al. |
| 5,622,871 A | 4/1997 | May et al. |
| 5,707,802 A | 1/1998 | Sandhu et al. |
| 5,714,993 A | 2/1998 | Keoshkerian et al. |
| 5,788,967 A | 8/1998 | Henkin |
| 5,849,741 A | 12/1998 | Watanabe et al. |
| 5,859,006 A | 1/1999 | Daugan |
| 5,869,516 A | 2/1999 | Arlt et al. |
| 5,993,782 A | 11/1999 | Gardner |
| 6,207,703 B1 | 3/2001 | Ponikau |
| 6,228,660 B1 | 5/2001 | May et al. |
| 6,387,639 B1 | 5/2002 | Posner et al. |
| 6,506,801 B1 | 1/2003 | Yee et al. |
| 6,929,925 B1 | 8/2005 | Zuker et al. |
| 7,109,042 B2 | 9/2006 | May et al. |
| 7,144,585 B1 | 12/2006 | Mukai et al. |
| 7,670,849 B2 | 3/2010 | Henkin |

(Continued)

FOREIGN PATENT DOCUMENTS

| | | |
|---|---|---|
| EP | 0967214 A1 | 12/1999 |
| WO | WO-9626940 A1 | 9/1996 |

(Continued)

OTHER PUBLICATIONS

Van Der Vekens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
El-Zaatari et al., Baseline Levels of Plasma Sonic Hedgehog Vary Widely but are Reduced in Subject with Pancreatic Cancer, Gastroenterology, May 2011, vol. 140, No. 5, Suppl. 1, p. S-854. (Year: 2011).*
Abbott Axsym system. Theophylline II package insert. Abbott Laboratories. 2003.
Agarwal, et al. A simple method for simultaneous estimation of zinc and copper in erythrocytes. Bio. Tr. Elem. Res. 1985;7: 199-208.
Ajani, et al. Alcohol consumption and risk of coronary heart disease by diabetes status. Circulation. Aug. 1, 2000;102(5):500-5.
Anholt, et al. Molecular neurobiology of olfaction. Crit. Rev. Neurobiol. 1993;7:1-22.
Asakura, et al. cAMP and cGMP in the human parotid saliva. Arch. Otorhinolaryngol. 1980;226:145-154.

(Continued)

*Primary Examiner* — Gary Counts
(74) *Attorney, Agent, or Firm* — Wilson Sonsini Goodrich & Rosati

(57) ABSTRACT

Disclosed herein are methods for diagnosing a subject with loss and/or distortion of taste or smell, e.g., hyposmia, dysosmia, anosmia, phantosmia, hypogeusia, dysgeusia, phantogeusia, and/or ageusia. Also disclosed herein are methods and compositions for treating a subject for loss and/or distortion of taste or smell, e.g., hyposmia, dysosmia, anosmia, phantosmia, hypogeusia, dysgeusia, phantogeusia, and/or ageusia.

12 Claims, 15 Drawing Sheets

(56) References Cited

U.S. PATENT DOCUMENTS

| | | | |
|---|---|---|---|
| 8,293,489 | B2 | 10/2012 | Henkin |
| 8,506,934 | B2 | 8/2013 | Henkin |
| 8,580,801 | B2 | 11/2013 | Henkin |
| 8,663,938 | B2 | 3/2014 | Henkin |
| 8,968,706 | B2 | 3/2015 | Henkin |
| 9,719,988 | B2 | 8/2017 | Henkin |
| 2003/0055039 | A1 | 3/2003 | Ikeya et al. |
| 2004/0209843 | A1 | 10/2004 | Inoue et al. |
| 2005/0288265 | A1 | 12/2005 | Locher et al. |
| 2006/0275801 | A1 | 12/2006 | Henkin |
| 2008/0029084 | A1 | 2/2008 | Costantino et al. |
| 2008/0200484 | A1 | 8/2008 | Liu et al. |
| 2008/0318913 | A1 | 12/2008 | Fox et al. |
| 2010/0022563 | A1 | 1/2010 | Henkin |
| 2010/0227875 | A1 | 9/2010 | Henkin |
| 2011/0023870 | A1 | 2/2011 | Wermeling |
| 2011/0166166 | A1 | 7/2011 | Henkin |
| 2012/0178768 | A1 | 7/2012 | Henkin |
| 2013/0011849 | A1 | 1/2013 | Henkin |
| 2013/0225595 | A1 | 8/2013 | Gillies et al. |
| 2014/0073654 | A1 | 3/2014 | Henkin |
| 2015/0297601 | A1 | 10/2015 | Henkin |
| 2015/0366869 | A1 | 12/2015 | Henkin |
| 2016/0030435 | A1 | 2/2016 | Henkin |

FOREIGN PATENT DOCUMENTS

| | | | |
|---|---|---|---|
| WO | WO-9641194 A1 | 12/1996 | |
| WO | WO-9703675 A1 | 2/1997 | |
| WO | WO-9703985 A1 | 2/1997 | |
| WO | WO-9743287 A1 | 11/1997 | |
| WO | WO-9817668 A1 | 4/1998 | |
| WO | WO-9849166 A1 | 11/1998 | |
| WO | WO-9901135 A1 | 1/1999 | |
| WO | WO-9921562 A1 | 5/1999 | |
| WO | WO-9930697 A2 | 6/1999 | |
| WO | WO-0148477 A1 | 7/2001 | |
| WO | WO-0182931 A1 | 11/2001 | |
| WO | WO-03025224 A1 | 3/2003 | |
| WO | WO-03025224 A3 | 10/2003 | |
| WO | WO-2006085102 A1 | 8/2006 | |
| WO | WO-2007044375 A2 | 4/2007 | |
| WO | WO-2008141438 A1 | 11/2008 | |
| WO | WO-2009115235 A1 | 9/2009 | |
| WO | WO-2010147981 A1 | 12/2010 | |
| WO | WO-2012016845 A2 | 2/2012 | |
| WO | WO-2012016889 A2 | 2/2012 | |
| WO | WO-2012154975 A2 | 11/2012 | |
| WO | WO-2014055801 A1 | 4/2014 | |
| WO | WO-2014059197 A1 | 4/2014 | |
| WO | WO-2015126944 A1 | 8/2015 | |

OTHER PUBLICATIONS

Atkinson, et al. The pathogenesis of insulin-dependent diabetes mellitus. New Engl. J. Med. 1994;331:1428-1436.

Bakalyar, et al. Identification of a specialized adenylyl cyclase that may mediate odorant detection. Science. Dec. 7, 1990;250(4986):1403-6.

Bogardus, et al. Relationships between insulin secretion, insulin action, and fasting plasma glucose concentration in nondiabetic and noninsulin-dependent diabetic subjects. J Clin Invest. Oct. 1984;74(4):1238-46.

Borisy, et al. High-affinity cAMP phosphodiesterase and adenosine localized in sensory organs. Brain Res. May 7, 1993;610(2):199-207.

Breer. Molecular reaction cascades in olfactory signal transduction. J Steroid Biochem Mol Biol. Oct. 1991;39(4B):621-5.

Bromley, et al. Smell and taste disorders: a primary care approach. Amer. Fam. Physician. 2000;61:427-436.

Cai, et al. Neuronal cyclic AMP controls the developmental loss in ability of axons to regenerate. J. Neurosci. 2001;21:4731-4739.

Cai, et al. Prior exposure to neurotrophins blocks inhibition of axonal regeneration by MAG and myelin via a cAMP dependent mechanism. Neuron. 1999;22:89-101.

Carlsson, et al. Alcohol consumption and the increase of Type II diabetes: Finnish twin cohort study. Diabetes Care. 2003, 26: 2785-2790.

Cho, et al. Development of udenafil-loaded microemulsions for intranasal delivery: in vitro and in vivo evaluations. Int J Pharm. Feb. 28, 2012;423(2):153-60. doi: 10.1016/j.ijpharm.2011.12.028. Epub Dec. 23, 2011.

Chou. Wake up and smell the coffee. Caffeine, coffee, and the medical consequences. West J Med. Nov. 1992;157(5):544-53.

Church, et al. Hyposmia associated with atopy. Ann. Aller. 1978;40:105-109.

Cicinelli, et al. Post-stroke reorganization of brain motor output to the hand: a 2-4 month follow-up with focal magnetic transcranial stimulation. Electroencephalogr Clin Neurophysiol. Dec. 1997;105(6):438-50.

Co-pending U.S. Appl. No. 15/327,190, filed Jan. 18, 2017.

Co-pending U.S. Appl. No. 15/635,979, filed Jun. 28, 2017.

Cullen, et al. Disorders of smell and taste. Med. Clin. North Amer. 1999;83:57-74.

Davidson, et al. Smell impairment: can it be reversed? Postgrad. Med. 1995;98:107-109, 112-118.

Deems, et al. Smell and taste disorders, a study of 750 patients from the University of Pennsylvania Smell and Taste Center. Arch. Otolaryngol. Head Neck Surg. 1991;177:519-528.

Doerty, et al. Carbonic anhydrase (CA) activity in nasal mucus appears to be a marker for loss of smell (hyposmia) in humans. J. Invest. Med. 1997;45:237A.

Doty, et al. Human odor intensity perception: correlation with frog epithelial adenylate cyclase activity and transepithelial voltage response. Brain Res. Sep. 10, 1990;527(1):130-4.

Draheim, et al., Anti-Inflammatory Potential of the Selective Phosphodiesterase 4 Inhibitor N-(3,5-Dichloro-pyrid-4-yl)-[1-(4-fluorobenzyl)-5-hydroxy-indole-3-yl]glyoxylic Acid Amide (AWD 12-281) in Human Cell Preparations, The Journal of Pharmacology and Experimental Therapeutics, 308(2): 555-563, 2004.

Elshafeey AH, et al. Intranasal microemulsion of sildenafil citrate: in vitro evaluation and in vivo pharmacokinetic study in rabbits. AAPS PharmSciTech. 2009;10(2):361-7. doi: 10.1208/s12249-009-9213-6. Epub Mar. 31, 2009.

European search report and opinion dated Feb. 12, 2016 for EP Application No. 13843665.

FDA. Guidance for industry. Estimating the maximum safe starting dose in initial clinical trials for therapeutics in adult healthy volunteers. Center for Drug Evaluation and Research. Jul. 2005.

Firestein, et al. Regulation of sensory neuron precursor proliferation by cyclic GMP]dependent protein kinase. J. Neurochem. 1998;71:1846-1853.

Firestein, et al. Single odor-sensitive channels in olfactory receptor neurons are also gated by cyclic nucleotides. J. Neurosci. 1991;11:3565-72.

Franz, et al. Evidence-based nutrition principles and recommendations for diabetes and related complications. Diabetes Care. 2002, 25:148-198.

Gillespie, et al. Pharmacologic Management of Chronic Rhinosinusitis, Alone or with Nasal Polyposis. Current Allergy and Asthma Reports, 2004, vol. 4, No. 6, pp. 478-485.

Glenert, et al. A simple assay for cyclic adenosine 3':5'-monophosphate in human saliva. J. Cyclic Nucleotide Protein Phosphor. Res. 1985;10:451-461.

Guidance for Industry. Nasal Spray and Inhalation Solution, Suspension, and Spray Drug Products—Chemistry, Manufacturing, and Controls Documentation. US Department of Health and Human Services. CDER. Jul. 2002. 49 pages.

Hardwick, et al. The effect of PGI2 and theophylline on the response of platelets subjected to shear stress. Blood. Oct. 1981;58(4):678-81.

Harris, et al. Clinical evaluation and symptoms of chemosensory impairment: one thousand consecutive cases from the Nasal Dysfunction Clinic in San Diego. Amer. J. Rhinol 2006;20:101-108.

(56) References Cited

OTHER PUBLICATIONS

Henkin. Concepts of therapy in taste and smell dysfunction: repair of sensory receptor function as primary treatment. Olfaction and Taste XI, (Kurihara, K., Suzuki, N., Ogawa, H., Eds.), Springer Verlag, 1994, pp. 568-573.
Henkin. Dichotomous changes in cAMP and cGMP in human parotid saliva after oral theophylline. FASEB J. 2003;17:A1028.
Henkin. Drug-induced taste and smell diorders. Incidence, mechanisms and management related primarily to treatment of sensory receptor dysfunction. Drug safety. 1994; 11(5):318-377.
Henkin. Effects of ACTH, adrenocorticosteroids and thyroid hormone on sensory function, in Anatomical Neuroendocrinology, (Stumpf, W.E., Grant, L.D., Eds.), Karger, A.G. , Basel, 1975, pp. 298-316.
Henkin, et al. A double blind study of the effects of zinc sulfate on taste and smell dysfunction. Amer. J. Med. Sci. 1976;272: 285-299.
Henkin, et al. A zinc protein isolated from human parotid saliva. Proc. Nat. Acad. Sci. USA 1975;72:488-492.
Henkin, et al. Aberrant signaling in the olfactory system: a mechanism for smell loss. FASEB Journal, vol. 18, No. 4-5, pp. Abst. 792.7, 2004.
Henkin, et al. Age related changes in cyclic nucleotides in saliva and nasal mucus possible feedback mechanism in development of gustatory and olfactory receptor function. FASEB J. 2005;19:A1368.
Henkin, et al. cAMP and cGMP in human parotid saliva: relationships to taste and smell dysfunction, gender and age. Amer. J. Med. Sci. 2007;334:431-440.
Henkin, et al. cAMP and cGMP in nasal mucus related to severity of smell loss in patients with smell dysfunction. Clinical Invest. Med. 2008;31:E78-E84.
Henkin, et al. cAMP and cGMP in nasal mucus: relationships to taste and smell dysfunction, gender and age. Clinical Invest. Med. 2008;31:E71-E77.
Henkin, et al. Decreased parotid saliva gustin/carbonic anhydrase VI secretion: an enzyme disorder manifested by gustatory and olfactory dysfunction. Amer. J. Med. Sci. 1999;318:380-391.
Henkin, et al. Decreased parotid salivary cyclic nucleotides related to smell loss severity in patients with taste and smell dysfunction. Metabolism. Dec. 2009;58(12):1717-23. doi: 10.1016/j.metabol. 2009.05.027. Epub Jul. 23, 2009.
Henkin, et al. Effective treatment of smell loss with theophylline. Exper. Biol. 2008;22:B976.2.
Henkin, et al. Efficacy of exogenous zinc in treatment of patients with carbonic anhydrase VI deficiency. Amer. J. Med. Sci. 1999;318:392-404.
Henkin, et al. Fractionation of human parotid saliva. J. Biol. Chem. 1978;253:7556-7565.
Henkin, et al. Hypogeusia, dysgeusia, hyposmia and dysosmia following influenza-like infection. Ann. Otol. Rhin. Laryngol. 1975;84:672-682.
Henkin, et al. Idiopathic hypogeusia with dysgeusia, hyposmia and dysosmia: a new syndrome. J. Amer. Med. Assoc. 1971;217:434-440.
Henkin, et al. Insulin receptors as well as insulin are present in saliva and nasal mucus. Journal of Investingative Medicine. 2006; 54(Suppl. 2):S378.
Henkin, et al. Interleukin 6 in hyposmia. JAMA Otolaryngol Head Neck Surg. Jul. 2013;139(7):728-34. doi: 10.1001/jamaoto.2013. 3392.
Henkin, et al. Intranasal theophylline treatment of hyposmia and hypogeusia: a pilot study. Arch Otolaryngol Head Neck Surg. Nov. 2012;138(11):1064-70. doi: 10.1001/2013.jamaoto.342.
Henkin, et al. Nasal seroproteins: a new frontier in the exploration of physiology and pathology of nasal and sinus disease. New Frontiers in Immunobiology. 2000; pp. 127-152.
Henkin; et al., "Olfactory Hallucinations without Clinical Motor Activity: A Comparison of Unirhinal with Birhinal Phantosmia. Brain Sci. Nov. 15, 2013;3(4):1483-553. doi: 10.3390/brainsci3041483."

Henkin, et al. Rapid changes in taste and smell function following transcranial magnetic stimulation (TCMS) in humans: relationship to CAN plasticity. FASEB J. 2002; 16:A878.
Henkin, et al. Treatment of abnormal chemsensation in human taste and smell. In: Norris DM, ed. Perception of Behavioral Chemicals. Amsterdam, netherlands: Elsevier/North Holland Biomedical Press; 1981:227-265.
Henkin. Evaluation and treatment of human olfactory dysfunction, in Otolaryngology (English, G.M. Ed.), Lippincott, Philadelphia, 1993, vol. 2, pp. 1-86.
Henkin. Olfaction in human disease. In: English GM, ed. Loose-leaf Series of Otolaryngology. New York, NY: Harper and Row; 1982:1-39.
Henkin, R.I. et al. "Is Increased IL-6 the Result or Cause of Smell Loss in Patients with Hyposmia?", FASEB Journal, 2009, vol. 23 (Meeting Abstract Supplement), Abstract 835.1.
Henkin, R.I. et al. "New Data on Human Cytokine Changes with Age", FASEB Journal, 2009, vol. 23 (Meeting Abstract Supplement), Abstract 571.9.
Henkin, R.I. et al. "Taste and smell function in chronic disease: A review of clinical and biochemical evaluations of taste and smell dysfunction in over 5000 patients at The Taste and Smell Clinic in Washington, DC", American Journal of Otolaryngology—Head and Neck Medicine and Surgery, 2013, vol. 34, pp. 477-489.
Henkin. Taste and smell disorders, human. Encyclopedia of Neuroscience, 3rd Ed., (Adelman, G., Smith, B.H., Eds.), Birkhauser, Boston, 2004.
Henkin. The definition of primary and accessory areas of olfaction as the basis for a classification of decreased olfactory acuity, in Olfaction and Taste II, (Hayashi, T. Ed.), Pergamon Press, London, 1967, pp. 235-252.
Henkin. The role of adrenal corticosteroids in sensory processes, in Adrenal Gland, (Blaschko, H., Sayers, G., Smith, A.D., Eds.), Handbook of Physiology. Endocrinology, Washington, DC. Amer. Physiol. Soc., Sect. 7, vol. VI, 1975, pp. 209-230.
Henkin. Zinc, saliva and taste: Interrelationships of gustin, nerve growth factor, saliva and zinc, in Zinc and Copper in Clinical Medicine, (Hambidge, K.M., Nichols, B.L., Eds.), Spectrum Publ. Inc., Jamaica, NY, 1978, pp. 35-48.
Huque, et al. Odorant- and guanine nucleotide-stimulated phosphoinositide turnover in olfactory cilia. Biochem Biophys Res Commun. May 29, 1986;137(1):36-42.
International preliminary report on patentability and written opinion dated Aug. 4, 2009 for PCT Application No. US2008/052712.
International search report and written opinion dated Apr. 8, 2014 for PCT/US2014/014940.
International search report and written opinion dated May 29, 2015 for PCT Application No. US2015/016381.
International search report and written opinion dated Nov. 14, 2006 for PCT Application No. PCT/US2006/016846.
International search report and written opinion dated Dec. 5, 2013 for PCT/US2013/064416.
International search report and written opinion dated Dec. 12, 2013 for PCT/US2013/063331.
Kanamori, et al. Origin of cyclic adenosine monophosphate in saliva. J. Dent. Res. 1975;54:535-539.
Kim, et al. Defects in the peripheral taste structure and function in the MRL/lpr mouse model of autoimmune disease. PLoS One. 2012;7(4):e35588. doi: 10.1371/journal.pone.0035588. Epub Apr. 19, 2012.
Krägelund, et al. N-terminal Pro-B-type natriuretic-peptide and long-term mortality in stable coronary heart disease. New Engl. J. Med. 2006; 252:666-675.
Kublik, et al. Nasal delivery systems and their effect on deposition and absorption. Adv Drug Deliv Rev. Jan. 5, 1998;29(1-2):157-177.
Kulkarni, et al. Formulation and characterization of nasal sprays. An examination of nasal sprat formulation parameters and excipients and their influence on key in vitro tests. Inhalation. Jun. 2012; 10-15.
Kurihara, et al. High activity of adenyl cyclase in olfactory and gustatory organs. Biochem Biophys Res Commun. Jul. 11, 1972;48(1):30-4.

(56) References Cited

OTHER PUBLICATIONS

Lancet, et al. Molecular transduction in smell and taste. Cold Spring Harb Symp Quant Biol. 1988;53 Pt 1:343-8.

Law, et al. Distribution of calmodulin in taste buds. Life Sci. 1985; 36:1189-1195.

Law, et al. Low parotid saliva calmodulin in patients with taste and smell dysfunction. Biochem Med Metab Biol. Aug. 1986;36(1):118-24.

Law, et al. Zinc deficiency decreases the activity of calmodulin regulated cyclic nucleotide phosphodiesterases in vivo in selected rat tissues. Biol Trace Elem Res. Aug. 1988;16(3):221-6.

Lee, et al. Thiolated chitosan nanoparticles enhance anti-inflammatory effects of intranasally delivered theophylline. Respir Res. Aug. 24, 2006;7:112.

Levin, et al. Soluble endoglin and other circulating antiangiogenic factors in preeclampsia. New Engl. J. Medicine. 2006;355:992-1005.

Levy, et al. Increased brain activation in response to odors in patients with hyposmia after theophylline treatment demonstrated by fMRI. J. Comp. Asst. Tomog. 1998;22:760-770.

Lindheimer, et al. Explaining and predicting preeclampsia. New Engl. J. Medicine. 2006;355:1056-1058.

Liu, et al. Sonic hedgehog exerts distinct, stage-specific effects on tongue and taste papilla development. Developmental Biology. vol. 276, Issue 2, Dec. 15, 2004, pp. 280-300.

Lnthavong, et al., A Numerical Study of Spray Particle Deposition in a Human Nasal Cavity, Aerosol Science and Technology, 40(11): 1034-1045. 2006.

Lowe, et al. Contribution of the ciliary cyclic nucleotide-gated conductance to olfactory transduction in the salamander. J Physiol. Mar. 1993;462:175-96.

Maggie et al., TT Virus in the Nasal Secretions of Children with Acute Respiratory Diseases: Relations to Viremia and Disease Severity, J Virology, Feb. 2003, 77(4):2418-2425.

Maitra, et al. The pancreas in Pathological Basis of Disease. 7th Edition. Elsevier. 2004; pp. 1155-1207.

Margolskee, Robert F. Molecular mechanisms of taste transduction. Pure and applied chemistry. 2002; 74(7):1125-1133.

Margolskee. The biochemistry and molecular biology of taste transduction. Curr Opin Neurobiol. Aug. 1993;3(4):526-31.

Mcauley, et al. Diagnosing insulin resistance in the general population. Diabetes Care. Mar. 2001;24(3):460-4.

Meret, et al. Simultaneous direct estimation by atomic absorption spectrophotometry of copper and zinc in serum, urine, and cerebrospinal fluid. Clin Chem. May 1971;17(5):369-73.

Misaka, et al. Taste buds have a cyclic nucleotide-activated channel, CNGgust. J Biol Chem. Sep. 5, 1997;272(36):22623-9.

Moharram, et al. Growth factor regulation in human olfactory system function: the role of transcranial magnetic stimulation (TCMS). FASEB J. 2004; 18(4):A201.

Moon, et al. Regulation of intracellular cyclic GMP levels in olfactory sensory neurons. J. Neurochem. 2005;95:200-9.

MWV Healthcare MK Sprayer. Product Information. 2013. 2 pages.

Nakajima, et al. Studies on cyclic nucleotides in brochopulmonary diseases with special reference to cAMP, cGMP in patients with nasal allergy and bronchial asthma. Acta Med. Kinki Univ., 4, 257-272, 1979.

Nakamura, et al. Proceedings of the 25th Japanese Symposium on Taste and Smell: 1. Current and Ca influx induced by intracellular cAMP in the newt olfactory receptor. Chem Sense. 1991; 17:85-116.

Neumann, et al. Regeneration of sensory axons within the injured spinal cord induced by intraganglionic cAMP elevation. Neuron. 2002;34:885-893.

Notice of Allowance dated Mar. 30, 2017 for U.S. Appl. No. 14/152,927.

Notice of allowance dated Apr. 2, 2013 for U.S. Appl. No. 12/649,320.

Notice of allowance dated Jun. 25, 2012 for U.S. Appl. No. 12/523,040.

Notice of allowance dated Oct. 10, 2013 for U.S. Appl. No. 13/618,882.

Notice of allowance dated Oct. 19, 2009 for U.S. Appl. No. 11/415,942.

Notice of allowance dated Oct. 28, 2014 for U.S. Appl. No. 13/932,613.

Notice of allowanced dated Aug. 7, 2013 for U.S. Appl. No. 12/508,530.

Notice of allowanced dated Oct. 9, 2013 for U.S. Appl. No. 12/508,530.

Office action dated Jan. 14, 2011 for U.S. Appl. No. 12/649,320.

Office action dated Jan. 14, 2014 for U.S. Appl. No. 13/932,613.

Office Action dated Jan. 30, 2017 for U.S. Appl. No. 14/775,796.

Office action dated Mar. 9, 2012 for U.S. Appl. No. 12/508,530.

Office Action dated Mar. 15, 2017 for U.S. Appl. No. 14/601,387.

Office action dated Mar. 18, 2015 for U.S. Appl. No. 13/421,277.

Office Action dated Mar. 20, 2017 for U.S. Appl. No. 13/421,277.

Office action dated Apr. 17, 2007 for U.S. Appl. No. 11/415,942.

Office action dated Apr. 17, 2008 for U.S. Appl. No. 11/415,942.

Office action dated Apr. 27, 2015 for U.S. Appl. No. 14/152,927.

Office action dated May 5, 2016 for U.S. Appl. No. 14/601,387.

Office action dated May 25, 2011 for U.S. Appl. No. 12/649,320.

Office action dated May 26, 2009 for U.S. Appl. No. 11/415,942.

Office Action dated May 30, 2017 for U.S. Appl. No. 14/433,300.

Office action dated Jun. 16, 2016 for U.S. Appl. No. 13/421,277.

Office action dated Jul. 26, 2012 for U.S. Appl. No. 12/508,530.

Office action dated Aug. 10, 2012 for U.S. Appl. No. 12/649,320.

Office action dated Aug. 15, 2014 for U.S Appl. No. 13/932,613.

Office action dated Oct. 8, 2014 for U.S. Appl. No. 14/152,927.

Office action dated Oct. 17, 2007 for U.S. Appl. No. 11/415,942.

Office action dated Oct. 17, 2016 for U.S. Appl. No. 14/433,300.

Office Action dated Oct. 19, 2017 for U.S. Appl. No. 13/421,277.

Office Action dated Oct. 24, 2017 for U.S. Appl. No. 14/775,796.

Office action dated Nov. 12, 2008 for U.S. Appl. No. 11/415,942.

Office action dated Nov. 12, 2015 for U.S. Appl. No. 13/421,277.

Office action dated Nov. 30, 2015 for U.S. Appl. No. 14/152,927.

Office action dated Aug. 22, 2016 for U.S. Appl. No. 14/152,927.

Office action dated Aug. 25, 2016 for U.S. Appl. No. 14/775,796.

Pace, et al. Odorant-sensitive adenylate cyclase may mediate olfactory reception. Nature. 1985;316:255-8.

Papathanassiu, et al. cAMP is present in human nasal mucus and may act as a growth factor in cells of the olfactory epithelium. FASEB J. 2002;16:A1153.

Pelangaris, et al. Oncogenic co-operation in beta-cell tumorigenesis. Endocr Relat Cancer. Dec. 2001;8(4):307-14.

Philips, et al. Factors determining the appearance of glucose in upper and lower respiratory tract secretions. Intensive Care Med. Dec. 2003;29(12):2204-10.

Poehling, et al., Accuracy and Impact of a Point of a Care Rapid Influenza Test in Young Children With Respiratory Illnesses, Arch Pediatr Adolsec Med., 2006, vol. 160(7):713-718.

Rickli, et al. Carbonic anhydrases from human erythrocytes. Preparation and properties of two enzymes. J Biol Chem. Apr. 1964;239:1065-78.

Riste, et al. High prevalence of Type 2 diabetes in all ethnic groups, including Europeans, in a British Inner City. Diabetes Care. 2001;24:1377-1383.

Rock, et al. Inhibitors of the proteosome block the degradation of most cell proteins and the generation of peptides presented on MHC class 1 molecules. Cell. 1994;78:761-771.

Rosezweig, et al. Possible novel mechanism for bitter taste mediated through cGMP. J. Neurophysiol. 1999;81: 1661-5.

Sano, et al. Immuno PCR: very sensitive antigen detection by means of specific antibody-DNA conjugates. Science. 1992;258:120-122.

Schaeffer, et al. Detection of cAMP in parotid saliva of normal individuals. J. Dent. Res. 1973;52:629.

Schechter, et al. Abnormalities of taste and smell following head trauma. J. Neurol. Neurosurg. Psychiat. 1974;37:802-810.

Schechter, et al. Idiopathic hypogeusia: a description of the syndrome and a single blind study with zinc sulfate, in Internat. Rev. Neurobiol. Suppl. 1., (Pfeiffer, C., Ed.), Academic Press, NY, 1972, pp. 125-133.

Schiffman, et al. Methyl xanthines enhance taste: evidence for modulation of taste by adenosine receptor. Pharmacol Biochem Behav. Feb. 1985;22(2):195-203.

(56) References Cited

OTHER PUBLICATIONS

Seal, et al. Point-of-care nucleic acid lateral flow tests. IVD Techology. 2006;41-51.

Seiden, et al. Office management of taste and smell disorders. Otolaryngol. Clin. North Amer. 1992;25:817-835.

Shepherd, et al. Sensory transduction entering the mainstream of membrane signaling. Cell. 1991;67:845-851.

Shin, et al. Virus-induced Type 1 IFN stimulates generation of immunoproteasomes at the site of infection. J. Clin. Invest. 2006;116(11):3006-3014.

Shirley, et al. Olfactory adenylate cyclase of the rat. Stimulation by odorants and inhibition by Ca2+. Biochem J. Dec. 1, 1986;240(2):605-7.

Sklar, et al. The odorant-sensitive adenylate cyclase of olfactory receptor cells. Differential stimulation by distinct classes of odorants. J Biol Chem. Nov. 25, 1986;261(33):15538-43.

Sobottka, et al. Disseminated Encephalitozoon (Septata) intestinalis infection in a patient with AIDS: novel diagnostic approaches and autopsy-confirmed parasitological cure following treatment with albendazole. J Clin Microbiol. Nov. 1995;33(11):2948-52.

Spivey, et al. Comparative Analysis of Manual Versus Automated Actuation Parameters for Droplet Size Determination by Laser Diffraction for Spray Devices. Catalent Pharma Solutions. 2008. 1 page.

Suzuki. Proceedings of the 21st Japanese Symposium on Taste and Smell: cyclic nucleotides as intracellular messengers in the olfactory transduction process. Chem Sense. 1988; 13:311-332.

Temmel, et al. Characteristics of olfactory disorders in relation to major causes of olfactory loss. Arch. Otolaryngol. Head Neck Surg. 2002;128:635-641.

The Expert Committee. Report of the Expert Committee on the Diagnosis and Classification of Diabetes Mellitus. Diabetes Care. 2003;26:S5-S20.

Thompson. Cyclic nucleotide phosphodiesterase: pharmacology, biochemistry and function. Pharmacol. Ther. 1991;51:13-33.

Vaughan. Second wind for second-messenger research. Bioscience. 1987; 37:642-646.

Velicu, et al. Insulin is present in human saliva and nasal mucus. Journal of Investingative Medicine. 2006; 54:S385.

Velicu, et al. On the antiapoptotic mechanism of action of theophylline in restoring smell function in patients with hyposmia. J. Invest. Med. 2005;53(Suppl. 2):5402.

Voegels, et al. Expression of interleukins in patients with nasal polyposis. Otolaryngology—Head and Neck Surgery, 2005, vol. 132, No. 4, pp. 613-616.

Weinstock, et al. Olfactory dysfunction in humans with deficient guanine nucleotide-binding protein. Nature. Aug. 14-20, 1986;322(6080):635-6.

Weyer, et al. The natural history of insulin secretory dysfunction and insulin resistance in the pathogenesis of type 2 diabetes mellitus. J Clin Invest. Sep. 1999;104(6):787-94.

Will, et al. Cigarette smoking and diabetes mellitus from a large prospective cohort study. Int. J. Epidemiol. 2001; 30: 540-546.

Williams, G. Diabetes. In Endocrine Disorder. Oxford Testbook of Medicine. vol. 2, 4th Edition, Oxford Univ. Press 2003, pp. 317-359.

Woods, et al. Effect of hyperglycaemia on glucose concentration of human nasal secretions. Clin Sci (Lond). May 2004;106(5):527-33.

Wysocki, et al. National Geographic Smell Survey: Effects of age are heterogeneous. Ann. NY Acad. Sci. 1989;561:12-28.

Extended European Search Report and Search Opinion dated Sep. 29, 2017 for European Patent Application No. EP15751827.5.

Liu et al. Multiple Shh signaling centers participate in fungiform papilla and taste bud formation and maintenance. Dev Biol. Oct. 1, 2013;382(1):82-97.

EP 15 751 827.5 Office Action dated Nov. 8, 2018.

* cited by examiner

ମETHODS AND COMPOSITIONS FOR
DIAGNOSING AND TREATING LOSS
AND/OR DISTORTION OF TASTE OR
SMELL

This application is a National Stage entry of International Application No. PCT/US2015/016381, filed Feb. 18, 2015, which claims the benefit of U.S. Provisional Application Nos.: 61/941,199, filed on Feb. 18, 2014; 62/026,298, filed on Jul. 18, 2014; and 62/075,337, filed on Nov. 5, 2014; each of which are incorporated herein by reference in their entireties.

BACKGROUND OF THE DISCLOSURE

Hyposmia is a reduced ability to smell and detect odors. Dysosmia is a distortion of the sense of smell. Anosmia is a complete loss of ability to smell and detect odors. Phantosmia is a distortion of the sense of smell, for example, the perception of a smell in the absence of an odor. Hypogeusia is a reduced ability to taste things. Dysgeusia is a distortion of the sense of taste. Ageusia is a complete loss of ability to detect or recognize tastens. Phantogeusia is a distortion of the sense of taste for example, the perception of a taste in the absence of a tasten. There is a need in the art for methods for diagnosing and treating these conditions.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY OF THE DISCLOSURE

Disclosed herein are methods comprising (a) obtaining one or more biological samples from a subject; (b) measuring a level of one or more members of the hedgehog signaling pathway in the one or more biological samples from the subject; (c) diagnosing the subject with loss or distortion of taste or smell based upon the level of one or more members of the hedgehog signaling pathway that is lower than a threshold level; and (d) treating the subject diagnosed with loss or distortion of taste or smell.

Also disclosed herein are methods comprising (a) obtaining one or more biological samples from the subject; (b) measuring a level of one or more members of the hedgehog signaling pathway in the one or more biological samples from the subject; and (c) diagnosing the subject with loss or distortion of taste or smell based upon the level of one or more members of the hedgehog signaling pathway that is lower than a threshold level; wherein the diagnosing is computer implemented.

Further disclosed herein are methods comprising (a) obtaining one or more biological samples from the subject; (b) measuring a level of one or more members of the hedgehog signaling pathway in the one or more biological samples from the subject, wherein the measuring is performed by ELISA; and (c) diagnosing the subject with loss or distortion of taste or smell based upon the level of one or more members of the hedgehog signaling pathway that is lower than a threshold level.

Disclosed herein are methods of evaluating the improvement in, decline in, no change in, diminution in and/or distortion in taste and/or smell, the method comprising: (a) treating the subject with one or more drugs; (b) obtaining one or more biological samples from the subject; (c) measuring a level of one or more members of the hedgehog signaling pathway in one or more biological samples from the subject; (d) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level; and (e) treating the subject with increased, lower, and/or the same one or more drugs.

Additionally disclosed herein are methods of evaluating the improvement in, decline in, no change in, diminution in and/or distortion in taste and/or smell, the method comprising: (a) treating the subject with one or more drugs; (b) obtaining one or more biological samples from the subject; (c) measuring a level of one or more members of the hedgehog signaling pathway in the one or more biological samples from the subject, wherein the measuring is performed by ELISA; and (d) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level.

Further disclosed here are methods of evaluating the improvement in, decline in, no change in, diminution in and/or distortion in taste and/or smell, the method comprising: (a) treating the subject with one or more drugs; (b) obtaining one or more biological samples from the subject; (c) measuring a level of one or more members of the hedgehog signaling pathway in one or more biological samples from the subject; and (d) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level; wherein the diagnosing is computer implemented.

In some embodiments, the subject has taste loss. In some embodiments, the subject has taste loss that is selected from a group consisting of: hypogeusia, dysgeusia, phantosmia, and ageusia. In some embodiments, the subject has smell loss. In some embodiments, the subject has smell loss that is selected from a group consisting of: hyposmia, dysosmia, phantogeusia, and anosmia.

In some embodiments, the methods further comprise treating the subject.

In some embodiments, the one or more biological samples comprises a whole blood sample, a serum sample, a plasma sample, a urine sample, a saliva sample, a mucus sample, a perspiration sample, or any combination thereof. In some embodiments, the one or more biological samples comprise a saliva sample. In some embodiments, the one or more biological samples comprise a mucus sample.

In some embodiments, the one or more members of the hedgehog signaling pathway is selected from a group consisting of: Sonic Hedgehog (SHH), Desert Hedgehog (DHH), Indian hedgehog (IHH), and any combination thereof. In some embodiments, the threshold level is an average level for one or more members of the hedgehog signaling pathway as measured in a control population comprising subjects with normal olfactory and/or gustatory function. In some embodiments, the level of one or more members of the hedgehog signaling pathway is at least one order of magnitude lower than said threshold level. In some embodiments, the measuring comprises using one or more antibodies that bind one or more members of the hedgehog signaling pathway.

In some embodiments, the methods further comprise evaluating the subject's gustatory and/or olfactory function by determining a detection threshold (DT) score, a recognition threshold (RT) score, a magnitude estimation (ME) score, or any combination thereof with a forced-choice, three-stimuli, stepwise-staircase technique using one or more olfaction testing compounds. In some embodiments, the method further comprises treating the subject, wherein the treating comprises administering at least one therapeutic agent. In some embodiments, the at least one therapeutic agent comprises theophylline, riociguat, forskolin, or any combination thereof. In some embodiments, the at least one therapeutic agent comprises theophylline. In some embodiments, the at least one therapeutic agent is in a composition or dosage unit. In some embodiments, the composition or dosage unit is steroid-free. In some embodiments, the one or more therapeutic agents comprise an effective amount of one or more phosphodiesterase inhibitors. In some embodiments, the one or more phosphodiesterase inhibitors comprise a non-selective phosphodiesterase inhibitor, a phosphodiesterase-1 selective inhibitor, a phosphodiesterase-2 selective inhibitor, a phosphodiesterase-3 selective inhibitor, a phosphodiesterase-4 selective inhibitor, a phosphodiesterase-5 selective inhibitor, a phosphodiesterase-10 selective inhibitor, or any combination thereof.

In some embodiments, the administering is intranasal administration. In some embodiments, the treatment results in increasing the level of one or more members of the hedgehog signaling pathway.

Further disclosed herein is a method of diagnosing loss or distortion of taste or smell in a subject, the method comprising: (a) obtaining one or more biological samples from the subject; (b) measuring a level of one or more members of the hedgehog signaling pathway in one or more biological samples from the subject; and (c) diagnosing the subject with loss or distortion of taste or smell based on one or more of: (i) a level of Sonic Hedgehog (SHH) that ranges from about greater than 0 pg/mL to about 8,500 pg/mL; (ii) a level of Indian hedgehog (IHH) that ranges from about greater than 0 pg/mL about to 1.0 pg/mL; or (iii) a level of Desert Hedgehog (DHH) that ranges from about greater than 0 pg/mL to about 5.0 pg/mL.

Also disclosed herein are methods of treating loss or distortion of taste or smell in a subject, the method comprising increasing or maintaining a level of one or more members of the hedgehog signaling pathway.

In some embodiments, the one or more members of the hedgehog signaling pathway are selected from a group consisting of: Sonic Hedgehog (SHH), Desert Hedgehog (DHH), Indian hedgehog (IHH), and any combination thereof. In some embodiments, the increasing or maintaining the level of one or more members of the hedgehog signaling pathway comprises giving the subject one or more cyclic adenosine monophosphate activators and/or cyclic guanosine monophosphate activators. In some embodiments, the one or more cyclic adenosine monophosphate activators and/or cyclic guanosine monophosphate activators are given in combination with one or more additional therapeutic agents. In some embodiments, the one or more cyclic guanosine monophosphate activators is riociguat. In some embodiments, the riociguat is present in an amount ranging from greater than 0.0 μg to less than or equal to about 250 μg. In some embodiments, the one or more additional therapeutic agents comprise an effective amount of one or more phosphodiesterase inhibitors. In some embodiments, the one or more phosphodiesterase inhibitors comprise a non-selective phosphodiesterase inhibitor, a phosphodiesterase-1 selective inhibitor, a phosphodiesterase-2 selective inhibitor, a phosphodiesterase-3 selective inhibitor, a phosphodiesterase-4 selective inhibitor, a phosphodiesterase-5 selective inhibitor, a phosphodiesterase-10 selective inhibitor, or combinations thereof. In some embodiments, the one or more additional therapeutic agents comprises theophylline in an amount ranging from greater than 0 mg to less than or equal to about 45 mg.

In some embodiments, the method comprises administering to the subject one or more additional therapeutic agents, wherein the one or more additional therapeutic agents comprises forskolin in an amount ranging from greater than 0 mg to less than or equal to about 500 mg.

Also disclosed herein are pharmaceutical dosage units comprising one or more cyclic guanosine monophosphate activators and one or more cyclic adenosine monophosphate activators. In some embodiments, the pharmaceutical dosage comprises one or more cyclic guanosine monophosphate activators selected from a group consisting of 3-(5'-hydroxymethyl-2'-furyl)-1-benzylindazole (YC-1), YC-1 derivatives, anthranilic acids derivatives, ataciguat (HMR1766), benzydamine analogs, CFM1517, A-350619, nitrovasodilators, molsidomine, nitroxyl (HNO), BAY 41-2272, BAY 41-8543, BAY 58-2667, cinaciguat (BAY 58-2667), riociguat (BAY 63-2521), and combinations thereof. In some embodiments, the one or more cyclic guanosine monophosphate activators is riociguat. In some embodiments, the one or more cyclic adenosine monophosphate activators is selected from a group consisting of: 3-(5'-hydroxymethyl-2'-furyl)-1-benzylindazole (YC-1), glucagon, PDE inhibitors, prostaglandin E1 (PGE1), forskolin, β-adrenergic agonists, and combinations thereof. In some embodiments, the one or more cyclic adenosine monophosphate activators comprises forskolin. In some embodiments, the cyclic adenosine monophosphate activators is theophylline. In some embodiments, the dosage unit is steroid-free.

In some embodiments, the effective amount of the one or more phosphodiesterase inhibitors is, individually, a positive amount selected from the group consisting of less than about 100 mg, less than about 75 mg, less than about 50 mg, less than about 25 mg, less than about 20 mg, less than about 10 mg, less than about 5 mg, less than about 1 mg, less than about 0.5 mg, or less than about 0.1 mg.

In some embodiments, the method, composition, or unit dose, is an intranasal composition, and/or the administration or treating is an intranasal administration or treatment. In some embodiments, the method of treating appetite loss comprises administering to a subject in need thereof, a dose of a PDE inhibitor. In some embodiments, the dose of a PDE inhibitor is effective to ameliorate appetite loss associated with taste and/or smell loss. In some embodiments, the effective amount of the one or more PDE inhibitors is, individually, a positive amount selected from the group consisting of less than about 100 mg, less than about 75 mg, less than about 50 mg, less than about 25 mg, less than about 20 mg, less than about 10 mg, less than about 5 mg, less than about 1 mg, less than about 0.5 mg, or less than about 0.1 mg.

In some embodiments, the subject in need is a cancer patient. In some embodiments, the cancer patient is undergoing chemotherapy. In some embodiments, the cancer patient is undergoing radiation therapy. In some embodiments, the PDE inhibitor comprises a selective PDE inhibitor. In some embodiments, the PDE inhibitor comprises a non-selective PDE inhibitor. In some embodiments, the non-selective PDE inhibitor comprises theophylline. In some embodiments, the method does not comprise administering a steroid. In some embodiments, the PDE inhibitor is administered intranasally.

In some embodiments, the method further comprises administering an antiemetic. In some embodiments, the antiemetic is selected from a group consisting of 5-HT3 receptor antagonists, Dopamine antagonists, NK1 receptor antagonist, Antihistamines (HI histamine receptor antagonists), Cannabinoids, Benzodiazepines, Anticholinergics, and steroids. In some embodiments, the antiemetic is selected from a group consisting of Dolasetron (Anzemet), Granisetron (Kytril, Sancuso), Ondansetron (Zofran), Tropisetron (Setrovel, Navoban), Palonosetron (Aloxi), Mirtazapine (Remeron), Domperidone (Motilium), Olanzapine (Zyprexa), Droperidol, haloperidol, chlorpromazine, prochlorperazine, Alizapride, Prochlorperazine (Compazine, Stemzine, Buccastem, Stemetil, Phenotil), Metoclopramide (Reglan), Aprepitant (Emend), Casopitant, Cyclizine, Diphenhydramine (Benadryl), Dimenhydrinate (Gravol, Dramamine), Doxylamine, Meclizine (Bonine, Antivert), Promethazine (Pentazine, Phenergan, Promacot), Hydroxyzine (Vistaril), Cannabis, Dronabinol (Marinol), synthetic cannabinoids such as Nabilone (Cesamet) or the JWH series, Sativex, Midazolam, Lorazepam (Ativan), Hyoscine (also known as scopolamine), Dexamethasone (Decadron), Trimethobenzamide, Ginger, Emetrol, Propofol, Muscimol, Peppermint, and Ajwain. In some embodiments, the antiemetic is, individually, a positive amount from 0.1 mg to 500 mg. In some embodiments, the antiemetic is, individually, a positive amount selected from the group consisting of 0.3-0.6 mg, 0.5 mg, 25-50 mg, 25-100 mg, 25 mg, 12.5-25 mg, 0.5-2 mg, 0.25-2 mg, 0.5-2.5 mg, 2.5-5 mg, 1-3 mg, 1-5 mg, 5-15 mg, 4 mg, 8 mg, 8-20 mg, 250-500 mg, 12.5-25 mg, 25-50 mg, 50-100 mg, 5-10 mg, 10-30 mg, 10 mg, 100 mg, 0.1-1 mg, 4-8 mg, and 1-4 mg.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE DISCLOSURE

Figure 1:
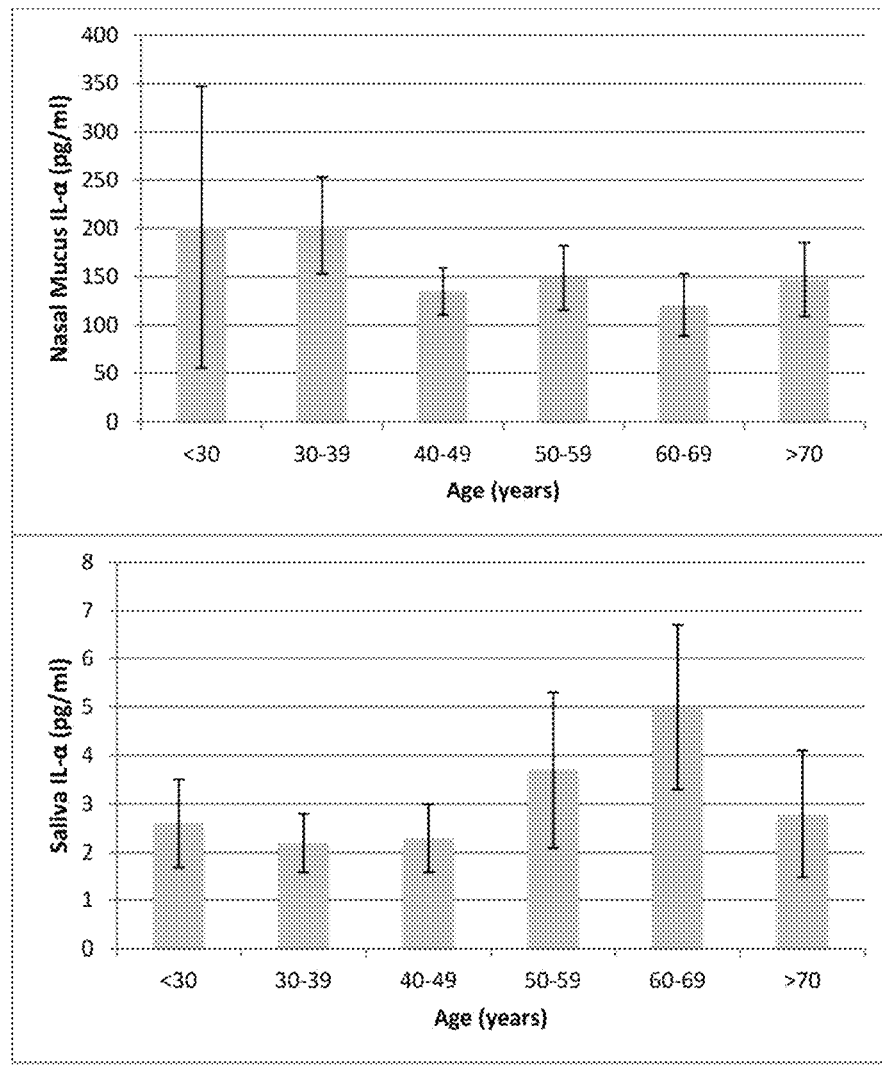
FIG. 1: Saliva and nasal mucus IL-1α by age (in pg/ml) in patients with hyposmia. Levels of IL-1α are shown on the ordinate, age in 10 yr groups on the abscissa. Mean levels are shown by the height of the blue bar with SEM indicated. Values were not obtained for blood plasma or urine.
Figure 2:
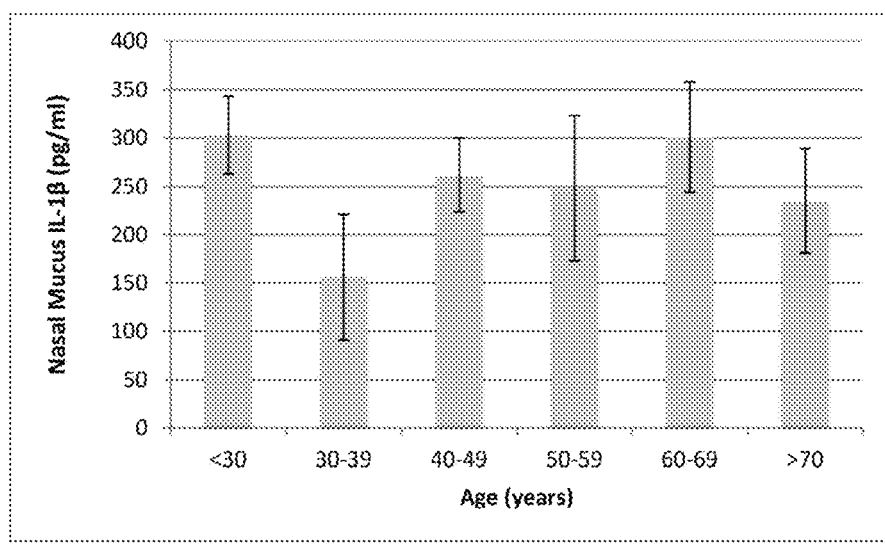
FIG. 2: Nasal mucus IL-1β by age. The figure is structured as in FIG. 1. Values were not obtained in saliva, blood plasma or urine.
Figure 3:
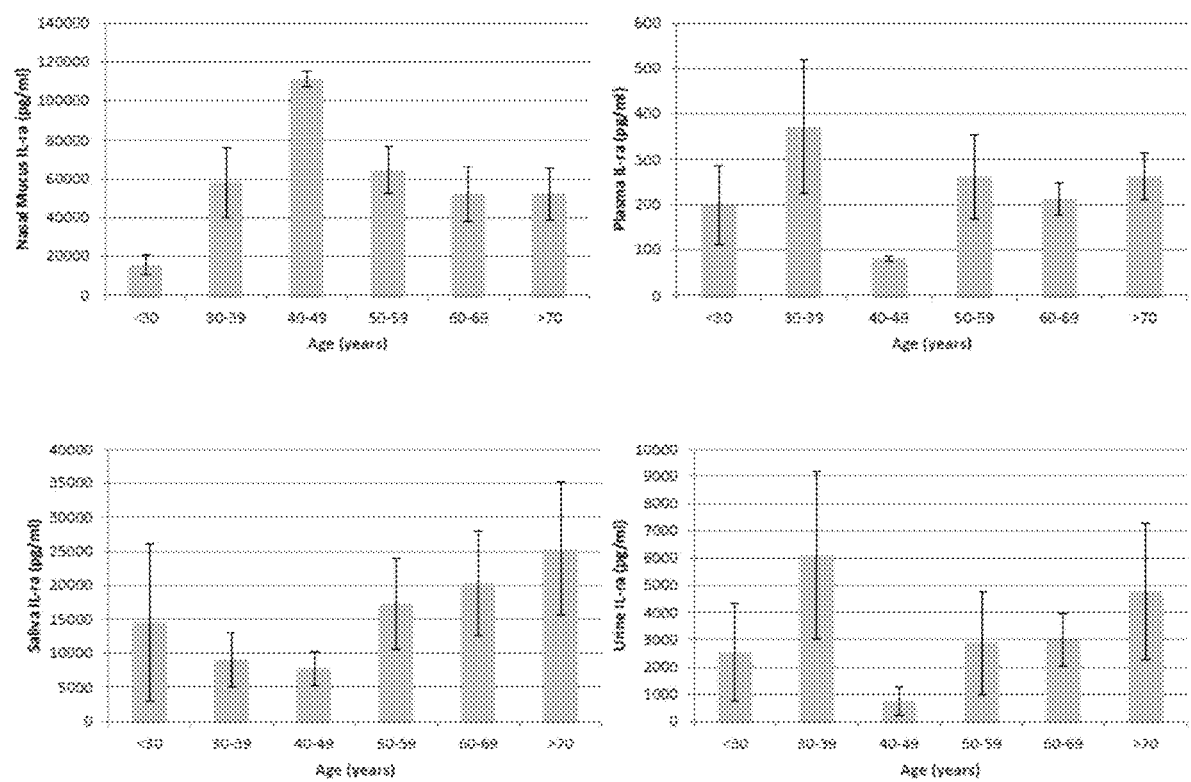
FIG. 3: Blood plasma, urine, saliva and nasal mucus IL-1ra by age. The figures are structured as in FIG. 1.
Figure 4:
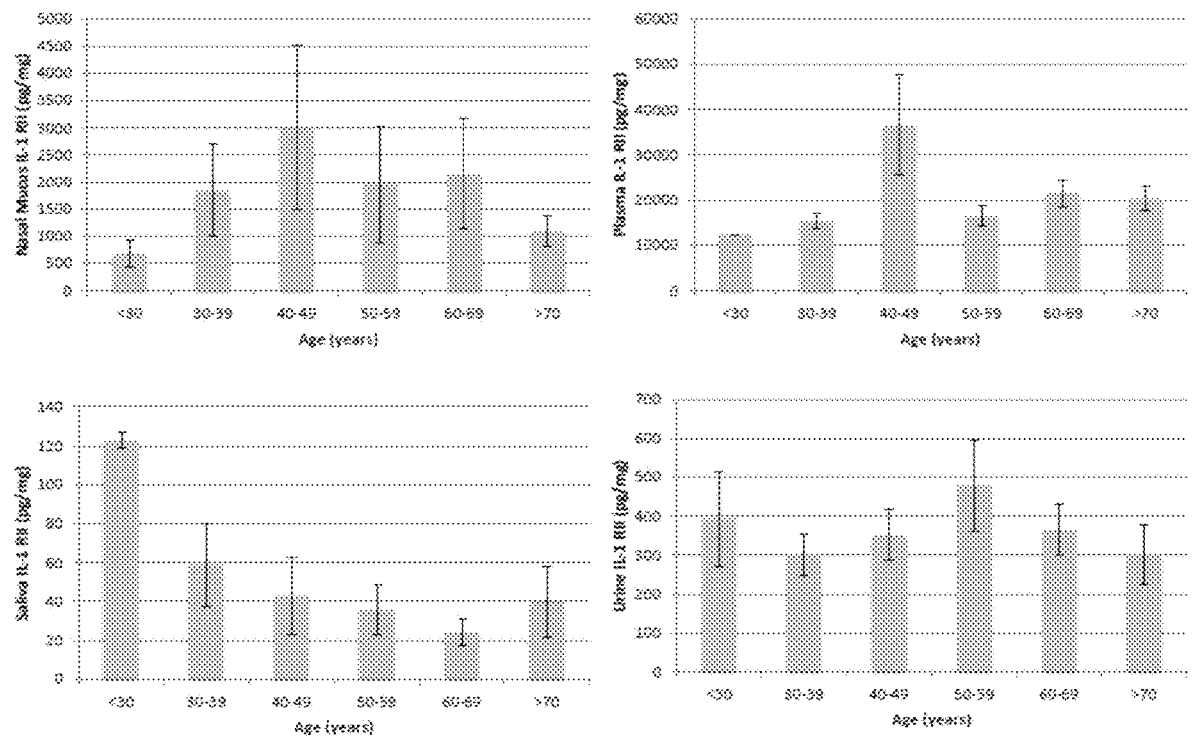
FIG. 4: Blood plasma, urine, saliva and nasal mucus IL-1 RII by age. The figures are structured as in FIG. 1.
Figure 5:
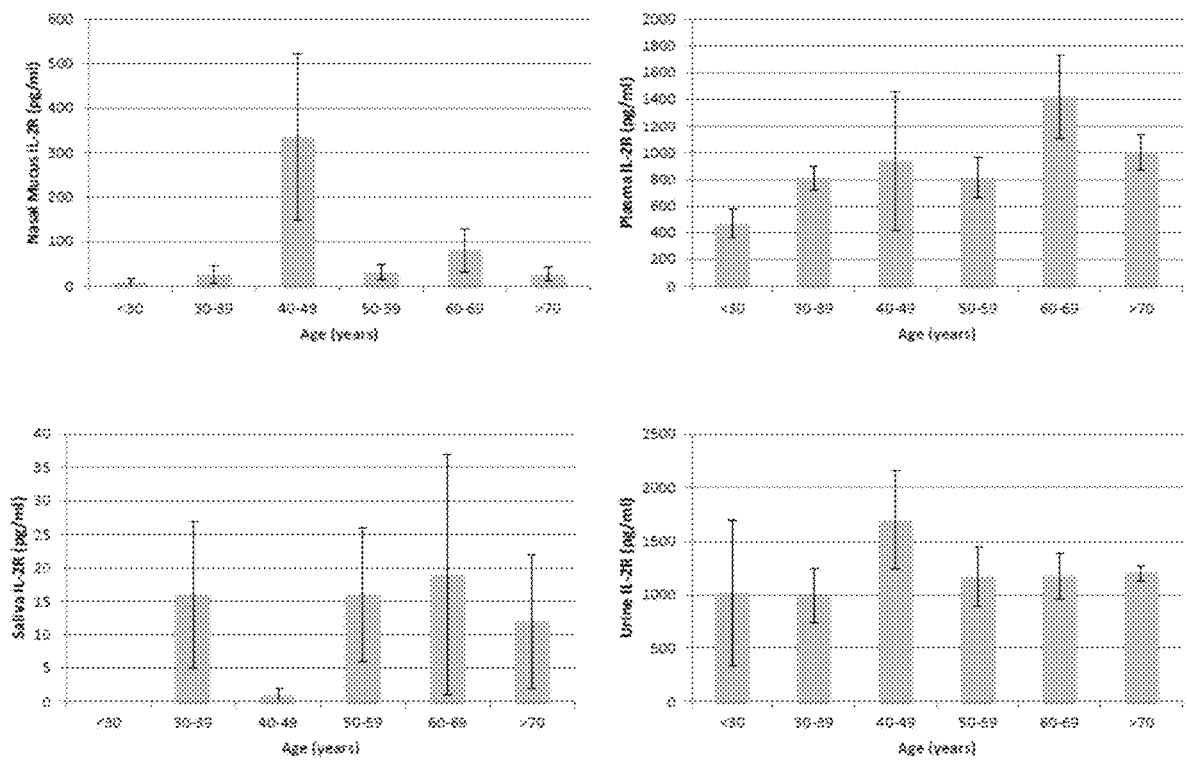
FIG. 5: Blood plasma, urine, saliva and nasal mucus IL-2R by age. The figures are structured as in FIG. 1.
Figure 6:
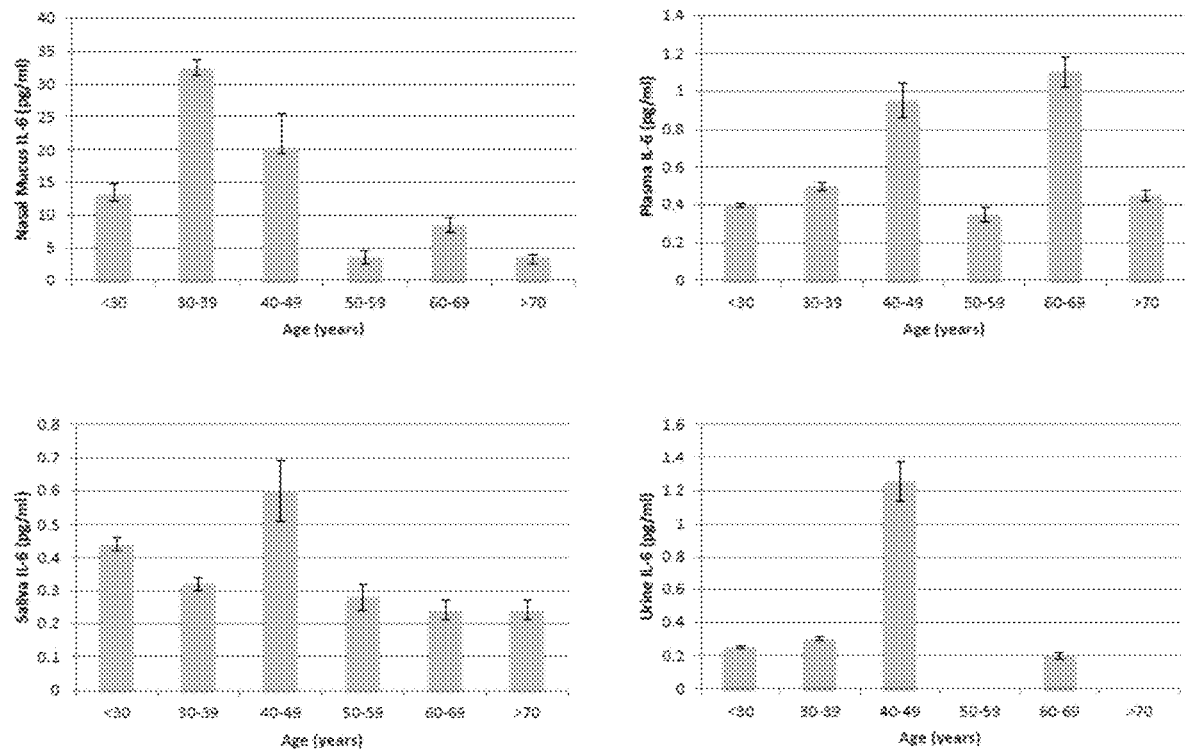
FIG. 6: Blood plasma, urine, saliva and nasal mucus IL-6 by age. The figures are structured as in FIG. 1.
Figure 7:
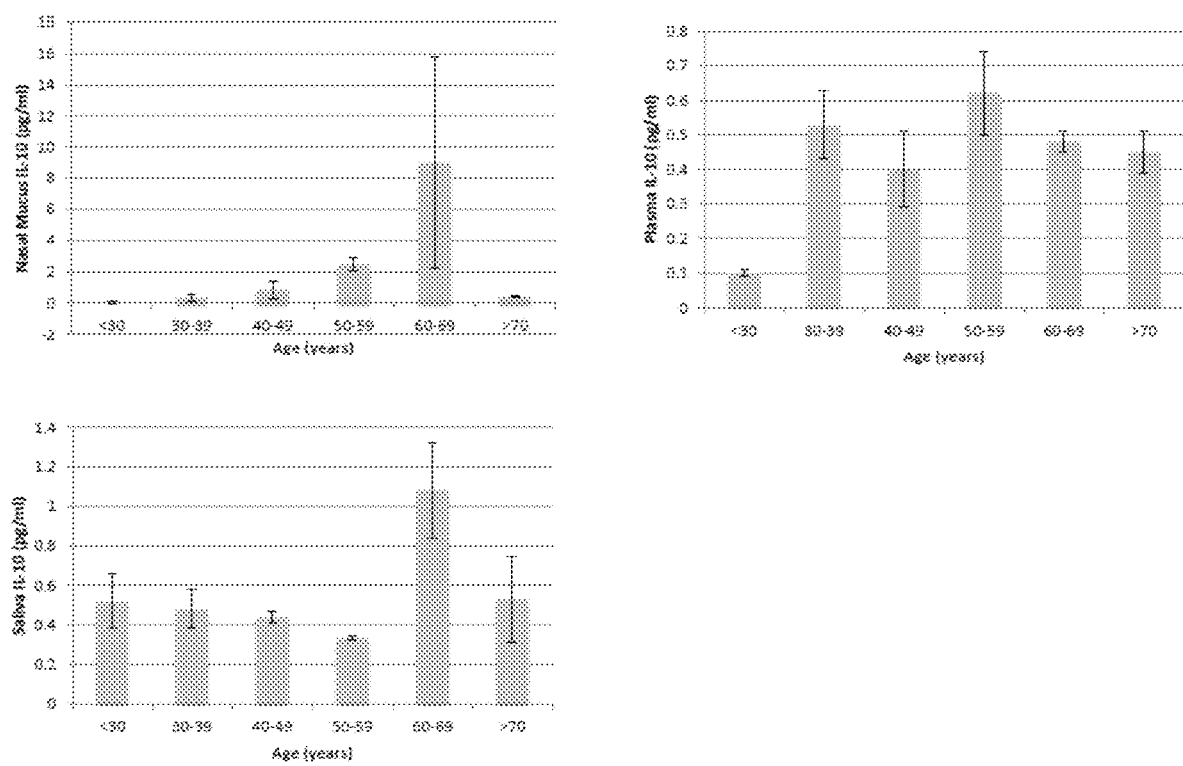
FIG. 7: Blood plasma, saliva and nasal mucus IL-10 by age. The figures are structured as in FIG. 1. Values were not obtained in urine.
Figure 8:
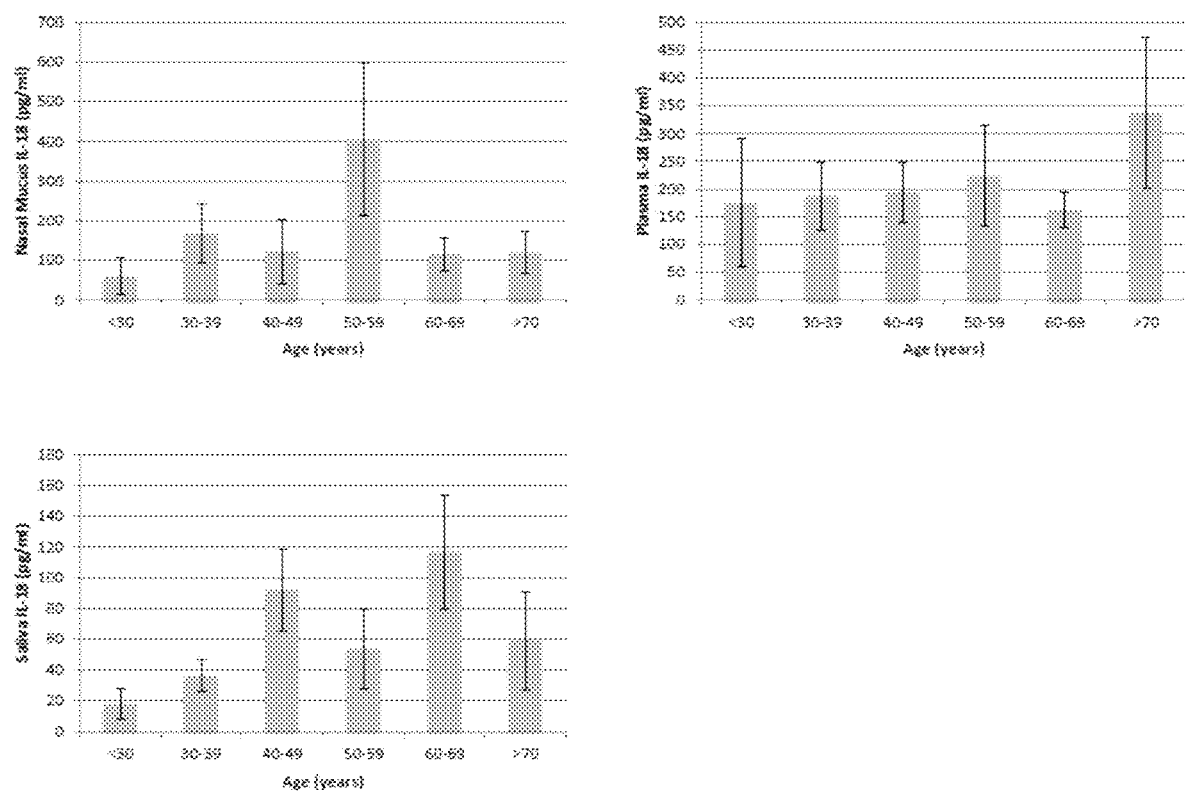
FIG. 8: Blood plasma, saliva and nasal mucus IL-18 by age. The figures are structured as in FIG. 1. Values were not obtained in urine.
Figure 9:
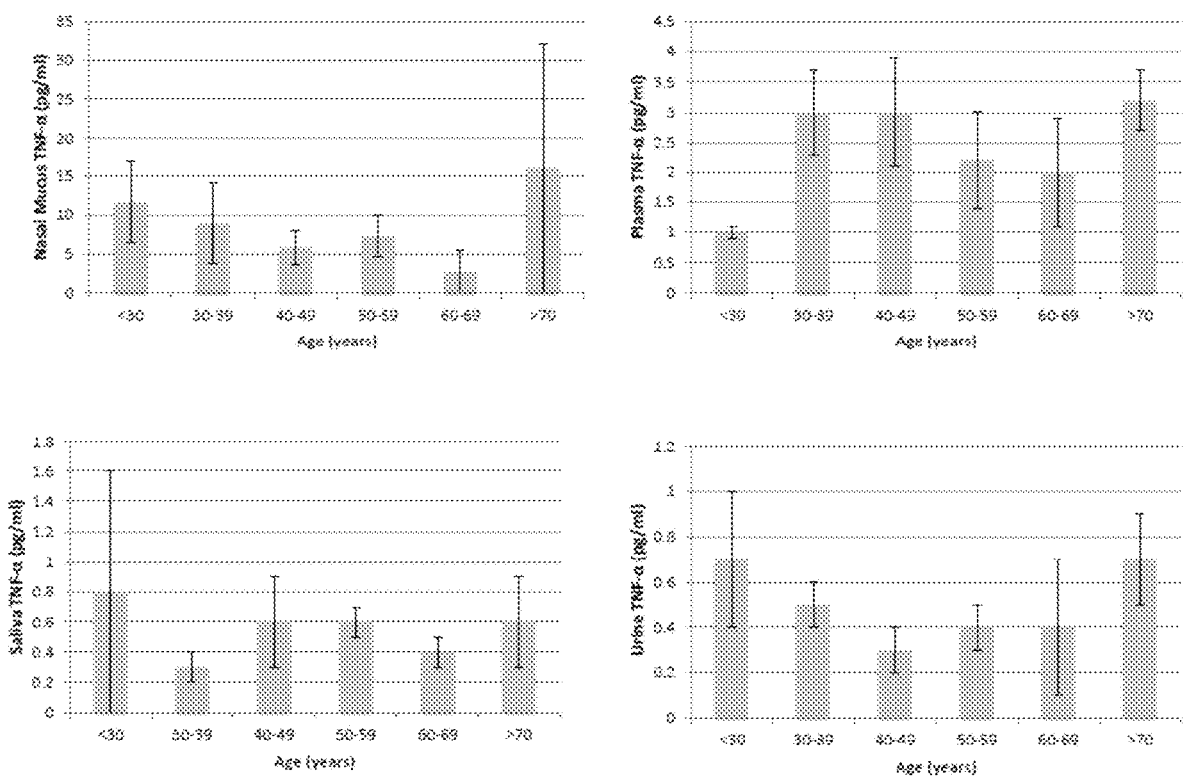
FIG. 9: Plasma, urine, saliva and nasal mucus in TNF-α by age. The figures are structured as in FIG. 1.
Figure 10:
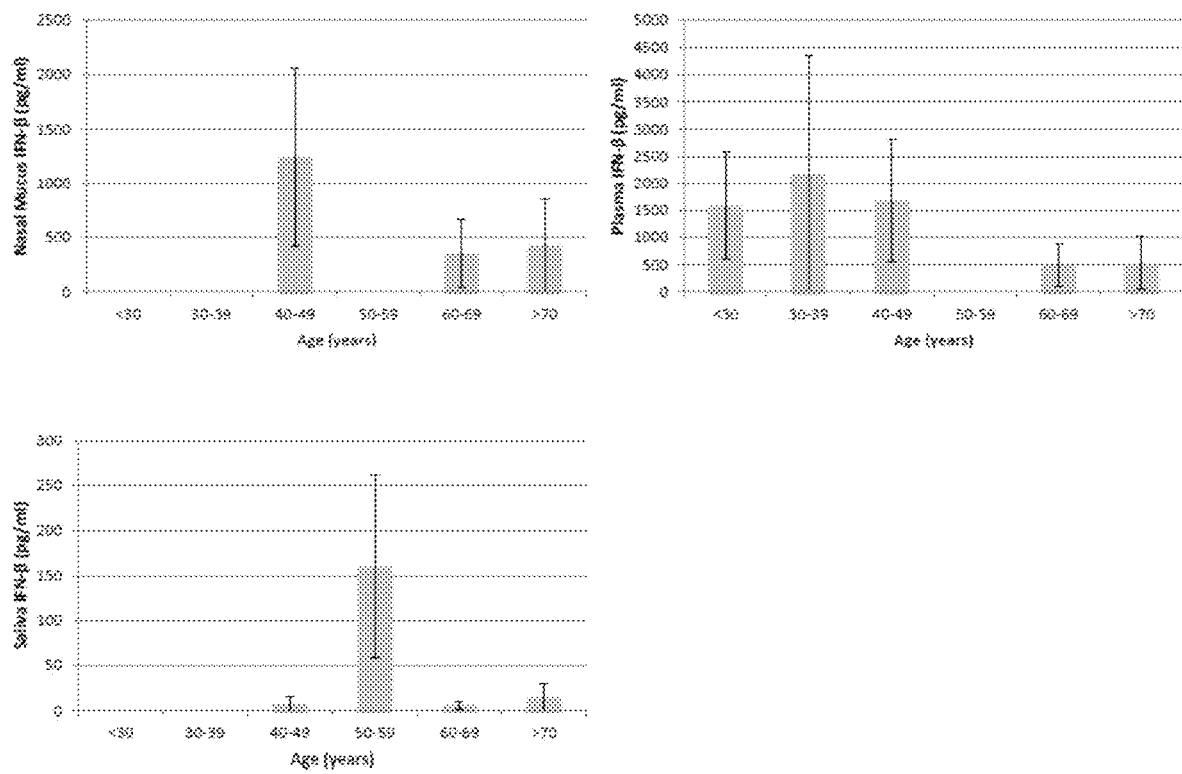
FIG. 10: Blood plasma, saliva and nasal mucus IFN-β by age. The figures are structured as in FIG. 1. Values were not obtained in urine.
Figure 11:
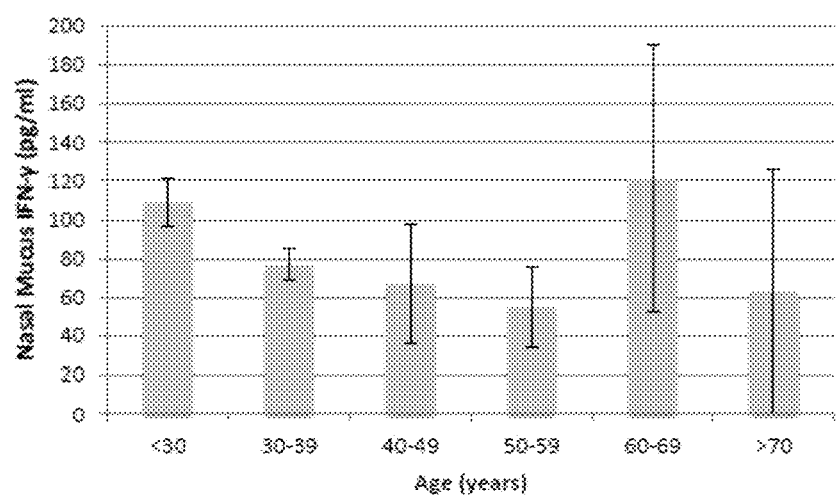
FIG. 11: Nasal mucus in IFN-γ by age. The figures are structured as in FIG. 1. Values were not obtained in blood plasma, urine or saliva.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Definitions

The term "about" as used herein and its grammatical equivalents, in relation to a reference numerical value can include a range of values plus or minus 10% from that value. For example the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

The term "diagnosis" as used herein and its grammatical equivalents can mean the testing of subjects to determine if they have a particular trait for use in a clinical decision. Diagnosis can include testing of subjects at risk of developing a particular disease resulting from infection by an infectious organism or a non-infectious disease, such as cancer or a metabolic disease. Diagnosis can also include testing of subjects who have developed particular symptoms to determine the cause of the symptoms. Diagnosis can also include prognosis, monitoring progress of a disease, and monitoring the efficacy of therapeutic regimens. The result of a diagnosis can be used to classify patients into groups for performance of clinical trials for administration of certain therapies.

The term "drug" as used herein and its grammatical equivalents can mean any compounds of any degree of complexity that perturbs a biological state, whether by known or unknown mechanisms and whether or not they are used therapeutically. Drugs thus can include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; pesticides; herbicides; and insecticides. The term "drug" as used herein and its grammatical equivalents can also refer to its free-base, acid, salts, esters, and mixtures thereof. If a drug is a salt, it can refer to a pharmaceutically acceptable salt, including but not limited to the salts found in the "Handbook of Pharmaceutical Salts: Properties, Selection, and Use," R. Heinrich Stahl and Camile G. Wermuth, eds., Wiley-VCH, $2^{nd}$ Edition (2011), incorporated herein by reference in its entirety. For example, the drugs can be formulated into, but not limited to, hydrochloride salts, hydrobromide salts, hydroiodide salts, fumaric acid salts, maleic acid salts, amino acid salts, mineral acid salts, addition salts, nitrate salts, phosphate salts, succinate salts, maleate salts, fumarate salts, citrate salts, tartrate salts, gluconate salts, lactate salts, lactobionate salts, lauryl sulfate salts, glutamate salts, acetamidobenzoate salts, potassium salts, sodium salts, calcium salts, tromethamine salts, 2-aminoethanol salts, lysine salts, and/or arginine salts.

The term "treating" as used herein and its grammatical equivalents can include achieving a therapeutic benefit and/or a prophylactic benefit. Therapeutic benefit can be eradication or amelioration of the underlying disorder being treated. Also, a therapeutic benefit can be achieved with the eradication or amelioration of one or more of the physiological symptoms associated with the underlying disorder such that an improvement can be observed in the patient, notwithstanding that the patient may still be afflicted with the underlying disorder. For prophylactic benefit, the compositions can be administered to a patient at risk of developing a particular disease, or to a patient reporting one or more of the physiological symptoms of a disease, even though a diagnosis of this disease may not have been made.

"Therapeutically effective amount" as used herein and its grammatical equivalents can refer to the amount of an active ingredient, with or without additional active ingredients, which can be effective to achieve its intended purpose. While individual patient needs may vary, determination of optimal ranges for effective amounts of the compounds and compositions is within the skill of an ordinary practitioner of the art. Generally, the dosage required to provide an effective amount of the composition, and which can be adjusted by one of ordinary skill in the art, can vary depending on the age, health, physical condition, sex, weight, extent of the dysfunction of the recipient, frequency of treatment and the nature, and scope of the dysfunction.

The terms "patient" or "subject" as used herein and its grammatical equivalents can include mammals, such as humans, including those in need of treatment thereof. Depending on the context, the terms "patient" and "subject" can sometimes be used interchangeably.

The term "average" as used herein and its grammatical equivalents can refer to the mathematical mean. Typically the mean can be calculated by the adding together a defined group of numbers and dividing the sum by the number of members in the group. For example, the mean of the group of numbers 1, 2, 3, 4, and 5 is 3 ((1+2+3+4+5)/(5) is 3).

The term "activator" as used herein and its grammatical equivalents can be used to describe a substance that leads to an increase in another e.g., measured substance. For example, a cAMP activator can lead to an increase the level of cAMP; a cGMP activator can lead to an increase the level of cGMP; or a SHH activator can lead to an increase the level of SHH.

The term "level" as used herein and its grammatical equivalents, when used in context with measuring, can refer to e.g., the level of a nucleic acid, a protein, cells, etc. For example, SHH levels can mean SHH protein or SHH nucleic acid levels. In some cases, e.g., when the term "level" refers to proteins, the term "level" can also refer to enzymatic activity. In some cases, e.g., when the term "level" refers to concentration, the term "level" can also refer to the concentration of substance (e.g., expressed as per protein) or the amount of substance (e.g., expressed as per protein).

The terms "dosage" and "dosage amounts" as used herein and its grammatical equivalents can mean that the referenced drug(s) can be formulated into any type of dosage forms suitable for oral administration, transmucosal administration, buccal administration, inhalation administration, intranasal administration, parental administration, intravenous administration, subcutaneous administration, intramuscular administration, sublingual administration, transdermal administration, and rectal administration.

The term "specific PDE inhibitor" or "selective PDE inhibitor" as used herein and their grammatical equivalents can be used to describe selectivity over one specific subtype of PDE receptor, e.g., has a preference to inhibit one specific PDE receptor subtype, but can also exhibit a certain degree of promiscuity. The degree of promiscuity can vary, but is less than 50%, for example, 49%, 45%, 40%, 35%, 30%, 25%, 20%, 15%, 10%, or 5% or less.

The term "communication medium" as used herein and its grammatical equivalents can refer to any means of communicating information. Exemplary types of communication medium can include, but are not limited to written, printed, and electronic types of media. Other types of communication medium will be apparent to those skilled in the relevant arts without departing from the spirit and scope of the present disclosure.

The term "combination thereof" as used herein and its grammatical equivalents can refer to one or more members of the recited group. For example, if the group comprises A, B, or any combination thereof, each of A individually, B individually, and the group A and B are contemplated.

The term "olfactometry" as used herein and its grammatical equivalents can refer to the testing and measurement of the sensitivity of the sense of smell. For example, olfactometry can be measured by determination of detection (DT) and recognition (RT) thresholds, magnitude estimation (ME) and hedonic evaluation (H) for four odors (pyridine, nitrobenzene, thiophene and amyl acetate). Additionally, abnormalities of smell function can consist of increased DT and/or RT above normal (decreased sensitivity) and/or decreased ME (decreased sensitivity) for one or more of the odors presented or decreased unpleasantness for odors of pyridine and thiophene or increased unpleasantness for odors of nitrobenzene or amyl acetate.

The term "subjective improvement" as used herein and its grammatical equivalents can refer to measurements of improvement in perception for all external odors based upon a scale of 1-100 with 100 indicating complete recovery of normal smell function with responses from 1-100 scaled appropriately. "Subjective improvement" and its grammatical equivalents can refer to the improvement in flavor perception as can be measured by responses of a 1-100 scale with 100 indicating that all flavors of food were considered normal and responses <100 scaled consistently less. Subjective improvement in taste function can also be measured with changes in taste for salt, sweet, sour and bitter tastants measured on the same 1-100 scale with 100 indicating return to normal for each of the four tastants considered and responses <100 scaled consistently less.

METHOD EMBODIMENTS

The loss or distortion of taste or smell is a problem affecting potentially millions of people. However, there are no good biochemical markers that can be used to effectively diagnose this loss or distortion of taste or smell. There are also no good treatment options currently on the market to treat loss or distortion of taste or smell.

Disclosed herein are methods for diagnosing and/or treating a subject with loss and/or distortion of taste or smell, e.g., hyposmia, dysosmia, anosmia, phantosmia, hypogeusia, dysgeusia, phantogeusia, and/or ageusia. The methods can comprise (a) obtaining one or more biological samples from the subject; (b) measuring a level of one or more members of the hedgehog signaling pathway in one or more biological samples from the subject; and (c) diagnosing the subject with loss and/or distortion of taste or smell, e.g., hyposmia, dysosmia, anosmia, phantosmia, hypogeusia, dysgeusia, phantogeusia, and/or ageusia based upon a level of one or more members of the hedgehog signaling pathway that can be lower than a threshold level. The methods of this invention can further comprise at least one of: (a) treating the subject diagnosed with loss and/or distortion of taste or smell, e.g., hyposmia, dysosmia, anosmia, phantosmia, hypogeusia, dysgeusia, phantogeusia, and/or ageusia; (b) transferring the diagnosed result via a communication medium; and (c) computer implementing the diagnosis.

Also disclosed herein are methods of evaluating the improvement in, decline in, and/or no change in, taste and/or smell, e.g., hyposmia, dysosmia, anosmia, phantosmia, hypogeusia, dysgeusia, phantogeusia, and/or ageusia in a subject. The methods can comprise (a) treating the subject with one or more drugs; (b) obtaining one or more biological samples from the subject; (c) measuring a level of one or more members of the hedgehog signaling pathway in one or more biological samples from the subject; and (d) diagnosing the subject with an improvement in, decline in, no change in, diminution in and/or distortion in taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level.

The methods described herein can comprise analyzing one or more biological samples from a subject to determine a level of one or more biological substances. The one or more biological samples can comprise one or more bodily fluids. The one or more bodily fluids can comprise, for example, a whole blood sample, a serum sample, a plasma sample, a urine sample, a saliva sample, a mucus sample, a perspiration sample, or any combination thereof. In some instances, the one or more biological samples can comprise the mucus sample. More specifically, the mucus sample can comprise a nasal mucus sample. Use of nasal specimens (e.g., the nasal mucus sample) can provide a minimally invasive manner of obtaining biological samples for analysis. In other cases, the one or more biological samples can comprise the saliva sample. Use of saliva sample can provide an alternative minimally invasive manner of obtaining biological samples for analysis. Another minimally invasive way to extract a bodily fluid from a patient is by collecting a perspiration sample. Methods to collect perspiration samples are within the abilities of a person of skill in the art. Some patients may prefer to have a blood test. In these instances, the bodily fluids can be whole blood, plasma, or serum samples, and can be used separately or in combination with each other. The results of this analysis can be suitable for use in diagnosis, prognosis, and determination of suitability of therapeutic interventions.

The term "one or more members of the hedgehog signaling pathway" as used herein and its grammatical equivalents can include known or unknown members of the hedgehog signaling pathway. For example, known members of the hedgehog signaling pathway can include the currently known members of the hedgehog signaling pathway, Sonic Hedgehog (SHH), Desert Hedgehog (DHH), and Indian hedgehog (IHH). Unknown members of the hedgehog signaling pathway can be found by comparing the homology of nucleic acid and proteins sequences. Although, the invention is directed towards the all of the members of the hedgehog signaling pathway, specific hedgehog members can be of significant influence. Therefore, it is contemplated that the invention can focus on SHH, DHH, IHH, or any combination thereof. For example, the embodiments disclosed herein can be focused on SHH.

The term "biological substance" as used herein and its grammatical equivalents can include cells and/or their extra-cellular and/or intra-cellular constituent(s). For example, biological substances can include pathogens, metabolites, DNA, RNA, lipids, proteins, carbohydrates, receptors, enzymes, hormones, growth factors, growth inhibitory factors, cells, organs, tissues, portions of cells, tissues, and/or organs, subcellular organelles, chemically reactive molecules like $H^+$, superoxides, ATP, citric acid, protein albumin, as well as combinations or aggregate representations of these types of biological variables. In addition, biological substances can include therapeutic agents such as, but not limited to, methotrexate, steroids, non-steroidal anti-inflammatory drugs, soluble TNF-alpha receptor, TNF-alpha antibody, and interleukin-1 receptor antagonists.

Biological substances can comprise one or more members of the hedgehog signaling pathway selected from a group consisting of SHH, DHH, and IHH. The level of one or more members of the hedgehog signaling pathway can indicate whether a subject has loss and/or distortion of taste or smell, e.g., hyposmia, dysosmia, anosmia, phantosmia, hypogeusia, dysgeusia, phantogeusia, and/or ageusia. As disclosed herein, the "level of one or more members of the hedgehog signaling pathway" can refer to its biological levels, e.g., nucleic acid and/or protein.

Biological substances can comprise cytokines, such a pro-inflammatory cytokines or anti-inflammatory cytokines. Pro-inflammatory cytokines can include IL-1α, IL-1β, IL-6, IL-18, TNF-α, or any combination thereof. Anti-inflammatory cytokines can include IL-1ra, IL-10, IFN-γ, IFN-β, or any combination thereof. The balance of pro- and anti-inflammatory cytokines can also indicate whether a subject has loss and/or distortion of taste or smell, e.g., hyposmia, dysosmia, anosmia, phantosmia, hypogeusia, dysgeusia, phantogeusia, and/or ageusia.

Biological substances can comprise cytokine receptors such as type I cytokine receptors, type II cytokine receptors, members of the immunoglobulin superfamily, members of the tumor necrosis factor receptor family, chemokine receptors, and or TGF beta receptors. A cytokine receptor can include IL-1 RII and/or IL-2R.

Biological substances can comprise eosinophils. Biological substances can also comprise IgE protein. Biological substances can comprise cyclic nucleotides (e.g., cAMP and cGMP). Biological substances can also comprise nitric oxide (NO).

The levels of the one or more biological substances can be compared, individually, to a threshold level. Threshold levels, as described herein, can be an average level for a particular biological substance as measured in a control population comprising subjects with normal taste and/or smell function. For example, if the level of the biological substance is above or below the threshold level for the biological substance, the subject can be diagnosed with and/or treated for loss and/or distortion of taste or smell, e.g., hyposmia, dysosmia, anosmia, phantosmia, hypogeusia, dysgeusia, phantogeusia, and/or ageusia. In certain cases, the level of one or more members of the hedgehog signaling pathway is at least one order of magnitude lower than said threshold level. For example, 2, 3, 4, 5, 10, 15, 16, 17, 18, 19, 20, 21, 22, 23, 24, 25, 26, 26, 27, 28, 29, 30, 31, 32, 33, 34, 35, 36, 37, 38, 39, 40, 41, 42, 43, 44, 45, 50, 60, 70 80, 90, 100, 150, 200, 250, 300, 400, 500, 600, 700, 800, 900, or 1000 or more orders of magnitude lower than said threshold level.

Sample Collection

The methods as described herein can use one or more biological samples. The biological sample can be collected from various sources by various methods, including but not limited to those described throughout. These one or more biological samples can be collected from a subject for analysis. The one or more biological samples can comprise one or more bodily fluids. For example, the one or more bodily fluids can comprise a whole blood sample, a serum sample, a plasma sample, a urine sample, a saliva sample, a mucus sample, a perspiration sample, or any combination thereof. One of the most easily accessible bodily fluids is mucus, which can be a nasal mucus sample; this invention contemplates using nasal mucus samples. Another easily accessible bodily fluid can be saliva and is specifically contemplated in the embodiments as disclosed herein. Additionally, because blood sample are sometimes easily accessible as well, the one or more bodily fluids can comprise a plasma sample, a serum sample, a whole blood sample, or any combination thereof. Another easily accessible bodily fluid that can be used in the invention is a perspiration sample.

If the one or more biological specimens is, for example, from the nasal area (e.g., a nasal mucus sample), the sample of nasal secretions can be collected directly from the nose into a collection tube or device. Alternative collection methods are also contemplated. For example, a sample of nasal secretion can be collected on a sample collection device by passing it into the nostril of a patient. The device can be inserted sequentially into each nostril of the patient and advanced parallel to the hard palate with slow rotation. The device can then be typically transferred to a transport tube, such as a glass or plastic test tube. The transport tube can include a suitable volume of a sterile medium such as ethanol or the like.

Other bodily fluids, such as a saliva sample can be obtained, for example, by draining, spitting, suction, and/or swabbing, to collect saliva, for example, mixed saliva. In order to better promote collection, gustatory or masticatory stimulation can be used to increase the flow of saliva. Another collection method can be by the use of a modified Lashley cup placed over the Stensen's duct, or with lingual stimulation with lemon juice to obtain parotid saliva, for example, pure saliva.

As previously described above, a blood sample can be collected, for example, by venipuncture, or finger sticking. Whole blood samples can be collected, for example, in a tube (e.g., a vacuum tube, a capillary tube), a syringe, or a bag. Plasma and serum samples can be derived from blood samples, e.g., by centrifugation.

A urine sample can be collected, e.g., in a cup, or in a 24-hour collection.

A perspiration sample can be collected, e.g., in a tube, and can be further purified for analysis. Collection can occur by any known method. In particular, a sweat sample can be collected using a special sweat stimulation procedure. For example, (a) a sweat-stimulating liquid can be applied to the skin creating a stimulated area; (b) an electrode can be placed on the stimulated area; (c) the stimulated area can be exposed to a weak electrical; and (d) sweat can be collected from the stimulated area into a plastic coil of tubing or onto a piece of gauze or filter paper.

A nasal sample collection device can be a swab, a wooden spatula, bibulous materials such as a cotton ball, filter, or gauze pad, an absorbent-tipped applicator, capillary tube, or a pipette. A swab can be used as a sample collection device, and the sample processing element can comprise a swab holder or a swab processing insert. The swab holder or swab processing insert can be tapered or angled to allow a single sample processing element to accommodate all types of swabs by allowing swabs with different amounts of fiber, or that are wound to different levels of tightness, to be held securely within the holder or insert. In certain cases, the swab holder or swab processing insert can securely hold the swab to provide stability. Nasal samples can also be collected from spontaneous discharge from the nasal cavity.

Samples can be collected from individuals repeatedly (e.g., once a day, once a week, once a month, biannually or annually) over a period of time (e.g., a day, a week, a month, more than one month, biannually, annually, several years, etc.) Obtaining numerous samples from an individual over a period of time can be used to verify results from earlier detections and/or to identify an alteration as a result of, for example, drug treatment. Samples can be obtained from humans or non-humans.

Analysis

Once the samples are collected, they can be used to determine levels of one or more relevant biological substances.

One or more biological samples can be collected and analyzed using one or more analytical techniques including enzymatic technique, ELISA, fluorometric technique, mass spectrography, visible spectrophotometric techniques, HPLC, GLC, PCR, protein and nucleic acid sequencing, and/or other similar techniques. The analysis can comprise determining the presence and/or level of one or more biological substance in the one or more biological samples. Once this analysis is complete, a diagnosis and/or treatment can be added.

Polymerase Chain Reaction (PCR)

The polymerase chain reaction (PCR) is a process for amplifying one or more desired specific nucleic acid sequences found in a nucleic acid. Because large amounts of a specific sequence can be produced by this process, it can be used for improving the efficiency of cloning DNA or messenger RNA and for amplifying a target sequence to facilitate detection thereof.

PCR involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction would be a discrete nucleic acid duplex with termini corresponding to the ends of the specific primers employed.

Any source of nucleic acid, in purified or non-purified form, can be utilized as the starting nucleic acid or acids, provided it contains or is suspected of containing the specific nucleic acid sequence desired. Thus, the process may employ, for example, DNA or RNA, including messenger RNA, which DNA or RNA can be single stranded or double stranded. In addition, a DNA-RNA hybrid which contains one strand of each can be utilized. A mixture of any of these nucleic acids may also be employed, or the nucleic acid produced from a previous amplification reaction herein using the same or different primers can be so utilized. The specific nucleic acid sequence to be amplified can be only a fraction of a larger molecule or can be present initially as a discrete molecule, so that the specific sequence constitutes the entire nucleic acid. It is not necessary that the sequence to be amplified be present initially in a pure form; it can be a minor fraction of a complex mixture, such as a portion of the β-globin gene contained in whole human DNA or a portion of nucleic acid sequence due to a particular microorganism which organism might constitute only a minor fraction of a particular biological sample. The starting nucleic acid may contain more than one desired specific nucleic acid sequence which can be the same or different. Therefore, it is useful not only for producing large amounts of one specific nucleic acid sequence, but also for amplifying simultaneously more than one different specific nucleic acid sequence located on the same or different nucleic acid molecules.

The nucleic acid or acids can be obtained from any source, for example, from plasmids such as pBR322, from cloned DNA or RNA, or from natural DNA or RNA from any source, including but not limited to, bacteria, yeast, viruses, and higher organisms such as plants or animals. DNA or RNA can be extracted from, including but not limited to, blood (whole blood, plasma, serum), tissue material such as chorionic villi or amniotic cells. The DNA or RNA can be cell-free DNA or RNA.

It will be understood that the word primer as used may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection can be 100% homologous with the end of the desired sequence to be amplified.

An appropriate agent can be added for inducing or catalyzing the primer extension reaction and the reaction can be allowed to occur under conditions known in the art. The inducing agent can be any compound or system which will function to accomplish the synthesis of primer extension products, including, but not limited to, enzymes. Suitable enzymes for this purpose can include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis can be initiated at the 3' end of each primer and proceed in the 5' direction along the template strand, until synthesis terminates, producing molecules of different lengths. There can be inducing agents, however, which initiate synthesis at the 5' end and proceed in the other direction, using the same process as described above.

The newly synthesized strand and its complementary nucleic acid strand can form a double-stranded molecule which can be used in the succeeding steps of the process. In the next step, the strands of the double-stranded molecule can be separated to provide single-stranded molecules. New nucleic acid can be synthesized on the single-stranded molecules. Additional inducing agent, nucleotides and primers can be added if necessary for the reaction to proceed under the conditions prescribed above. Again, the synthesis can be initiated at one end of the oligonucleotide primers and can proceed along the single strands of the template to produce additional nucleic acid. After this step, half of the extension product can consist of the specific nucleic acid sequence bounded by the two primers. The steps of strand separation and extension product synthesis can be repeated as often as needed to produce the desired quantity of the specific nucleic acid sequence. The amount of the specific nucleic acid sequence produced can accumulate in an exponential fashion. After the appropriate length of time has passed to produce the desired amount of the specific nucleic acid sequence, the reaction can be halted by inactivating the enzymes in any known manner or separating the components of the reaction.

Amplification can be useful when the amount of nucleic acid available for analysis is small, as, for example, in the prenatal diagnosis of sickle cell anemia using DNA obtained from fetal cells or from maternal plasma/serum/blood. Amplification can be particularly useful if such an analysis can be to be done on a small sample using non-radioactive detection techniques that can be inherently insensitive, or where radioactive techniques are employed but where rapid detection can be desirable.

Any known techniques for nucleic acid (e.g., DNA and RNA) amplification can be used with the assays described herein. Some amplification techniques are the polymerase chain reaction (PCR) methodologies which can include, but are not limited to, solution PCR and in situ PCR.

The invention is not limited to the use of straightforward PCR. A system of nested primers can be used for example. Other suitable amplification methods known in the field can also be applied such as, but not limited to, ligase chain reaction (LCR), strand displacement amplification (SDA), self-sustained sequence replication (3SR), array based test, digital PCR, and TAQMAN™.

As used herein "amplification" may refer to any in vitro method for increasing the number of copies of a nucleic acid sequence, e.g., with the use of a DNA polymerase. Nucleic acid amplification can result in the incorporation of nucleotides into a DNA molecule or primer thereby forming a new DNA molecule complementary to a DNA template. The newly formed DNA molecule and its template can be used as templates to synthesize additional DNA molecules. As used herein, one amplification reaction may consist of many rounds of DNA replication. DNA amplification reactions can include, for example, polymerase chain reactions (PCR). One PCR reaction may consist of 5-100 "cycles" of denaturation, annealing, and synthesis of a DNA molecule.

Nucleic Acid Sequencing

Nucleic acid sequencing can be used for detection of a biological substance in a biological sample. Nucleic acid sequencing enables detection of the presence or absence of nucleic acids, determining the levels of nucleic acids, and also determining the exact nucleotide sequences. The methods can be performed by any known methods, for example, Maxam-Gilbert sequencing, Sanger sequencing, shotgun sequencing, bridge PCR, massively parallel signature sequencing (MPSS), polony sequencing, 454 pyrosequencing, Illumina (Solexa) sequencing, SOLiD sequencing, Ion Torrent semiconductor sequencing, DNA nanoball sequencing, heliscope single molecule sequencing, and/or single molecule real time (SMRT) sequencing. Other sequencing methods can be used such as nanopore DNA sequencing, tunneling currents DNA sequencing, sequencing by hybridization, sequencing with mass spectrometry, microfluidic Sanger sequencing, microscopy-based techniques, RNAP sequencing, and/or in vitro virus high-throughput sequencing. These methods are disclosed in the literature.

Fluorescence Microscopy

Fluorescence microscopy can be used for detection of a biological substance in a biological sample. Fluorescence microscopy can enable the molecular composition of the structures being observed to be identified through the use of fluorescently-labeled probes of high chemical specificity such as antibodies. It can be done by directly conjugating a fluorophore to a protein and introducing this back into a cell. Fluorescent analogs can behave like the native protein and can therefore serve to reveal the distribution and behavior of this protein in the cell. Along with NMR, infrared spectroscopy, circular dichroism and other techniques, protein intrinsic fluorescence decay and its associated observation of fluorescence anisotropy, collisional quenching and resonance energy transfer are techniques for protein detection. Microscopy can also be used to detect and enumerate cells, such as eosinophils.

The naturally fluorescent proteins can be used as fluorescent probes. The jellyfish aequorea victoria produces a naturally fluorescent protein known as green fluorescent protein (GFP). The fusion of these fluorescent probes to a target protein enables visualization by fluorescence microscopy and quantification by flow cytometry. Without limiting the scope of the present invention, some of the probes are as following:

Labels:

Sensitivity and safety (compared to radioactive methods) of fluorescence has led to an increasing use for specific labeling of nucleic acids, proteins and other biomolecules. Besides fluorescein, other fluorescent labels cover the whole range from 400 to 820 nm. By way of example only, some of the labels can be: fluorescein and its derivatives, carboxyfluoresceins, rhodamines and their derivatives, atto labels, fluorescent red and fluorescent orange: Cy3/Cy5 alternatives, lanthanide complexes with long lifetimes, long wavelength labels—up to 800 nm, DY cyanine labels, and phycobili proteins.

Conjugates:

Antibody conjugates can be generated with specificity for virtually any epitope and are therefore, applicable to imaging a wide range of biomolecules. By way of example only, some of the conjugates can be: isothiocyanate conjugates, streptavidin conjugates, and/or biotin conjugates.

Enzyme Substrates:

By way of example only, some of the enzyme substrates can be fluorogenic and chromogenic substrates.

Micro- and Nanoparticles:

By way of example only, some of the fluorochromes can be: FITC (green fluorescence, excitation/emission=506/529 nm), rhodamine B (orange fluorescence, excitation/emission=560/584 nm), and nile blue A (red fluorescence, excitation/emission=636/686 nm). Fluorescent nanoparticles can be used for various types of immunoassays. Fluorescent nanoparticles can be based on different materials, such as, polyacrylonitrile, and polystyrene etc.

Molecular Rotors:

Fluorescent molecular rotors are sensors of microenvironmental restriction that become fluorescent when their rotation is constrained. Few examples of molecular constraint can include increased dye (aggregation), binding to antibodies, or being trapped in the polymerization of actin.

IEF-Markers:

IEF (isoelectric focusing) is an analytical tool for the separation of ampholytes, mainly proteins. An advantage for IEF-Gel electrophoresis with fluorescent IEF-marker is the possibility to directly observe the formation of gradient. Fluorescent IEF-marker can also be detected by UV-absorption at 280 nm (20° C.).

Any or all of these fluorescent probes can be used for the detection of biological substances in the nasal mucus. A peptide library can be synthesized on solid supports and, by using coloring receptors, subsequent dyed solid supports can be selected one by one. If receptors cannot indicate any color, their binding antibodies can be dyed. The methods can not only be used on protein receptors, but also on screening binding ligands of synthesized artificial receptors and screening new metal binding ligands as well. Automated methods for HTS and FACS (fluorescence activated cell sorter) can also be used. A FACS machine originally runs cells through a capillary tube and separate cells by detecting their fluorescent intensities.

Immunoassays

Immunoassay can be used for detecting a biological substance in a biological sample. In immunoblotting like the western blot of electrophoretically separated proteins a single protein can be identified by its antibody. Immunoassay can be competitive binding immunoassay where analyte competes with a labeled antigen for a limited pool of antibody molecules (e.g., radioimmunoassay, EMIT). Immunoassay can be non-competitive where antibody is present in excess and is labeled. As analyte antigen complex is increased, the amount of labeled antibody-antigen complex may also increase (e.g., ELISA). Antibodies can be polyclonal if produced by antigen injection into an experimental animal, or monoclonal if produced by cell fusion and cell culture techniques. In immunoassay, the antibody may serve as a specific reagent for the analyte antigen.

Without limiting the scope and content of the present invention, some of the types of immunoassays can be, by way of example only, RIAs (radioimmunoassay), enzyme immunoassays like ELISA (enzyme-linked immunosorbent assay), EMIT (enzyme multiplied immunoassay technique), microparticle enzyme immunoassay (MEIA), LIA (luminescent immunoassay), and FIA (fluorescent immunoassay).

These techniques can be used to detect biological substances in the nasal specimen. The antibodies—either used as primary or secondary ones—can be labeled with radioisotopes (e.g., 125I), fluorescent dyes (e.g., FITC) or enzymes (e.g., HRP or AP) which may catalyze fluorogenic or luminogenic reactions.

EMIT (Enzyme Multiplied Immunoassay Technique):

EMIT is a competitive binding immunoassay that avoids a separation step. EMIT is a type of immunoassay in which the protein can be labeled with an enzyme, and the enzyme-protein-antibody complex can be enzymatically inactivated, allowing quantitation of unlabeled protein.

ELISA (Enzyme Linked Immunosorbent Assay):

The invention can also use ELISA to detect biological substances in the nasal specimen. ELISA is based on selective antibodies attached to solid supports combined with enzyme reactions to produce systems capable of detecting low levels of proteins. It is also known as enzyme immunoassay or EIA. The protein can be detected by antibodies that have been made against it, that is, for which it is the antigen. Monoclonal antibodies are often used.

The test may require the antibodies to be fixed to a solid surface, such as the inner surface of a test tube, and a preparation of the same antibodies coupled to an enzyme. The enzyme can be one (e.g., (3-galactosidase) that produces a colored product from a colorless substrate. The test, for example, can be performed by filling the tube with the antigen solution (e.g., protein) to be assayed. Any antigen molecules present may bind to the immobilized antibody molecules. The antibody-enzyme conjugate can be added to the reaction mixture. The antibody part of the conjugate binds to any antigen molecules that were bound previously, creating an antibody-antigen-antibody "sandwich". After washing away any unbound conjugate, the substrate solution can be added. After a set interval, the reaction can be stopped (e.g., by adding 1 N NaOH) and the concentration of colored product formed can be measured in a spectrophotometer. The intensity of color can be proportional to the concentration of bound antigen.

ELISA can also be adapted to measure the concentration of antibodies, in which case, the wells can be coated with the appropriate antigen. The solution (e.g., serum) containing antibody can be added. After it has had time to bind to the immobilized antigen, an enzyme-conjugated anti-immunoglobulin can be added, consisting of an antibody against the antibodies being tested for. After washing away unreacted reagent, the substrate can be added. The intensity of the color produced can be proportional to the amount of enzyme-labeled antibodies bound (and thus to the concentration of the antibodies being assayed).

Radioimmunoassay:

Some embodiments of the invention can include radioimmunoassays to detect biological substances in the biological samples, e.g., in the nasal specimen. Radioactive isotopes can be used to study in vivo metabolism, distribution, and binding of small amount of compounds. Radioactive isotopes of $^1H$, $^{12}C$, $^{31}P$, $^{32}S$, and $^{127}I$ in body can be used, such as $^3H$, $^{14}C$, $^{32}P$, $^{35}S$, and $^{125}I$.

In receptor fixation method in 96-well plates, receptors can be fixed in each well by using antibody or chemical methods and radioactive labeled ligands can be added to each well to induce binding. Unbound ligands can be washed out and then the standard can be determined by quantitative analysis of radioactivity of bound ligands or that of washed-out ligands. Then, addition of screening target compounds may induce competitive binding reaction with receptors. If the compounds show higher affinity to receptors than standard radioactive ligands, most of radioactive ligands would not bind to receptors and can be left in solution. Therefore, by analyzing quantity of bound radioactive ligands (or washed-out ligands), testing compounds' affinity to receptors can be indicated.

The filter membrane method can be needed when receptors cannot be fixed to 96-well plates or when ligand binding needs to be done in solution phase. In other words, after ligand-receptor binding reaction in solution, if the reaction solution can be filtered through nitrocellulose filter paper, small molecules including ligands may go through it and only protein receptors can be left on the paper. Only ligands that strongly bound to receptors may stay on the filter paper and the relative affinity of added compounds can be identified by quantitative analysis of the standard radioactive ligands.

Fluorescence Immunoassays:

The invention can also include fluorescence immunoassays for detecting a biological substance in a biological sample. Fluorescence based immunological methods can be based upon the competitive binding of labeled ligands versus unlabeled ones on highly specific receptor sites. Fluorescence immunoassays can also be used to detect and enumerate cells, such as eosinophils.

The fluorescence technique can be used for immunoassays based on changes in fluorescence lifetime with changing analyte concentration. This technique may work with short lifetime dyes like fluorescein isothiocyanate (FITC) (the donor) whose fluorescence can be quenched by energy transfer to eosin (the acceptor). A number of photoluminescent compounds can be used, such as cyanines, oxazines, thiazines, porphyrins, phthalocyanines, fluorescent infrared-emitting polynuclear aromatic hydrocarbons, phycobiliproteins, squaraines and organo-metallic complexes, hydrocarbons and azo dyes.

Fluorescence based immunological methods can be, for example, heterogenous or homogenous. Heterogenous immunoassays can comprise physical separation of bound from free labeled analyte. The analyte or antibody can be attached to a solid surface. The technique can be competitive (for a higher selectivity) or noncompetitive (for a higher sensitivity). Detection can be direct (only one type of antibody used) or indirect (a second type of antibody can be used). Homogenous immunoassays can comprise no physical separation. Double-antibody fluorophore-labeled antigen can participate in an equilibrium reaction with antibodies directed against both the antigen and the fluorophore. Labeled and unlabeled antigen may compete for a limited number of anti-antigen antibodies.

Some of the fluorescence immunoassay methods can include simple fluorescence labeling method, fluorescence resonance energy transfer (FRET), time resolved fluorescence (TRF), and scanning probe microscopy (SPM). The simple fluorescence labeling method can be used for receptor-ligand binding, enzymatic activity by using pertinent fluorescence, and as a fluorescent indicator of various in vivo physiological changes such as pH, ion concentration, and electric pressure. TRF is a method that can selectively measure fluorescence of the lanthanide series after the emission of other fluorescent molecules is finished. TRF can be used with FRET and the lanthanide series can become donors or acceptors. In scanning probe microscopy, in the capture phase, for example, at least one monoclonal antibody can adhere to a solid phase and a scanning probe microscope can be utilized to detect antigen/antibody complexes which can be present on the surface of the solid phase. The use of scanning tunneling microscopy can eliminate the need for labels which normally can be utilized in many immunoassay systems to detect antigen/antibody complexes.

Nuclear Magnetic Resonance (NMR)

The invention can also include NMR for detecting a biological substance in a biological sample. NMR spectroscopy can determine the structures of biological macromolecules like proteins and nucleic acids at atomic resolution. In addition, it can be possible to study time dependent phenomena with NMR, such as intramolecular dynamics in macromolecules, reaction kinetics, molecular recognition or protein folding. Heteronuclei like $^{15}N$, $^{13}C$ and $^2H$, can be incorporated in proteins by uniform or selective isotopic labeling. Additionally, some new information about structure and dynamics of macromolecules can be determined with these methods.

X-Ray Crystallography

The invention can also include X-ray crystallography for detecting a biological substance in a biological sample. X-ray crystallography is a technique in which the pattern produced by the diffraction of X-rays through the closely spaced lattice of atoms in a crystal is recorded and then analyzed to reveal the nature of that lattice. This generally can lead to an understanding of the material and molecular structure of a substance. The spacing in the crystal lattice can be determined using Bragg's law. X-ray diffraction can be commonly carried out using single crystals of a material, but if these are not available, microcrystalline powdered samples may also be used which may require different equipment.

Fluorescence Spectroscopy

The invention can also include fluorescence spectroscopy for detecting a biological substance in a biological sample. By way of example only, conventional fluorometry is measurement of emission light intensities at defined wavelengths for a certain emission maxima of a fluorophore. Total fluorometry is a collection of data for a continuum of absorption as well as emission wavelengths. Fluorescence polarization is when polarized light is used for excitation and binding of fluorochrome-labeled antigens to specific antibodies. Line narrowing spectroscopy is low-temperature solid-state spectroscopy that derives its selectivity from the narrow-line emission spectra.

Time-dependent fluorescence spectroscopy can comprise time-resolved measurements containing more information than steady-state measurements, since the steady-state values represent the time average of time-resolved determinations. It is a single photon timing technique where the time between an excitation light pulse and the first photon emitted by the sample is measured.

Matrix Assisted Laser Desorption Ionization Time-of-Flight Mass Spectrometry (MALDI TOF-MS)

The invention can include MALDI TOF-MS for detecting a biological substance in a biological sample. MALDI TOF-MS provides accurate mass determinations and primary sequence information. Improved mass resolution in MALDI TOF-MS can be obtained by the utilization of a single-stage or a dual-stage reflectron (RETOF-MS). In the reflectron mass spectrum, the isotopic multiplet can be well resolved producing a full width half maximum (FWHM) mass resolution of about 3400. Mass resolutions up to 6000 (FWHM) can be obtained for peptides up to about 3000 Da with RETOF-MS. Enhancing the mass resolution can also increase the mass accuracy when determining the ion's mass.

Both linear and reflectron MALDI-TOF-MS can be utilized for molecular weight determinations of molecular ions and enzymatic digests leading to structural information of proteins. These digests are typically mass analyzed with or without purification prior to molecular weight determinations. Varieties of methodologies have been developed to obtain primary sequence information for proteins and peptides utilizing MALDI TOF-MS. Two different approaches can be taken. The first method is known as protein ladder sequencing and can be employed to produce structurally informative fragments of the analyte prior to insertion into the TOF mass spectrometer and subsequent analysis. The second approach can utilize the phenomenon of metastable ion decay that occurs inside the TOF mass spectrometer to produce sequence information.

The ladder sequencing with TOF-MS consists of either a time-dependent or concentration-dependent chemical degradation from either the N- or C-terminus of the protein/peptide into fragments, each of which differs by one amino acid residue. The mixture can be mass analyzed in a single MALDI-TOF-MS experiment with mass differences between adjacent mass spectral peaks corresponding to a specific amino acid residue. The order of occurrence in the mass spectrum defines the sequence of amino acids in the original protein/peptide.

Post-source decay with RETOF-MS MALDI is an ionization technique that produces intact protonated pseudomolecular ion species. A significant degree of metastable ion decay can occur after ion acceleration and prior to detection. The ion fragments produced from the metastable ion decay of peptides and proteins typically can include both neutral molecule losses (such as water, ammonia and portions of the amino acid side chains) and random cleavage at peptide bonds. In-source decay with linear TOF-MS is an alternative approach to RETOF-MS for studying metastable ion decay of MALDI generated ions. Primary structural information for peptides and proteins can be obtained by this method. Coherent mass spectral peaks can be produced from these metastable decayed ions giving rise to significant structural information for peptides and proteins.

Surface-Enhanced Laser Desorption Ionization-Time of Flight (SELDI-TOF)

The invention can include SELDI TOF-MS for detecting a biological substance in a biological sample. This technique can utilize stainless steel or aluminum-based supports, or chips, engineered with chemical (hydrophilic, hydrophobic, pre-activated, normal-phase, immobilized metal affinity, and cationic or anionic) or biological (antibody, antigen binding fragments (e.g., scFv), DNA, enzyme, or receptor) bait surfaces of 1-2 mm in diameter. These varied chemical and biochemical surfaces can allow differential capture of proteins based on the intrinsic properties of the proteins themselves. Solubilized tissue or body fluids in volumes as small as 0.1 µl can be directly applied to these surfaces, where proteins with affinities to the bait surface may bind. Following a series of washes to remove non-specifically or weakly bound proteins, the bound proteins can be laser desorbed and ionized for MS analysis. Masses of proteins ranging from small peptides of less than 1000 Da up to proteins of greater than 300 kDa can be calculated based on time-of-flight. As mixtures of proteins can be analyzed within different samples, a unique sample fingerprint or signature may result for each sample tested. Consequently, patterns of masses rather than actual protein identifications can be produced by SELDI analysis. These mass spectral patterns can be used to differentiate patient samples from one another, such as diseased from normal.

UV-Vis

The invention can include optical absorption spectroscopy (UV/VIS) for detecting a biological substance in a biological sample. UV/VIS provides light absorption data which helps in the determination of concentration of macromolecules such as, proteins, DNA, nucleotides etc. Organic dyes can be used to enhance the absorption and to shift the absorption into the visible range (e.g., coomassie blue reagents). Resonance raman spectroscopy (RRS) can be used to study molecular structure and dynamics. RRS helps in investigating specific parts of macromolecules by using different excitation wavelengths.

Liquid Chromatography (LC)

The invention can include LC for detecting a biological substance in a biological sample. Examples of LC are but not limited to, affinity chromatography, gel filtration chromatography, anion exchange chromatography, cation exchange chromatography, diode array-LC and high performance liquid chromatography (HPLC).

Gel filtration chromatography can separate proteins, peptides, and oligonucleotides on the basis of size. Molecules may move through a bed of porous beads, diffusing into the beads to greater or lesser degrees. Smaller molecules may diffuse further into the pores of the beads and therefore move through the bed more slowly, while larger molecules may enter less or not at all and thus move through the bed more quickly. Both molecular weight and three dimensional shapes contribute to the degree of retention. Gel Filtration Chromatography can be used for analysis of molecular size, for separations of components in a mixture, or for salt removal or buffer exchange from a preparation of macromolecules.

Affinity chromatography is the process of bioselective adsorption and subsequent recovery of a compound from an immobilized ligand. This process can allow for the specific and efficient purification of many diverse proteins and other compounds. Ion exchange chromatography can separate molecules based on differences between the overall charges of the proteins. It can be used for the purification of protein, oligonucleotides, peptides, or other charged molecules.

HPLC can be used in the separation, purification and detection of biological substances in the nasal mucus. Crude tissue extracts can be loaded directly onto the HPLC system and mobilized by gradient elution. Rechromatography under the identical conditions can be an option if further purification is warranted or necessary. Reversed phase chromatography (RPC) can be utilized in the process of protein structure determination. HPLC can be coupled with MS. The HPLC method described in Henkin et al., *New Frontiers in Immunobiology,* 2000, pp. 127-152, is incorporated herein in its entirety.

The size-exclusion chromatography (SEC) and ion-exchange chromatography (IEC) can be used for separation and purification of biologically active proteins, such as enzymes, hormones, and antibodies. In liquid affinity chromatography (LAC), interaction can be based on binding of the protein due to mimicry of substrate, receptor, etc. The protein can be eluted by introducing a competitive binding agent or altering the protein configuration which may facilitate dissociation. A procedure that can be used in the separation of membrane proteins is the use of nonionic detergents, such as Triton X-100, or protein solubilization by organic solvents with IEC.

Diode array detector-liquid chromatography (DAD-LC) provides complete, multiple spectra for each HPLC peak which, by comparison, can provide indication of peak purity. These data can also assign presence of tyr, trp, phe, and possibly others (his, met, cys) and can quantitate these amino acids by 2nd derivative or multi-component analysis. By a post-column derivatization, DAD-LC can also identify and quantitate cys, his and arg in individual peptides. Thus, it can be possible to analyze for 6 of the 20 amino acids of each separated peptide in a single LC run, and information can be obtained about presence or absence of these amino acids in a given peptide in a single step. This can be assisted by knowing the number of residues in each peptide.

Electrophoresis

The invention can include electrophoresis for detecting a biological substance in a biological sample. Electrophoresis can be gel electrophoresis or capillary electrophoresis.

Gel Electrophoresis:

Gel electrophoresis is a technique that can be used for the separation of proteins. During electrophoresis, macromolecules are forced to move through pores when an electrical current is applied. Their rate of migration through the electric field depends on strength of the field, size and shape of the molecules, relative hydrophobicity of the samples, and on an ionic strength and temperature of a buffer in which the molecules are moving. After staining, the separated macromolecules in each lane can be seen in a series of bands spread from one end of the gel to the other. Using this technology can be possible to separate and identify protein molecules that differ by as little as a single amino acid. Also, gel electrophoresis can allow determination of crucial properties of a protein such as its isoelectric point and approximate molecular weight. Electrofocusing or isoelectric focusing is a technique for separating different molecules by their electric charge differences (if they have any charge). It is a type of zone electrophoresis that takes advantage of the fact that a molecule's charge changes as the pH of its surroundings changes.

Capillary Electrophoresis:

Capillary electrophoresis is a collection of a range of separation techniques which may involve the application of high voltages across buffer filled capillaries to achieve separations. The variations can include separation based on size and charge differences between analytes (termed capillary zone electrophoresis (CZE) or free solution CE (FSCE)), separation of neutral compounds using surfactant micelles (micellar electrokinetic capillary chromatography (MECC) or sometimes referred to as MEKC) sieving of solutes through a gel network (capillary gel electrophoresis, GCE), separation of cations (or anions) based on electrophoretic mobility (capillary isotachophoresis, CITP), and separation of zwitterionic solutes within a pH gradient (capillary isoelectric focusing, CIEF). Capillary electrochromatography (CEC) can be an associated electrokinetic separation technique which involves applying voltages across capillaries filled with silica gel stationary phases. Separation selectivity in CEC can be any combination of both electrophoretic and chromatographic processes. Many of the CE separation techniques can rely on the presence of an electrically induced flow of solution (electroosmotic flow, EOF) within the capillary to pump solutes towards the detector.

Arrays

The invention can include arrays for detecting a biological substance in a biological sample. Arrays can involve performing parallel analysis of multiple samples against known protein targets. The development of various microarray platforms can enable and accelerate the determination of protein abundance, localization, and interactions in a cell or tissue. Microarrays can provide a platform that allows identification of protein interaction or function against a characterized set of proteins, antibodies, or peptides. Protein-based chips can array proteins on a small surface and can directly measure the levels of proteins in tissues using fluorescence-based imaging. Proteins can be arrayed on either flat solid phases or in capillary systems (microfluidic arrays), and several different proteins can be applied to these arrays. In addition to the use of antibodies as array probes, single-stranded oligonucleotides, whose specificity is optimized by in vitro elution (aptamers), offer a viable alternative. Nonspecific protein stains can be then used to detect bound proteins.

Arrays can include, but are not limited to, bead arrays, bead based arrays, bioarrays, bioelectronic arrays, cDNA arrays, cell arrays, DNA arrays, gene arrays, gene expression arrays, frozen cell arrays, genome arrays, high density oligonucleotide arrays, hybridization arrays, microcantilever arrays, microelectronic arrays, multiplex DNA hybridization arrays, nanoarrays, oligonucleotide arrays, oligosaccharide arrays, planar arrays, protein arrays, solution arrays, spotted arrays, tissue arrays, exon arrays, filter arrays, macroarrays, small molecule microarrays, suspension arrays, theme arrays, tiling arrays, and transcript arrays.

Sensors

The invention can include sensors for detecting a biological substance in a biological sample. Sensors can be used for both in vivo and in vitro detection. Sensors can be chemical sensors, optical sensors, and biosensors. Chemical sensors can be miniaturized analytical devices which may deliver real-time and online information on the presence of specific compounds or ions in complex samples. Optical sensors can be based on measurement of either intrinsic optical properties of analytes, or of optical properties of indicator dyes or labeled biomolecules attached to solid supports. Biosensors can be affinity biosensor based on capabilities of enzymes to convert substrates into products or catalytic biosensors. Biosensors can detect antibody and analyte complexes using a variety of physical methods. Some biosensors can measure the change in surface charge that occurs when analyte is bound to antibodies or other binding agents, which in turn are bound to a surface. Other biosensors can use binding agents attached to a surface and measure a change in a physical property of the support, other than surface charge, upon binding of analyte. Some biosensor techniques can use a specific property of a labeled binding agent or antigen to produce a measurable change.

Methods for Identifying Proteins from a Library Screen

Protein identification methods by way of example only can include low-throughput sequencing through Edman degradation, mass spectrometry techniques, peptide mass fingerprinting, de novo sequencing, and antibody-based assays. The protein quantification assays can include fluorescent dye gel staining, tagging or chemical modification methods (i.e., isotope-coded affinity tags (ICATS), combined fractional diagonal chromatography (COFRADIC)). The purified protein may also be used for determination of three-dimensional crystal structure, which can be used for modeling intermolecular interactions. Common methods for determining three-dimensional crystal structure can include x-ray crystallography and NMR spectroscopy. Detailed below are a few of the methods for identifying proteins in the present invention.

Protein Sequencing:

N-terminal sequencing can aid in the identification of unknown proteins, can confirm recombinant protein identity and fidelity (reading frame, translation start point, etc.), can aid the interpretation of NMR and crystallographic data, can demonstrate degrees of identity between proteins, or can provide data for the design of synthetic peptides for antibody generation, etc. N-terminal sequencing can utilize the Edman degradative chemistry, sequentially removing amino acid residues from the N-terminus of the protein and identifying them by reverse-phase HPLC. Sensitivity can be at the level of 100 s femtomoles and long sequence reads (20-40 residues) can often be obtained from a few 10 s picomoles of starting material. Pure proteins (>90%) can generate easily interpreted data, but insufficiently purified protein mixtures may also provide useful data, subject to rigorous data interpretation. N-terminally modified (especially acetylated) proteins cannot be sequenced directly, as the absence of a free primary amino-group prevents the Edman chemistry. However, limited proteolysis of the blocked protein (e.g., using cyanogen bromide) may allow a mixture of amino acids to be generated in each cycle of the instrument, which can be subjected to database analysis in order to interpret meaningful sequence information. C-terminal sequencing can be a post-translational modification, affecting the structure and activity of a protein. Various disease situations can be associated with impaired protein processing and C-terminal sequencing provides an additional tool for the investigation of protein structure and processing mechanisms.

Proteome Analyses:

Proteomics can be identified primarily by computer search algorithms that assign sequences to a set of empirically acquired mass/intensity data which are generated from conducting electrospray ionization (ESI), matrix-assisted laser desorption/ionization (MALDI-TOF), or three-dimensional quadrupole ion traps on the protein of interest.

Diagnosis

Generally, the compositions and methods of this disclosure can provide for the diagnosis or treatment of smell loss and/or distortion (e.g., hyposmia, dysosmia, anosmia) and/or taste loss and/or distortion (e.g., hypogeusia, dysgeusia, ageusia) by detecting one or more members of the hedgehog signaling pathway in one or more biological samples.

Examples of Biological Substances

Various substances that can be analyzed and/or measured in the methods disclosed herein can include, by way of example only, proteins, carbohydrates, lipids, hormones (e.g., leptin, ghrelin) in control of appetite, cholesterol and other lipids and lipid carrying proteins in control of lipid metabolism, growth factors (e.g., hepatic growth factor, granulocyte colony growth factor, brain derived neurotrophic factor), and antibodies, liver enzymes (e.g., SGOT, SGPT) therapeutic and recreational drugs of abuse, trace metals [either excess as in toxicity (e.g., lead, mercury, arsenic) or in deficiency diseases involving zinc, copper, magnesium] and most other substances found in plasma, erythrocytes, urine, saliva, and perspiration. Each metabolite in nasal mucus may reflect both physiological and pathological changes in human body metabolism specific to each metabolite and may reflect the manner in which nasal mucus provides information both on human body metabolism such as provided by plasma, erythrocytes, urine, saliva, and perspiration or information relatively unique to nasal mucus.

Biological substances can comprise one or more members of the hedgehog signaling pathway selected from a group consisting of SHH, DHH, and IHH. The level of one or more members of the hedgehog signaling pathway can indicate whether a subject has loss and/or distortion of taste or smell, e.g., hyposmia, dysosmia, anosmia, phantosmia, hypogeusia, dysgeusia, phantogeusia, and/or ageusia.

Biological substances can comprise cytokines, such a pro-inflammatory cytokines or anti-inflammatory cytokines. Pro-inflammatory cytokines can include IL-1α, IL-1β, IL-6, IL-18, TNF-α, or any combination thereof. Anti-inflammatory cytokines can include IL-1ra, IL-10, IFN-γ, IFN-β, or any combination thereof. The balance of pro- and anti-inflammatory cytokines can indicate whether a subject has loss and/or distortion of taste or smell, e.g., hyposmia, dysosmia, anosmia, phantosmia, hypogeusia, dysgeusia, phantogeusia, and/or ageusia.

Biological substances can comprise cytokine receptors such as type I cytokine receptors, type II cytokine receptors, members of the immunoglobulin superfamily, members of the tumor necrosis factor receptor family, chemokine receptors, and or TGF-beta receptors. For example, a cytokine receptor can be IL-1 RII and/or IL-2R.

Biological substances can comprise eosinophils. Biological substances can comprise IgE protein. Biological substances can comprise cyclic nucleotides (e.g., cAMP, cGMP). Biological substances can comprise nitric oxide (NO).

The identification and analysis of biological substances as disclosed herein can have numerous therapeutic and diagnostic applications. Clinical applications can include, for example, detection of loss and/or distortion of taste or smell, e.g., hyposmia, dysosmia, anosmia, phantosmia, hypogeusia, dysgeusia, phantogeusia, and/or ageusia; distinguishing the underlying cause of the loss and/or distortion of taste or smell, e.g., hyposmia, dysosmia, anosmia, phantosmia, hypogeusia, dysgeusia, phantogeusia, and/or ageusia to inform prognosis, selection of therapy, and/or prediction of therapeutic response; monitoring of therapy associated with efficacy and toxicity; and detection of recurrence of the loss and/or distortion of taste or smell, e.g., hyposmia, dysosmia, anosmia, phantosmia, hypogeusia, dysgeusia, phantogeusia, and/or ageusia.

The presence or increase or decrease of biological substances' concentration can allow the physician to diagnose loss and/or distortion of taste or smell, e.g., hyposmia, dysosmia, anosmia, phantosmia, hypogeusia, dysgeusia, phantogeusia, and/or ageusia and/or to predict the efficacy of treatment regimes.

The diagnosis of loss and/or distortion of taste or smell, e.g., hyposmia, dysosmia, anosmia, phantosmia, hypogeusia, dysgeusia, phantogeusia, and/or ageusia as disclosed herein can be used to enable or assist in the pharmaceutical drug development process for therapeutic agents. The analysis can be used to diagnose patients enrolling in a clinical trial. The diagnosis can indicate the state of the loss and/or distortion of taste or smell, e.g., hyposmia, dysosmia, anosmia, phantosmia, hypogeusia, dysgeusia, phantogeusia, and/or ageusia in patients undergoing treatment in clinical trials, and show changes in the state during the treatment. The diagnosis can demonstrate the efficacy of a treatment, and can be used to stratify patients according to their responses to various therapies.

The methods herein can be used to evaluate the efficacy of treatments over time. For example, biological samples can be obtained from a patient over a period of time as the patient is undergoing treatment. The biological substances from the different samples can be compared to each other to determine the efficacy of the treatment. Also, the methods described herein can be used to compare the efficacies of different therapies and/or responses to one or more treatments in different populations (e.g., different age groups, ethnicities, family histories, cause of loss and/or distortion of taste or smell, etc.).

General Methods for Diagnosis

Generally, the compositions and methods of this disclosure can provide for evaluating a subject's gustatory and/or olfactory function by determining a detection threshold (DT) score, a recognition threshold (RT) score, a magnitude estimation (ME) score, or any combination thereof. These score can be determined as previously described in Henkin, R. I., Schecter, P. J., Friedewald, W. T., DeMets, D. L., Raff, M. S, incorporated herein by reference in its entirety. A double blind study of the effects of zinc sulfate on taste or smell dysfunction. Amer. J. Med. Sci. 1976; 272:285-299, incorporated herein by reference in its entirety. Some methods are described in Henkin, R. I., Levy, L. M., and Fordyce, A. Taste and smell function in chronic disease: a review of clinical and biochemical evaluations of taste and smell dysfunction in over 5000 patients at The Taste and Smell Clinic in Washington, D.C. Am. J. Otolaryngol. 2013 September-October; 34(5):477-489, incorporated herein by reference in its entirety.

For example, patients can be initially diagnosed with suspected hyposmia, if their sensory dysfunction manifests as either loss of taste (i.e., flavor) and/or smell function. This subjective response can be documented by objective psychophysical measurements of olfactory function administered to each patient by use of a forced-choice, three-stimuli, stepwise-staircase technique in a fixed, controlled design as previously described herein and in Henkin, R. I. Evaluation and treatment of human olfactory dysfunction, in Otolaryngology (English, G. M. Ed.), Lippincott, Philadelphia, 1993, Vol. 2, pp. 1-86 (incorporated by reference herein in its entirety).

In some cases four test odors can be used; they can be pyridine (dead-fish odor), nitrobenzene (bitter-almond odor), thiophene (petroleum-like odor) and amyl acetate (banana-oil odor). Detection thresholds (DT), recognition thresholds (RT) and magnitude estimation (ME) values for each odor can be determined as previously described. Thresholds can be converted into bottle units (BU) as previously described and results reported as M±SEM of correct responses for each odor in each treatment group; ME can be reported in % and results calculated to obtain M±SEM for each treatment group for all correct responses using data for the four highest odor concentrations presented (from $10^{-2M}$—an absolute odor concentration).

In addition, each patient can be graded using the hedonic (H) value of each odor presented for these same odor concentrations (from $10^{-2M}$—an absolute odor concentration using a −100-0-+100 scale). If they consider a pleasant odor pleasant ("they wished to smell the odor again") they can be graded the odor as +1-+100 with respect to pleasantness; if they consider the odor unpleasant ("they did not wish to smell the odor again") they graded the odor as −1--100 with respect to unpleasantness; if they do not consider the odor either pleasant or unpleasant they can be graded the odor as neutral or 0. Results can be obtained by calculating the arithmetical sum of each correct recognition response for each odor with respect to its pleasantness, unpleasantness or neutrality. Arithmetic M±SEM can be obtained for each treatment group for each odor presented. These score may then be compared to a reference or threshold levels. This comparison can be used in aiding the diagnosis of hyposmia. Some methods are described in Henkin, R. I., Levy, L. M., and Fordyce, A. Taste and smell function in chronic disease: a review of clinical and biochemical evaluations of taste and smell dysfunction in over 5000 patients at The Taste and Smell Clinic in Washington, D.C. Am. J. Otolaryngol. 2013 September-October; 34(5): 477-489, incorporated herein by reference in its entirety.

Additionally, the present disclosure can provide for the measurement of levels of one or more biological substances associated with loss and/or distortion of taste or smell, e.g., hyposmia, dysosmia, anosmia, phantosmia, hypogeusia, dysgeusia, phantogeusia, and/or ageusia. These levels may also be compared to a threshold level, wherein the comparison can be also used to aid in the diagnosis of loss and/or distortion of taste or smell, e.g., hyposmia, dysosmia, anosmia, phantosmia, hypogeusia, dysgeusia, phantogeusia, and/or ageusia. The level of these biological substances can include but not be limited to the level of one or more members of the hedgehog signaling pathway.

For example, these members of the hedgehog signaling pathway can be SHH, DHH, and/or IHH, and/or any combination thereof can be decreased or eliminated. In some cases the hedgehog member can be SHH, DHH, IHH, or any combination thereof. The threshold for determining a decrease of the level of SHH in biological fluids can vary, for example, SHH levels can be or about: 0 pg/mL, greater than 0 pg/mL to less than less than 1 pg/mL, 1 pg/mL to 25 pg/mL, 15 pg/mL to 30 pg/mL, 20 pg/mL to 40 pg/mL; 35 pg/mL to 50 pg/mL; 45 pg/mL to 100 pg/mL; 75 pg/mL to 150 pg/mL, 125 pg/mL to 1000 pg/mL, 900 pg/mL to 2500 pg/mL, 2000 pg/mL to 5000 pg/mL, 4000 pg/mL to 7500 pg/mL, 6000 pg/mL to 10,000 pg/mL. The threshold for determining a decrease of the level of DHH in biological fluids can vary, for example, DHH can be or about: 0 pg/mL, greater than 0 pg/mL to 0.1 pg/mL, 0.05 pg/mL to 0.15 pg/mL, 0.125 pg/mL to 0.2 pg/mL, 0.15 pg/mL to 0.30 pg/mL, 0.25 pg/mL to 0.5 pg/mL, 0.4 pg/mL to 0.7 pg/mL, 0.6 pg/mL to 0.75 pg/mL, 0.725 pg/mL to 0.9 pg/mL, 0.8 pg/mL to 1.0 pg/mL, 0.9 pg/mL to 1.1 pg/mL, 1.0 pg/mL to 1.3 pg/mL, 1.2 pg/mL to 1.5 pg/mL, 1.4 pg/mL to 2.0 pg/mL, 1.9 pg/mL to 2.5 pg/mL, 2.4 pg/mL to 3.0 pg/mL, 2.9 pg/mL to 3.5 pg/mL, 3.4 pg/mL to 3.8 pg/mL, 3.7 pg/mL to 3.9 pg/mL, 3.85 pg/mL to 5.0 pg/mL, less than 5.0 pg/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL. The threshold for determining a decrease of the level of IHH in biological fluids can vary, for example, IHH can be or about: 0 pg/mL, greater than 0 pg/mL to 0.1 pg/mL, 0.05 pg/mL to 0.15 pg/mL, 0.125 pg/mL to 0.2 pg/mL, 0.15 pg/mL to 0.30 pg/mL, 0.25 pg/mL to 0.5 pg/mL, 0.4 pg/mL to 0.7 pg/mL, 0.6 pg/mL to 0.75 pg/mL, 0.725 pg/mL to 0.9 pg/mL, 0.8 pg/mL to 1.0 pg/mL, less than 1.0 pg/mL, less than 2.0 pg/mL, less than 5.0 pg/mL, less than 10.0 pg/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL.

The present disclosure can also provide for the measurement of levels of one or more biological substances associated with loss and/or distortion of taste or smell, e.g., hyposmia, dysosmia, anosmia, phantosmia, hypogeusia, dysgeusia, phantogeusia, and/or ageusia. The level of these biological substances can include but are not limited to IL-1α, IL-1β, IL-1ra, IL-1 RII, IL-1α, IL-1β, IL-1ra, IL-1 RII, IL-2, IL-2R, IL-6, IL-10, IL-18, TNF-α, IFN-β, IFN-γ, cytokines, IgE, or eosinophils.

For example, molecules such as IL-1α, IL-1β, IL-1ra, IL-1 RII, IL-1α, IL-1β, IL-1ra, IL-1 RII, IL-2, IL-2R, IL-6, IL-10, IL-18, TNF-α, IFN-β, IFN-γ, or any combination thereof can be elevated. In some cases the molecule can be IL-6. In some cases the threshold for determining elevation about 15 pg/mL to about 45 pg/mL and wherein higher levels of the molecules described herein may indicate that the subject has hyposmia. The threshold can be 0.1, 0.2, 0.3, 0.4, 0.5, 0.6, 0.7, 0.8, 0.9, 1, 2, 3, 4, 5, 10, 15, 16, 17, 18, 19, 20, 21, 22, 23, 24, 25, 26, 26, 27, 28, 29, 30, 31, 32, 33, 34, 35, 36, 37, 38, 39, 40, 41, 42, 43, 44, 45, 50, 60, 70 80, 90 or 100 pg/mL. The level of IL-6 wherein the threshold level of IL-6 can be from or from about: 0.05 pg/mL to 50 pg/mL and about 0.05 pg/mL to about 50 pg/mL, for example, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL, or 40 pg/mL to 60 pg/mL, or 50 pg/mL to 70 pg/mL, or 60 pg/mL to 80 pg/mL, or 70 pg/mL to 90 pg/mL, or 80 pg/mL to 100 pg/mL. By way of example only, and not to be construed as limiting in any way, the range for IHH in salvia, urine, and plasma, can be or about: 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL; and in mucus, can be or about 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL, or 40 pg/mL to 60 pg/mL, or 50 pg/mL to 70 pg/mL, or 60 pg/mL to 80 pg/mL, or 70 pg/mL to 90 pg/mL, or 80 pg/mL to 100 pg/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL.

Measurements or testing of one or more biological substances can be compared to thresholds or can be compared to level or amounts of other biological substances.

For example, elevated levels of IgE in biological samples can be used in aiding the diagnosis of loss and/or distortion of taste or smell, e.g., hyposmia, dysosmia, anosmia, phantosmia, hypogeusia, dysgeusia, phantogeusia, and/or ageusia. The threshold level can be 75 kU/L. The threshold may also be 75 kU/L-125 kU/L. The threshold may also be 45, 55, 65, 75, 76, 77, 78, 79, 80, 85, 90, 95, 100, 105, 110, 115, 120, 125, 150, 175, 200 kU/L. The threshold may also be higher than 75 kU/L, 100 kU/L, or 125 kU/L and about 75 kU/L, about 100 kU/L, or about 125 kU/L. Elevated levels of IgE can be elevated above a threshold value. Elevated levels may indicate that a subject has a loss and/or distortion of taste or smell, e.g., hyposmia, dysosmia, anosmia, phantosmia, hypogeusia, dysgeusia, phantogeusia, and/or ageusia. A subject may have loss and/or distortion of taste or smell, e.g., hyposmia, dysosmia, anosmia, phantosmia, hypogeusia, dysgeusia, phantogeusia, and/or ageusia if the subject's IgE values are measured above 45, 55, 65, 75, 76, 77, 78, 79, 80, 85, 90, 95, 100, 105, 110, 115, 120, 125, 150, 175, 200 kU/L. A subject may have loss and/or distortion of taste or smell, e.g., hyposmia, dysosmia, anosmia, phantosmia, hypogeusia, dysgeusia, phantogeusia, and/or ageusia if the subject's IgE values are measured above 75 kU/L, 100 kU/L, or 125 kU/L and about 75 kU/L, about 100 kU/L, or about 125 kU/L. A subject's IgE value can be determined by any suitable assay as described herein. For example, the level of IgE can be measured using a fluorescence polarization assay.

Elevated levels of eosinophils in biological samples, e.g., blood samples, can be used in aiding the diagnosis of hyposmia. The threshold level can be 200 cells/HPF. The threshold may also be 200 cells/HPF-400 cells/HPF. The threshold may also be 50-600 cells/HPF. The threshold may also be 50, 100, 200, 210, 220, 230, 240, 250, 260, 270, 280, 290, 300, 310, 320, 330, 340, 350, 360, 370, 380, 390 or 400, 420, 440, 460, 480, 500, 520, 540, 560, 580 or 600 cells/HPF. The threshold may also be 300 cells/HPF (high powered field), 350 cells/HPF, or 400 cells/HPF and about 300 cells/HPF, 350 cells/HPF, or 400 cells/HPF. Elevated level of eosinophils can be elevated about a threshold value. Elevated levels may indicate that a subject has a hyposmia. A subject may have hyposmia if the subject's eosinophils count or levels is above 50, 100, 200, 210, 220, 230, 240, 250, 260, 270, 280, 290, 300, 310, 320, 330, 340, 350, 360, 370, 380, 390 or 400, 420, 440, 460, 480, 500, 520, 540, 560, 580 or 600 cells/HPF. A subject may have hyposmia if the subject's eosinophils count or levels is above 300 cells/HPF (high powered field), 350 cells/HPF, or 400 cells/HPF and about 300 cells/HPF, 350 cells/HPF, or 400 cells/HPF. A subject' eosinophils count can be determined by any suitable assay as described herein, including, but not limited to, microscopy or Coulter counter.

Figure 12:
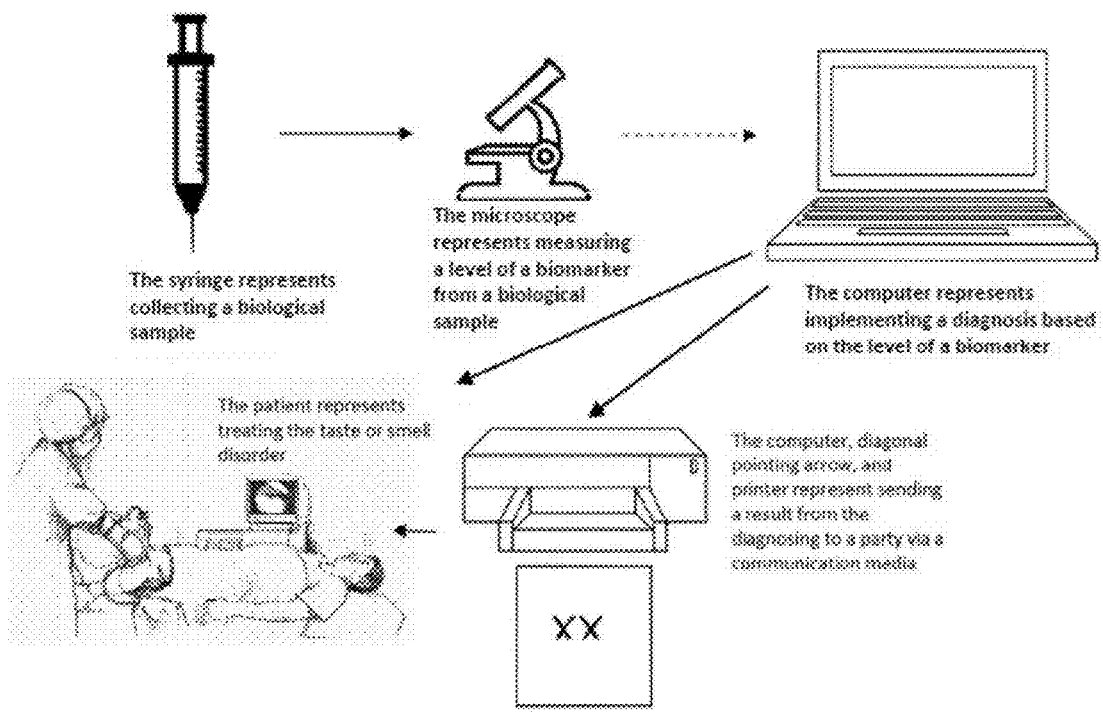
FIG. 12: Illustrates an exemplary course of events related to a method of diagnosing a taste or smell disorders.

FIG. 12 illustrates an exemplary practice of the diagnostic methods disclosed herein. A sample is collected from a subject, as illustrated by a syringe representing an means disclosed herein for the collection of a biological sample. The method of collecting the biological sample will depend upon the type of biological sample collected. The biological sample can be analyzed to measure a level of one or more biomarkers from the biological sample using a microscope, or any other means to measure the biomarker level. The levels for each of the one or more biomarkers can be used in a computer implemented diagnosis. The resulting diagnosis based on the biomarker analysis can be sent to a party via a communication media, represented by the computer, diagonal pointing arrow, and printer. Based on the results of the diagnosis, the patient can be treated for a taste or smell disorder.

Methods for Diagnosis, Evaluation, and/or Treatment

The Hedgehog signaling pathway is known to be a key regulator of animal development, particularly during late stages of embryogenesis and metamorphosis. Mammals are have three Members of the hedgehog signaling pathway, Sonic Hedgehog (SHH), Desert Hedgehog (DHH), and Indian hedgehog (IHH). The pathway is implicated in the development of some cancers. However, the role of members of the hedgehog signaling pathway in diagnosing and treating loss and/or distortion of taste or smell, e.g., hyposmia, dysosmia, anosmia, phantosmia, hypogeusia, dysgeusia, phantogeusia, and/or ageusia, has yet to be determined.

In one aspect, disclosed herein are methods of diagnosing loss and/or distortion of taste or smell, e.g., hyposmia, dysosmia, anosmia, phantosmia, hypogeusia, dysgeusia, phantogeusia, and/or ageusia in a subject, the methods comprising (a) obtaining one or more biological samples from the subject; (b) measuring a level of one or more members of the hedgehog signaling pathway in one or more biological samples from the subject; and (c) diagnosing the subject with loss and/or distortion of taste or smell, e.g., hyposmia, dysosmia, anosmia, phantosmia, hypogeusia, dysgeusia, phantogeusia, and/or ageusia based upon the level of one or more members of the hedgehog signaling pathway that can be lower than a threshold level. Disclosed herein are also methods of evaluating the improvement in, decline in, and/or no change in taste and/or smell, e.g., hyposmia, dysosmia, anosmia, phantosmia, hypogeusia, dysgeusia, phantogeusia, and/or ageusia in a subject, the methods comprising (a) treating the subject with one or more drugs; (b) obtaining one or more biological samples from the subject; (c) measuring a level of one or more members of the hedgehog signaling pathway in one or more biological samples from the subject; and (d) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level. The threshold level can be an average level for the one or more members of the hedgehog signaling pathway as measured in a control population comprising subjects with normal olfactory and/or taste function. The level of one or more members of the hedgehog signaling pathway can be at least one order of magnitude lower than said threshold level. For example, 2, 3, 4, 5, 10, 15, 16, 17, 18, 19, 20, 21, 22, 23, 24, 25, 26, 26, 27, 28, 29, 30, 31, 32, 33, 34, 35, 36, 37, 38, 39, 40, 41, 42, 43, 44, 45, 50, 60, 70 80, 90, 100, 150, 200, 250, 300, 400, 500, 600, 700, 800, 900, or 1000 or more orders of magnitude lower than said threshold level. The methods of this invention can further comprise at least one of: (a) treating the subject diagnosed with loss and/or distortion of taste or smell, e.g., hyposmia, dysosmia, anosmia, phantosmia, hypogeusia, dysgeusia, phantogeusia, and/or ageusia; (b) transferring the diagnosed result via a communication medium; and (c) computer implementing the diagnosis.

Some patients can be diagnosed with loss and/or distortion of taste or smell, e.g., hyposmia, dysosmia, anosmia, phantosmia, hypogeusia, dysgeusia, phantogeusia, and/or ageusia without comparing the levels of members of the hedgehog signaling pathway to a threshold number. Disclosed herein are methods of diagnosing loss and/or distortion of taste or smell, e.g., hyposmia, dysosmia, anosmia, phantosmia, hypogeusia, dysgeusia, phantogeusia, and/or ageusia in a subject, the methods comprising obtaining one or more biological samples from the subject; measuring a level of one or more members of the hedgehog signaling pathway in one or more biological samples from the subject; and diagnosing the subject with loss and/or distortion of taste or smell, e.g., hyposmia, dysosmia, anosmia, phantosmia, hypogeusia, dysgeusia, phantogeusia, and/or ageusia based on one or more of: (i) the level of Sonic Hedgehog (SHH) that is or about greater than 0 pg/mL to 8,500 pg/mL;

(ii) the level of Indian hedgehog (IHH) that is or about greater than 0 pg/mL to 1.0 pg/mL; and (iii) the level of Desert Hedgehog (DHH) that is or about greater than 0 pg/mL to 5.0 pg/mL.

In order to evaluative the improvement in, decline in, and/or no change of patients (e.g., patient response) to drugs, e.g., theophylline (e.g., nasal and/or oral), cGMP activators (e.g., riociguat), and/or cAMP activators (e.g., forskolin), any drug described in herein, and any combination thereof, the inventor has developed appropriate methods. For example, a patients' response to drugs can be determined by methods of evaluating the improvement in, decline in, and/or no change in taste and/or smell, e.g., hyposmia, dysosmia, anosmia, phantosmia, hypogeusia, dysgeusia, phantogeusia, and/or ageusia in a subject, the methods comprising (a) treating the subject with one or more drugs; (b) obtaining one or more biological samples from the subject; (c) measuring a level of one or more members of the hedgehog signaling pathway in one or more biological samples from the subject; and (d) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level. For instance, if a subject does not responds to drugs, the method of (a) treating the subject with one or more drugs; (b) obtaining one or more biological samples from the subject; and (c) measuring a level of one or more members of the hedgehog signaling pathway in one or more biological samples from the subject; can lead to (d) diagnosing the subject with no change in taste and/or smell, e.g., hyposmia, dysosmia, anosmia, phantosmia, hypogeusia, dysgeusia, phantogeusia, and/or ageusia based upon the level of one or more members of the hedgehog signaling pathway that can be the same or about the same as a threshold level. In another example, if the subject responds negatively to drug treatment, the method of (a) treating the subject with one or more drugs, (b) obtaining one or more biological samples from the subject; and (c) measuring a level of one or more members of the hedgehog signaling pathway in one or more biological samples from the subject; can lead to (d) diagnosing the subject with decrease in taste and/or smell, e.g., hyposmia, dysosmia, anosmia, phantosmia, hypogeusia, dysgeusia, phantogeusia, and/or ageusia based upon the level of one or more members of the hedgehog signaling pathway that can be lower than a threshold level. In further example, if the subject responds positively to drug treatment, the method of (a) treating the subject with one or more drugs; (b) obtaining one or more biological samples from the subject; and (c) measuring a level of one or more members of the hedgehog signaling pathway in one or more biological samples from the subject; can lead to (d) diagnosing the subject with increase in taste and/or smell, e.g., hyposmia, dysosmia, anosmia, phantosmia, hypogeusia, dysgeusia, phantogeusia, and/or ageusia based upon the level of one or more members of the hedgehog signaling pathway that can be higher than a threshold level. In some embodiments, (b) and (c) are performed before and/or after (a). For example, the methods described herein can comprise evaluating the improvement in, decline in, and/or no change in taste and/or smell, e.g., hyposmia, dysosmia, anosmia, phantosmia, hypogeusia, dysgeusia, phantogeusia, and/or ageusia in a subject, the methods comprising (a) obtaining one or more biological samples from the subject; (b) measuring a level of one or more members of the hedgehog signaling pathway in one or more biological samples from the subject; (c) treating the subject with one or more drugs; (d) obtaining one or more biological samples from the subject; (e) measuring a level of one or more members of the hedgehog signaling pathway in one or more biological samples from the subject; and (f) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level. In another example, the methods described herein can comprise evaluating the improvement in, decline in, and/or no change in taste and/or smell, e.g., hyposmia, dysosmia, anosmia, phantosmia, hypogeusia, dysgeusia, phantogeusia, and/or ageusia in a subject, the methods comprising (a) obtaining one or more biological samples from the subject; (b) measuring a level of one or more members of the hedgehog signaling pathway in one or more biological samples from the subject; (c) treating the subject with one or more drugs; and (d) diagnosing the subject with an improvement in, decline in, no change in, diminution in and/or distortion, taste and/or smell, e.g., hyposmia, dysosmia, anosmia, phantosmia, hypogeusia, dysgeusia, phantogeusia, and/or ageusia based upon the level of one or more members of the hedgehog signaling pathway that can be above, lower, and/or the same, than a threshold level. Without being bound by theory, in many instances, taste and smell function can improve simultaneously, however, in some instances, taste function may improve when smell function declines, and smell function may improve when taste function declines. In additional embodiments, the method can further comprise one or more of the following: (a) patients described herein can be treated with more drugs (e.g., increase in dosage), can be treated with less drugs (e.g., decrease in dosage), maintained on the same drug (e.g., same dosage), switched to a different drug (e.g., from a PDE inhibitor to a cGMP activator), and/or combinations thereof; (b) the measuring a level of one or more members of the hedgehog signaling pathway can be performed by an antibody-based assay, for example, ELISA; (c) the diagnosis can be computer implemented; and (d) any combination thereof.

In order to effectively measure levels of members of the hedgehog signaling pathway in subjects, one or more biological samples can be needed. As described in detail above, various methods for retrieving and preparing biological samples are known and can be used to extract and prepare biological samples for testing. Also as described above, the one or more biological samples can comprise one or more bodily fluids. The one or more bodily fluids can also comprise a whole blood sample, a serum sample, a plasma sample, a urine sample, a saliva sample, a mucus sample, a perspiration sample, or any combination thereof. If a single bodily fluid is used, the one or more bodily fluids can also comprise a mucus sample (e.g., a nasal mucus sample), a plasma sample, a serum sample, a whole blood sample, and/or a perspiration sample.

The one or more members of the hedgehog signaling pathway can be selected from a group consisting of: Sonic Hedgehog (SHH), Desert Hedgehog (DHH), and/or Indian hedgehog (IHH). The one or more members of the hedgehog signaling pathway can be SHH, DHH, IHH, or any combination thereof. Although a mammalian (e.g., human) hedgehog can be measured, it is also contemplated that a non-mammalian hedgehog can be measured.

The measuring of the level of members of the hedgehog signaling pathway can be performed by using methods in the art. Methods incorporating the use of antibodies can be particularly useful. However, this is not to be construed as limiting the methods of measuring based on antibody tests. The measuring of the level of one or more members of the hedgehog signaling pathway can comprise using one or more antibodies that bind one or more members of the hedgehog signaling pathway. The measuring can further comprise one or more antibodies that bind one or more members of the hedgehog signaling pathway wherein the one or more antibodies are used in an immunostain, an immunoprecipitation, an immunoelectrophoresis, an immunoblot, a western blot, or a spectrophotometry assay. It is contemplated that the methods can also further comprise one or more antibodies that bind one or more members of the hedgehog signaling pathway wherein the one or more antibodies are used in the spectrophotometry assay that can be an EMIT (Enzyme Multiplied Immunoassay Technique) assay or an ELISA (Enzyme Linked Immunosorbent Assay). Some examples of measuring techniques are described throughout the specification. For example, the methods can comprise using one or more techniques that are fluorescence microscopy, a radioimmunoassay, a fluorescence immunoassay, mass spectrometry, liquid chromatography, electrophoresis, or any combination thereof.

To assess if a subject has loss and/or distortion of taste or smell, e.g., hyposmia, dysosmia, anosmia, phantosmia, hypogeusia, dysgeusia, phantogeusia, and/or ageusia, based on levels of one or more members of the hedgehog signaling pathway, a threshold comparison, e.g., a basal level can be used. Thus, the threshold level can be an average level for one or more members of the hedgehog signaling pathway as measured in a control population comprising subjects with normal olfactory and/or gustatory function. The level of one or more members of the hedgehog signaling pathway can be at least one order of magnitude lower than said threshold level. For example, 2, 3, 4, 5, 10, 15, 16, 17, 18, 19, 20, 21, 22, 23, 24, 25, 26, 26, 27, 28, 29, 30, 31, 32, 33, 34, 35, 36, 37, 38, 39, 40, 41, 42, 43, 44, 45, 50, 60, 70 80, 90, 100, 150, 200, 250, 300, 400, 500, 600, 700, 800, 900, or 1000 or more orders of magnitude lower than said threshold level.

Levels of pro-inflammatory cytokines, in combination or individually with members of the hedgehog signaling pathway levels and/or other biological markers, can be helpful in diagnosing a subject with loss and/or distortion of taste or smell, e.g., hyposmia, dysosmia, anosmia, phantosmia, hypogeusia, dysgeusia, phantogeusia, and/or ageusia. For example, some methods can further comprise measuring a level of one or more pro-inflammatory cytokines in at least one or more of the biological samples. The methods can also comprise measuring a level of one or more pro-inflammatory cytokines selected from a group consisting of: IL-1α, IL-1β, IL-6, IL-18, TNF-α, or any combination thereof. Alternatively, the methods can also comprise measuring a level of one or more pro-inflammatory cytokines wherein the one or more pro-inflammatory cytokines can comprise IL-6. The methods can also comprise measuring the level of IL-6 wherein the threshold level of IL-6 can be 0.1, 0.2, 0.3, 0.4, 0.5, 0.6, 0.7, 0.8, 0.9, 1, 2, 3, 4, 5, 10, 15, 16, 17, 18, 19, 20, 21, 22, 23, 24, 25, 26, 26, 27, 28, 29, 30, 31, 32, 33, 34, 35, 36, 37, 38, 39, 40, 41, 42, 43, 44, 45, 50, 60, 70 80, 90 or 100 pg/mL. The level of IL-6 wherein the threshold level of IL-6 can be from or from about: 0.05 pg/mL to 50 pg/mL and about 0.05 pg/mL to about 50 pg/mL, for example, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL, or 40 pg/mL to 60 pg/mL, or 50 pg/mL to 70 pg/mL, or 60 pg/mL to 80 pg/mL, or 70 pg/mL to 90 pg/mL, or 80 pg/mL to 100 pg/mL. By way of example only, and not to be construed as limiting in any way, the range for IL-6 in salvia, urine, and plasma, can be or about: 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL; and in mucus, can be or about 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL, or 40 pg/mL to 60 pg/mL, or 50 pg/mL to 70 pg/mL, or 60 pg/mL to 80 pg/mL, or 70 pg/mL to 90 pg/mL, or 80 pg/mL to 100 pg/mL.

To assess if a subject has loss and/or distortion of taste or smell, e.g., hyposmia, dysosmia, anosmia, phantosmia, hypogeusia, dysgeusia, phantogeusia, and/or ageusia, based on levels of one or more pro-inflammatory cytokines, a threshold comparison, e.g., a basal level, can be used. For example, the methods can further comprise measuring a level of one or more pro-inflammatory cytokines wherein diagnosing can be further based upon the level of at least one of the one or more pro-inflammatory cytokines being higher than an average pro-inflammatory cytokine level as measured in the control population comprising subjects with normal olfactory and/or gustatory function.

Levels of anti-inflammatory cytokines, in combination or individually with members of the hedgehog signaling pathway levels and/or other biological markers, can be helpful in diagnosing a subject with loss and/or distortion of taste or smell, e.g., hyposmia, dysosmia, anosmia, phantosmia, hypogeusia, dysgeusia, phantogeusia, and/or ageusia. For example, the methods can further comprise measuring a level of one or more anti-inflammatory cytokines in at least one of the biological samples. The methods can also comprise measuring a level of one or more anti-inflammatory cytokines wherein the one or more anti-inflammatory cytokines can be selected from a group consisting of: IL-1ra, IL-10, IFN-γ, IFN-β, or combinations thereof.

To assess if a subject has loss and/or distortion of taste or smell, e.g., hyposmia, dysosmia, anosmia, phantosmia, hypogeusia, dysgeusia, phantogeusia, and/or ageusia, based on levels of one or more anti-inflammatory cytokines, a threshold comparison, e.g., a basal level, can be used. For example, the diagnosing can be further based upon the level of at least one of the one or more anti-inflammatory cytokines being lower than an average anti-inflammatory cytokine level as can be measured in the control population comprising subjects with normal olfactory and/or gustatory function.

Levels of other biological makers, in combination or individually with members of the hedgehog signaling pathway levels and/or other biological markers, can be helpful in diagnosing a subject with loss and/or distortion of taste or smell, e.g., hyposmia, dysosmia, anosmia, phantosmia, hypogeusia, dysgeusia, phantogeusia, and/or ageusia. For example, the methods can further comprise measuring a level of immunoglobulin E (IgE), eosinophils, cyclic adenosine monophosphate (cAMP), cyclic guanosine monophosphate (cGMP), nitric oxide (NO), IL-1 RII, IL-2R, or any combination thereof in at least one of the one or more biological samples.

To assess if a subject has loss and/or distortion of taste or smell, e.g., hyposmia, dysosmia, anosmia, phantosmia, hypogeusia, dysgeusia, phantogeusia, and/or ageusia, based on the level of IgE, a threshold comparison, e.g., a basal level, can be used. Thus, the methods can further comprise measuring the level of IgE, wherein diagnosing can be further based upon the level of IgE being higher than an average IgE level as measured in the control population comprising subjects with normal olfactory and/or gustatory function. The methods can further comprise measuring the level of IgE, wherein diagnosing can be further based upon the level of IgE being higher than 75 kU/L, 100 kU/L, or 125 kU/L and about 75 kU/L, about 100 kU/L, or about 125 kU/L. The methods can further comprise measuring the level of IgE, wherein measuring the level of IgE can comprise a fluorescence polarization assay.

To assess if a subject has loss and/or distortion of taste or smell, e.g., hyposmia, dysosmia, anosmia, phantosmia, hypogeusia, dysgeusia, phantogeusia, and/or ageusia, based on the level of eosinophils, a threshold comparison, e.g., a basal level, can be used. The methods can further comprise measuring the level of eosinophils, wherein diagnosing can be further based upon the level of eosinophils being higher than an average eosinophils level as measured in the control population comprising subjects with normal olfactory and/or gustatory function. The methods can further comprise the measuring the level of eosinophils, wherein diagnosing can be further based upon the level of eosinophils being higher than 300 cells/HPF (high powered field), 350 cells/HPF, or 400 cells/HPF and about 300 cells/HPF, 350 cells/HPF, or 400 cells/HPF. The measuring the level of eosinophils can be performed with a Coulter counter.

To assess if a subject has loss and/or distortion of taste or smell, e.g., hyposmia, dysosmia, anosmia, phantosmia, hypogeusia, dysgeusia, phantogeusia, and/or ageusia, based on the level of NO, a threshold comparison, e.g., a basal level, can be used. The methods can further comprise measuring the level of NO, wherein diagnosing can be further based upon the level of NO being lower than an average NO level as measured in the control population comprising subjects with normal olfactory and/or gustatory function.

To assess if a subject has loss and/or distortion of taste or smell, e.g., hyposmia, dysosmia, anosmia, phantosmia, hypogeusia, dysgeusia, phantogeusia, and/or ageusia, based on the level of cAMP, a threshold comparison, e.g., a basal level, can be used. The methods can further comprise measuring the level of cAMP, wherein diagnosing can be further based upon the level of cAMP being lower than an average cAMP level as measured in the control population comprising subjects with normal olfactory and/or gustatory function.

To assess if a subject has loss and/or distortion of taste or smell, e.g., hyposmia, dysosmia, anosmia, phantosmia, hypogeusia, dysgeusia, phantogeusia, and/or ageusia, based on the level of cGMP, a threshold comparison, e.g., a basal level, can be used. The methods can further comprise measuring the level of cGMP, wherein diagnosing can be further based upon the level of cGMP being lower than an average cGMP level as measured in the control population comprising subjects with normal olfactory and/or gustatory function.

The inventors have found that decreased levels of members of the hedgehog signaling pathway can be used to diagnose and recommend treating subjects with loss and/or distortion of taste or smell, e.g., hyposmia, dysosmia, anosmia, phantosmia, hypogeusia, dysgeusia, phantogeusia, and/or ageusia. For example, the subject can be diagnosed with loss and/or distortion of taste or smell, e.g., hyposmia, dysosmia, anosmia, phantosmia, hypogeusia, dysgeusia, phantogeusia, and/or ageusia based on one or more of: (a) the level of SHH that can be or about: 0 pg/mL, greater than 0 pg/mL to less than less than 1 pg/mL, 1 pg/mL to 25 pg/mL, 15 pg/mL to 30 pg/mL, 20 pg/mL to 40 pg/mL; 35 pg/mL to 50 pg/mL; 45 pg/mL to 100 pg/mL; 75 pg/mL to 150 pg/mL, 125 pg/mL to 1000 pg/mL, 900 pg/mL to 2500 pg/mL, 2000 pg/mL to 5000 pg/mL, 4000 pg/mL to 7500 pg/mL, 6000 pg/mL to 10,000 pg/mL; (b) the level of IHH that can be or about: 0 pg/mL, greater than 0 pg/mL to 0.1 pg/mL, 0.05 pg/mL to 0.15 pg/mL, 0.125 pg/mL to 0.2 pg/mL, 0.15 pg/mL to 0.30 pg/mL, 0.25 pg/mL to 0.5 pg/mL, 0.4 pg/mL to 0.7 pg/mL, 0.6 pg/mL to 0.75 pg/mL, 0.725 pg/mL to 0.9 pg/mL, 0.8 pg/mL to 1.0 pg/mL, less than 1.0 pg/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL; (c) the level of DHH that can be or about: 0 pg/mL, greater than 0 pg/mL to 0.1 pg/mL, 0.05 pg/mL to 0.15 pg/mL, 0.125 pg/mL to 0.2 pg/mL, 0.15 pg/mL to 0.30 pg/mL, 0.25 pg/mL to 0.5 pg/mL, 0.4 pg/mL to 0.7 pg/mL, 0.6 pg/mL to 0.75 pg/mL, 0.725 pg/mL to 0.9 pg/mL, 0.8 pg/mL to 1.0 pg/mL, 0.9 pg/mL to 1.1 pg/mL, 1.0 pg/mL to 1.3 pg/mL, 1.2 pg/mL to 1.5 pg/mL, 1.4 pg/mL to 2.0 pg/mL, 1.9 pg/mL to 2.5 pg/mL, 2.4 pg/mL to 3.0 pg/mL, 2.9 pg/mL to 3.5 pg/mL, 3.4 pg/mL to 3.8 pg/mL, 3.7 pg/mL to 3.9 pg/mL, 3.85 pg/mL to 5.0 pg/mL, less than 5.0 pg/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL.

The inventors have also found that measuring the level of particular biological markers can, for example, be used to diagnose and treat subjects with loss and/or distortion of taste or smell, e.g., hyposmia, dysosmia, anosmia, phantosmia, hypogeusia, dysgeusia, phantogeusia, and/or ageusia. The methods can further comprise diagnosing the subject with loss and/or distortion of taste or smell, e.g., hyposmia, dysosmia, anosmia, phantosmia, hypogeusia, dysgeusia, phantogeusia, and/or ageusia can be based upon one or more measurements: (a) the level of IL-1α that can be or about: 125 pg/mL to 195 pg/mL, 150 pg/mL to 170 pg/mL, 120 pg/mL to 170 pg/mL, or 150 pg/mL to 195 pg/mL, or 185 pg/mL to 500 pg/mL (e.g., by way of example only, in nasal mucus from about: 15 pg/mL to 30 pg/mL, or 25 pg/mL to 50 pg/mL, or 45 pg/mL to 75 pg/mL, or 70 pg/mL to 100 pg/mL, or 90 pg/mL to 150 pg/mL, or 125 pg/mL to 200 pg/mL, or 150 pg/mL to 250 pg/mL, or from 200 pg/mL to 300 pg/mL, or from 250 pg/mL to 350 pg/mL, or 300 pg/mL to 400 pg/mL, or 350 pg/mL to 450 pg/mL, or 400 pg/mL to 500 pg/mL; and in saliva from 0.1 pg/mL to 0.5 pg/mL, or 0.25 pg/mL to 0.75 pg/mL, or 0.6 pg/mL to 0.9 pg/mL, or 0.7 pg/mL to 1.0 pg/mL, or 0.9 pg/mL to 1.5 pg/mL, or 1.25 pg/mL to 2.0 pg/mL, or 1.75 pg/mL to 2.5 pg/mL, or 2.4 pg/mL to 3.0 pg/mL, 2.7 pg/mL to 3.5 pg/mL or 3.4 pg/mL to 4.5 pg/mL, or 4.0 pg/mL to 5.0 pg/mL, or 4.6 pg/mL to 5.5 pg/mL, or 5.4 pg/mL to 6.0 pg/mL, or 5.9 pg/mL to 6.5 pg/mL, or 6.4 pg/mL to 7.0 pg/mL, or 6.9 pg/mL to 7.5 pg/mL, or 7.4 pg/mL to 8.0 pg/mL, or 7.9 pg/mL to 8.5 pg/mL, or 8.4 pg/mL to 9.0 pg/mL, or 8.9 pg/mL to 9.5 pg/mL, or 9.4 pg/mL to 10.0 pg/mL; (b) the level of IL-1β that can be or about: 10 pg/mL to 30 pg/mL, 25 pg/mL to 50 pg/mL, 45 pg/mL to 100 pg/mL, 90 pg/mL to 150 pg/mL, 140 pg/mL to 200 pg/mL, 195 pg/mL to 300 pg/mL, 220 pg/mL to 275 pg/mL, 220 pg/mL to 300 pg/mL, or 195 pg/mL to 275 pg/mL, 250 pg/mL to 300 pg/mL, 290 pg/mL to 350 pg/mL, 340 pg/mL to 400 pg/mL, 390 pg/mL to 450 pg/mL, 440 pg/mL to 500 pg/mL; (c) the level of IL-1ra that can be or about: 50 pg/mL to 150,000 pg/mL, e.g., 30,000 pg/mL to 90,000 pg/mL, 45,000 pg/mL to 75,000 pg/mL, 45,000 pg/mL to 90,000 pg/mL, or 30,000 pg/mL to 75,000 pg/mL (e.g., by way of example only, in plasma, from about: 1 pg/mL to 25 pg/mL, 20 pg/mL to 40 pg/mL, 30 pg/mL to 60 pg/mL, 50 pg/mL to 100 pg/mL, 75 pg/mL to 150 pg/mL, 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL, 475 pg/mL to 550 pg/mL, 525 pg/mL to 600 pg/mL, 575 pg/mL to 650 pg/mL, 625 pg/mL to 700 pg/mL; in urine, from: 100 pg/mL to 500 pg/mL, 400 pg/mL to 1000 pg/mL, 900 pg/mL to 1500 pg/mL, 1400 pg/mL to 2000 pg/mL, 1900 pg/mL to 2500 pg/mL, 2400 pg/mL to 3000 pg/mL, 2900 pg/mL to 3500 pg/mL, 3400 pg/mL to 4000 pg/mL, 3900 pg/mL to 4500 pg/mL, 4400 pg/mL to 5000 pg/mL, 4900 pg/mL to 5500 pg/mL, 5400 pg/mL to 6000 pg/mL, 5900 pg/mL to 6500 pg/mL, 6400 pg/mL to 7000 pg/mL, 6900 pg/mL to 7500 pg/mL, 7400 pg/mL to 8000 pg/mL, 7900 pg/mL to 8500 pg/mL, 8400 pg/mL to 9000 pg/mL, 8900 pg/mL to 9500 pg/mL, 9400 pg/mL to 10,000 pg/mL; in nasal mucus from: 2500 pg/mL to 4000 pg/mL, 3500 pg/mL to 6000 pg/mL, 5000 pg/mL to 10,000 pg/mL, 9000 pg/mL to 15,000 pg/mL, 14,000 pg/mL to 20,000 pg/mL, 19,000 pg/mL to 25,000 pg/mL, 24,000 pg/mL to 30,000 pg/mL, 29,000 pg/mL to 35,000 pg/mL, 34,000 pg/mL to 40,000 pg/mL, 39,000 pg/mL to 45,000 pg/mL, 44,000 pg/mL to 50,000 pg/mL, 49,000 pg/mL to 55,000 pg/mL, 54,000 pg/mL to 60,000 pg/mL, 59,000 pg/mL to 65,000 pg/mL, 64,000 pg/mL to 70,000 pg/mL, 69,000 pg/mL to 75,000 pg/mL, 74,000 pg/mL to 80,000 pg/mL, 79,000 pg/mL to 85,000 pg/mL, 84,000 pg/mL to 90,000 pg/mL, 89,000 pg/mL to 95,000 pg/mL, 94,000 pg/mL to 100,000 pg/mL, 104,000 pg/mL to 110,000 pg/mL, 109,000 pg/mL to 115,000 pg/mL, 114,000 pg/mL to 120,000 pg/mL, 119,000 pg/mL to 120,000 pg/mL, 119,000 pg/mL to 125,000 pg/mL, 124,000 pg/mL to 130,000 pg/mL, 129,000 pg/mL to 135,000 pg/mL, 134,000 pg/mL to 140,000 pg/mL, 139,000 pg/mL to 145,000 pg/mL, 144,000 pg/mL to 150,000 pg/mL); (d) the level of IL-1 RII that can be or about: 960 pg/mL to 2600 pg/mL, 1370 pg/mL to 2190 pg/mL, 1370 pg/mL to 2600 pg/mL, or 960 pg/mL to 2190 pg/mL; (e.g., by way of example only, in saliva, from about: 1 pg/mL to 5 pg/mL, 5 pg/mL to 10 pg/mL, 9 pg/mL to 15 pg/mL, 14 pg/mL to 20 pg/mL, or 19 pg/mL to 25 pg/mL, or 24 pg/mL to 30 pg/mL, or 29 pg/mL to 35 pg/mL, or 34 pg/mL to 40 pg/mL, or 39 pg/mL to 45 pg/mL, 44 pg/mL to 50 pg/mL, or 49 pg/mL to 55 pg/mL, or 54 pg/mL to 60 pg/mL, or 59 pg/mL to 65 pg/mL, or 64 pg/mL to 70 pg/mL, or 69 pg/mL to 75 pg/mL, 74 pg/mL to 80 pg/mL, or 79 pg/mL to 85 pg/mL, or 84 pg/mL to 90 pg/mL, or 89 pg/mL to 95 pg/mL, or 94 pg/mL to 100 pg/mL, or 99 pg/mL to 105 pg/mL, 104 pg/mL to 110 pg/mL, or 109 pg/mL to 105 pg/mL, or 104 pg/mL to 110 pg/mL, or 109 pg/mL to 115 pg/mL, or 114 pg/mL to 120 pg/mL, or 119 pg/mL to 125 pg/mL, 124 pg/mL to 130 pg/mL, or 129 pg/mL to 135 pg/mL, or 134 pg/mL to 140 pg/mL, or 139 pg/mL to 145 pg/mL, or 144 pg/mL to 150 pg/mL, or 149 pg/mL to 200 pg/mL; in urine, from: 25 pg/mL to 75 pg/mL, 50 pg/mL to 100 pg/mL, 75 pg/mL to 150 pg/mL, 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL, 475 pg/mL to 550 pg/mL, 525 pg/mL to 600 pg/mL, 575 pg/mL to 650 pg/mL, 625 pg/mL to 700 pg/, 690 pg/mL to 750 pg/mL, 740 pg/mL to 800 pg/mL; in nasal mucus, from: 100 pg/mL to 500 pg/mL, 400 pg/mL to 1000 pg/mL, 900 pg/mL to 1500 pg/mL, 1400 pg/mL to 2000 pg/mL, 1900 pg/mL to 2500 pg/mL, 2400 pg/mL to 3000 pg/mL, 2900 pg/mL to 3500 pg/mL, 3400 pg/mL to 4000 pg/mL, 3900 pg/mL to 4500 pg/mL, 4400 pg/mL to 5000 pg/mL, 4900 pg/mL to 5500 pg/mL, 5400 pg/mL to 6000 pg/mL; in plasma, from: 5000 pg/mL to 10,000 pg/mL, 9000 pg/mL to 15,000 pg/mL, 14,000 pg/mL to 20,000 pg/mL, 19,000 pg/mL to 25,000 pg/mL, 24,000 pg/mL to 30,000 pg/mL, 29,000 pg/mL to 35,000 pg/mL, 34,000 pg/mL to 40,000 pg/mL, 39,000 pg/mL to 45,000 pg/mL, 44,000 pg/mL to 50,000 pg/mL, 49,000 pg/mL to 55,000 pg/mL, 54,000 pg/mL to 60,000 pg/mL, 59,000 pg/mL to 65,000 pg/mL, 64,000 pg/mL to 70,000 pg/mL); (e) the level of IL-2 that can be or about: 0 pg/mL, 0.1 pg/mL, 0.2 pg/mL, 0.3 pg/mL, or 0.5 pg/mL; (f) the level of IL-2R that can be or about: 0 to 200 pg/mL, 50 to 150 pg/mL, 0 to 150 pg/mL, or 50 to 200 pg/mL (e.g., by way of example only, in saliva, from 0.1 pg/mL to 0.5 pg/mL, or 0.25 pg/mL to 0.75 pg/mL, or 0.6 pg/mL to 0.9 pg/mL, or 0.7 pg/mL to 1.0 pg/mL, or 0.9 pg/mL to 1.5 pg/mL, or 1.25 pg/mL to 2.0 pg/mL, or 1.75 pg/mL to 2.5 pg/mL, or 2.4 pg/mL to 3.0 pg/mL, 2.7 pg/mL to 3.5 pg/mL or 3.4 pg/mL to 4.5 pg/mL, or 4.0 pg/mL to 5.0 pg/mL, or 4.6 pg/mL to 5.5 pg/mL, or 5.4 pg/mL to 6.0 pg/mL, or 5.9 pg/mL to 6.5 pg/mL, or 6.4 pg/mL to 7.0 pg/mL, or 6.9 pg/mL to 7.5 pg/mL, or 7.4 pg/mL to 8.0 pg/mL, or 7.9 pg/mL to 8.5 pg/mL, or 8.4 pg/mL to 9.0 pg/mL, or 8.9 pg/mL to 9.5 pg/mL, or 9.4 pg/mL to 10.0 pg/mL, from 9.0 pg/mL to 15.0 pg/mL, or 14.0 pg/mL to 20.0 pg/mL, or 19.0 pg/mL to 25.0 pg/mL, or 24.0 pg/mL to 30.0 pg/mL, or 29.0 pg/mL to 35.0 pg/mL, or 34.0 pg/mL to 40.0 pg/mL, or 39.0 pg/mL to 45.0 pg/mL, or 44.0 pg/mL to 50.0 pg/mL; in nasal mucus from: 0.1 pg/mL to 3 pg/mL, 2.5 pg/mL to 4 pg/mL, 3.5 pg/mL to 6 pg/mL, 5 pg/mL to 10 pg/mL, 9 pg/mL to 15 pg/mL, 14 pg/mL to 20 pg/mL, or 19 pg/mL to 25 pg/mL, or 24 pg/mL to 30 pg/mL, or 29 pg/mL to 35 pg/mL, or 34 pg/mL to 40 pg/mL, or 39 pg/mL to 45 pg/mL, 44 pg/mL to 50 pg/mL, or 49 pg/mL to 55 pg/mL, or 54 pg/mL to 60 pg/mL, or 59 pg/mL to 65 pg/mL, or 64 pg/mL to 70 pg/mL, or 69 pg/mL to 75 pg/mL, 74 pg/mL to 80 pg/mL, or 79 pg/mL to 85 pg/mL, or 84 pg/mL to 90 pg/mL, or 89 pg/mL to 95 pg/mL, or 94 pg/mL to 100 pg/mL, or 99 pg/mL to 105 pg/mL, 104 pg/mL to 110 pg/mL, or 109 pg/mL to 105 pg/mL, or 104 pg/mL to 110 pg/mL, or 109 pg/mL to 115 pg/mL, or 114 pg/mL to 120 pg/mL, or 119 pg/mL to 125 pg/mL, 124 pg/mL to 130 pg/mL, or 129 pg/mL to 135 pg/mL, or 134 pg/mL to 140 pg/mL, or 139 pg/mL to 145 pg/mL, or 144 pg/mL to 150 pg/mL, 149 pg/mL to 200 pg/mL, 190 pg/mL to 250 pg/mL, 240 pg/mL to 300 pg/mL, 290 pg/mL to 350 pg/mL, 340 pg/mL to 400 pg/mL, 390 pg/mL to 450 pg/mL, 440 pg/mL to 500 pg/mL; in urine and plasma from: 50 pg/mL to 100 pg/mL, 75 pg/mL to 150 pg/mL, 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL, 475 pg/mL to 550 pg/mL, 525 pg/mL to 600 pg/mL, 575 pg/mL to 650 pg/mL, 625 pg/mL to 700 pg/mL, 675 pg/mL to 750 pg/mL, 725 pg/mL to 800 pg/mL, 775 pg/mL to 850 pg/mL, 825 pg/mL to 900 pg/mL, 875 pg/mL to 950 pg/mL, 925 pg/mL to 1000 pg/mL, 950 pg/mL to 1100 pg/mL, 1075 pg/mL to 1200 pg/mL, 1175 pg/mL to 1300 pg/mL, 1275 pg/mL to 1400 pg/mL, 1375 pg/mL to 1500 pg/mL; 1475 pg/mL to 1600 pg/mL, 1575 pg/mL to 1700 pg/mL, 1675 pg/mL to 1800 pg/mL, 1775 pg/mL to 1900 pg/mL, 1875 pg/mL to 2000 pg/mL); (g) the level of IL-6 that can be or about: 0.1 pg/mL to 2.2 pg/mL, 0.6 pg/mL to 1.7 pg/mL, 0.6 pg/mL to 2.2 pg/mL, or 0.1 pg/mL to 1.7 pg/mL (e.g., by way of example only in salvia, urine, and plasma, can be or about: 0.005 pg/mL to 0.01 pg/mL, 0.0075 pg/mL to 0.015 pg/mL, 0.0125 pg/mL to 0.02 pg/mL, 0.015 pg/mL to 0.03 pg/mL, 0.025 pg/mL to 0.04 pg/mL, 0.035 pg/mL to 0.045 pg/mL, 0.044 pg/mL to 0.051 pg/mL, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL; and in nasal mucus, can be or about 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL, or 40 pg/mL to 60 pg/mL, or 50 pg/mL to 70 pg/mL, or 60 pg/mL to 80 pg/mL, or 70 pg/mL to 90 pg/mL, or 80 pg/mL to 100 pg/mL); (h) the level of IL-10 that can be or about: 0 pg/mL to 3.5 pg/mL, 0.8 pg/mL to 2.7 pg/mL, 0.8 pg/mL to 3.5 pg/mL, or 0 pg/mL to 2.7 pg/mL (e.g., by way of example only, in nasal mucus, plasma, and saliva, can be from about: 0.005 pg/mL to 0.01 pg/mL, 0.0075 pg/mL to 0.015 pg/mL, 0.0125 pg/mL to 0.02 pg/mL, 0.015 pg/mL to 0.03 pg/mL, 0.025 pg/mL to 0.04 pg/mL, 0.035 pg/mL to 0.045 pg/mL, 0.044 pg/mL to 0.051 pg/mL, 0.05 pg/mL to 0.1 pg/mL, or 0.75 pg/mL to 0.125 pg/mL, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL; and in nasal mucus, can be or about 0.05 pg/mL to 0.1 pg/mL, or 0.75 pg/mL to 0.125 pg/mL, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL); (i) the level of IL-18 that can be or about: 40 pg/mL to 290 pg/mL, 100 pg/mL to 230 pg/mL, 40 pg/mL to 230 pg/mL, or 100 pg/mL to 290 pg/mL (e.g., by way of example only, in nasal mucus and saliva, can be from about: 0.1 pg/mL to 0.5 pg/mL, or 0.25 pg/mL to 0.75 pg/mL, or 0.6 pg/mL to 0.9 pg/mL, or 0.7 pg/mL to 1.0 pg/mL, or 0.9 pg/mL to 1.5 pg/mL, or 1.25 pg/mL to 2.0 pg/mL, or 1.75 pg/mL to 2.5 pg/mL, or 2.4 pg/mL to 3.0 pg/mL, 2.7 pg/mL to 3.5 pg/mL or 3.4 pg/mL to 4.5 pg/mL, or 4.0 pg/mL to 5.0 pg/mL, or 4.6 pg/mL to 5.5 pg/mL, or 5.4 pg/mL to 6.0 pg/mL, or 5.9 pg/mL to 6.5 pg/mL, or 6.4 pg/mL to 7.0 pg/mL, or 6.9 pg/mL to 7.5 pg/mL, or 7.4 pg/mL to 8.0 pg/mL, or 7.9 pg/mL to 8.5 pg/mL, or 8.4 pg/mL to 9.0 pg/mL, or 8.9 pg/mL to 9.5 pg/mL, or 9.4 pg/mL to 10.0 pg/mL, from 9.0 pg/mL to 15.0 pg/mL, or 14.0 pg/mL to 20.0 pg/mL, or 19.0 pg/mL to 25.0 pg/mL, or 24.0 pg/mL to 30.0 pg/mL, or 29.0 pg/mL to 35.0 pg/mL, or 34.0 pg/mL to 40.0 pg/mL, or 39.0 pg/mL to 45.0 pg/mL, or 44.0 pg/mL to 50.0 pg/mL, 50 pg/mL to 100 pg/mL, 75 pg/mL to 150 pg/mL, 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL, 475 pg/mL to 550 pg/mL, 525 pg/mL to 600 pg/mL, 575 pg/mL to 650 pg/mL; in plasma from: 10 pg/mL to 30 pg/mL, 20 pg/mL to 40 pg/mL, 35 pg/ml to 60 pg/mL, 50 pg/mL to 100 pg/mL, 75 pg/mL to 150 pg/mL, 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL, 475 pg/mL to 550 pg/mL, 525 pg/mL to 600 pg/mL, 575 pg/mL to 650 pg/mL, 625 pg/mL to 700 pg/mL, 675 pg/mL to 750 pg/mL, 725 pg/mL to 800 pg/mL, 775 pg/mL to 850 pg/mL, 825 pg/mL to 900 pg/mL, 875 pg/mL to 950 pg/mL, 925 pg/mL to 1000 pg/mL; (j) the level of TNF-α that can be or about: 3 pg/mL to 13 pg/mL, 6 pg/mL to 10 pg/mL, 6 pg/mL to 13 pg/mL, or 3 pg/mL to 10 pg/mL (e.g., by way of example only, in nasal mucus, plasma, saliva, and urine, can be about from: greater than 0 to 0.025, 0.02 to 0.06, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL; and in nasal mucus, can be or about 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, or 5 pg/mL to 7 pg/mL, or 6 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL); (k) the level of IFN-β that can be or about: 0 pg/mL to 910 pg/mL, 230 pg/mL to 680 pg/mL, 230 pg/mL to 910 pg/mL, or 0 pg/mL to 680 pg/mL (e.g., by way of example only, in saliva can be from about: 0 to 0.025, 0.02 to 0.06, 0.05 pg/mL to 0.1 pg/mL, or 0.75 pg/mL to 0.125 pg/mL, or 0.1 pg/mL to 0.2 pg/mL, or 0.15 pg/mL to 0.3 pg/mL, or 0.2 pg/mL to 0.4 pg/mL, or 0.3 pg/mL to 0.5 pg/mL, or 0.4 pg/mL to 0.6 pg/mL, or 0.5 pg/mL to 0.7 pg/mL, or 0.6 pg/mL to 0.8 pg/mL, or 0.7 pg/mL to 0.9 pg/mL, or 0.8 pg/mL to 1.0 pg/mL, or 0.5 pg/mL to 2.0 pg/mL, or 1.5 pg/mL to 3.0 pg/mL, or 2.5 pg/mL to 4.0 pg/mL, or 3.5 pg/mL to 5.0 pg/mL, or 4 pg/mL to 6 pg/mL, 5 pg/mL to 8 pg/mL, or 7 pg/mL to 9 pg/mL, or 8 pg/mL to 10 pg/mL, or 9 pg/mL to 11 pg/mL, or 10 pg/mL to 12 pg/mL, or 11 pg/mL to 13 pg/mL, or 11 pg/mL to 13 pg/mL, or 12 pg/mL to 16 pg/mL, or 15 pg/mL to 25 pg/mL, or 20 pg/mL to 40 pg/mL, or 30 pg/mL to 50 pg/mL; 49 pg/mL to 55 pg/mL, or 54 pg/mL to 60 pg/mL, or 59 pg/mL to 65 pg/mL, or 64 pg/mL to 70 pg/mL, or 69 pg/mL to 75 pg/mL, 74 pg/mL to 80 pg/mL, or 79 pg/mL to 85 pg/mL, or 84 pg/mL to 90 pg/mL, or 89 pg/mL to 95 pg/mL, or 94 pg/mL to 100 pg/mL, or 99 pg/mL to 105 pg/mL, 104 pg/mL to 110 pg/mL, or 109 pg/mL to 105 pg/mL, or 104 pg/mL to 110 pg/mL, or 109 pg/mL to 115 pg/mL, or 114 pg/mL to 120 pg/mL, or 119 pg/mL to 125 pg/mL, 124 pg/mL to 130 pg/mL, or 129 pg/mL to 135 pg/mL, or 134 pg/mL to 140 pg/mL, or 139 pg/mL to 145 pg/mL, or 144 pg/mL to 150 pg/mL; 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL; in nasal mucus and plasma from about: 50 pg/mL to 100 pg/mL, 75 pg/mL to 150 pg/mL, 125 pg/mL to 200 pg/mL, 175 pg/mL to 250 pg/mL, 225 pg/mL to 300 pg/mL, 275 pg/mL to 350 pg/mL, 325 pg/mL to 400 pg/mL, 375 pg/mL to 450 pg/mL, 425 pg/mL to 500 pg/mL, 475 pg/mL to 550 pg/mL, 525 pg/mL to 600 pg/mL, 575 pg/mL to 650 pg/mL, 625 pg/mL to 700 pg/mL; in plasma, from: 100 pg/mL to 500 pg/mL, 400 pg/mL to 1000 pg/mL, 900 pg/mL to 1500 pg/mL, 1400 pg/mL to 2000 pg/mL, 1900 pg/mL to 2500 pg/mL, 2400 pg/mL to 3000 pg/mL, 2900 pg/mL to 3500 pg/mL, 3400 pg/mL to 4000 pg/mL, 3900 pg/mL to 4500 pg/mL, 4400 pg/mL to 5000 pg/mL, 4900 pg/mL to 5500 pg/mL, 5400 pg/mL to 6000 pg/mL, 5900 pg/mL to 6500 pg/mL, 6400 pg/mL to 7000 pg/mL, 6900 pg/mL to 7500 pg/mL, 7400 pg/mL to 8000 pg/mL, 7900 pg/mL to 8500 pg/mL, 8400 pg/mL to 9000 pg/mL, 8900 pg/mL to 9500 pg/mL, 9400 pg/mL to 10,000 pg/mL; or (1) the level of IFN-γ that can be or about: 55 pg/mL to 110 pg/mL, 70 pg/mL to 95 pg/mL, 70 pg/mL to 110 pg/mL, 55 pg/mL to 95 pg/mL, 0.1 pg/mL to 3 pg/mL, 2.5 pg/mL to 4 pg/mL, 3.5 pg/mL to 6 pg/mL, 5 pg/mL to 10 pg/mL, 9 pg/mL to 15 pg/mL, 14 pg/mL to 20 pg/mL, or 19 pg/mL to 25 pg/mL, or 24 pg/mL to 30 pg/mL, or 29 pg/mL to 35 pg/mL, or 34 pg/mL to 40 pg/mL, or 39 pg/mL to 45 pg/mL, 44 pg/mL to 50 pg/mL, or 49 pg/mL to 55 pg/mL, or 54 pg/mL to 60 pg/mL, or 59 pg/mL to 65 pg/mL, or 64 pg/mL to 70 pg/mL, or 69 pg/mL to 75 pg/mL, 74 pg/mL to 80 pg/mL, or 79 pg/mL to 85 pg/mL, or 84 pg/mL to 90 pg/mL, or 89 pg/mL to 95 pg/mL, or 94 pg/mL to 100 pg/mL, or 99 pg/mL to 105 pg/mL, 104 pg/mL to 110 pg/mL, or 109 pg/mL to 105 pg/mL, or 104 pg/mL to 110 pg/mL, or 109 pg/mL to 115 pg/mL, or 114 pg/mL to 120 pg/mL, or 119 pg/mL to 125 pg/mL, 124 pg/mL to 130 pg/mL, or 129 pg/mL to 135 pg/mL, or 134 pg/mL to 140 pg/mL, or 139 pg/mL to 145 pg/mL, or 144 pg/mL to 150 pg/mL, 149 pg/mL to 200 pg/mL.

The methods can be based upon 2, 3, 4, 5, 6, 7, 8, 9, 10, 11, or 12 of one or more measurements.

The methods can further comprise evaluating the subject's gustatory and/or olfactory function by determining a detection threshold (DT) score, a recognition threshold (RT) score, a magnitude estimation (ME) score, or any combination thereof with a forced-choice, three-stimuli, stepwise-staircase technique using one or more gustatory and/or olfaction testing compounds. Gustatory testing compounds can comprise any substance that is salty, sweet, bitter, sour, or umami, for example, sugar (such as sucrose, glucose, fructose, and lactose), salt (such as sodium chloride), acids (such as hydrochloric acid and citric acid), quinine (e.g., quinine sulfate), and monosodium glutamate. Any substances that can evoke a salty, sweet, bitter, sour, or umami sensation, can be used as a test substance, and therefore is explicitly contemplated. The one or more olfaction testing compounds can comprise pyridine, nitrobenzene, thiophene, amyl acetate, or any combination thereof. The diagnosing can be further based upon the DT score being higher than an average DT score as measured in the control population comprising subject with normal olfactory function, the RT score being higher than an average RT score as measured in the control population comprising subject with normal olfactory function, and/or the ME score being lower than an average ME score as measured in the control population comprising subject with normal olfactory function.

After diagnosing a subject with loss and/or distortion of taste or smell, e.g., hyposmia, dysosmia, anosmia, phantosmia, hypogeusia, dysgeusia, phantogeusia, and/or ageusia, based on one or more of the previously described diagnostics methods, subjects can be treated to ameliorate and/or cure their loss and/or distortion of taste or smell, e.g., hyposmia, dysosmia, anosmia, phantsomia, hypogeusia, dysgeusia, phantogeusia, and/or ageusia conditions. The diagnostic methods are supplemented with treatment of loss and/or distortion of taste or smell, e.g., hyposmia, dysosmia, anosmia, phantsomia, hypogeusia, dysgeusia, phantogeusia, and/or ageusia. The diagnostic methods can further comprise treating the loss and/or distortion of taste or smell, e.g., hyposmia, dysosmia, anosmia, phantsomia, hypogeusia, dysgeusia, phantogeusia, and/or ageusia in the subject diagnosed with loss and/or distortion of taste or smell, e.g., hyposmia, dysosmia, anosmia, phantsomia, hypogeusia, dysgeusia, phantogeusia, and/or ageusia can be a subject in need thereof.

The methods of this invention can further comprise at least one of: (a) treating the subject diagnosed with loss and/or distortion of taste or smell, e.g., hyposmia, dysosmia, anosmia, phantsomia, hypogeusia, dysgeusia, phantogeusia, and/or ageusia; (b) transferring the e.g., diagnosed, result via a communication medium; and/or (c) computer implementing the diagnosis.

The treating can comprise administering to the subject e.g., in need thereof, at least one therapeutic agent.

The at least one therapeutic agent can be a PDE inhibitor. "Phosphodiesterase inhibitor" or "PDE inhibitor" can refer to any compound that inhibits a phosphodiesterase enzyme, isozyme or allozyme. The term can refer to selective or non-selective inhibitors of cyclic guanosine 3',5'-monophosphate phosphodiesterases (cGMP-PDE) and/or cyclic adenosine 3',5'-monophosphate phosphodiesterases (cAMP-PDE).

Theophylline and papaverine are representative members of non-selective PDE inhibitors that can be prescribed orally to treat asthma and chronic obstructive pulmonary disease (COPD) through the relaxation of smooth muscle in the airways. Theophylline has anti-inflammatory effects on the airways that can be useful to combat the abnormal inflammation seen in asthmatics. Most importantly, this anti-inflammatory effect can be obtained at levels in the blood well below that which causes the common side effects seen in most people. Patients with emphysema and chronic bronchitis can also be helped with theophylline when their symptoms are partially related to reversible airway narrowing.

Theophylline is a methylxanthine derivative; other non-selective phosphodiesterase inhibitors in this class can include caffeine, IBMX (3-isobutyl-1-methylxanthine, aminophylline, doxophylline, cipamphylline, theobromine, pentoxifylline (oxpentifylline) and diprophylline.

PDE1 selective inhibitors formerly known as calcium- and calmodulin-dependent phosphodiesterases can include eburnamenine-14-carboxylic acid ethyl ester (vinpocetine), which can be used to induce vasorelaxation on cerebral smooth muscle tissue. Other PDE-1 selective inhibitors can include compound KS505a, bepril, flunarizine, amiodarone, zaprinast, 8-methoxymethyl IPMX, SCH 51866, Nimodipine, and IC224.

PDE2 decreases aldosterone secretion and can play an important role in the regulation of elevated intracellular concentrations of cAMP and cGMP in platelets. Several regions of the brain can express PDE2 and rat experiments indicate that inhibition of PDE2 enhances memory. PDE2 may play a role in regulation of fluid and cell extravasation during inflammatory conditions as PDE2 can be localized to microvessels, especially venous capillary and endothelial cells, but apparently not to larger vessels. PDE2 can also be a pharmacological target for pathological states such as sepsis or in more localized inflammatory responses such as thrombin-induced edema formation in the lung. PDE-2 selective inhibitors can include EHNA (erythro-9-(2-hydroxy-3-nonyl) adenine), 9-(6-phenyl-2-oxohex-3-yl)-2-(3,4-dimethoxybenzyl)-purin-6-one (PDP), and BAY 60-7750.

The PDE3 family hydrolyzes cAMP and cGMP, but in a manner suggesting that in vivo, the hydrolysis of cAMP can be inhibited by cGMP. They also are distinguished by their ability to be activated by several phosphorylation pathways including the PKA and PI3K/PKB pathways. PDE3A can be relatively highly expressed in platelets, as well as in cardiac myocytes and oocytes. PDE3B can be a major PDE in adipose tissue, liver, and pancreas, as well as in several cardiovascular tissues. Both PDE3A and PDE3B can be highly expressed in vascular smooth muscle cells and may likely modulate contraction.

PDE3 inhibitors can mimic sympathetic stimulation to increase cardiac inotropy, chronotropy and dromotropy. PDE3 inhibitors can also antagonize platelet aggregation, increase myocardial contractility, and/or enhance vascular and airway smooth muscle relaxation. PDE3A can be a regulator of this process and PDE3 inhibitors can effectively prevent aggregation of platelets. Cilastazol (Pletal), is approved for treatment of intermittent claudication. Without being limited by theory, the mechanism of Cilastazol action is thought to involve inhibition of platelet aggregation along with inhibition of smooth muscle proliferation and vasodilation. PDE3-selective inhibitors can include enoximone, milrinone (Primacor), amrinone, cilostamide, cilostazol (Pletal), trequinsin, inamrinone, anagrelide, pimobendan, lixazinone, and dihydro-pyridazinone.

PDE4 inhibitors can effectively suppress release of inflammatory mediators (e.g., cytokines) and can inhibit the production of reactive oxygen species and immune cell infiltration. PDE4-selective inhibitors can include mesembrine; rolipram; Ibudilast, a neuroprotective and bronchodilator drug used mainly in the treatment of asthma and stroke; roflumilast (Daxas), cilomilast (Airflo), piclamilast, luteolin, drotaverine, and denbufylline. PDE4 inhibitors can be effective in treating asthma, arthritis, and psoriasis.

PDE5s can regulate vascular smooth muscle contraction and can be the molecular target for drugs that can be used to treat erectile dysfunction and/or pulmonary hypertension. In the lung, inhibition of PDE5 can oppose smooth muscle vasoconstriction. PDE5 inhibitors can be used to treat pulmonary hypertension.

PDE5-selective inhibitors can include sildenafil, tadalafil, vardenafil, udenafil and avanafil, dipyridamole, icariin, 4-Methylpiperazine, Pyrazolo Pyrimidin-7-1, cilomilast, and zaprinast.

PDE6-selective inhibitors can include zaprinast, dipyridamole, vardenafil, and tadalafil.

PDE7-selective inhibitors can include quinazoline type PDE7 inhibitor, dipyridamole, and thiadiazole.

PDE8-selective inhibitors can include dipyridamole.

PDE9-selective inhibitors can include zaprinast.

PDE10-selective inhibitors can include papaverine, OMS824, PF-2545920, and dipyridamole.

PDE11-selective inhibitors can include tadalafil, zaprinast, and dipyridamole.

PDE inhibitors can inhibit cellular apoptosis. Without being limited by theory, the mechanism of apoptosis inhibition can include inhibition of TNF alpha, TRAIL and their metabolites. PDE inhibitors can activate the production and secretion of nitric oxide in tissues, which can induce vasorelaxation or vasodilation of blood vessels (e.g., peripheral blood vessels, thereby inhibiting intermittent claudication; the distal extremities; and in the penile region, contributing to penile erection).

PDE inhibitors useful in the present invention can include, for example, filaminast, piclamilast, rolipram, Org 20241, MCI-154, roflumilast, toborinone, posicar, lixazinone, zaprinast, sildenafil, pyrazolopyrimidinones (such as those disclosed in WO 98/49166), motapizone, pimobendan, zardaverine, siguazodan, CI-930, EMD 53998, imazodan, saterinone, loprinone hydrochloride, 3-pyridinecarbonitrile derivatives, denbufyllene, albifylline, torbafylline, doxofylline, theophylline, pentoxofylline, nanterinone, cilostazol, cilostamide, MS 857, piroximone, milrinone, aminone, tolafentrine, dipyridamole, papaverine, E4021, thienopyrimidine derivatives (such as those disclosed in WO 98/17668), triflusal, ICOS-351, tetrahydropiperazino[1,2-b]beta-carboline-1,4-dione derivatives (such as those disclosed in U.S. Pat. No. 5,859,006, WO 97/03985 and WO 97/03675), carboline derivatives, (such as those disclosed in WO 97/43287), 2-pyrazolin-5-one derivatives (such as those disclosed in U.S. Pat. No. 5,869,516), fused pyridazine derivatives (such as those disclosed in U.S. Pat. No. 5,849,741), quinazoline derivatives (such as those disclosed in U.S. Pat. No. 5,614,627), anthranilic acid derivatives (such as those disclosed in U.S. Pat. No. 5,714,993), imidazoquinazoline derivatives (such as those disclosed in WO 96/26940), and the like, incorporated herein by reference in their entirety. Also included are those phosphodiesterase inhibitors disclosed in WO 99/21562 and WO 99/30697, incorporated herein by reference in their entirety. It is contemplated that at certain times, the intranasal composition does not comprise a PDE5 selective inhibitor.

Theophylline is an exemplary PDE inhibitor that can be administered according to the methods disclosed herein. For example, 20 µg/naris of theophylline can be administered twice daily. 40 µg/naris of theophylline can also be administered once daily. 40 µg/naris of theophylline can also be administered twice daily. 80 µg/naris of theophylline can also be administered once daily. 80 µg/naris of theophylline can also be administered twice daily.

The administration of an effective amount of a PDE inhibitor such as theophylline by intranasal administration may not produce a detectable blood level of the PDE inhibitor. The overall level of PDE inhibition can be measured by methods known in the art. For example, methods that can be used to determine the level of PDE, measure the downstream targets of PDE. Commercial tests can also be used. For example, a phosphodiesterase assay can be used as described in Lu et al., *Cell Physiology*, 2012, V302:C59-C66, incorporated herein by reference in its entirety. The administration of an effective amount of a PDE inhibitor by intranasal administration can produce blood concentrations of the PDE inhibitor that can be less than 5 mg/dl, 2 mg/dl, 1 mg/dl, 500 µg/dl, 250 µg/dl, 100 µg/dl, 50 µg/dl, 25 µg/dl, 10 µg/dl, 5 µg/dl, or 1 µg/dl.

Intranasal administration of an effective amount of a PDE inhibitor such as theophylline can increase taste or smell acuity. The increase in taste or smell acuity can be at least 5%, 10%, 20%, 30%, 40%, 50%, 75%, or 100% compared to the untreated state. Taste or smell acuity can be increased to at least 5%, 10%, 20%, 30%, 40%, 50%, 75%, or 100% of the acuity of normal individuals. Taste or smell acuity can be measured objectively, while in other embodiments taste or smell acuity can be measured subjectively. According to the NIH (www.nlm.nih.gov/medlinepluse/druginfo/meds/a681006.html) the use of PDE inhibitors such as theophylline can be associated with side effects such as upset stomach, stomach pain, diarrhea, headache, restlessness, insomnia, irritability, vomiting, increased or rapid heart rate, irregular heartbeat, seizures, and/or skin rash. Intranasal administration of PDE inhibitors such as theophylline can cause fewer side effects than other routes of administration. Intranasal administration of PDE inhibitors such as theophylline can cause less severe side effects than other routes of administration.

PDE inhibitors such as theophylline can be administered alone or in combination with one or more other active ingredients; for example, 1, 2, 3, 4, 5, 6, 7, 8, 9, 10 or more other active ingredients, such as any drug disclosed herein. For example, other selective or non-selective PDE inhibitors can be used, or drugs such as forskolin and riociguat can be used.

The at least one PDE inhibitor can be a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof. The at least one PDE inhibitor can be a non-selective PDE inhibitor that can be a methylxanthine derivative. The methylxanthine derivative can be caffeine, theophylline, doxophylline, cipamphylline, neuphylline, pentoxiphylline, or diprophylline. The methylxanthine derivative can be theophylline. The PDE 1 inhibitor can be vinpocetine, compound KS505a, bepril, flunarizine, amiodarone, zaprinast, 8-methoxymethyl IPMX, SCH 51866, Nimodipine, or IC224. The PDE 2 inhibitor can be EHNA. The PDE 3 inhibitor can be enoximone, milrinone (Primacor), amrinone, cilostamide, cilostazol (Pletal), trequinsin, inamrinone, anagrelide, pimobendan, lixazinone, or dihydro-pyridazinone. The PDE 4 inhibitor can be mesembrine, rolipram, ibudilast, roflumilast (Daxas), cilomilast (Airflo), piclamilast, luteolin, drotaverine, or denbufylline. The PDE 5 inhibitor can be sildenafil, tadalafil, vardenafil, udenafil and avanafil, dipyridamole, icariin, 4-Methylpiperazine, Pyrazolo Pyrimidin-7-1, cilomilast, or zaprinast. The PDE6-selective inhibitors can be zaprinast, dipyridamole, vardenafil, or tadalafil. The PDE7-selective inhibitors can be quinazoline type PDE7 inhibitor, dipyridamole, or thiadiazole. The PDE8-selective inhibitors can be dipyridamole. The PDE9-selective inhibitors can be zaprinast. The PDE 10 inhibitor can be papaverine, OMS824 (from Omeros Corporation), and/or PF-2545920 (from Pfizer). The PDE11-selective inhibitors can be tadalafil, zaprinast, or dipyridamole. Any combination of one or more PDE inhibitors, as described herein, can be used.

Forskolin is a labdane diterpene that is produced by the plant *Coleus forskohlii*. Forskolin can be used to raise levels of cAMP levels. The mechanism can comprise activating adenylyl cyclase.

Riociguat, also known as BAY 63-2521, can be used as a guanylate cyclase (sGC) stimulator. At specific milligram oral dosages, riociguat is believed to be helpful in treating two forms of pulmonary hypertension (PH): chronic thromboembolic pulmonary hypertension (CTEPH) and pulmonary arterial hypertension (PAH).

The methods described herein can further comprise treating the subject, i.e., in need thereof, with at least one therapeutic agent, wherein the at least one therapeutic agent can be a non-selective PDE inhibitor, forskolin, and/or riociguat. Various combinations are contemplated. By way of example, several methods are disclosed herein. The methods can further comprise treating the subject in need thereof with at least one therapeutic agent, wherein the at least one therapeutic agent can be a selective PDE inhibitor, forskolin, and/or riociguat. The methods can further comprise treating the subject in need thereof with at least one therapeutic agent, wherein the at least one therapeutic agent can be a non-selective PDE inhibitor, theophylline, and/or riociguat. The methods can further comprise treating the subject in need thereof with at least one therapeutic agent, wherein the at least one therapeutic agent can comprise a selective PDE inhibitor, theophylline, and/or riociguat. The methods can further comprise treating the subject in need thereof with at least one therapeutic agent, wherein the at least one therapeutic agent can comprise a non-selective PDE inhibitor and/or riociguat. The methods can further comprise treating the subject in need thereof with at least one therapeutic agent, wherein the at least one therapeutic agent can comprise a selective PDE inhibitor and/or riociguat. The methods can further comprise treating the subject in need thereof with at least one therapeutic agent, wherein the at least one therapeutic agent can comprise theophylline and/or riociguat. The methods can further comprise at least one therapeutic agent, wherein the at least one therapeutic agent can comprise forskolin and/or riociguat. The methods can further comprise at least one therapeutic agent, wherein the at least one therapeutic agent can comprise theophylline, forskolin, and/or riociguat. The methods can further comprise at least one therapeutic agent, wherein the at least one therapeutic agent can comprise riociguat. The methods can further comprise at least one therapeutic agent, wherein the at least one therapeutic agent can comprise theophylline. The methods can further comprise at least one therapeutic agent, wherein the at least one therapeutic agent can comprise forskolin. The methods can further comprise at least one therapeutic agent, wherein the at least one therapeutic agent can comprise a non-selective PDE inhibitor. The methods can further comprise at least one therapeutic agent, wherein the at least one therapeutic agent can comprise a selective PDE inhibitor.

Riociguat can be used to effectively treat loss and/or distortion of taste or smell, e.g., hyposmia, dysosmia, anosmia, phantosmia, hypogeusia, dysgeusia, phantogeusia, and/ or ageusia. In particular, effective dosages of riociguat can differ from high to low levels. Riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, and about 235 µg to less than 250 µg.

Theophylline can be used to effectively treat loss and/or distortion of taste or smell, e.g., hyposmia, dysosmia, anosmia, phantosmia, hypogeusia, dysgeusia, phantogeusia, and/or ageusia. In particular, effective dosages of theophylline can differ from high to low levels. Theophylline can be given and/or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg.

Forskolin can be used to effectively treat loss and/or distortion of taste or smell, e.g., hyposmia, dysosmia, anosmia, phantosmia, hypogeusia, dysgeusia, phantogeusia, and/or ageusia. In particular, effective dosages of forskolin can differ from high to low levels. Forskolin can be given and/or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

Any combination of riociguat, theophylline, and/or forskolin can be given to a subject e.g., in need thereof. In certain cases, a particular combination of riociguat, theophylline, and/or forskolin can exhibit synergistic effects when treating conditions, compared to when treating with riociguat, theophylline, and/or forskolin alone. In other cases, a particular combination of riociguat, theophylline, and/or forskolin can exhibit synergistic effects when treating conditions, compared to when treating with riociguat, theophylline, and/or forskolin in pairs. The conditions can be disease. The condition can be loss and/or distortion of taste or smell, e.g., hyposmia, dysosmia, anosmia, phantosmia, hypogeusia, dysgeusia, phantogeusia, and/or ageusia. The methods can comprise treating subjects with one or more therapeutic agents, wherein: (a) riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, and about 235 µg to less than 250 µg; (b) theophylline can be given and/or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg; and (c) forskolin can be given and/or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

The cytochrome P450 superfamily (CYP) can be a large and diverse group of enzymes that catalyze the oxidation of organic substances. CYPs are the major enzymes involved in drug metabolism and bioactivation. The inventors have found that by inhibiting CYPs, the effect of the therapeutic agents of this invention can be prolonged and have a more profound effect. This can allow for lower dosing and delivery via a multitude of different routes of administration. The inventors have also found that different routes of administration may circumvent drug resistance.

The methods can further comprise treating a subject in need thereof, wherein the treating can comprise administering to a subject, an effective amount of cytochrome p450 inhibitors. The methods can further comprise administering to a subject, an effective amount of cytochrome p450 inhibitors, wherein the cytochrome p450 inhibitors can fully or partially inhibit a cytochrome selected from a group consisting of: CYP1, CYP1A1, CYP1A2, CYP1B1, CYP2, CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1, CYP3, CYP3A4, CYP3A5, CYP3A7, CYP3A43, CYP4, CYP4A11, CYP4A22, CYP4B1, CYP4F2, CYP4F3, CYP4F8, CYP4F11, CYP4F12, CYP4F22, CYP4V2, CYP4X1, CYP4Z1, CYP5, CYP5A1, CYP7, CYP7A1, CYP7B1, CYP8, CYP8A1, CYP8B1, CYP11, CYP11A1, CYP11B1, CYP11B2, CYP17, CYP17A1, CYP19, CYP19A1, CYP20, CYP20A1, CYP21, CYP21A2, CYP24, CYP24A1, CYP26, CYP26A1, CYP26B1, CYP26C1, CYP27, CYP27A1, CYP27B1, CYP27C1, CYP39, CYP39A1, CYP46, CYP46A1, CYP5, and CYP51A1. The methods can also further comprise administering to a subject, an effective amount of cytochrome p450 inhibitors, wherein the cytochrome p450 inhibitor can fully or partially inhibit CYP1. The methods can also further comprise administering to a subject, an effective amount of cytochrome p450 inhibitors, wherein the cytochrome p450 inhibitor can fully or partially inhibit CYP1A2. The CYP1A2 inhibitor can be selected from a group consisting of: fluoroquinolone, selective serotonin reuptake inhibitor (SSRI), calcium channel blocker, herbal tea, naringenin, H2-receptor antagonist, antiarrhythmic agent, interferon, xanthotoxin, mibefradil, cumin, turmeric, and isoniazid. The one or more CYP1A2 inhibitor can be grapefruit juice. The one or more CYP1A2 inhibitor can be naringenin.

β-adrenergic agonists are a class of sympathomimetic agents which can act upon the beta adrenoceptors. Stimulation with β-adrenergic agonists can activate adenylate cyclase and raise intracellular cAMP levels. The inventors have found that treatment with β-adrenergic agonists can ameliorate loss and/or distortion of taste or smell, e.g., hyposmia, dysosmia, anosmia, phantosmia, hypogeusia, dysgeusia, phantogeusia, and/or ageusia. The methods can further comprise treating a subject in need thereof, wherein the treating can comprise administering to a subject, an effective amount of one or more β-adrenergic agonists. The one or more β-adrenergic agonists can be a $β_1$-adrenergic agonist and/or β2-adrenergic agonist. The methods can also further comprise one or more β-adrenergic agonists, wherein the one or more β-adrenergic agonists can be a $β_1$-adrenergic agonist. The one or more β-adrenergic agonists can be a $β_1$-adrenergic agonist selected from a group consisting of dobutamine, isoproterenol, xamoterol and epinephrine. The one or more β-adrenergic agonists can be a $β_2$-adrenergic agonist. The one or more β-adrenergic agonists can be a $β_2$-adrenergic agonist selected from a group consisting of albuterol, levalbuterol, fenoterol, formoterol, isoproterenol ($β_1$ and $β_2$), metaproterenol, salmeterol, terbutaline, clenbuterol, isoetarine, pirbuterol, procaterol, ritodrine, and epinephrine. The one or more β-adrenergic agonists can be selected from a group consisting of: arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol.

Anti-inflammatory cytokines can be used to ameliorate loss and/or distortion of taste or smell, e.g., hyposmia, dysosmia, anosmia, phantosmia, hypogeusia, dysgeusia, phantogeusia, and/or ageusia. The methods can also further comprise treating, wherein the treating can comprise administering to a subject in need thereof, an effective amount of one or more anti-inflammatory cytokines. The one or more anti-inflammatory cytokines can comprise IL-1ra, IL-10, IFN-γ, IFN-β, or any combination thereof.

Antibodies or the like, e.g., antibody mimetics and antibody fragments can be used to ameliorate loss and/or distortion of taste or smell, e.g., hyposmia, dysosmia, anosmia, phantosmia, hypogeusia, dysgeusia, phantogeusia, and/or ageusia. The methods can also further comprise treating, wherein the treating can comprise administration of an effective amount of an antibody, antibody fragment, or antibody mimetic that can inhibit one of the one or more pro-inflammatory cytokines. The antibody, antibody fragment, or antibody mimetic can bind to one of the one or more pro-inflammatory cytokines. The antibody, antibody fragment, or antibody mimetic can bind to a receptor for at least one of the one or more pro-inflammatory cytokines. The antibody can be a monoclonal antibody. The monoclonal antibody can be a recombinant antibody, a chimeric antibody, a human monoclonal antibody, or a humanized monoclonal antibody. The antibody fragment can be a FAB fragment, a FAB2 fragment, a Fv fragment, a ScFv fragment, an antibody light chain, or an antibody heavy chain. The antibody mimetic can be an affibody molecule, an affilin, an affitin, an anticalins, an avimers, a DARPins, a fynomer, a Kunitz domain peptide, or a monobody.

It is contemplated that the methods comprise a antibody, antibody fragment, or antibody mimetic can bind to IL-6. The antibody, antibody fragment, or antibody mimetic can bind to a receptor for IL-6. The antibody, antibody fragment, or antibody mimetic can be tociluzumab, sarilumab, elsilimomab, siltuximab, sirukumab, BMS-945429, CDP6038, VX30, ARGX-109, or FM101. The inhibitor can be lunasin. The methods can also encompass antibodies, antibody fragments, or antibody mimetics that can bind to IL-1α. The antibody, antibody fragment, or antibody mimetic can bind to a receptor for IL-1α. The inhibitor can be IL-1RA. The antibody, antibody fragment, or antibody mimetic can bind to IL-1β. The antibody, antibody fragment, or antibody mimetic can bind to a receptor for IL-1β. The antibody, antibody fragment, or antibody mimetic can be canakinumab. The antibody, antibody fragment, or antibody mimetic can bind to TNF-α. The antibody, antibody fragment, or antibody mimetic can bind to a receptor for TNF-α. The antibody, antibody fragment, or antibody mimetic can be infliximab, adalimumab, certolizumab pegol, or golimumab. The inhibitor can be etanercept, a xanthine derivative, bupropion, or a 5-HT2A agonist. The inhibitor can be the xanthine derivative that can be pentoxifylline. The inhibitor can be the 5-HT2A agonist that can be (R)-DOI (2,5-dimethoxy-4-iodoamphetamine), TCB-2 (1-[(7R)-3-bromo-2,5-dimethoxybicyclo[4.2.0]octa-1,3,5-trien-7-yl]methanamine), LSD (lysergic acid diethylamide), or LSZ (Lysergic acid 2,4-dimethylazetidide).

The methods can further comprise administration of a composition or dosage unit that can be steroid-free.

Another aspect of this invention can be to restore the levels of members of the hedgehog signaling pathway to a therapeutically effective level. This can be achieved by various methods, including but not limited to those already known in the art. The treatment can comprise increasing the level of one or more members of the hedgehog signaling pathway by administration of an effective amount of one or more members of the hedgehog signaling pathway. The increasing the level of one or more members of the hedgehog signaling pathway can also comprise administration of an effective amount of the one or more exogenous members of the hedgehog signaling pathway. The increasing the level of one or more members of the hedgehog signaling pathway can also comprise activating expression of an effective amount of one or more members of the hedgehog signaling pathway. The activating expression of an effective amount of one or more members of the hedgehog signaling pathway can be done by genetic manipulation of genes responsible for the expression of one or more members of the hedgehog signaling pathway. The activating expression of an effective amount of one or more members of the hedgehog signaling pathway can also be effectuated through a therapeutic agent. The treatment can directly or indirectly affect levels of one or more members of the hedgehog signaling pathway.

The methods of this invention can include different routes of administration for the one or more therapeutic agents. Known methods in the art can be used to make different formulations. The one or more therapeutic agents or composition comprising one or more therapeutic agents can be suitable for administration by a methods selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. Because of the ease of use, the one or more therapeutic agents or composition comprising one or more therapeutic agents can be suitable for oral administration, inhalational administration, intranasal administration, or any combination thereof.

The subject of this invention can be a mammal. For example, the subject can be a human. The subject can be a subject in need thereof.

Methods for Treating

The inventors have found that loss and/or distortion of taste or smell, e.g., hyposmia, dysosmia, anosmia, phantosmia, hypogeusia, dysgeusia, phantogeusia, and/or ageusia can be treated by altering levels of one or more members of the hedgehog signaling pathway.

Disclosed herein are methods of treating loss and/or distortion of taste or smell, e.g., hyposmia, dysosmia, anosmia, phantosmia, hypogeusia, dysgeusia, phantogeusia, and/or ageusia in a subject, the methods comprising increasing and/or maintaining the level of one or more members of the hedgehog signaling pathway.

The one or more members of the hedgehog signaling pathway can be selected from a group consisting of: SHH, DHH, and IHH. The one or more members of the hedgehog signaling pathway can be SHH, DHH, IHH, or any combination thereof.

The one or more members of the hedgehog signaling pathway can be increased and/or maintained by increasing cGMP levels. The increasing and/or maintaining the level of one or more members of the hedgehog signaling pathway can comprise giving the subject one or more cGMP activators. The one or more cGMP activators can be given in combination with one or more additional therapeutic agents. The cGMP activator can be riociguat. The one or more additional therapeutic agents can comprise one or more non-selective PDE inhibitors and/or forskolin, or combinations thereof. The one or more additional therapeutic agents can comprise one or more selective PDE inhibitors and/or forskolin, or combinations thereof.

The methods can further comprise administering to the subject one or more additional therapeutic agents, wherein the one or more additional therapeutic agents can comprise riociguat given or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 pg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, and about 235 µg to less than 250 µg.

The methods can further comprise administering to the subject one or more additional therapeutic agents, wherein the one or more additional therapeutic agents can comprise theophylline given or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg.

The methods can further comprise administering to the subject one or more additional therapeutic agents, wherein the one or more additional therapeutic agents can comprise forskolin given or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

Any combination of riociguat, theophylline, and/or forskolin can be given to a subject to raise the level of one or more members of the hedgehog signaling pathway. In certain cases, a particular combination of riociguat, theophylline, and/or forskolin can exhibit synergistic effects compared to when treating with riociguat, theophylline, and/or forskolin alone. In other cases, a particular combination of riociguat, theophylline, and/or forskolin can exhibit synergistic effects compared to when treating with riociguat, theophylline, and/or forskolin in pairs. The methods can further comprise administering to the subject one or more additional therapeutic agents, wherein the one or more additional therapeutic agents can comprise: (a) riociguat given or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 pg to about 180 µg, about 170 µg to about 200 µg, about 200 µg to about 230 µg, about 215 µg to about 240 µg, and about 235 µg to less than 250 µg; (b) theophylline given or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg; and (c) forskolin given or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

The methods can further comprise comprising one or more non-selective PDE inhibitors wherein the one or more non-selective PDE inhibitors can comprise theophylline. The methods can also further comprise one or more non-selective PDE inhibitors, wherein the one or more selective PDE inhibitors can be selected from a group consisting of: a PDE-1 selective inhibitor, a PDE-2 selective inhibitor, a PDE-3 selective inhibitor, a PDE-4 selective inhibitor, a PDE-5 selective inhibitor, or any combination thereof.

The maintaining and/or increasing the level of one or more members of the hedgehog signaling pathway can comprise administration of an effective amount of one or more members of the hedgehog signaling pathway. The maintaining and/or increasing the level of one or more members of the hedgehog signaling pathway can also comprise administration of an effective amount of the one or more exogenous members of the hedgehog signaling pathway. The maintaining and/or increasing the level of one or more members of the hedgehog signaling pathway can also comprise activating expression of an effective amount of one or more members of the hedgehog signaling pathway. The activating expression of an effective amount of one or more members of the hedgehog signaling pathway can be effectuated by genetic manipulation of one or more genes responsible for the expression of one or more members of the hedgehog signaling pathway. The activating expression of an effective amount of one or more members of the hedgehog signaling pathway can also be effectuated through a therapeutic agent. The therapeutic agent can directly affect the levels of one or more members of the hedgehog signaling pathway. The therapeutic agent can indirectly affect the levels of one or more members of the hedgehog signaling pathway.

The one or more therapeutic agents or composition comprising one or more therapeutic agents can be suitable for administration by a methods selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. Because of the ease of use, the one or more therapeutic agents or composition comprising one or more therapeutic agents can be suitable for oral administration, inhalational administration, intranasal administration, or any combination thereof.

The inventors have found that loss and/or distortion of taste or smell, e.g., hyposmia, dysosmia, anosmia, phantosmia, hypogeusia, dysgeusia, phantogeusia, and/or ageusia can be effectively ameliorated by increasing the levels of one or more members of the hedgehog signaling pathway while effecting levels of nitric oxide (NO), TNF alpha (TNF-α), TNF-related apoptosis-inducing ligand (TRAIL), interleukin-1 (IL-1), interleukin-1 receptor antagonist (IL-1RA), and/or interleukin-10 (IL-10). In some cases, the combination can lead to synergistic effects.

Disclosed herein are also methods of treating loss and/or distortion of taste or smell, e.g., hyposmia, dysosmia, anosmia, phantosmia, hypogeusia, dysgeusia, phantogeusia, and/or ageusia in a subject in need thereof, the methods comprising administering to the subject one or more therapeutic agents or a composition comprising one or more therapeutic agents sufficient to effectuate: (a) maintenance and/or increase in one or more members of the hedgehog signaling pathway; (b) at least one or more of the following: (i) an increase in nitric oxide (NO); (ii) a decrease in TNF alpha (TNF-α); (iii) a decrease in TNF-related apoptosis-inducing ligand (TRAIL); (iv) a decrease in interleukin-1 (IL-1); (v) a decrease in interleukin-1 receptor antagonist (IL-1RA); and (vi) an increase of interleukin-10 (IL-10); and (c) stem cell differentiation.

The one or more therapeutic agents can comprise one or more cGMP activators, one or more cAMP activators, or any combination thereof.

The methods can further comprise one or more cGMP activators, wherein the one or more cGMP activators can be selected from a group consisting of 3-(5'-hydroxymethyl-2'-furyl)-1-benzylindazole (YC-1), YC-1 derivatives, anthranilic acids derivatives, ataciguat (HMR1766), benzydamine analogs, CFM1517, A-350619, nitrovasodilators, molsidomine, nitroxyl (HNO), BAY 41-2272, BAY 41-8543, BAY 58-2667, cinaciguat (BAY 58-2667), and riociguat (BAY 63-2521). The one or more cGMP activators can be riociguat.

The methods can further comprise one or more cAMP activators wherein the one or more cAMP activators can be selected from a group consisting of 3-(5'-hydroxymethyl-2'-furyl)-1-benzylindazole (YC-1), glucagon, PDE inhibitors, prostaglandin E1 (PGE1; pharmaceutically known as alprostadil), forskolin, and 3-adrenergic agonists. The methods can further comprise one or more cAMP activators wherein the one or more cAMP activators can comprise one or more PDE inhibitors and/or forskolin. The methods can further comprise one or more cAMP activators wherein the one or more cAMP activators can be forskolin.

The methods can further comprise one or more cAMP activators wherein the one or more cAMP activators can be one or more PDE inhibitors. The one or more PDE inhibitors can comprise a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof. The one or more PDE inhibitors can be a selective PDE inhibitor. The one or more PDE inhibitors can comprise a non-selective PDE inhibitor that can be a methylxanthine derivative. The methylxanthine derivative can be caffeine, theophylline, doxophylline, cipamphylline, neuphylline, pentoxiphylline, or diprophylline. The methylxanthine derivative can be theophylline. The PDE 1 inhibitor can be vinpocetine, compound KS505a, bepril, flunarizine, amiodarone, zaprinast, 8-methoxymethyl IPMX, SCH 51866, Nimodipine, or IC224. The PDE 2 inhibitor that can be EHNA. The PDE 3 inhibitor can be enoximone, milrinone (Primacor), amrinone, cilostamide, cilostazol (Pletal), trequinsin, inamrinone, anagrelide, pimobendan, lixazinone, or dihydro-pyridazinone. The PDE 4 inhibitor can be mesembrine, rolipram, ibudilast, roflumilast (Daxas), cilomilast (Airflo), piclamilast, luteolin, drotaverine, or denbufylline. The PDE 5 inhibitor can be sildenafil, tadalafil, vardenafil, udenafil and avanafil, dipyridamole, icariin, 4-Methylpiperazine, Pyrazolo Pyrimidin-7-1, cilomilast, or zaprinast.

The PDE6-selective inhibitors can be zaprinast, dipyridamole, vardenafil, or tadalafil. The PDE7-selective inhibitors can be quinazoline type PDE7 inhibitor, dipyridamole, or thiadiazole. The PDE8-selective inhibitors can be dipyridamole. The PDE9-selective inhibitors can be zaprinast. The PDE 10 inhibitor can be papaverine, OMS824 (from Omeros Corporation), and/or PF-2545920 (from Pfizer). The PDE11-selective inhibitors can be tadalafil, zaprinast, or dipyridamole.

The one or more therapeutic agents can comprise a non-selective PDE inhibitor, forskolin, and riociguat. The one or more therapeutic agents can comprise a selective PDE inhibitor, forskolin, and riociguat. Various combinations are also contemplated. For example, the one or more therapeutic agents can comprise a non-selective PDE inhibitor, theophylline, and riociguat. The one or more therapeutic agents can comprise a selective PDE inhibitor, theophylline, and riociguat. The one or more therapeutic agents can comprise a non-selective PDE inhibitor and riociguat. The one or more therapeutic agents can comprise a selective PDE inhibitor and riociguat. The one or more therapeutic agents can comprise theophylline and riociguat. The one or more therapeutic agents can comprise forskolin and riociguat. The one or more therapeutic agents can comprise theophylline, forskolin, and riociguat.

The methods of this invention can comprise one or more therapeutic agents, wherein the one or more therapeutic agents can be steroid-free.

Riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, less than 250 µg and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, about 235 µg to less than about 250 µg.

Theophylline can be given and/or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg.

Forskolin can be given and/or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, 2 mg to greater than 0 mg and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, about 2 mg to greater than about 0 mg.

Any combination of riociguat, theophylline, and/or forskolin can be given to a subject to raise the level of one or more members of the hedgehog signaling pathway and/or NO, TNF-α, TRAIL, IL-1, IL-1RA, and/or IL-10. In certain cases, a particular combination of riociguat, theophylline, and/or forskolin can exhibit synergistic effects compared to when treating with riociguat, theophylline, and/or forskolin alone. In other cases, a particular combination of riociguat, theophylline, and/or forskolin can exhibit synergistic effects compared to when treating with riociguat, theophylline, and/or forskolin in pairs. The methods can comprise methods wherein (a) riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, and about 235 µg to less than 250 pg; (b) theophylline can be given and/or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg; and (c) forskolin can be given and/or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

The increasing and/or maintaining the level of one or more members of the hedgehog signaling pathway can comprise administering an effective amount of one or more members of the hedgehog signaling pathway. The increasing and/or maintaining the level of one or more members of the hedgehog signaling pathway can comprise administering an effective amount of one or more exogenous members of the hedgehog signaling pathway. The increasing and/or maintaining the level of one or more members of the hedgehog signaling pathway can comprise activating expression of an effective amount of one or more members of the hedgehog signaling pathway. The activating expression of an effective amount of one or more members of the hedgehog signaling pathway can be effectuated by genetic manipulation of one or more genes responsible for the expression of one or more members of the hedgehog signaling pathway The activating expression of an effective amount of one or more members of the hedgehog signaling pathway can be effectuated through a therapeutic agent. The therapeutic agent can directly affect the levels of one or more members of the hedgehog signaling pathway. The therapeutic agent can indirectly affect the levels of one or more members of the hedgehog signaling pathway.

The one or more therapeutic agents or composition comprising one or more therapeutic agents can be suitable for administration by a method selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. Because of ease of use, the one or more therapeutic agents or composition comprising one or more therapeutic agents can be suitable for oral administration, inhalational administration, intranasal administration, or any combination thereof.

The one or more therapeutic agents or compositions can show an unexpected efficacy when formulated as a liquid above a specific pH. Sometimes, any combination of one or more therapeutic agents when formulated above a specific pH can result in synergistic effects. The one or more therapeutic agents or composition comprising one or more therapeutic agents can be a liquid. The one or more therapeutic agents or composition comprising one or more therapeutic agents can have a pH of greater than 7.0. The one or more therapeutic agents or composition comprising one or more therapeutic agents can have a pH of greater than 7.1. The one or more therapeutic agents or composition comprising one or more therapeutic agents can have a pH of greater than 7.5. The one or more therapeutic agents or composition comprising one or more therapeutic agents can have a pH of greater than 8.0. The one or more therapeutic agents or composition comprising one or more therapeutic agents can have a pH of greater than 9.0.

Excipients can be added to one or more therapeutic agents or compositions. The excipients that can be used in the invention can include those found in the Handbook of Pharmaceutical Excipients, Sixth Edition (2009), Eds. R. C. Rowe, P. J. Shesky, and M. E. Quinn, incorporated herein by reference in its entirety. For example, it is contemplated that the following excipients can be added separately or in any combination, to one or more therapeutic agents or composition: Acacia, Acesulfame Potassium, Acetic Acid—Glacial, Acetone, Acetyltributyl Citrate, Acetyltriethyl Citrate, Adipic Acid, Agar, Albumin, Alcohol, Alginic Acid, Aliphatic Polyesters, Alitame, Almond Oil, Alpha Tocopherol, Aluminum Hydroxide Adjuvant, Aluminum Monostearate, Aluminum Oxide, Aluminum Phosphate Adjuvant, Ammonia Solution, Ammonium Alginate, Ammonium Chloride, Ascorbic Acid, Ascorbyl Palmitate, Aspartame, Attapulgite, Bentonite, Benzalkonium Chloride, Benzethonium Chloride, Benzoic Acid, Benzyl Alcohol, Benzyl Benzoate, Boric Acid, Bronopol, Butylated Hydroxyanisole, Butylated Hydroxytoluene, Butylene Glycol, Butylparaben, Calcium Acetate, Calcium Alginate, Calcium Carbonate, Calcium Chloride, Calcium Hydroxide, Calcium Lactate, Calcium Phosphate—Dibasic Anhydrous, Calcium Phosphate—Dibasic Dihydrate, Calcium Phosphate—Tribasic, Calcium Silicate, Calcium Stearate, Calcium Sulfate, Canola Oil, Carbomer, Carbon Dioxide, Carboxymethylcellulose Calcium, Carboxymethylcellulose Sodium, Carrageenan, Castor Oil, Castor Oil—Hydrogenated, Cellulose—Microcrystalline, Cellulose—Microcrystalline and Carboxymethylcellulose Sodium, Cellulose—Powdered, Cellulose—Silicified Microcrystalline, Cellulose Acetate, Cellulose Acetate Phthalate, Ceratonia, Ceresin, Cetostearyl Alcohol, Cetrimide, Cetyl Alcohol, Cetylpyridinium Chloride, Chitosan, Chlorhexidine, Chlorobutanol, Chlorocresol, Chlorodifluoroethane (HCFC), Chlorofluorocarbons (CFC), Chloroxylenol, Cholesterol, Citric Acid Monohydrate, Coconut Oil, Colloidal Silicon Dioxide, Coloring Agents, Copovidone, Corn Oil, Corn Starchand Pregelatinized Starch, Cottonseed Oil, Cresol, Croscarmellose Sodium, Crospovidone, Cyclodextrins, Cyclomethicone, Denatonium Benzoate, Dextrates, Dextrin, Dextrose, Dibutyl Phthalate, Dibutyl Sebacate, Diethanolamine, Diethyl Phthalate, Difluoroethane (HFC), Dimethicone, Dimethyl Ether, Dimethyl Phthalate, Dimethyl Sulfoxide, Dimethylacetamide, Disodium Edetate, Docusate Sodium, Edetic Acid, Erythorbic Acid, Erythritol, Ethyl Acetate, Ethyl Lactate, Ethyl Maltol, Ethyl Oleate, Ethyl Vanillin, Ethylcellulose, Ethylene Glycol Stearates, Ethylene Vinyl Acetate, Ethylparaben, Fructose, Fumaric Acid, Gelatin, Glucose—Liquid, Glycerin, Glyceryl Behenate, Glyceryl Monooleate, Glyceryl Monostearate, Glyceryl Palmitostearate, Glycine, Glycofurol, Guar Gum, Hectorite, Heptafluoropropane (HFC), Hexetidine, Hydrocarbons (HC), Hydrochloric Acid, Hydrophobic Colloidal Silica, Hydroxyethyl Cellulose, Hydroxyethylmethyl Cellulose, Hydroxypropyl Betadex, Hydroxypropyl Cellulose, Hydroxypropyl Cellulose—Low-substituted, Hydroxypropyl Starch, Hypromellose, Hypromellose Acetate Succinate, Hypromellose Phthalate, Imidurea, Inulin, Iron Oxides, Isomalt, Isopropyl Alcohol, Isopropyl Myristate, Isopropyl Palmitate, Kaolin, Lactic Acid, Lactitol, Lactose—Anhydrous, Lactose—Inhalation, Lactose—Monohydrate, Lactose—Monohydrate and Corn Starch, Lactose—Monohydrate and Microcrystalline Cellulose, Lactose—Monohydrate and Povidone, Lactose—Monohydrate and Powdered Cellulose, Lactose—Spray-Dried, Lanolin, Lanolin—Hydrous, Lanolin Alcohols, Lauric Acid, Lecithin, Leucine, Linoleic Acid, Macrogol 15 Hydroxystearate, Magnesium Aluminum Silicate, Magnesium Carbonate, Magnesium Oxide, Magnesium Silicate, Magnesium Stearate, Magnesium Trisilicate, Maleic Acid, Malic Acid, Maltitol, Maltitol Solution, Maltodextrin, Maltol, Maltose, Mannitol, Medium-chain Triglycerides, Meglumine, Menthol, Methionine, Methylcellulose, Methylparaben, Mineral Oil, Mineral Oil—Light, Mineral Oil and Lanolin Alcohols, Monoethanolamine, Monosodium Glutamate, Monothioglycerol, Myristic Acid, Myristyl Alcohol, Neohesperidin Dihydrochalcone, Neotame, Nitrogen, Nitrous Oxide, Octyldodecanol, Oleic Acid, Oleyl Alcohol, Olive Oil, Palmitic Acid, Paraffin, Peanut Oil, Pectin, Pentetic Acid, Petrolatum, Petrolatum and Lanolin Alcohols, Phenol, Phenoxyethanol, Phenylethyl Alcohol, Phenylmercuric Acetate, Phenylmercuric Borate, Phenylmercuric Nitrate, Phospholipids, Phosphoric Acid, Polacrilin Potassium, Poloxamer, Polycarbophil, Polydextrose, Poly (DL-Lactic Acid), Polyethylene Glycol, Polyethylene Oxide, Polymethacrylates, Poly(methyl vinylether/maleic anhydride), Polyoxyethylene Alkyl Ethers, Polyoxyethylene Castor Oil Derivatives, Polyoxyethylene Sorbitan Fatty Acid Esters, Polyoxyethylene Stearates, Polyoxylglycerides, Polyvinyl Acetate Phthalate, Polyvinyl Alcohol, Potassium Alginate, Potassium Alum, Potassium Benzoate, Potassium Bicarbonate, Potassium Chloride, Potassium Citrate, Potassium Hydroxide, Potassium Metabisulfite, Potassium Sorbate, Povidone, Propionic Acid, Propyl Gallate, Propylene Carbonate, Propylene Glycol, Propylene Glycol Alginate, Propylparaben, Propylparaben Sodium, Pyrrolidone, Raffinose, Saccharin, Saccharin Sodium, Safflower Oil, Saponite, Sesame Oil, Shellac, Simethicone, Sodium Acetate, Sodium Alginate, Sodium Ascorbate, Sodium Benzoate, Sodium Bicarbonate, Sodium Borate, Sodium Carbonate, Sodium Chloride, Sodium Citrate Dihydrate, Sodium Cyclamate, Sodium Formaldehyde Sulfoxylate, Sodium Hyaluronate, Sodium Hydroxide, Sodium Lactate, Sodium Lauryl Sulfate, Sodium Metabisulfite, Sodium Phosphate—Dibasic, Sodium Phosphate—Monobasic, Sodium Propionate, Sodium Starch Glycolate, Sodium Stearyl Fumarate, Sodium Sulfite, Sodium Thiosulfate, Sorbic Acid, Sorbitan Esters (Sorbitan Fatty Acid Esters), Sorbitol, Soybean Oil, Starch, Starch—Pregelatinized, Starch—Sterilizable Maize, Stearic Acid, Stearyl Alcohol, Sucralose, Sucrose, Sucrose Octaacetate, Sugar—Compressible, Sugar—Confectioner's, Sugar Spheres, Sulfobutylether b-Cyclodextrin, Sulfur Dioxide, Sulfuric Acid, Sunflower Oil, Suppository Bases—Hard Fat, Tagatose, Talc, Tartaric Acid, Tetrafluoroethane (HFC), Thaumatin, Thimerosal, Thymol, Titanium Dioxide, Tragacanth, Trehalose, Triacetin, Tributyl Citrate, Tricaprylin, Triethanolamine, Triethyl Citrate, Triolein, Vanillin, Vegetable Oil—Hydrogenated, Vitamin E Polyethylene Glycol Succinate, Water, Wax—Anionic Emulsifying, Wax—Carnauba, Wax—Cetyl Esters, Wax—Microcrystalline, Wax—Nonionic Emulsifying, Wax—White, Wax—Yellow, Xanthan Gum, Xylitol, Zein, Zinc Acetate, and/or Zinc Stearate.

The one or more therapeutic agents or composition comprising one or more therapeutic agents can further comprise one or more excipients. The one or more therapeutic agents or composition comprising one or more therapeutic agents can further comprise one or more excipients wherein the one or more excipients can be selected from a group consisting of: detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

The one or more therapeutic agents can comprise one or more cytochrome p450 inhibitors. The one or more therapeutic agents or composition comprising one or more therapeutic agents can further comprise one or more cytochrome p450 inhibitors wherein the one or more cytochrome p450 inhibitors can fully or partially inhibit a cytochrome p450 selected from a group consisting of: CYP1, CYP1A1, CYP1A2, CYP1B1, CYP2, CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1, CYP3, CYP3A4, CYP3A5, CYP3A7, CYP3A43, CYP4, CYP4A11, CYP4A22, CYP4B1, CYP4F2, CYP4F3, CYP4F8, CYP4F11, CYP4F12, CYP4F22, CYP4V2, CYP4X1, CYP4Z1, CYP5, CYP5A1, CYP7, CYP7A1, CYP7B1, CYP8, CYP8A1, CYP8B1, CYP11, CYP11A1, CYP11B1, CYP11B2, CYP17, CYP17A1, CYP19, CYP19A1, CYP20, CYP20A1, CYP21, CYP21A2, CYP24, CYP24A1, CYP26, CYP26A1, CYP26B1, CYP26C1, CYP27, CYP27A1, CYP27B1, CYP27C1, CYP39, CYP39A1, CYP46, CYP46A1, CYP51, and CYP51A1. The one or more cytochrome p450 inhibitors can fully or partially inhibit CYP1. The one or more cytochrome p450 inhibitors can fully or partially inhibit CYP1A2. The one or more CYP1A2 inhibitor can be selected from a group consisting of: fluoroquinolone, selective serotonin reuptake inhibitor (SSRI), calcium channel blocker, herbal tea, naringenin, H2-receptor antagonist, antiarrhythmic agent, interferon, xanthotoxin, mibefradil, cumin, turmeric, and isoniazid. The one or more CYP1A2 inhibitor can be grapefruit juice. The one or more CYP1A2 inhibitor can be naringenin.

The one or more therapeutic agents or composition comprising one or more therapeutic agents can further comprise one or more β-adrenergic agonists. The one or more j-adrenergic agonists can be a $β_1$-adrenergic agonist and/or $β_2$-adrenergic agonist. The one or more therapeutic agents or composition can comprise one or more β-adrenergic agonists wherein the one or more β-adrenergic agonists can be a $β_1$-adrenergic agonist. The one or more therapeutic agents or composition can comprise one or more β-adrenergic agonists wherein the one or more β-adrenergic agonists can be a $β_1$-adrenergic agonist selected from a group consisting of: dobutamine, isoproterenol, xamoterol and epinephrine. The one or more therapeutic agents or composition can comprise one or more β-adrenergic agonists wherein the one or more β-adrenergic agonists can be a $β_2$-adrenergic agonist. The one or more therapeutic agents or composition can comprise one or more β-adrenergic agonists wherein the one or more β-adrenergic agonists can be $β_2$-adrenergic agonist selected from a group consisting of: albuterol, levalbuterol, fenoterol, formoterol, isoproterenol ($β_1$ and $β_2$), metaproterenol, salmeterol, terbutaline, clenbuterol, isoetarine, pirbuterol, procaterol, ritodrine, and epinephrine. The one or more therapeutic agents or composition can comprise one or more β-adrenergic agonists wherein the one or more β-adrenergic agonists can be selected from a group consisting of: arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol.

Drug Compositions for Treatment

The inventors have found that loss and/or distortion of taste or smell, e.g., hyposmia, dysosmia, anosmia, phantosmia, hypogeusia, dysgeusia, phantogeusia, and/or ageusia can be effectively ameliorated by using a pharmaceutical dosage unit comprising one or more cGMP activator and/or one or more cAMP activator. In some cases, the combination of cGMP and cAMP activators can produce a synergistic effect.

In an additional aspect of the invention, disclosed herein is a pharmaceutical dosage unit comprising one or more cGMP activators, one or more cAMP activators, and any combination thereof.

The pharmaceutical dosage unit can comprise one or more cGMP activators wherein the one or more cGMP activators can be selected from a group consisting of 3-(5'-hydroxymethyl-2'-furyl)-1-benzylindazole (YC-1), YC-1 derivatives, anthranilic acids derivatives, ataciguat (HMR1766), benzydamine analogs, CFM1517, A-350619, nitrovasodilators, molsidomine, nitroxyl (HNO), BAY 41-2272, BAY 41-8543, BAY 58-2667, cinaciguat (BAY 58-2667), and riociguat (BAY 63-2521). The pharmaceutical dosage unit can also comprise one or more cGMP activators wherein the one or more cGMP activators can be riociguat.

The pharmaceutical dosage unit can comprise one or more cAMP activators wherein the one or more cAMP activators can be selected from a group consisting of: 3-(5'-hydroxymethyl-2'-furyl)-1-benzylindazole (YC-1), glucagon, PDE inhibitors, prostaglandin E1 (PGE1; pharmaceutically known as alprostadil), forskolin, and β-adrenergic agonists. The pharmaceutical dosage unit can also comprise one or more cAMP activators wherein the one or more cAMP activators can comprise one or more PDE inhibitors and/or forskolin. The pharmaceutical dosage unit can also comprise one or more cAMP activators wherein the one or more cAMP activators can comprise forskolin.

The pharmaceutical dosage unit can further comprise one or more PDE inhibitors. The one or more PDE inhibitors can comprise a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof. The one or more PDE inhibitors can comprise a selective PDE inhibitor. The one or more PDE inhibitor can be a non-selective PDE inhibitor that can be a methylxanthine derivative. The methylxanthine derivative can be caffeine, theophylline, doxophylline, cipamphylline, neuphylline, pentoxiphylline, or diprophylline. The methylxanthine derivative can be theophylline. The PDE 1 inhibitor can be vinpocetine, compound KS505a, bepril, flunarizine, amiodarone, zaprinast, 8-methoxymethyl IPMX, SCH 51866, Nimodipine, or IC224. The PDE 2 inhibitor can be EHNA. The PDE 3 inhibitor can be enoximone, milrinone (Primacor), amrinone, cilostamide, cilostazol (Pletal), trequinsin, inamrinone, anagrelide, pimobendan, lixazinone, or dihydro-pyridazinone. The PDE 4 inhibitor can be mesembrine, rolipram, ibudilast, roflumilast (Daxas), cilomilast (Airflo), piclamilast, luteolin, drotaverine, or denbufylline. The PDE 5 inhibitor can be sildenafil, tadalafil, vardenafil, udenafil and avanafil, dipyridamole, icariin, 4-Methylpiperazine, Pyrazolo Pyrimidin-7-1, cilomilast, or zaprinast. The PDE6-selective inhibitors can be zaprinast, dipyridamole, vardenafil, or tadalafil. The PDE7-selective inhibitors can be quinazoline type PDE7 inhibitor, dipyridamole, or thiadiazole. The PDE8-selective inhibitors can be dipyridamole. The PDE9-selective inhibitors can be zaprinast. The PDE 10 inhibitor can be papaverine, OMS824 (from Omeros Corporation), and/or PF-2545920 (from Pfizer). The PDE11-selective inhibitors can be tadalafil, zaprinast, or dipyridamole.

The pharmaceutical dosage unit can comprise a non-selective PDE inhibitor, forskolin, and riociguat. The dosage unit can comprise a selective PDE inhibitor, forskolin, and riociguat. Various combination can be used. For example, the dosage unit can comprise a non-selective PDE inhibitor, theophylline, and riociguat. The dosage unit can comprise a selective PDE inhibitor, theophylline, and riociguat. The dosage unit can comprise a non-selective PDE inhibitor and riociguat. The dosage unit can comprise a selective PDE inhibitor and riociguat. The dosage unit can comprise theophylline, forskolin, and riociguat. The dosage unit can comprise theophylline and riociguat. The dosage unit can comprise forskolin and riociguat. The dosage unit can comprise riociguat.

The invention can include a dosage unit, wherein the dosage unit can be steroid-free.

Riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 pg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, less than 250 µg and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, about 235 µg to less than about 250 µg.

Theophylline can be given and/or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg.

Forskolin can be given and/or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, 2 mg to greater than 0 mg and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, about 2 mg to greater than about 0 mg.

It is contemplated that riociguat, theophylline, and/or forskolin can be combined. In certain cases, a particular combination of riociguat, theophylline, and/or forskolin can exhibit synergistic effects, compared to compositions with riociguat, theophylline, and/or forskolin alone. In other cases, a particular combination of riociguat, theophylline, and/or forskolin can exhibit synergistic effects compared to compositions with riociguat, theophylline, and/or forskolin in pairs. The pharmaceutical dosage unit can be a dosage unit wherein (a) riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, and about 235 µg to less than 250 pg; (b) theophylline can be given and/or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 pg; and (c) forskolin can be given and/or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

The dosage unit or composition comprising the dosage unit can be suitable for administration by a method selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. For ease of use, the dosage unit or composition comprising the dosage unit can be suitable for oral administration, inhalational administration, intranasal administration, or any combination thereof. The dosage unit or composition comprising the dosage unit can also be a liquid.

The dosage unit or composition can be affected by pH. The dosage unit can exhibit synergistic effects when the pH is above a particular threshold. For example, the dosage unit or composition can have a pH of greater than 7.0. The dosage unit or composition can have a pH of greater than 7.1. The dosage unit or composition can have a pH of greater than 7.5. The dosage unit or composition can have a pH of greater than 8.0. The dosage unit or composition can have a pH of greater than 9.0.

Excipients can be added to one or more therapeutic agents or compositions. The excipients that can be used in the invention can include those found in the Handbook of Pharmaceutical Excipients, Sixth Edition (2009), Eds. R. C. Rowe, P. J. Shesky, and M. E. Quinn, incorporated herein by reference in its entirety. For example, it is contemplated that the following excipients can be added separately or in any combination, to one or more therapeutic agents or composition: Acacia, Acesulfame Potassium, Acetic Acid—Glacial, Acetone, Acetyltributyl Citrate, Acetyltriethyl Citrate, Adipic Acid, Agar, Albumin, Alcohol, Alginic Acid, Aliphatic Polyesters, Alitame, Almond Oil, Alpha Tocopherol, Aluminum Hydroxide Adjuvant, Aluminum Monostearate, Aluminum Oxide, Aluminum Phosphate Adjuvant, Ammonia Solution, Ammonium Alginate, Ammonium Chloride, Ascorbic Acid, Ascorbyl Palmitate, Aspartame, Attapulgite, Bentonite, Benzalkonium Chloride, Benzethonium Chloride, Benzoic Acid, Benzyl Alcohol, Benzyl Benzoate, Boric Acid, Bronopol, Butylated Hydroxyanisole, Butylated Hydroxytoluene, Butylene Glycol, Butylparaben, Calcium Acetate, Calcium Alginate, Calcium Carbonate, Calcium Chloride, Calcium Hydroxide, Calcium Lactate, Calcium Phosphate—Dibasic Anhydrous, Calcium Phosphate—Dibasic Dihydrate, Calcium Phosphate—Tribasic, Calcium Silicate, Calcium Stearate, Calcium Sulfate, Canola Oil, Carbomer, Carbon Dioxide, Carboxymethylcellulose Calcium, Carboxymethylcellulose Sodium, Carrageenan, Castor Oil, Castor Oil—Hydrogenated, Cellulose—Microcrystalline, Cellulose—Microcrystalline and Carboxymethylcellulose Sodium, Cellulose—Powdered, Cellulose—Silicified Microcrystalline, Cellulose Acetate, Cellulose Acetate Phthalate, Ceratonia, Ceresin, Cetostearyl Alcohol, Cetrimide, Cetyl Alcohol, Cetylpyridinium Chloride, Chitosan, Chlorhexidine, Chlorobutanol, Chlorocresol, Chlorodifluoroethane (HCFC), Chlorofluorocarbons (CFC), Chloroxylenol, Cholesterol, Citric Acid Monohydrate, Coconut Oil, Colloidal Silicon Dioxide, Coloring Agents, Copovidone, Corn Oil, Corn Starchand Pregelatinized Starch, Cottonseed Oil, Cresol, Croscarmellose Sodium, Crospovidone, Cyclodextrins, Cyclomethicone, Denatonium Benzoate, Dextrates, Dextrin, Dextrose, Dibutyl Phthalate, Dibutyl Sebacate, Diethanolamine, Diethyl Phthalate, Difluoroethane (HFC), Dimethicone, Dimethyl Ether, Dimethyl Phthalate, Dimethyl Sulfoxide, Dimethylacetamide, Disodium Edetate, Docusate Sodium, Edetic Acid, Erythorbic Acid, Erythritol, Ethyl Acetate, Ethyl Lactate, Ethyl Maltol, Ethyl Oleate, Ethyl Vanillin, Ethylcellulose, Ethylene Glycol Stearates, Ethylene Vinyl Acetate, Ethylparaben, Fructose, Fumaric Acid, Gelatin, Glucose—Liquid, Glycerin, Glyceryl Behenate, Glyceryl Monooleate, Glyceryl Monostearate, Glyceryl Palmitostearate, Glycine, Glycofurol, Guar Gum, Hectorite, Heptafluoropropane (HFC), Hexetidine, Hydrocarbons (HC), Hydrochloric Acid, Hydrophobic Colloidal Silica, Hydroxyethyl Cellulose, Hydroxyethylmethyl Cellulose, Hydroxypropyl Betadex, Hydroxypropyl Cellulose, Hydroxypropyl Cellulose—Low-substituted, Hydroxypropyl Starch, Hypromellose, Hypromellose Acetate Succinate, Hypromellose Phthalate, Imidurea, Inulin, Iron Oxides, Isomalt, Isopropyl Alcohol, Isopropyl Myristate, Isopropyl Palmitate, Kaolin, Lactic Acid, Lactitol, Lactose—Anhydrous, Lactose—Inhalation, Lactose—Monohydrate, Lactose—Monohydrate and Corn Starch, Lactose—Monohydrate and Microcrystalline Cellulose, Lactose—Monohydrate and Povidone, Lactose—Monohydrate and Powdered Cellulose, Lactose—Spray-Dried, Lanolin, Lanolin—Hydrous, Lanolin Alcohols, Lauric Acid, Lecithin, Leucine, Linoleic Acid, Macrogol 15 Hydroxystearate, Magnesium Aluminum Silicate, Magnesium Carbonate, Magnesium Oxide, Magnesium Silicate, Magnesium Stearate, Magnesium Trisilicate, Maleic Acid, Malic Acid, Maltitol, Maltitol Solution, Maltodextrin, Maltol, Maltose, Mannitol, Medium-chain Triglycerides, Meglumine, Menthol, Methionine, Methylcellulose, Methylparaben, Mineral Oil, Mineral Oil—Light, Mineral Oil and Lanolin Alcohols, Monoethanolamine, Monosodium Glutamate, Monothioglycerol, Myristic Acid, Myristyl Alcohol, Neohesperidin Dihydrochalcone, Neotame, Nitrogen, Nitrous Oxide, Octyldodecanol, Oleic Acid, Oleyl Alcohol, Olive Oil, Palmitic Acid, Paraffin, Peanut Oil, Pectin, Pentetic Acid, Petrolatum, Petrolatum and Lanolin Alcohols, Phenol, Phenoxyethanol, Phenylethyl Alcohol, Phenylmercuric Acetate, Phenylmercuric Borate, Phenylmercuric Nitrate, Phospholipids, Phosphoric Acid, Polacrilin Potassium, Poloxamer, Polycarbophil, Polydextrose, Poly (DL-Lactic Acid), Polyethylene Glycol, Polyethylene Oxide, Polymethacrylates, Poly(methyl vinylether/maleic anhydride), Polyoxyethylene Alkyl Ethers, Polyoxyethylene Castor Oil Derivatives, Polyoxyethylene Sorbitan Fatty Acid Esters, Polyoxyethylene Stearates, Polyoxylglycerides, Polyvinyl Acetate Phthalate, Polyvinyl Alcohol, Potassium Alginate, Potassium Alum, Potassium Benzoate, Potassium Bicarbonate, Potassium Chloride, Potassium Citrate, Potassium Hydroxide, Potassium Metabisulfite, Potassium Sorbate, Povidone, Propionic Acid, Propyl Gallate, Propylene Carbonate, Propylene Glycol, Propylene Glycol Alginate, Propylparaben, Propylparaben Sodium, Pyrrolidone, Raffinose, Saccharin, Saccharin Sodium, Safflower Oil, Saponite, Sesame Oil, Shellac, Simethicone, Sodium Acetate, Sodium Alginate, Sodium Ascorbate, Sodium Benzoate, Sodium Bicarbonate, Sodium Borate, Sodium Carbonate, Sodium Chloride, Sodium Citrate Dihydrate, Sodium Cyclamate, Sodium Formaldehyde Sulfoxylate, Sodium Hyaluronate, Sodium Hydroxide, Sodium Lactate, Sodium Lauryl Sulfate, Sodium Metabisulfite, Sodium Phosphate—Dibasic, Sodium Phosphate—Monobasic, Sodium Propionate, Sodium Starch Glycolate, Sodium Stearyl Fumarate, Sodium Sulfite, Sodium Thiosulfate, Sorbic Acid, Sorbitan Esters (Sorbitan Fatty Acid Esters), Sorbitol, Soybean Oil, Starch, Starch—Pregelatinized, Starch—Sterilizable Maize, Stearic Acid, Stearyl Alcohol, Sucralose, Sucrose, Sucrose Octaacetate, Sugar—Compressible, Sugar—Confectioner's, Sugar Spheres, Sulfobutylether b-Cyclodextrin, Sulfur Dioxide, Sulfuric Acid, Sunflower Oil, Suppository Bases—Hard Fat, Tagatose, Talc, Tartaric Acid, Tetrafluoroethane (HFC), Thaumatin, Thimerosal, Thymol, Titanium Dioxide, Tragacanth, Trehalose, Triacetin, Tributyl Citrate, Tricaprylin, Triethanolamine, Triethyl Citrate, Triolein, Vanillin, Vegetable Oil—Hydrogenated, Vitamin E Polyethylene Glycol Succinate, Water, Wax—Anionic Emulsifying, Wax—Carnauba, Wax—Cetyl Esters, Wax—Microcrystalline, Wax—Nonionic Emulsifying, Wax—White, Wax—Yellow, Xanthan Gum, Xylitol, Zein, Zinc Acetate, and/or Zinc Stearate.

The dosage unit or composition comprising the dosage unit can further comprise one or more excipients. The dosage unit or composition can further comprise one or more excipients, wherein the one or more excipients can be selected from a group consisting of: detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

The dosage unit or composition can further comprise one or more cytochrome p450 inhibitors. The dosage unit or composition can further comprise one or more cytochrome p450 inhibitors wherein the one or more cytochrome p450 inhibitors can fully or partially inhibit a cytochrome p450 selected from a group consisting of: CYP1, CYP1A1, CYP1A2, CYP1B1, CYP2, CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1, CYP3, CYP3A4, CYP3A5, CYP3A7, CYP3A43, CYP4, CYP4A11, CYP4A22, CYP4B1, CYP4F2, CYP4F3, CYP4F8, CYP4F11, CYP4F12, CYP4F22, CYP4V2, CYP4X1, CYP4Z1, CYP5, CYP5A1, CYP7, CYP7A1, CYP7B1, CYP8, CYP8A1, CYP8B1, CYP1 1, CYP11A1, CYP11B1, CYP11B2, CYP17, CYP17A1, CYP19, CYP19A1, CYP20, CYP20A1, CYP21, CYP21A2, CYP24, CYP24A1, CYP26, CYP26A1, CYP26B1, CYP26C1, CYP27, CYP27A1, CYP27B1, CYP27C1, CYP39, CYP39A1, CYP46, CYP46A1, CYP51, and CYP51A1. The dosage unit or composition can also comprise one or more cytochrome p450 inhibitors wherein the one or more cytochrome p450 inhibitors can fully or partially inhibit CYP1. The dosage unit or composition can also comprise one or more cytochrome p450 inhibitors wherein the one or more cytochrome p450 inhibitors can fully or partially inhibit CYP1A2. The dosage unit or composition can also comprise one or more CYP1A2 inhibitors wherein the one or more CYP1A2 inhibitors can be selected from a group consisting of: fluoroquinolone, selective serotonin reuptake inhibitor (SSRI), calcium channel blocker, herbal tea, naringenin, H2-receptor antagonist, antiarrhythmic agent, interferon, xanthotoxin, mibefradil, cumin, turmeric, and isoniazid. The dosage unit or composition can also further comprise one or more CYP1A2 inhibitors wherein the one or more CYP1A2 inhibitors can be grapefruit juice. The dosage unit or composition can also further comprise one or more CYP1A2 inhibitors wherein the one or more CYP1A2 inhibitors can be naringenin.

The dosage unit or composition can further comprise one or more β-adrenergic agonists. The dosage unit or composition can also further comprise one or more β-adrenergic agonists wherein the one or more β-adrenergic agonists can be a $β_1$-adrenergic agonist and/or $β_2$-adrenergic agonist. The dosage unit or composition can also further comprise one or more β-adrenergic agonists wherein the one or more β-adrenergic agonists can be a $β_1$-adrenergic agonist. The dosage unit or composition can also further comprise one or more β-adrenergic agonists wherein the one or more β-adrenergic agonists can be a $β_1$-adrenergic agonist selected from a group consisting of: dobutamine, isoproterenol, xamoterol and epinephrine. The dosage unit or composition can also further comprise one or more β-adrenergic agonists wherein the one or more β-adrenergic agonists can be a $β_2$-adrenergic agonist. The dosage unit or composition can also further comprise one or more β-adrenergic agonists wherein the one or more β-adrenergic agonists can be a $β_2$-adrenergic agonist selected from a group consisting of: albuterol, levalbuterol, fenoterol, formoterol, isoproterenol ($β_1$ and $β_2$), metaproterenol, salmeterol, terbutaline, clenbuterol, isoetarine, pirbuterol, procaterol, ritodrine, and epinephrine. The dosage unit or composition can also further comprise one or more β-adrenergic agonists wherein the one or more β-adrenergic agonists can be selected from a group consisting of: arbutamine, befunolol, bromoacetylaprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol.

Diagnosing and Treating Loss and/or Distortion of Taste or Smell

Also disclosed are methods of diagnosing loss and/or distortion of taste or smell in a subject, the methods comprising (a) obtaining one or more biological samples from the subject; (b) measuring a level of one or more members of the hedgehog signaling pathway in the one or more biological samples from the subject; (c) diagnosing the subject with loss and/or distortion of taste or smell based upon the level of one or more members of the hedgehog signaling pathway that is lower than a threshold level; and (d) administering to the subject a treatment for taste or smell disorder. Any of the methods of diagnosing loss and/or distortion of taste or smell disclosed herein can be used in combination with any of the pharmaceutical dosage units or composition disclosed herein.

Making Drug Compositions

In an additional aspect of the invention, disclosed herein are methods of making a pharmaceutical dosage unit comprising combining one or more cGMP activators and one or more cAMP activators, in any combination thereof.

The methods can comprise one or more cGMP activators wherein the one or more cGMP activators can be selected from a group consisting of: 3-(5'-hydroxymethyl-2'-furyl)-1-benzylindazole (YC-1), YC-1 derivatives, anthranilic acids derivatives, ataciguat (HMR1766), benzydamine analogs, CFM1517, A-350619, nitrovasodilators, molsidomine, nitroxyl (HNO), BAY 41-2272, BAY 41-8543, BAY 58-2667, cinaciguat (BAY 58-2667), and riociguat (BAY 63-2521). The methods can also comprise one or more cGMP activators wherein the one or more cGMP activators can comprise riociguat. The methods can comprise one or more cAMP activators wherein the one or more cAMP activators can be selected from a group consisting of: 3-(5'-hydroxymethyl-2'-furyl)-1-benzylindazole (YC-1), glucagon, PDE inhibitors, prostaglandin E1 (PGE1; pharmaceutically known as alprostadil), forskolin, and β-adrenergic agonists.

The methods can comprise one or more cAMP activators wherein the one or more cAMP activators can further comprise one or more PDE inhibitors and/or forskolin.

The methods can comprise one or more cAMP activators wherein the one or more cAMP activators can be forskolin.

The one or more PDE inhibitors can be a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof. The methods can also comprise one or more PDE inhibitors wherein the one or more one or more PDE inhibitors can be a selective PDE inhibitor. The methods can also comprise one or more PDE inhibitors wherein the one or more PDE inhibitors can be a non-selective PDE inhibitor that can be a methylxanthine derivative. The methods can also comprise methylxanthine derivative that can be caffeine, theophylline, doxophylline, cipamphylline, neuphylline, pentoxiphylline, or diprophylline. The methods can also comprise the methylxanthine derivative that can be theophylline. The methods can also comprise a PDE 1 inhibitor can be vinpocetine, compound KS505a, bepril, flunarizine, amiodarone, zaprinast, 8-methoxymethyl IPMX, SCH 51866, Nimodipine, or IC224. The methods can also comprise a PDE 2 inhibitor that can be EHNA. The methods can also comprise a PDE 3 inhibitor that can be enoximone, milrinone (Primacor), amrinone, cilostamide, cilostazol (Pletal), trequinsin, inamrinone, anagrelide, pimobendan, lixazinone, or dihydro-pyridazinone. The methods can also comprise a PDE 4 inhibitor that can be mesembrine, rolipram, ibudilast, roflumilast (Daxas), cilomilast (Airflo), piclamilast, luteolin, drotaverine, or denbufylline. The methods can also comprise a PDE 5 inhibitor that can be sildenafil, tadalafil, vardenafil, udenafil and avanafil, dipyridamole, icariin, 4-Methylpiperazine, Pyrazolo Pyrimidin-7-1, cilomilast, or zaprinast. The methods can also comprise a PDE6-selective inhibitors that can be zaprinast, dipyridamole, vardenafil, or tadalafil. The methods can also comprise a PDE7-selective inhibitors that can be quinazoline type PDE7 inhibitor, dipyridamole, or thiadiazole. The methods can also comprise a PDE8-selective inhibitors that can be dipyridamole. The methods can also comprise a PDE9-selective inhibitors can be zaprinast. The methods can also comprise a PDE 10 inhibitor that can be papaverine, OMS824 (from Omeros Corporation), and/or PF-2545920 (from Pfizer). The methods can also comprise a PDE11-selective inhibitors that can be tadalafil, zaprinast, or dipyridamole.

The dosage unit can be formed by combining a non-selective PDE inhibitor, forskolin, and riociguat. The dosage unit can be formed by combining a selective PDE inhibitor, forskolin, and riociguat. The dosage unit can be formed by combining a non-selective PDE inhibitor, theophylline, and riociguat. The dosage unit can be formed by combining a selective PDE inhibitor, theophylline, and riociguat. The dosage unit can be formed by combining a non-selective PDE inhibitor and riociguat. The dosage unit can be formed by combining a selective PDE inhibitor and riociguat. The dosage unit can be formed by combining theophylline and riociguat. The dosage unit can be formed by combining forskolin and riociguat. The dosage unit can be formed by combining theophylline, forskolin, and riociguat.

Riociguat can be combined or present in an amount selected from a group consisting of: greater than 0.0 μg to 1 μg, 0.5 μg to 2 μg, 1.5 μg to 3.0 μg, 2.5 μg to 10 μg, 5 μg to 15 μg, 12.5 μg to 30 μg, 25 μg to 50 μg, 40 μg to 80 μg, 60 μg to 100 μg, 90 μg to 120 μg, 110 μg to 130 μg, 125 μg to 150 μg, 140 μg to 180 μg, 170 μg to 200 μg, 200 μg to 230 μg, 215 μg to 240 μg, 235 μg to less than 250 μg, less than 250 μg and greater than about 0.0 μg to about 1 μg, about 0.5 μg to about 2 μg, about 1.5 μg to about 3.0 μg, about 2.5 μg to about 10 μg, about 5 μg to about 15 μg, about 12.5 μg to about 30 μg, about 25 μg to about 50 μg, about 40 μg to about 80 μg, about 60 μg to about 100 μg, about 90 μg to about 120 μg, about 110 μg to about 130 μg, about 125 μg to about 150 μg, about 140 μg to about 180 μg, about 170 μg to about 200 μg, about 200 μg to about 230 μg, about 215 μg to about 240 μg, about 235 μg to less than about 250 μg.

Theophylline can be combined or present in an amount selected from a group consisting of: less than 45 mg, 30 mg, 15 mg, 10 mg, 5 mg, 1 mg, 500 μg, 250 μg, 120 μg, 80 μg, 40 μg, or 20 μg and less than about 45 mg, about 30 mg, about 15 mg, about 10 mg, about 5 mg, about 1 mg, about 500 μg, about 250 μg, about 120 μg, about 80 μg, about 40 μg, or about 20 μg.

Forskolin can be combined or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 20.5 mg, 30.5 mg to 1 mg, 2 mg to greater than 0 mg and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, about 2 mg to greater than about 0 mg.

In some aspects of the invention, riociguat, theophylline, and forskolin can be combined. For example, (a) riociguat can be combined or present in an amount selected from a group consisting of: greater than 0.0 μg to 1 μg, 0.5 μg to 2 μg, 1.5 μg to 3.0 μg, 2.5 μg to 10 μg, 5 μg to 15 μg, 12.5 μg to 30 μg, 25 μg to 50 μg, 40 μg to 80 μg, 60 μg to 100 μg, 90 μg to 120 μg, 110 μg to 130 μg, 125 μg to 150 μg, 140 μg to 180 μg, 170 μg to 200 μg, 200 μg to 230 μg, 215 μg to 240 μg, 235 μg to less than 250 μg, and less than 250 μg, and greater than about 0.0 μg to about 1 μg, about 0.5 μg to about 2 μg, about 1.5 μg to about 3.0 μg, about 2.5 μg to about 10 μg, about 5 μg to about 15 μg, about 12.5 μg to about 30 μg, about 25 μg to about 50 μg, about 40 μg to about 80 μg, about 60 μg to about 100 μg, about 90 μg to about 120 μg, about 110 μg to about 130 μg, about 125 μg to about 150 μg, about 140 μg to about 180 μg, about 170 μg to about 200 μg, about 200 μg to about 230 μg, about 215 μg to about 240 μg, and about 235 μg to less than 250 μg; (b) theophylline can be combined or present in an amount selected from a group consisting of: less than 45 mg, 30 mg, 15 mg, 10 mg, 5 mg, 1 mg, 500 μg, 250 μg, 120 μg, 80 μg, 40 μg, or 20 μg and less than about 45 mg, about 30 mg, about 15 mg, about 10 mg, about 5 mg, about 1 mg, about 500 μg, about 250 μg, about 120 μg, about 80 μg, about 40 μg, or about 20 μg; and (c) forskolin can be combined or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

The dosage unit or composition comprising the dosage unit can be formed into a dosage unit suitable for administration by a method selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. For ease of use, the dosage unit or composition comprising the dosage unit can be formed into a dosage unit suitable for oral administration, inhalational administration, nasal administration, or any combination thereof. The dosage unit or composition comprising the dosage unit can be a liquid.

The dosage unit or composition comprising the dosage unit can have a pH of greater than 7.0. For example, the dosage unit or composition comprising the dosage unit can have a pH of greater than 7.1. The dosage unit or composition comprising the dosage unit can have a pH of greater than 7.5. The dosage unit or composition comprising the dosage unit can have a pH of greater than 8.0. The dosage unit or composition comprising the dosage unit can have a pH of greater than 9.0.

The dosage unit or composition comprising the dosage unit can further comprise one or more excipients. The dosage unit can be formed to comprise one or more excipients, wherein the one or more excipients can be selected from a group consisting of: detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

The dosage unit or composition comprising the dosage unit can further comprise combining one or more cytochrome p450 inhibitors. The dosage unit or composition comprising the dosage unit can also comprise one or more cytochrome p450 inhibitors wherein the cytochrome p450 inhibitors can fully or partially inhibit a cytochrome selected from a group consisting of: CYP1, CYP1A1, CYP1A2, CYP1B1, CYP2, CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1, CYP3, CYP3A4, CYP3A5, CYP3A7, CYP3A43, CYP4, CYP4A11, CYP4A22, CYP4B, CYP4F2, CYP4F3, CYP4F8, CYP4F11, CYP4F12, CYP4F22, CYP4V2, CYP4X1, CYP4Z1, CYP5, CYP5A1, CYP7, CYP7A1, CYP7B1, CYP8, CYP8A1, CYP8B1, CYP11, CYP11A1, CYP11B1, CYP11B2, CYP17, CYP17A1, CYP19, CYP19A1, CYP20, CYP20A, CYP21, CYP21A2, CYP24, CYP24A1, CYP26, CYP26A1, CYP26B1, CYP26C1, CYP27, CYP27A1, CYP27B, CYP27C, CYP39, CYP39A1, CYP46, CYP46A 1, CYP51, and CYP51A1. The dosage unit or composition comprising the dosage unit can also comprise one or more cytochrome p450 inhibitors wherein the cytochrome p450 inhibitors can fully or partially inhibit CYP1. The dosage unit or composition comprising the dosage unit can also comprise one or more cytochrome p450 inhibitors wherein the cytochrome p450 inhibitors can fully or partially inhibit CYP1A2. The dosage unit or composition comprising the dosage unit can also comprise one or more CYP1A2 inhibitors wherein the CYP1A2 inhibitors can be selected from a group consisting of: fluoroquinolone, selective serotonin reuptake inhibitor (SSRI), calcium channel blocker, herbal tea, naringenin, H2-receptor antagonist, antiarrhythmic agent, interferon, xanthotoxin, mibefradil, cumin, turmeric, and isoniazid. The dosage unit or composition comprising the dosage unit can also comprise one or more CYP1A2 inhibitors wherein the CYP1A2 inhibitors can be grapefruit juice. The dosage unit or composition comprising the dosage unit can also comprise one or more CYP1A2 inhibitors wherein the CYP1A2 inhibitors can be naringenin.

The dosage unit or composition comprising the dosage unit can further comprise combining one or more β-adrenergic agonists. The dosage unit or composition comprising the dosage unit can also comprise combining one or more β-adrenergic agonists wherein the one or more β-agonists can be a $β_1$-adrenergic agonist and/or β2-adrenergic agonist. The dosage unit or composition comprising the dosage unit can also comprise one or more β-adrenergic agonists wherein the one or more β-agonists can be a $β_1$-adrenergic agonist. The dosage unit or composition comprising the dosage unit can also comprise one or more β-adrenergic agonists wherein the one or more β-agonists can be a $β_1$-adrenergic agonist selected from a group consisting of dobutamine, isoproterenol, xamoterol and epinephrine. The dosage unit or composition comprising the dosage unit can also comprise one or more β-adrenergic agonists wherein the one or more β-agonists can be a $β_2$-adrenergic agonist. The dosage unit or composition comprising the dosage unit can also comprise one or more β-adrenergic agonists wherein the one or more β-agonists can be a $β_2$-adrenergic agonist selected from a group consisting of: albuterol, levalbuterol, fenoterol, formoterol, isoproterenol ($β_1$ and $β_2$), metaproterenol, salmeterol, terbutaline, clenbuterol, isoetarine, pirbuterol, procaterol, ritodrine, and epinephrine. The dosage unit or composition comprising the dosage unit can also comprise one or more β-adrenergic agonists wherein the one or more β-agonists can be selected from a group consisting of: arbutamine, befunolol, bromoacetylaprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol.

Kits for Diagnosis and/or Treatment

A kit that can be used to diagnose loss and/or distortion of taste or smell, e.g., hyposmia, dysosmia, anosmia, phantosmia, hypogeusia, dysgeusia, phantogeusia, and/or ageusia is contemplated as part of the invention.

In an additional aspect of the invention, disclosed herein is a kit that can comprise: (a) antibodies that bind one or more members of the hedgehog signaling pathway; and (b) an insert that describes how to diagnose a subject with loss and/or distortion of taste or smell, e.g., hyposmia, dysosmia, anosmia, phantosmia, hypogeusia, dysgeusia, phantogeusia, and/or ageusia based upon the level of one or more members of the hedgehog signaling pathway that can be lower than a threshold level.

The antibodies can be SHH specific antibodies. The antibodies can be IHH specific antibodies. The antibodies can be DHH specific antibodies.

The kit can further comprise an ELISA assay.

The kit can further comprise one or more therapeutic agents capable of maintaining and/or increasing one or more members of the hedgehog signaling pathway.

Drug Compositions Comprising Riociguat

Riociguat is believed to be helpful in treating two forms of pulmonary hypertension (PH): chronic thromboembolic pulmonary hypertension (CTEPH) and pulmonary arterial hypertension (PAH). However, the dosages can be typically in the milligram range and can be given as an oral dosage. However, if the dosage form is changed, for example, into a form suitable for nasal administration, riociguat can be given at a much lower dosage (in the microgram or lower range). Additionally, when riociguat is presented in other dosage forms, it can be effective in treating other diseases, such as pulmonary hypertension, loss and/or distortion of taste or smell, e.g., hyposmia, dysosmia, anosmia, phantosmia, hypogeusia, dysgeusia, phantogeusia, and/or ageusia.

In an additional aspect of the invention, disclosed herein is a pharmaceutical dosage unit comprising riociguat. A pharmaceutical dosage unit with riociguat in the microgram or lower range, e.g., below 250 micrograms, is also disclosed.

The riociguat can be suitable for administration by a method selected from a group consisting of: transmucosal administration, inhalation administration, intranasal administration, parental administration, intravenous administration, subcutaneous administration, intramuscular administration, sublingual administration, transdermal administration, and rectal administration. For ease of use, the ricociguat can be suitable for administration by inhalation administration, intranasal administration, intravenous administration, or any combination thereof.

Riociguat can be present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 255 µg to less than 250 µg, less than 250 µg and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, about 235 µg to less than about 250 µg. Riociguat can be present in an amount less than 250 µg to greater than 0 or about less than 250 µg to greater than 0. Riociguat can be present in an amount less than 200 µg to greater than 0 or about less than 200 µg to greater than 0. Riociguat can be present in an amount less than 150 µg to greater than 0 or about less than 150 µg to greater than 0. Riociguat can be present in an amount less than 100 µg to greater than 0 or about less than 100 µg to greater than 0. Riociguat can be present in an amount less than 50 µg to greater than 0 or about less than 50 µg to greater than 0.

It is contemplated that the dosage unit can be steroid-free.

Methods of Treatment Comprising Riociguat

Although ricociguat can be effective in treating pulmonary hypertension with milligram oral dosages. The inventors have found that when ricociguat is reformulated, some conditions, including but not limited to pulmonary hypertension, bone-related disorders, loss and/or distortion of taste or smell, e.g., hyposmia, dysosmia, anosmia, phantosmia, hypogeusia, dysgeusia, phantogeusia, and/or ageusia, can be treated with microgram dosages.

In an additional aspect of the invention, disclosed herein are methods for treating disease comprising treating a subject in need thereof, with riociguat.

For example, the subject can be treated for pulmonary hypertension. The subject can also be treated for chronic thromboembolic pulmonary hypertension. The subject can also be treated for pulmonary arterial hypertension. The subject can also be treated for bone related disorders.

The ricociguat can be given by transmucosal administration, inhalation administration, intranasal administration, parental administration, intravenous administration, subcutaneous administration, intramuscular administration, sublingual administration, transdermal administration, and rectal administration. For ease, the ricociguat can be given by inhalation administration, intranasal administration, intravenous administration, or any combination thereof.

The riociguat can be given and/or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, less than 250 µg and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, about 235 µg to less than about 250 µg. The riociguat can be given and/or present in an amount less than 250 µg to greater than 0 or about less than 250 µg to greater than 0. The riociguat can be given and/or present in an amount less than 200 µg to greater than 0 or about less than 200 µg to greater than 0. The riociguat can be given and/or present in an amount less than 150 µg to greater than 0 or about less than 150 µg to greater than 0. The riociguat can be given and/or present in an amount less than 100 µg to greater than 0 or about less than 100 µg to greater than 0. The riociguat can be given and/or present in an amount less than 50 µg to greater than 0 or about less than 50 µg to greater than 0.

Treating Appetite Loss

Cancer patients undergoing chemotherapy can often lose significant amounts of body weight. This loss of weight can be at least partially attributed to decrease in appetite (also known as anorexia).

It is also contemplated by the methods described herein that appetite loss can be treated with one or more therapeutic agents. This decrease in appetite loss may or may not be associated with a disease or a treatment of disease. For example, anorexia is generally can be treated by the methods disclosed herein. The appetite loss can result from cancer, with or without chemotherapy treatment. Other diseases that can result in appetite loss and can be treated by the methods disclosed herein include but are not limited to Addison's disease, amyloidosis, asthma, cancer, cat scratch disease, acute lymphoblastic leukemia, coxsackie virus, dementia, depression, encopresis, gastroespophageal reflux disease, acid reflux, infectious mononucleosis, kidney failure, legionnaires' disease, leigh's disease, peptic ulcer, postpartum depression, psychotic disorders, rheumatoid arthritis, rocky mountain spotted fever, stress, anthrax, anorexia nervosa, pernicious anemia, alcohol withdrawal, migraine headaches, vitamin B12 deficiency, acute mountain sickness, stroke, thyroid diseases, yellow fever, liver disease, chronic obstructive pulmonary disease, heart failure, hepatitis, HIV, pregnancy, bowel disease, disease of the gastrointestinal tract (e.g., gallbladder disease, crohn's disease, irritable bowel syndrome, appendicitis), brain damage (e.g., from trauma), hormone (endocrine) disease, inflammation (e.g., from chronic infectious or chronic inflammatory diseases, or loss of taste. The appetite loss that results from each of these diseases can be treated individually. Furthermore, medication or drugs (e.g., including but not limited to digoxin, cocaine, codeine, demerol, morphine, antibiotics, amphetamines, methamphetamine, chemotherapy agents, common cold medicines, and cough & stuffy nose decongestants) related appetite loss can also be treated by the methods disclosed herein. Other appetite loss associated with infections such as flu, mumps, syphilis, vasculitis, giardiasis, listeriosis, AIDS/HIV, pneumonia, chickenpox, strep throat, yellow fever, typhoid fever, leishmaniasis, gastroenteritis, mononucleosis, schistosomiasis, cat scratch fever, coxsackie disease, hookworm disease, Rocky Mountain spotted fever, and food poisoning—*E. coli* enteritis, can be treated by the methods described herein.

Disclosed herein is a method of treating appetite loss that can comprise administering to a subject in need thereof a dose of one or more therapeutic agents, e.g., a PDE inhibitor. The subject can be a subject in need thereof. For example, a subject with appetite loss and/or with any of the diseases (or taking any of the medications or drugs) listed above can be a subject in need thereof. For example, the subject in need thereof can be a cancer patient. The cancer patient may or may not be undergoing chemotherapy.

One or more therapeutic agents can be used to treat appetite loss. For example, PDE inhibitors can be used to treat appetite loss. The one or more PDE inhibitors can be a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof. The methods can also comprise one or more PDE inhibitors wherein the one or more one or more PDE inhibitors can be a selective PDE inhibitor. The methods can also comprise one or more PDE inhibitors wherein the one or more PDE inhibitors can be a non-selective PDE inhibitor that can be a methylxanthine derivative. The methods can also comprise methylxanthine derivative that can be caffeine, theophylline, doxophylline, cipamphylline, neuphylline, pentoxiphylline, or diprophylline. The methods can also comprise the methylxanthine derivative that can be theophylline. The methods can also comprise a PDE 1 inhibitor can be vinpocetine, compound KS505a, bepril, flunarizine, amiodarone, zaprinast, 8-methoxymethyl IPMX, SCH 51866, Nimodipine, or IC224. The methods can also comprise a PDE 2 inhibitor that can be EHNA. The methods can also comprise a PDE 3 inhibitor that can be enoximone, milrinone (Primacor), amrinone, cilostamide, cilostazol (Pletal), trequinsin, inamrinone, anagrelide, pimobendan, lixazinone, or dihydro-pyridazinone. The methods can also comprise a PDE 4 inhibitor that can be mesembrine, rolipram, ibudilast, roflumilast (Daxas), cilomilast (Airflo), piclamilast, luteolin, drotaverine, or denbufylline. The methods can also comprise a PDE 5 inhibitor that can be sildenafil, tadalafil, vardenafil, udenafil and avanafil, dipyridamole, icariin, 4-Methylpiperazine, Pyrazolo Pyrimidin-7-1, cilomilast, or zaprinast.

The methods can also comprise a PDE6-selective inhibitors that can be zaprinast, dipyridamole, vardenafil, or tadalafil. The methods can also comprise a PDE7-selective inhibitors that can be quinazoline type PDE7 inhibitor, dipyridamole, or thiadiazole. The methods can also comprise a PDE8-selective inhibitors that can be dipyridamole. The methods can also comprise a PDE9-selective inhibitors can be zaprinast. The methods can also comprise a PDE 10 inhibitor that can be papaverine, OMS824 (from Omeros Corporation), and/or PF-2545920 (from Pfizer). The methods can also comprise a PDE11-selective inhibitors that can be tadalafil, zaprinast, or dipyridamole.

The methods can further comprise administering to the subject one or more additional therapeutic agents, wherein the one or more additional therapeutic agents can comprise riociguat given or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 µg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 µg to about 230 µg, about 215 µg to about 240 µg, and about 235 µg to less than 250 µg.

The methods can further comprise administering to the subject one or more additional therapeutic agents, wherein the one or more additional therapeutic agents can comprise theophylline given or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 µg.

The methods can further comprise administering to the subject one or more additional therapeutic agents, wherein the one or more additional therapeutic agents can comprise forskolin given or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

Any combination of riociguat, theophylline, and/or forskolin can be given to a subject. In certain cases, a particular combination of riociguat, theophylline, and/or forskolin can exhibit synergistic effects compared to when treating with riociguat, theophylline, and/or forskolin alone. In other cases, a particular combination of riociguat, theophylline, and/or forskolin can exhibit synergistic effects compared to when treating with riociguat, theophylline, and/or forskolin in pairs. The methods can further comprise administering to the subject one or more additional therapeutic agents, wherein the one or more additional therapeutic agents can comprise: (a) riociguat given or present in an amount selected from a group consisting of: greater than 0.0 µg to 1 µg, 0.5 µg to 2 µg, 1.5 µg to 3.0 µg, 2.5 µg to 10 µg, 5 µg to 15 µg, 12.5 µg to 30 µg, 25 µg to 50 µg, 40 µg to 80 µg, 60 µg to 100 µg, 90 µg to 120 µg, 110 µg to 130 µg, 125 µg to 150 µg, 140 µg to 180 µg, 170 µg to 200 µg, 200 µg to 230 µg, 215 µg to 240 µg, 235 pg to less than 250 µg, and less than 250 µg, and greater than about 0.0 µg to about 1 µg, about 0.5 µg to about 2 µg, about 1.5 µg to about 3.0 µg, about 2.5 µg to about 10 µg, about 5 µg to about 15 µg, about 12.5 µg to about 30 µg, about 25 µg to about 50 µg, about 40 µg to about 80 µg, about 60 µg to about 100 µg, about 90 µg to about 120 µg, about 110 µg to about 130 µg, about 125 µg to about 150 µg, about 140 µg to about 180 µg, about 170 µg to about 200 µg, about 200 pg to about 230 µg, about 215 µg to about 240 µg, and about 235 µg to less than 250 µg; (b) theophylline given or present in an amount selected from a group consisting of: less than 45 mg, 30 mg, 15 mg, 10 mg, 5 mg, 1 mg, 500 µg, 250 µg, 120 µg, 80 µg, 40 µg, or 20 µg and less than about 45 mg, about 30 mg, about 15 mg, about 10 mg, about 5 mg, about 1 mg, about 500 µg, about 250 µg, about 120 µg, about 80 µg, about 40 µg, or about 20 pg; and (c) forskolin given or present in an amount selected from a group consisting of: less than 500 mg to 450 mg, 475 mg to 425 mg, 435 mg to 400 mg, 415 mg to 300 mg, 325 mg to 250 mg, 275 mg to 150 mg, 200 mg to 100 mg, 135 mg to 80 mg, 95 mg to 65 mg, 75 mg to 50 mg, 60 mg to 40 mg, 45 mg to 25 mg, 30 mg to 20 mg, 15 mg to 5 mg, 10 mg to 2.5 mg, 3.5 mg to 1 mg, and 2 mg to greater than 0 mg, and less than about 500 mg to about 450 mg, about 475 mg to about 425 mg, about 435 mg to about 400 mg, about 415 mg to about 300 mg, about 325 mg to about 250 mg, about 275 mg to about 150 mg, about 200 mg to about 100 mg, about 135 mg to about 80 mg, about 95 mg to about 65 mg, about 75 mg to about 50 mg, about 60 mg to about 40 mg, about 45 mg to about 25 mg, about 30 mg to about 20 mg, about 15 mg to about 5 mg, about 10 mg to about 2.5 mg, about 3.5 mg to about 1 mg, and about 2 mg to greater than 0 mg.

The one or more therapeutic agents can be an effective amount of one or more members of the hedgehog signaling pathway. For example, the methods can comprise administration of an effective amount of the one or more exogenous members of the hedgehog signaling pathway. The methods can also comprise activating expression of an effective amount of one or more members of the hedgehog signaling pathway. The activating expression of an effective amount of one or more members of the hedgehog signaling pathway can be effectuated by genetic manipulation of one or more genes responsible for the expression of one or more members of the hedgehog signaling pathway. The activating expression of an effective amount of one or more members of the hedgehog signaling pathway can also be effectuated through a therapeutic agent. The therapeutic agent can directly affect the levels of one or more members of the hedgehog signaling pathway. The therapeutic agent can indirectly affect the levels of one or more members of the hedgehog signaling pathway.

The one or more therapeutic agents or composition comprising one or more therapeutic agents can be suitable for administration by a methods selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. Because of the ease of use, the one or more therapeutic agents or composition comprising one or more therapeutic agents can be suitable for oral administration, inhalational administration, intranasal administration, or any combination thereof.

The one or more therapeutic agents can comprise one or more cGMP activators, one or more cAMP activators, or any combination thereof.

The methods can further comprise one or more cGMP activators, wherein the one or more cGMP activators can be selected from a group consisting of 3-(5'-hydroxymethyl-2'-furyl)-1-benzylindazole (YC-1), YC-1 derivatives, anthranilic acids derivatives, ataciguat (HMR1766), benzydamine analogs, CFM1517, A-350619, nitrovasodilators, molsidomine, nitroxyl (HNO), BAY 41-2272, BAY 41-8543, BAY 58-2667, cinaciguat (BAY 58-2667), and riociguat (BAY 63-2521). The one or more cGMP activators can be riociguat.

The methods can further comprise one or more cAMP activators wherein the one or more cAMP activators can be selected from a group consisting of 3-(5'-hydroxymethyl-2'-furyl)-1-benzylindazole (YC-1), glucagon, PDE inhibitors, prostaglandin E1 (PGE1; pharmaceutically known as alprostadil), forskolin, and β-adrenergic agonists. The methods can further comprise one or more cAMP activators wherein the one or more cAMP activators can comprise one or more PDE inhibitors and/or forskolin. The methods can further comprise one or more cAMP activators wherein the one or more cAMP activators can be forskolin.

The one or more therapeutic agents can comprise a non-selective PDE inhibitor, forskolin, and riociguat. The one or more therapeutic agents can comprise a selective PDE inhibitor, forskolin, and riociguat. Various combinations are also contemplated. For example, the one or more therapeutic agents can comprise a non-selective PDE inhibitor, theophylline, and riociguat. The one or more therapeutic agents can comprise a selective PDE inhibitor, theophylline, and riociguat. The one or more therapeutic agents can comprise a non-selective PDE inhibitor and riociguat. The one or more therapeutic agents can comprise a selective PDE inhibitor and riociguat. The one or more therapeutic agents can comprise theophylline and riociguat. The one or more therapeutic agents can comprise forskolin and riociguat. The one or more therapeutic agents can comprise theophylline, forskolin, and riociguat.

Treatment can also vary based on the disease and the severity of the conditions of the subject in need thereof. A physician can determine the appropriate dose of PDE inhibitor or other drugs that can be effective in treating appetite loss.

Also, the method can further comprise treating with an antiemetic. For example, the antiemetic can be selected from 5-HT3 receptor antagonists, Dopamine antagonists, NK1 receptor antagonist, Antihistamines (HI histamine receptor antagonists), Cannabinoids, Benzodiazepines, Anticholinergics, and steroids. The antiemetic can also be is selected from Dolasetron (Anzemet), Granisetron (Kytril, Sancuso), Ondansetron (Zofran), Tropisetron (Setrovel, Navoban), Palonosetron (Aloxi), Mirtazapine (Remeron), Domperidone (Motilium), Olanzapine (Zyprexa), Droperidol, haloperidol, chlorpromazine, prochlorperazine, Alizapride, Prochlorperazine (Compazine, Stemzine, Buccastem, Stemetil, Phenotil), Metoclopramide (Reglan), Aprepitant (Emend), Casopitant, Cyclizine, Diphenhydramine (Benadryl), Dimenhydrinate (Gravol, Dramamine), Doxylamine, Meclizine (Bonine, Antivert), Promethazine (Pentazine, Phenergan, Promacot), Hydroxyzine (Vistaril), Cannabis, Dronabinol (Marinol), synthetic cannabinoids such as Nabilone (Cesamet) or the JWH series, Sativex, Midazolam, Lorazepam (Ativan), Hyoscine (also known as scopolamine), Dexamethasone (Decadron), Trimethobenzamide, Ginger, Emetrol, Propofol, Muscimol, Peppermint, and Ajwain.

Dosages can be provided as described in the table below.

ANTIEMETIC DOSAGE GUIDELINES CHART

| ANTIEMETIC | SELECTED DOSE | SIDE EFFECTS | NOTES |
|---|---|---|---|
| Anticholinergics | | | |
| Seopalamine | 0.3-0.6 mg SC, IM, or IV May be repeated 3-4 times daily. 0.5 mg/24 h topical patch q3d (brand-dependent) | dry mouth, sedation, visual disturbances, memory dysfunction, dysphoria, occasionally confusion, disorientation, hallucinations | Good for patients with motion sickness or undergoing surgery affecting vestibular apparatus; apply 4 h prior to exposure |
| Anihistamines | | | |
| Diphenhydramine (Benadryl) | 25-50 mg po/IV q6-8 h prn | Sedation, dizziness, dry mouth, urinary retention, blurred vision | Diphenhydramine-1$^{st}$-line agent |
| Hydroxyine | 25-100 mg IM q4-6 h prn | | |
| [Atrax (HCL), Vistaril pamoate)] | 25 mg po tid-qid | | Class good for patients with motion sickness or undergoing surgery afffecting vesibular apparatus |
| Meclizine (Antivert) | 12.5-25 mg po tid-qid | | |
| Benzodiazepines | | | |
| Lorazepam (Atrivan) | 0.5-2 mg po/IV q4-6 h (dosages up to 4 mg have been used) | Sedation, amnesia, confusion, dizziness | |
| Midazolem (Versed) | 0.25-2 mg IV q5 h prn | | |
| Butyrophenones | | | |
| Droperidol (Inapsine) | 0.5-2.5 mg IV q4-6 h | Sedation, EPS, dizziness, blood pressure changes, confusion, agitation, akathisia | Droperidol-Black box warning-ECG monitoring required prior to admin & for 2-3 h p dose |
| Haloperidol (Haldol) | 1-3 mg po q3-6 h 1-5 mg IV/IM q2-6 h | | Haloperidol IV-see Haloperidol IV Protocol Opiod-induced N, V; N, V due to bowel obstruction |
| Cannabinoids | | | |
| Dronabinol (Marinol) | 5-15 mg/m$^3$ po q4-6 h maximum of 6 doses/d (available as 2.5 mg, 5 mg, and 10 mg caps) | Tachycardia, mood changes, dizziness, confusion, hallucinations, motor incoordination, amnesia, sedation, increased appetite | |
| Corticosteroids | | | |
| Dexamethasone (Decadron) | 4 mg po q6-24 h (usually × 24 h) (8 mg po-max single dose) 8-20 mg IV q12-24 h | Mood changes, increased appetite, psychosia, hyperglycemia (watch in diabetes), irritability, leukocytosis, fluid retention (esp. in cardiac patients) | Equivalent Glucocorticoid dosages. These are general approximations and may not apply to all diseases or routes of administration. Equivalent glucocorticoid doasages: Cortisone - 25 mg Hydrocortisone - 20 mg Prednisolone - 5 mg Prednisone - 5 mg Methylprednisolone - mg Dexamathasone - 0.75 mg May take time to work |
| Methylpredinisone (Solu-Medrol) | 250-500 mg IV q12-24 h | | |
| Phenothiazines | | | |
| Chlorpromazine (Thorazine) | 12.5-25 mg po q4-6 h prn 25-50 mg IM/IV q4-6 h 50-100 mg PR q6-8 h | Sedation, EPS, anticholinergic, side effects, hypotension (IV prochlorperazine and promethazine) | |
| Prochloperazine (Compazine) | 5-10 mg po IR q4-6 h 10-30 mg po SR q12 h (max rec daily dose = 40 mg) 5-10 mg IM/IV q4-6 h prn 25 mg PR q12 h | | IV rate not >5 mg/min Gnerally not recognized in children Effective first-line, currently unavailable |
| Promethazine (Phenergan)) | 12.5-25 mg po/IV/IM q4-6 h prn 25 mg pr q12 h | | IV rate not > 25 mg/min |
| Thiethylperazine (Torecan) | 10 mg po q8-24 h 10 mg IV q8-24 h | | |
| Serotonin Antagonists | | | |
| Dolasetron (Anzemet) | 100 mg po (1.8 mcg/kg) q24 h prn$^2$ PONV-12.5 mg IV/IM × 1 postop prn | Headache (most common), mild sedation, constipation, transiently elevated LFTs, dizziness, hiccups, ECG alterations (rare), EP reactions (rare) | Dolasetron & Granisetron-Not FDA-approved indication for more than 1 × dose |
| Granisetron (Kytril) | 0.1-1 mg IV/po q12-24 h (10 mcg/kg)$^2$ PONV-10-40 mcg/kg IV for 1-3 doses seperated by at least 10 min | | Only effective in acute phase, not useful beyond 24 h (in terms of chemotherapy) Ondansetron trials in hyperemesis gravidum, puritus associated with |

ANTIEMETIC DOSAGE GUIDELINES CHART

| ANTIEMETIC | SELECTED DOSE | SIDE EFFECTS | NOTES |
| --- | --- | --- | --- |
| Ondansetron (Zofran) | 4-8 mg po q8-24 h<br>4-8 mg IV q8-24 h (0.15 mg/kg)<br>PONV-1-4 mg IV × 1 post-op prn | | cholestatic jaundice.<br>All equally effective at equivalent doses-cost should be a factor in making a choice<br>Much more effective for vomitting than nausea |
| Substituted Benzamides | | | |
| Metoclopramide (Reglan)<br>Low dose<br>High dose | 10 mg po/IV q4-6 h (up to 20 mg used)<br>(usual dose = 10 mg IV q6)<br>1-3 mg/kg IV q2-6 h | Sedation, diahrrea, EPS, dizziness, anxiety, insomnia | Opioid-induced N.V.CI in bowel obstruction, GIB or perforation<br>Generally not recommended in children |
| Trimethobenzamide (Tigan) | | Sedation, diahrrea, headache, EPS (rare) | Trimethobenzamide not recommended in elderly |

Business Methods

Figure 13:
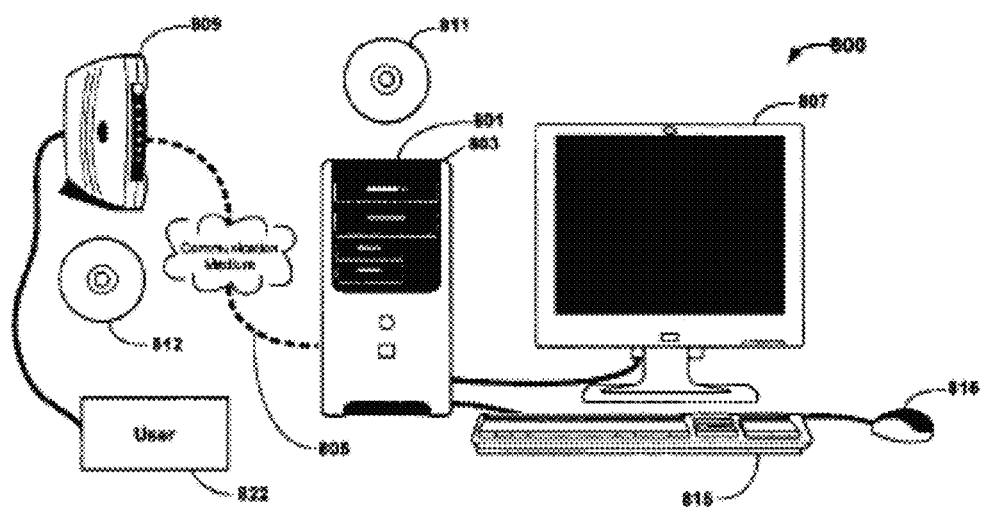
FIG. 13: Depicts a computer system useful for displaying, storing, retrieving, or calculating diagnostic results from a level of one or more biomarkers associated with taste or smell disorders; displaying, storing, retrieving, or calculating raw data from biomarker analysis; or displaying, storing, retrieving, or calculating any sample or subject information useful in the diagnostic methods disclosed herein.

One or more computers can be utilized in the diagnostic methods disclosed herein, such as a computer 800 as illustrated in FIG. 13. It is contemplated that the computer 800 can be uniquely designed for the task at hand, e.g., the computer is not a general computer. The computer 800 can be used for managing subject and sample information such as sample or subject tracking, database management, analyzing biomarker data, analyzing cytological data, storing data, billing, marketing, reporting results, or storing results. The computer may include a monitor 807 or other graphical interface for displaying data, results, billing information, marketing information (e.g., demographics), subject information, or sample information. The computer may also include data or information input 816, 815. The computer may include a processing unit 801 and fixed 803 or removable 811 media or any combination thereof. The computer can be accessed by a user in physical proximity to the computer, for example via a keyboard and/or mouse, or by a user 822 that does not necessarily have access to the physical computer through a communication medium 805 such as a modem, an internet connection, a telephone connection, or a wired or wireless communication signal carrier wave. In some cases, the computer can be connected to a server 809 or other communication device for relaying information from a user to the computer or from the computer to a user. In some cases, the user may store data or information obtained from the computer through a communication medium 805 on media, such as removable media 812. It is envisioned that data or diagnoses can be transmitted over such networks or connections for reception and/or review by a party. The receiving party can be, but is not limited to, an individual, a health care provider, or a health care manager. For example, a computer-readable medium includes a medium suitable for transmission of a result of an analysis of a biological sample, such as a level of one or more biomarker. The medium can include a result regarding a diagnosis of having a taste or smell disorder for a subject, wherein such a result is derived using the methods described herein.

Sample information can be entered into a database for the purpose of one or more of the following: inventory tracking, assay result tracking, order tracking, subject management, subject service, billing, and sales. Sample information may include, but is not limited to: subject name, unique subject identification, subject-associated medical professional, indicated assay or assays, assay results, adequacy status, indicated adequacy tests, medical history of the subject, preliminary diagnosis, suspected diagnosis, sample history, insurance provider, medical provider, third party testing center or any information suitable for storage in a database. Sample history may include but is not limited to: age of the sample, type of sample, method of acquisition, method of storage, or method of transport.

The database can be accessible by a subject, medical professional, insurance provider, third party, or any individual or entity granted access. Database access may take the form of electronic communication such as a computer or telephone. The database can be accessed through an intermediary such as a customer service representative, business representative, consultant, independent testing center, or medical professional. The availability or degree of database access or sample information, such as assay results, may change upon payment of a fee for products and services rendered or to be rendered. The degree of database access or sample information can be restricted to comply with generally accepted or legal requirements for patient or subject confidentiality.

EXAMPLES

Example 1: IL-6 in Hyposmia

Objective:
To determine IL-6 levels in biological fluids of patients with hyposmia.

Study Design:
This is a retrospective clinical study of patients who were evaluated for hyposmia.

Methods:
IL-6 was measured in plasma, urine, saliva, and nasal mucus in 59 patients with hyposmia of several etiologies and compared with levels measured in normal subjects. Measurements were made by use of a spectrophotometric ELISA assay.

Results:
IL-6 was present in all biological fluids studied. IL-6 levels in nasal mucus were greater than in any other biological fluid in both normal subjects and patients with hyposmia. Levels in patients with hyposmia were significantly greater than in normal subjects. IL-6 was selectively higher in nasal mucus in patients with hyposmia, for example, hyposmia following an influenza-like illness [post-influenza-like hyposmia and hypogeusia (PIHH)], in patients with burning mouth syndrome (BMS) and in patients with hyposmia following head injury.

Conclusion:

Elevated IL-6 in patients with hyposmia compared to normal subjects is reported herein. Since IL-6 is a pro-inflammatory cytokine, these changes can relate to local or systemic inflammatory processes which play roles either as a cause of or as a result of the pathological processes associated with hyposmia.

Introduction

Loss of smell (hyposmia) can be a symptom reflective of multiple chronic disease processes involving multiple organ systems including endocrine, vitamin, trace metal, metabolic, neurological, neurodegenerative, hematological, immunological and other organ systems. Hyposmia can reflect both local changes in the oral or nasal cavities affecting olfactory receptors, in the nerves connecting receptors to the brain or in the brain itself. The systemic changes associated with the major pathologies noted above can include hyposmia as a major symptom.

This study attempts to understand the multiple pathologies responsible for initiation and perpetuation of hyposmia by studying changes in secretions of the multiple organ systems in which hyposmia occurs. Specific biochemical moieties are associated with hyposmia onset and their replacement has corrected this symptom. For example, lack of thyroid hormone can induce hypothyroidism with its associated systemic symptoms, one of which can be hyposmia; administration of thyroid hormone can correct the systemic symptoms of hypothyroidism and the associated hyposmia. Zinc deficiency can induce multiple systemic symptoms and hyposmia which can be manifested by decreased gustin [carbonic anhydrase (CA) VI] secretion; administration of zinc ion to zinc deficient patients can correct both these systemic symptoms and the associated hyposmia associated with increased CA VI secretion.

The multiple biochemical moieties of these diverse organ systems which correct hyposmia in these various pathologies can be growth factors which stimulate olfactory epithelial stem cells to initiate maturation and renewal of the sensory cells responsible for normal olfaction to occur.

Olfaction is a complex process comprised of multiple component parts including receptors, nerves and brain. The local and systemic components of this complex process have not been fully explored. Cell signaling processes can be critical in any complex sensory system such as olfaction and can involve adenylyl cyclases, sonic hedgehog and cytokines. Here, levels of IL-6 in patients with hyposmia are investigated since no prior studies of this type among these patients have been reported.

IL-6, a proinflammatory cytokine, can be over produced in a spectrum of clinical illnesses and conditions including cardiovascular disease, osteoporosis, arthritis, Type II diabetes, renal disease, hepatitis, schizophrenia, preeclampsia, various neoplasms, periodontal disease, frailty, stress and functional decline. In these conditions, increased IL-6 can be found in blood plasma. IL-6 can be increased in both plasma and ventricular fluid following acute but not chronic head injury. Increased IL-6 can be found in cerebrospinal fluid following traumatic brain injury and can trigger nerve growth factor secretion in astrocytes. Increased IL-6 can be found in blood plasma of patients with persistent sciatic pain and IL-6 mRNA can be increased in rat spinal cord following peripheral nerve injury. Increased IL-6 can be found in plasma and in saliva of some patients with burning mouth syndrome (BMS); no IL-6 differences were reported in these patients with and without associated depression and perceived pain. However, stress hormones can regulate IL-6 expression in various ovarian carcinoma cells through a Src-dependent mechanism. Both specific and nonspecific factors can elicit changes in IL-6 in several biological fluids in several disease processes including neurological, inflammatory, and psychological stress.

To evaluate IL-6 in olfaction, IL-6 levels were investigated in plasma, urine, parotid saliva and nasal mucus among patients with hyposmia and were compared to similar measurements obtained in a group of normal subjects.

Methods

Subjects:

Subjects of the study were 59 patients, 26 men, 33 women, age 10-86 y, 54±2 y (Mean±SEM) who presented with various degrees of smell loss. Diagnoses of these patients included 24 with post-influenza-like hyposmia and hypogeusia (PIHH), seven with allergic rhinitis, seven with congenital smell loss, six with hyposmia related to idiopathic causes, five with head injury, four with drug induced hyposmia, three with phantageusia and hyposmia and three with hyposmia and BMS. All patients had loss of smell as manifested by subjective statements and by olfactometry measurements in which impaired smell function was determined in each patient. Olfactometry was performed using psychophysical techniques with four odorants (pyridine, nitrobenzene, thiophene and amyl acetate). These techniques have been validated by performance in a double-blind clinical trial. Olfactory impairment was determined by impaired detection thresholds (DT) and/or recognition thresholds (RT) (elevated above normal) and/or decreased magnitude estimation (ME) levels (below normal levels) for one or more of the four odorants.

By use of these techniques, smell loss was confirmed in each patient with 12 patients exhibiting Type I hyposmia (the most severe form of hyposmia with RTs=0 and ME=0 for all patients for all odors), 44 patients with Type II hyposmia (the next most severe form of hyposmia with DTs, RTs and MEs <normal for all patients) and 3 patients exhibiting Type III hyposmia (the least severe form of hyposmia with DTs and RTs=normal but MEs<normal).

Subjects of this study also included eight normal volunteers 4 men, 4 women, age 39-76 y, 60±8 y. All normal subjects were healthy and not taking any prescribed medications. All volunteers had normal smell function by subjective statements and by normal olfactometry.

Procedures:

At initial clinical evaluation, blood plasma was collected from each patient by venipuncture, placed in ice into tubes containing 100 µl of zinc free heparin, centrifuged at 3000 rpm for 10 min, the plasma removed and stored at −20° C. until assayed. Urine from each patient was collected over a 24-hour period in timed relationship to collection of blood plasma. Urine volume was measured and a 20 ml aliquot was stored at 4° C. until assayed. Parotid saliva was collected from each patient immediately after blood collection by placement of a Lashley cup over Stensen's duct with lingual stimulation with reconstituted lemon juice (Borden, Real Lemon, Stamford, Conn.). Saliva was collected in ice in plastic tubes over an 8-12 min period. Samples were stored at −20° C. until assayed. Nasal mucus was collected from each patient directly from the nasal cavity in 50 ml wide mouth plastic tubes over a period of two-five days in timed relationship to collection of blood, urine and saliva. After each daily collection nasal mucus was stored at 4° C. After total collection nasal mucus was transferred to plastic centrifuge tubes, centrifuged at 18K-20K×g for 40-55 min, the supernatant transferred to plastic PCR tubes and stored at −20° C. until assayed.

Similar collections of blood, urine, saliva and nasal mucus were also obtained from each normal volunteer.

IL-6 was measured by a spectrophotometric 96 plate ELISA assay obtained from R&D Systems (Minneapolis, Minn.). Tests were employed following the manufacturer's directions. Since measurements of IL-6 in nasal mucus were not previously performed various sample dilutions were developed to perform the assay. These studies reflect all measurements of IL-6 in these biological fluids made among patients.

All measurements were made without reference to origin of any collected sample. After all measurements were completed, values were matched with patients' records, sorted by diagnosis and compared to results obtained in normal subjects. Mean±SEM were determined for each patient diagnostic category and compared to similar results in normals. Differences were determined by Student t test with $p<0.05$ considered significant. Analysis of variance among patient diagnosis, smell loss type (I, II, III) and IL-6 levels in each biological fluid studied was performed with $p<0.05$ considered significant.

Results

Levels of IL-6 were measured in all biological fluids studied. Comparison of IL-6 levels in each biological fluid was compared between patients and normals. Patients demonstrated large, consistent and significant differences in IL-6 levels (Table 1). IL-6 in plasma, saliva, and nasal mucus in patients was significantly higher than in normals. Mean nasal mucus levels in patients were 2.6 times that in normals, mean saliva levels were 1.9 times that in normals and mean plasma levels were 7.9 times that in normals.

Comparison of IL-6 among patients categorized by etiology of loss with normals demonstrated that mean plasma IL-6 was significantly higher in all patients compared to normal controls; the highest level was found in BMS, the next in head injury, the third highest in PIHH and the lowest in patients with allergic rhinitis (Table 2). Mean urine IL-6 in patients was similar to normals in all patient categories except congenital hyposmia in whom levels were significantly lower than in normal controls. Mean saliva IL-6 was significantly above normal controls in patients with BMS, head injury and PIHH with the highest level in BMS. Mean nasal mucus IL-6 was elevated in patients with head injury, BMS, allergic rhinitis, phantageusia and PIHH but significantly so only in patients with BMS and PIHH. IL-6 levels in nasal mucus were highest in patients with head injury and BMS.

Comparative analysis of IL-6 levels in normal controls in plasma, urine, saliva and nasal mucus revealed a specific hierarchy (Table 1) different from that found in patients. Levels of IL-6 in nasal mucus were higher than in any other biological fluid being over 10 times that found in urine, saliva or in blood plasma. Levels were next highest in urine, then saliva and lowest in plasma. The ratio of nasal mucus:plasma was 97:1, of nasal mucus:saliva 34:1 and nasal mucus:urine 9:1.

Comparative analysis of IL-6 levels in patients also yielded a hierarchy of levels but with a somewhat different set of ratios than that found in normals. The highest level of IL-6 was also found in nasal mucus which was over 30 times the levels found in saliva, urine or in plasma. The next highest levels were found in plasma and urine (levels were similar) and the lowest level in saliva. The ratio of nasal mucus:plasma was 31:1 about ⅓ that found in normals, nasal mucus:saliva was 52:1, about 1½ times the ratio in normals and nasal mucus:urine was 32:1, about 3½ times the ratio found in normals.

There were no significant differences among IL-6 levels in plasma, saliva or nasal mucus with smell loss type and patient diagnosis.

Discussion

The present study is the first to demonstrate IL-6 elevations among patients with hyposmia. If these findings were to relate to similar results found in rheumatoid arthritis (RA) then elevated IL-6 could be considered a causal factor for initiation of hyposmia reflective of local and/or systemic immunological and/or inflammatory changes in blood, saliva or nasal mucus. This hypothesis is consistent with finding smell loss among patients with inflammatory RA. Among patients with hyposmia, chronic lymphocytic inflammation can be found in nasal mucous membranes of patients with PIHH. Elevated IL-6 can be found in nasal lavage fluid from patients with naturally acquired viral rhinitis. Paravirus and other viruses can be found in turbinate epithelial cells of patients with post viral olfactory dysfunction. Manifestation of herpes virus infection can be found in olfactory bulb neurons in mice as long as 200 days after they were initially experimentally infected as well as in astrocytes in the suspected portal of entry. However, histological changes which may occur in the olfactory epithelium, transmitting nerves or in the brain under these conditions have not been investigated. Treatment of RA with IL-6 inhibitors has been associated with diminution of both inflammation and IL-6 elevation. If IL-6 elevation in hyposmic patients were related to the cause of their pathology then treatment with IL-6 inhibitory drugs might be associated with improvement of their smell function.

Elevation of many substances locally or systemically can inhibit smell function including zinc, cadmium, drugs of several types, and several other chemical moieties. Elevated IL-6 could act as an endogenous substance regulating olfactory neuronal activity because it can regulate neuronal and glial cell activity. Thus, IL-6 elevations among patients with hyposmia and chronic head injury may relate to neurological as well as to inflammatory changes.

Finding elevated levels of IL-6 in both plasma and in saliva in some patients with BMS suggests not only a response to an inflammatory process but also a possible neurological process as well. Suggestion of a neurological rather than an inflammatory mechanism responsible for the pyrosis in BMS is consistent with the lack of obvious signs of oral inflammation among these patients. BMS can be considered a trigeminal small fibre neuropathy and treatment with an antioxidant, GABAergic drugs or repetitive transcranial magnetic stimulation can be used to alleviate this condition.

Results of the present study also illustrate that IL-6 levels in nasal mucus are higher than those in plasma, urine or saliva. This appears to be the first direct comparison of IL-6 levels in these biological fluids and the first demonstration that levels of IL-6 in nasal mucus in patients with hyposmia and in normal subjects are increased relative to that in plasma, urine or saliva. This finding is logically consistent with the abundance of microbial and antimicrobial agents normally present in nasal mucus. Active inflammatory agents in nasal mucus can include bacteria, viruses, fungi, and other substances including histamine whereas anti-inflammatory agents found can include lysozyme, lactoferrin and albumin. However, contrary to this supposition, the highest level of IL-6 in nasal mucus reported here was not in patients with allergic rhinitis in which these agents might be expected to be most active but in patients with head injury and BMS in whom no active local nasal inflammatory process presumably occurs although both patient groups exhibit hyposmia.

Possible mechanism(s) of the relationship(s) of IL-6 signaling to loss of smell are multiple. IL-6 can be part of a complex and sophisticated signaling system which plays multiple roles in body metabolism. IL-6 can be an inflammatory cytokine which drives acute phase proteins including C-reactive protein and fibrinogen, both proteins induced by systemic inflammation. It can be a factor in differentiation of B cells into antibody producing plasma cells. It can influence NF-κB and ATP-ubiquitin-dependent proteolytic pathways, it can activate TNF-α and thereby activate apoptotic pathways which could directly inhibit smell function. Neuropoietin, an IL-6 related cytokine which affects signaling through ciliary neurotrophic factor receptor, could directly inhibit smell function since inhibition of several ciliary factors have induced smell loss in patients with Kartagener's and Bardet-Biedl syndromes. Patients with Castleman's disease can overproduce IL-6 and treatment which inhibits either IL-6 or IL-6 receptor activity can alleviate symptoms of the disease. Il-6 deficient mice are incapable of mounting an inflammatory response. After binding to its receptor, the IL-6 receptor complex activates gp 130 signaling in cells that would not normally express IL-6 receptor, a mechanism that can play a role in pathophysiology of chronic inflammatory disorders.

These results suggest that both specific and nonspecific factors may increase IL-6 in both acute and chronic disease processes. These processes can include neurological and inflammatory processes and processes involving psychological stress. Indeed, stress hormones can regulate IL-6 expression in various ovarian carcinoma cells through a Src-dependent mechanism.

This is the first study of any type in which IL-6 measurements were obtained and compared in patients with chronic disease processes in several biological fluids (plasma, urine, saliva and nasal mucus) in a similar timed based study. These results offer an insight into the signaling processes present among some patients with hyposmia which may influence some of the complex processes responsible for their sensory changes.

TABLE 1

IL-6 IN PLASMA, URINE, PAROTID SALIVA AND NASAL MUCUS IN PATIENTS WITH HYPOSMIA AND IN NORMAL SUBJECTS

| BIOLOGICAL FLUIDS | NORMALS IL-6 (8) | PATIENTS IL-6 (59) |
|---|---|---|
| PLASMA | 0.12 ± 0.03* | 0.95 ± 0.10$^a$ |
| URINE | 1.26 ± 0.41 | 0.92 ± 0.17$^a$ |
| SALIVA | 0.30 ± 0.01 | 0.57 ± 0.05$^a$ |
| NASAL MUCUS | 11.6 ± 0.50 | 29.7 ± 3.80$^a$ |

IL-6 (pg/ml)
*Mean ± SEM
( ) Subject number
$^a$p < 0.001 with respect to normals

TABLE 2

IL-6 IN PLASMA, URINE, PAROTID SALIVA AND NASAL MUCUS IN PATIENTS WITH HYPOSMIA

| Etiology Biological Fluid: | Post Influenza (PIHH) (24) | Allergic Rhinitis (7) | Congentital (7) | Idiopathic (6) | Head Injury (5) | Drug Induced (4) | Phantageusia (3) | Burning Mouth Syndrome (BMS) (3) | Normal (6) |
|---|---|---|---|---|---|---|---|---|---|
| Plasma | 1.03 ± 0.15*,$^a$ | 0.62 ± 0.12$^{a,e11}$ | 0.72 ± 0.15$^{a,e11}$ | 1.03 ± 0.15$^a$ | 1.47 ± 0.56$^a$ | 0.70 ± 0.1$^{a,d1,e11}$ | 0.56 ± 0.08$^{a,e11}$ | 2.20 ± 0.60$^a$ | 0.12 ± 0.03$^a$ |
| Urine | 1.22 ± 0.38 | 0.71 ± 0.16 | 0.29 ± 0.06$^{d1}$ | 1.00 ± 0.40 | 0.83 ± 0.26 | 0.78 ± 0.26 | 0.44 ± 0.21 | 0.90 ± 0.50 | — |
| Saliva | 0.51 ± 0.05 | 0.39 ± 0.06 | 0.59 ± 0.14 | 0.55 ± 0.07 | 0.68 ± 0.18$^d$ | 0.53 ± 0.05$^{c1}$ | 0.45 ± 0.13 | 1.40 ± 0.70$^a$ | 0.34 ± 0.01$^a$ |
| Nasal Mucus | 29.7 ± 5.2 | 39.5 ± 18.2 | 19.6 ± 8.3$^{e11}$ | 13.6 ± 4.7$^{b11}$ | 54.4 ± 23.7 | 10.8 ± 4.0$^{b11}$ | 31.5 ± 23.0 | 50.9 ± 11.5$^b$ | 11.6 ± 0.50 |

*Mean ± SEM
( ) Subject number
Compared to normal
$^a$p < 0.001
$^b$p < 0.005
$^{c1}$p < 0.01
$^{d1}$p < 0.02
Compared to PIHH
$^{b11}$p < 0.005
$^{e11}$p < 0.05
Compared to BMS Example 2: Cytokine Changes in Nasal Mucus and Other Biological Fluids in Patients with Smell Loss Classified by Age Cytokine changes in nasal mucus and other biological fluids in patients with smell loss classified by age.

Background:

Cytokine activity in nasal mucus has not been studied in patients with smell loss (hyposmia). Cytokines have been reported to change with age with some known to increase, others to decrease and others not to change. However, most of these reported changes were observed in relationship to stimulated activities mainly in various hematological system functions. Therefore, we performed a survey of cytokine activity in several biological fluids including nasal mucus in patients with hyposmia classified by age.

Methods:

By use of sensitive 96 plate spectrophotometric ELISA techniques IL-1α, IL-1β, IL-1ra, IL-1 RII, IL-2, IL-2R, IL-6, IL-10, IL-18, TNF-α, IFN-β and IFN-γ were measured in nasal mucus, blood plasma, urine and parotid saliva in 79 subjects with hyposmia at progressive 10 year age groups from <30 y to >70 y.

Results:

IL-1ra levels in nasal mucus were the highest found in any biological fluid consistent with the role of this cytokine as an anti-inflammatory factor. Cytokines IL-1α, IL-1β and IFN-γ were present in nasal mucus consistent with their roles as inflammatory factors. These latter cytokines were absent in blood plasma, urine and saliva.

Conclusions:

Cytokine levels in nasal mucus suggest a complex interaction occurs between proinflammatory and anti-inflammatory cytokines among patients with hyposmia with the highest levels in the anti-inflammatory cytokine IL-1ra in nasal mucus. Cytokine levels varied with age in complex patterns. This is the first demonstration of several cytokines in nasal mucus in relationship to other biological fluids.

Introduction

Cytokines are cell signaling moieties activated by specific stimuli which lead to many physiological responses. However, these signaling proteins function in such multiple pathways that their specificity may not be clearly defined. We have been interested in the roles various cytokines play in patients with smell loss (hyposmia) and have published preliminary data related to changes that occur in cytokines with age among these patients who also exhibit anorexia and taste distortions.

However, the pathology associated with hyposmia is quite varied in relationship to multiple clinical conditions. Most patients develop hyposmia following a viral-type infection whereas others develop this symptom following head injury or associated with systemic and nasal symptoms of allergic rhinitis. We have attempted to determine some common biochemical threads underlying these diverse pathologies and in so doing we and others before us determined that smell loss has been attributed to changes in secretions from multiple organ systems including decreased levels of trace metals and vitamins, treatment with various therapeutic drugs and associated with various pathological conditions, including diabetes, other endocrine disorders, neurological disorders and liver disease. In an effort to define these putative common pathological threads underlying these various pathologies we undertook systematic studies of the multiple biochemical parameters putatively responsible for loss of smell function. To perform these studies we evaluated levels of trace metals in blood plasma and cyclic nucleotides in saliva and nasal mucus. These studies revealed that many patients with hyposmia exhibited lower than normal levels of zinc in their saliva and lower than normal levels of adenylyl cyclases in their saliva and nasal mucus.

Because hyposmia involves changes in sensory receptors, nerves and brain it was apparent that changes in cell signaling and thus, in cytokines, were involved in this complex system. For example, inhibition of sonic hedgehog secretion initiated loss of taste by inhibiting stem cell stimulation in taste buds which is responsible for growth and maturation of the elegant repertoire of cellular components initiating and maintaining normal taste function. Because cytokines play such a significant role in cell signaling we undertook a survey of several cytokines in blood plasma, urine, saliva and nasal mucus among a group of patients with hyposmia.

Cytokine levels have been previously reported by many investigators to change with age. In-vitro production of IL-1β, IL-6, TNF-α and IFN-γ by peripheral mononuclear cells was reported increased in aged compared to younger human subjects. Stimulated T cells from aged mice compared to young mice showed increased production of IFN-γ, decreased IL-2 but no differences in IL-4. Leukocytes from elderly humans produced higher amounts of IL-1, IL-6, IL-8 and TNF-α than from younger subjects, there was a decreased release of IL-2 and soluble IL-2R but IL-2R expression in the cell surface was not increased in the elderly. No age related differences were observed in absolute amounts of IL-1β and IL-6 after normalizing for circulatory monocytes and there was no age related decline in IL-2. Because of these results changes in cytokine levels by age appeared to be one factor by which changes in hyposmia might occur.

Results of our studies indicated that in patients with hyposmia levels of the anti-inflammatory cytokine IL-1ra in nasal mucus were higher than in any other cytokine contrasted with the presence of lesser but still large amounts of nasal mucus proinflammatory cytokines. These results suggest that a complex interplay between anti- and proinflammatory cytokines occurs among these patients and may play a role in their smell function.

Materials and Methods

Patients:

Subjects were 79 patients who presented to The Taste or Smell Clinic, Washington, D.C. with clinical complaints of smell loss. Other than smell loss patients were well and healthy. Patients were 44 women and 35 men, aged 53±5 y (Mean±SEM), range 21-83 y. Studies were approved by the Institutional Review Board of the Georgetown University Medical Center; all patients gave informed consent to participate in this study.

At initial clinical evaluation blood plasma was obtained by venipuncture and stored at −20° C. until assayed. A 24-hour urine was collected in direct timed relationship to collection of blood plasma; volume was measured and an aliquot stored at −20° C. until assayed. Parotid saliva was collected from each patient immediately after blood collection by placement of a modified Lashley cup over Stensen's duct with lingual stimulation with reconstituted lemon juice (Borden, Real Lemon, Stamford, Conn.) and stored at −20° C. until assayed. Nasal mucus was collected using spontaneous nasal discharge over two-five days, as previously described. After each daily collection samples were stored at 4° C. Samples were transferred to plastic tubes, centrifuged at 17K-19K×g for 40-55 min and the supernatant stored at −20° C. until assayed.

Cytokines and some of their receptors (IL-1α, IL-1β, IL-1ra, IL-1 RII, IL-2, IL-2R, IL-6, IL-10, IL-18, TNF-α, IFN-β and IFN-γ) were measured by sensitive spectrophotometric 96 plate ELISA assays obtained from R&D Systems (Minneapolis, Minn.). Tests were employed following the manufacturer's directions. Since no prior measurements of cytokines in nasal mucus were performed various sample dilutions had to be developed to perform this assay.

All measurements were made without reference to any specific clinical data including patient age. After all measurements were completed values were matched with patient records and sorted by age. Mean±SEM were determined for each cytokine with patients separated into progressive age groups of <30 y, 31-40 y, 41-50 y, 51-60 y, 61-70 y, and >70 y. Significance of differences was determined by Student t test with p<0.05 considered significant.

Results

IL-1α.

Values were obtained only in nasal mucus and saliva (Table 3). Levels of nasal mucus ranged from 24-92 times levels in saliva. For nasal mucus there was a small, gradual decrease with age. There was no apparent age related relationship observed with age in saliva.

IL-11.

Values were obtained only in nasal mucus (Table 3). Values in nasal mucus were generally higher than those found for IL-1α. There were no apparent age related relationships observed with age.

IL-1ra.

Values were obtained in each biological fluid (Table 3). Levels in nasal mucus were the highest found in any biological fluid. Levels in nasal mucus ranged from 80 to over 1000 times higher than those in plasma which were comparatively the lowest among fluids studied. IL-1ra levels in nasal mucus were almost 1000 times higher than levels in IL-1α and IL-1β. By age there was an inverted U shaped pattern for nasal mucus with the peak at age 40-49 y. There was a U shaped pattern in saliva with the nadir at a similar age with nasal mucus, 40-49 y.

IL-1 RII.

Values were obtained in each biological fluid (Table 3). Levels in nasal mucus were about 0.1-0.5% levels in plasma but 5-90 times levels in saliva and 2-9 times the level in urine. Levels in nasal mucus were about 0.2-0.4% values measured in IL-1ra but 5-17 times levels measured in IL-1α and varied from 5-17 times higher than levels of IL-1β. By age there was an inverted U shaped pattern for nasal mucus similar to that measured in IL-1ra with the peak at age 40-49 y and a similar inverted U shaped pattern in plasma with a peak at a similar age.

IL-2.

At dilutions used for this cytokine values were not obtained in any fluid.

IL-2R.

Values were measured in all biological fluids (Table 3). Levels in nasal mucus varied from 2%-36% below that measured in plasma, from 2%-20% below that measured in urine but from 5-335 times higher than that measured in saliva. Levels in nasal mucus were lower than those measured in IL-1α, IL-3, IL-1ra or IL-1 RII. There was a relative inverted U shaped pattern with age in nasal mucus with the peak again at age 40-49 y.

IL-6.

Values were measured in all biological fluids (Table 4). Levels in nasal mucus were higher than in any other of these biological fluids being 3-13 times levels in plasma, from 7-25 times levels in urine and 3-10 times levels in saliva. Levels in IL-6 were lower than those in IL-1α, IL-1β, IL-1ra, IL-1 RII and IL-2R. With respect to age levels in nasal mucus increased up to age 30-39 y and decreased thereafter.

IL-10.

Values were measured in nasal mucus, saliva and plasma but not in urine. Levels in nasal mucus were generally higher than in either saliva or plasma except at either end of the age range. Levels in nasal mucus ranged from 2-20 times higher than in plasma and 2-8 times higher in saliva. With respect to age there was a gradual increase in nasal mucus until age 60-69 y and then a decrease thereafter.

IL-18.

Values were measured in nasal mucus, saliva and plasma but not in urine, as with IL-10. Values in nasal mucus varied with respect to levels in plasma but were generally higher than levels in saliva by as much as a factor of seven. Levels in nasal mucus were higher than in IL-2R, IL-6 or IL-10 but lower than in IL-1α, IL-1β, IL-1ra or IL-1 RII. With respect to age there was again an inverted U shaped pattern in nasal mucus with a peak at age 50-59 y.

TNF-α.

Values were measured in all biological fluids (Table 4). Levels in nasal mucus were higher than in any of these biological fluids being 3-11 times higher than levels in plasma, 7-23 times levels in urine and 7-27 times levels in saliva. Levels of TNF-α in nasal mucus were higher than levels of IL-6 or IL-10 but lower than in IL-1α, IL-1β, IL-1ra, IL-1 RII and IL-18. With respect to age there was an approximate U shaped pattern in nasal mucus with a nadir at age 40-49 y albeit the lowest level was at age 60-69 y; highest levels were measured at both ends of the age range.

IFN-β.

Values were obtained in all biological fluids except for urine. Values in nasal mucus were generally similar to levels in plasma but higher than levels in saliva. Levels in nasal mucus were higher than levels in IL-2R, IL-6, IL-10, IL-18 or TNF-α but lower than levels in IL-1α, IL-1β, IL-1ra and IL-1 RII. Age related values in nasal mucus and saliva cannot be evaluated due to multiple missing data but there appears to be an inverted U shaped pattern in plasma with the peak at age 30-39 y.

IFN-γ.

Values were obtained only in nasal mucus. Levels were higher than in IL-2R, IL-6, IL-10 and TNF-α but lower than levels in IL-1α, IL-1β, IL-1ra and IL-1 RII. There can be a U shaped pattern with age with the nadir at age 50-59 y.

All numbers in Table 3 and Table 4 that are within a single cell should be read as one number.

Discussion

These data indicate that multiple cytokines in multiple biological fluids are present in patients with hyposmia but levels of each cytokine vary in each fluid. Levels in nasal mucus were generally the highest measured in any biological fluid with a specific pattern of activity.

This pattern appears related to a specific interplay between proinflammatory cytokines (e.g., IL-1α, IL-1β, IL-6, IL-18, TNF-α) and anti-inflammatory cytokines (e.g., IL-1ra, IL-10, IFN-γ) among hyposmic patients and suggest that while there are multiple etiological factors responsible for loss of smell, many of which have no apparent inflammatory component, e.g., following head injury or hypothyroidism, there can be an underlying physiological interplay among these nasal mucus cytokines.

Cytokine changes in nasal mucus suggest this complex interplay between proinflammatory cytokines and their competitive inhibitor anti-inflammatory components among patients with hyposmia. Since changes in nasal mucus can and do reflect changes in olfactory function these results are relevant to basic mechanisms underlying smell loss in these patients. The identities of proinflammatory cytokines in nasal mucus are consistent with the anatomical and pathological changes of chronic inflammation in the nasal mucus membranes as previously identified among these hyposmic patients. However, these results are contrasted with levels of IL-1ra, the competitive inhibitor of these proinflammatory cytokines, which are much higher in concentration than those of the proinflammatory cytokines suggesting an endogenous protective effect against acute or chronic inflammation among these patients. This result is consistent with treatment in hyposmic patients with theophylline or other phosphodiesterase inhibitors which improve smell function among these patients and also inhibiting secretion of TNF-α and other proinflammatory cytokines.

Cytokines are pleiotropic and redundant molecules with a wide variety of functions with overlapping activities in several cells. For example, TNF-α was initially considered to have mainly immunomodulatory and proinflammatory effects but more recent data suggest that TNF-α also has significant anti-inflammatory properties. On the other hand IL-10 inhibits synthesis of proinflammatory cytokines including IL-1, IL-6 and TNF-α by modulating liposaccharide induced fever and similar changes in animals.

IL-1 is a 17 KD proinflammatory cytokine synthesized from a variety of cell types associated with disease states or during perturbations such as immune responses. It is part of a family of cytokines which share a conserved 3-trefoil structure which binds to receptors belonging to the IL-1 receptor family. In most instances in which inflammation is activated IL-1 is the major protagonist. IL-18, usually considered a proinflammatory cytokine, has also been reported to play an antagonistic role to this activity of IL-1 but this action is still controversial. There is a naturally occurring IL-1 specific receptor antagonist, IL-1ra, which shares 40% amino acid homology with IL-1β, binds to IL-1 surface receptors with the same affinity as IL-1, does not possess agonist activity but acts as a competitive inhibitor of IL-1. Studies suggest that IL-1 plays a key role in triggering the cascade of inflammatory cellular responses with IL-1ra blocking endogenous IL activity.

IL-1ra in nasal mucus is the highest secreted cytokine among all biological fluid cytokines measured and highest among all the nasal mucus cytokines measured. This level in nasal mucus is about 800 times higher than the levels of IL-1α, over 400 times higher than the level of IL-1β, about 30 times the level of IL-1 RII and over 19000 times higher than the level of TNF-α.

With this context in mind evaluation of results of this study suggests a complex interplay occurs in nasal mucus in patients with hyposmia between proinflammatory cytokines IL-1α, IL-1β, IL-6, IL-18 and TNF-α and their competitive inhibitors IL-1ra, IL-10 and IFN-γ. These results suggest a mucosal balance between proinflammatory and anti-inflammatory cytokines among these patients suggesting some control of these elements in hyposmia. This contrasts with the imbalance between these proinflammatory and anti-inflammatory cytokines in patients with inflammatory bowel disease in which IL-1 is significantly greater than IL-1ra which has been related to a novel mechanism of chronic intestinal inflammation in chronic inflammatory bowel disease and the presence of hyposmia.

The increased proinflammatory cytokines in nasal mucus is consistent with the anatomical and pathological changes of inflammation in the nasal mucus membranes previously identified among patients with viral rhinitis and among these hyposmic patients. Theophylline treatment, which improved smell function among these patients, also inhibited secretion of TNF-α and other proinflammatory cytokines which support these observations. Since levels of IL-1ra, the major competitive inhibitor of these proinflammatory cytokines are much higher than those of the proinflammatory cytokines these results suggest an endogenous protective effect against acute or chronic inflammation occurs among these patients.

While the changes observed in this study relate to mucosal changes in cytokines released into nasal mucus by cells in nasal epithelial glands these changes may also relate in changes in central nervous system and anterior pituitary function. Changes in IL-1, IL-1ra and IL-10 μgene expression have all been shown to be increased during systemic inflammation in the central nervous system and anterior pituitary. These results suggest that IL-1ra can be secreted by the anterior pituitary as a systemic anti-inflammatory hormone released in response to IL-1β from multiple system sources consistent with the results we have observed among hyposmic patients. IL-18 μgene polymorphism has also been found among patients with allergic diseases.

Changes we measured in cytokine levels with age in each biological fluid are complex. Previous investigators reported that many factors influence cytokine changes in addition to age including caloric restriction, endotoxin presence, oxidative stress and hormonal states. Age changes in TNF-α have been reported to be predictive of insulin resistance. Thus, differences in levels in each biological fluid we studied may reflect not only differences in each cytokine with age but also other mechanisms related to multiple factors not identified in this study. Indeed, the most relevant aspect of this study relates not to age changes but to changes in cytokines in nasal mucus itself relative to changes in other biological fluids as related to patients with hyposmia. With these cytokine changes in nasal mucus these results suggest a complex interplay between proinflammatory cytokines and their competitive inhibitors occurs among patients with hyposmia. Since changes in nasal mucus can and do reflect changes in olfactory function these results are relevant to the basic mechanism(s) underlying smell loss in this group of patients. Indeed, antibodies to specific cytokines have been successful in disease treatment.

Among the cytokines measured there is an apparent hierarchy of levels among the various biological fluids studied. Nasal mucus IL-1ra is the most prevalent cytokine in any biological fluid studied although there are significant variations in these measurements. Urinary IL-1ra is the most prevalent urinary cytokine among all urinary cytokines studied. Plasma and saliva IL-1 RII are the most prevalent cytokines among the plasma and saliva levels measured.

Cytokine concentrations found in these biological fluids are relative to measurement techniques used. Because these results reflect cytokine levels under physiological conditions, albeit in patients with hyposmia, it is difficult to compare these results with those previously reported by most other investigators since they mainly reported age related changes in cytokine activity in hematological or tissue cell function in response to specific stimulatory and inhibitory substances. Inamizu, et al. reported macrophage IL-1 production decreased with age whereas in our studies there was no change with age in nasal mucus. Previous investigators reported decreased keratinocyte IL-1α production with age whereas our results show a generalized increase with age in IL-1α in each biological fluid studied. It is known that IL-1 stimulates IL-1ra production but the complex changes with age we demonstrate in either nasal mucus or saliva do not support the observation that IL-1 relates to increased levels in IL-1ra. IL-2R from older subjects have been reported to decline with age but in our studies there were increases in plasma, little change in urine and a complex pattern of change in nasal mucus. Beharka, et al. reported that IL-6 production does not increase with age whereas in our studies IL-6 in plasma increased, particularly at age 60-69 y, and in urine at age 49-49 y. IL-10 in our study increased with age in each fluid whereas Ye, et al. reported age-related declines in IL-10 in brain sections and glial cells in mice. Consistent with our studies, aged marine CD4[+] T cells produced more IL-10 than did young cells. There were no changes reported in IFN-γ production with age whereas we reported an increase in nasal mucus levels at age 60-69 y. Variable age related changes in TNF-α and interferon have been reported by many previous investigators. Changes in cytokine levels with age in several other biological fluids have been previously reported; Kawasaki, et al. reported that RANKL and OPG levels decreased in gingival crevicular fluid with age and Yamakawa, et al. reported an increase in IL-1β production in murine parotid acinar cells with age and they reported a decrease in IL-6.

This is the first study in which cytokine levels in several biological fluids in patients with hyposmia have been reported and the first in which cytokine levels in several biological fluids, measured in near time to each other, have been reported.

TABLE 3

CHANGES IN HUMAN CYTOKINE LEVELS WITH AGE

| Age y | Nasal Mucus | Saliva | Plasma | Urine | Nasal Mucus | Saliva | Plasma | Urine | Nasal Mucus | Saliva | Plasma | Urine |
|---|---|---|---|---|---|---|---|---|---|---|---|---|
| | IL-1α (pg/mL) | | | | IL-1β (pg/mL) | | | | IL-1ra (pg/mL) | | | |
| <30 | 201* | 2.5 | 0 | 0 | 303 | 0 | 0 | 0 | 15534 | 14573 | 198 | 2534 |
| 30-39 | 203 | 2.2 | 0 | 0 | 156 | 0 | 0 | 0 | 58226 | 9050 | 373 | 6099 |
| 40-49 | 135 | 2.3 | 0 | 0 | 262 | 0 | 0 | 0 | 111243 | 7767 | 80 | 746 |
| 50-59 | 149 | 3.7 | 0 | 0 | 248 | 0 | 0 | 0 | 64576 | 17319 | 262 | 2875 |
| 60-69 | 121 | 5 | 0 | 0 | 301 | 0 | 0 | 0 | 52132 | 20293 | 212 | 2992 |
| >70 | 147 | 2.8 | 0 | 0 | 235 | 0 | 0 | 0 | 52215 | 25371 | 262 | 4769 |
| <30 | 146† | 0.9 | 0 | 0 | 40 | 0 | 0 | 0 | 5065 | 11528 | 88 | 1800 |
| 30-39 | 50 | 0.6 | 0 | 0 | 65 | 0 | 0 | 0 | 18305 | 3908 | 148 | 3073 |
| 40-49 | 24 | 0.7 | 0 | 0 | 38 | 0 | 0 | 0 | 3919 | 2445 | 6 | 506 |
| 50-59 | 33 | 1.6 | 0 | 0 | 75 | 0 | 0 | 0 | 12145 | 6739 | 93 | 1887 |
| 60-69 | 32 | 1.7 | 0 | 0 | 57 | 0 | 0 | 0 | 14218 | 7722 | 35 | 959 |
| >70 | 38 | 1.3 | 0 | 0 | 54 | 0 | 0 | 0 | 13742 | 9726 | 52 | 2498 |
| | IL-1RII (pg/mL) | | | | IL-2 (pg/mL) | | | | IL-2R (pg/mL) | | | |
| <30 | 674* | 123 | 12323 | 394 | 0 | 0 | 0 | 0 | 9 | 0 | 467 | 1019 |
| 30-39 | 1844 | 59 | 15338 | 302 | 0 | 0 | 0 | 0 | 27 | 16 | 808 | 988 |
| 40-49 | 3003 | 43 | 36680 | 352 | 0 | 0 | 0 | 0 | 335 | 1 | 939 | 1698 |
| 50-59 | 1961 | 36 | 16495 | 478 | 0 | 0 | 0 | 0 | 31 | 16 | 814 | 1167 |
| 60-69 | 2153 | 24 | 21457 | 366 | 0 | 0 | 0 | 0 | 80 | 19 | 1418 | 1177 |
| >70 | 1087 | 40 | 20257 | 302 | 0 | 0 | 0 | 0 | 27 | 12 | 1003 | 1303 |
| <30 | 245† | 4 | 68 | 121 | 0 | 0 | 0 | 0 | 9 | 0 | 107 | 679 |
| 30-39 | 849 | 21 | 1699 | 52 | 0 | 0 | 0 | 0 | 20 | 11 | 89 | 255 |
| 40-49 | 1518 | 20 | 11143 | 64 | 0 | 0 | 0 | 0 | 188 | 1 | 523 | 454 |
| 50-59 | 1075 | 13 | 2311 | 117 | 0 | 0 | 0 | 0 | 17 | 10 | 153 | 275 |
| 60-69 | 1023 | 7 | 2921 | 66 | 0 | 0 | 0 | 0 | 48 | 18 | 312 | 216 |
| >70 | 288 | 18 | 2684 | 77 | 0 | 0 | 0 | 0 | 15 | 10 | 132 | 71 |

*Mean
†±SEM
0 Values were 0

TABLE 4

CHANGES IN HUMAN CYTOKINE LEVELS WITH AGE

| Age y | Nasal Mucus | Saliva | Plasma | Urine | Nasal Mucus | Saliva | Plasma | Urine | Nasal Mucus | Saliva | Plasma | Urine |
|---|---|---|---|---|---|---|---|---|---|---|---|---|
| | IL-6 (pg/mL) | | | | IL-10 (pg/mL) | | | | IL-18 (pg/mL) | | | |
| <30 | 1.1* | 0.11 | 0.08 | 0.05 | 0.03 | 0.52 | 0.1 | 0 | 60 | 18 | 175 | 0 |
| 30-39 | 2.7 | 0.08 | 0.1 | 0.06 | 0.32 | 0.48* | 0.53 | 0 | 167 | 36 | 187 | 0 |
| 40-49 | 1.7 | 0.15 | 0.19 | 0.25 | 0.84 | 0.44* | 0.4 | 0 | 122 | 92 | 195 | 0 |
| 50-59 | 0.3 | 0.07 | 0.07 | — | 2.47 | 0.33 | 0.62 | 0 | 405 | 54 | 224 | 0 |
| 60-69 | 0.7 | 0.06 | 0.22 | 0.04 | 8.99 | 1.08 | 0.48 | 0 | 116 | 117 | 163 | 0 |
| >70 | 0.3 | 0.06 | 0.09 | — | 0.42 | 0.53 | 0.45 | 0 | 119 | 59 | 338 | 0 |
| <30 | 0.5† | 0.02 | 0.01 | 0.01 | 0.1 | 0.14 | 0.01 | 0 | 46 | 10 | 116 | 0 |
| 30-39 | 0.14 | 0.03 | 0.02 | 0.01 | 1.22 | 0.10 | 0.1 | 0 | 74 | 10 | 62 | 0 |
| 40-49 | 1 | 0.09 | 0.09 | 0.12 | 0.56 | 0.03 | 0.11 | 0 | 80 | 27 | 54 | 0 |
| 50-59 | 0.1 | 0.04 | 0.04 | — | 0.4 | 0.01 | 0.12 | 0 | 193 | 26 | 90 | 0 |
| 60-69 | 0.12 | 0.03 | 0.08 | 0.02 | 6.8 | 0.24 | 0.03 | 0 | 41 | 37 | 32 | 0 |
| >70 | 0.08 | 0.03 | 0.03 | — | 0.02 | 0.22 | 0.06 | 0 | 53 | 32 | 136 | 0 |
| | INF-α (pg/mL) | | | | IFN-β (pg/mL) | | | | IFN-γ (pg/mL) | | | |
| <30 | 11.7* | 0.8 | 1 | 0.7 | 0 | 0 | 1584 | 0 | 109 | 0 | 0 | 0 |
| 30-39 | 8.9 | 0.3 | 3 | 0.5 | 0 | 0 | 2175 | 0 | 77 | 0 | 0 | 0 |
| 40-49 | 5.8 | 0.6 | 3 | 0.3 | 1239 | 8 | 1690 | 0 | 67 | 0 | 0 | 0 |
| 50-59 | 7.3 | 0.6 | 2.2 | 0.4 | — | 160 | — | 0 | 55 | 0 | 0 | 0 |
| 60-69 | 2.7 | 0.4 | 2 | 0.4 | 351 | 6 | 492 | 0 | 121 | 0 | 0 | 0 |
| >70 | 16.1 | 0.6 | 3.2 | 0.7 | 428 | 15 | 533 | 0 | 63 | 0 | 0 | 0 |
| <30 | 5.3† | 0.8 | 0.1 | 0.3 | 0 | 0 | 995 | 0 | 12 | 0 | 0 | 0 |
| 30-39 | 5.2 | 0.1 | 0.7 | 0.1 | 0 | 0 | 2175 | 0 | 8 | 0 | 0 | 0 |
| 40-49 | 2.2 | 0.3 | 0.9 | 0.1 | 819 | 8 | 1142 | 0 | 31 | 0 | 0 | 0 |

TABLE 4-continued

CHANGES IN HUMAN CYTOKINE LEVELS WITH AGE

| Age y | Nasal Mucus | Saliva | Plasma | Urine | Nasal Mucus | Saliva | Plasma | Urine | Nasal Mucus | Saliva | Plasma | Urine |
|---|---|---|---|---|---|---|---|---|---|---|---|---|
| 50-59 | 2.7 | 0.1 | 0.8 | 0.1 | — | 101 | — | 0 | 21 | 0 | 0 | 0 |
| 60-69 | 2.7 | 0.1 | 0.9 | 0.3 | 309 | 4 | 382 | 0 | 69 | 0 | 0 | 0 |
| >70 | 6.7 | 0.3 | 0.5 | 0.2 | 428 | 15 | 483 | 0 | 63 | 0 | 0 | 0 |

*Mean
†±SEM
0 Values were 0
— No sample obtained
$^{a}$p < 0.05 with respect to age 60-69 y

Example 3: IgE and Eosinophil Changes in Hyposmia

Patients with smell loss have multiple clinical and biochemical characteristics which define their pathology. In a recent reanalysis of data obtained at The Taste or smell Clinic in Washington, D.C. 28 patients were analyzed with taste or smell dysfunction. Each of the 28 patients has a significant abnormality in ability to taste or smell. Eight of the 28 patients (29%) have an elevated serum IgE level. Levels range from 128-781 kU/L (mean±SEM, 258±82). Four of these patients have a primary diagnosis of post influenza-like hyposmia and hypogeusia (PIHH); four have a primary diagnosis of allergic rhinitis. Patients are seven men, one woman, aged 35-71 y. Five of the 28 patients (18%) have an elevated plasma eosinophil level. Levels range from 3.7-11.9% of total white blood cells (mean±SEM, 6.1±2.3%) with eosinophil counts of 307-750 cells (mean±SEM, 462±176). Three of these patients have a diagnosis of PIHH, two have a diagnosis of allergic rhinitis. Patients are four men, one woman, aged 39-71 y. Two have both an elevated IgE and eosinophil count, one man, one woman, both with PIHH, age 39 and 71, respectively. These patients also have low levels of cAMP and cGMP in their saliva and nasal mucus.

Patients are treated and tested with theophylline to test if restoration of smell function can be restored. A comparison of this subpopulation of patients to larger group of patients is performed.

Example 4: Role of Nitric Oxide in Smell Loss

In this example the role of nitric oxide in smell loss is investigated. Phosphodiesterase (PDE) inhibitors may improve smell loss through other mechanisms, such as through nitric oxide (NO). Theophylline, a generalized PDE inhibitor, may increase nitric oxide (NO) at the same time that it increases cAMP and cGMP. Patients with hyposmia treated with theophylline may not only have increased nasal mucus cAMP and cGMP but also increased NO. NO through guanylate cyclase produces cGMP, whose elevation mediates, in part, NO stimulatory effects on smell loss. cGMP can be 1) degraded by PDE isoforms and 2) can be enhanced by PDE inhibition which maintains its presence.

To investigate this possibility, treatments with alternative pharmaceutical compositions, which may increase nitric oxide production, levels, effective amounts or half-life are administered to patients with hyposmia. Pharmaceutical compositions that are directed towards increase in cGMP and cAMP may also be administered.

Example 5: Cyclic Nucleotides in Saliva

Methods:

All studies were performed at The Taste and Smell Clinic, Washington, D.C. between February 2001 and July, 2005 and constitute studies on consecutive normal subjects and patients. Studies were approved by the Institutional Review Board of the Georgetown University Medical Center.

Parotid saliva was collected from 61 normal volunteers, aged 18-75 y [50+5 y (Mean±SEM)]. Normal volunteers were 40 men, aged 23-75 y (51±7 y) and 21 women, aged 18-69 y (49±4 y) who were well and healthy, without any acute or chronic disease and were not taking any medication. Parotid saliva was also collected from 253 patients, aged 9-83 y [55+3 y (mean±SEM)] with taste and smell dysfunction. Patients were 104 men, age 9-83 y (56+2 y) and 149 women, age 12-79 y (54±2 y).

Smell and taste function tests were obtained in all normal subjects and patients by use of standard three stimuli, forced choice, staircase fixed design measurements of detection (DT) and recognition (RT) thresholds and magnitude estimation (ME) for four tastants (NaCl for salt, for sweet, HCl for sour, urea for bitter) and four odorants (pyridine—"dead fish" odor, nitrobenzene—bitter almond odor, thiophene—petroleum odor, and amyl acetate—banana oil odor) previously described in detail with results confirmed and validated in a double-blind clinical trial and in the studies of other investigators. Normal subjects exhibited DT, RT and ME within normal range for all tastants and odorants tested.

Patients with taste and smell dysfunction exhibited a variety of sensory abnormalities secondary to several etiological factors. Etiology of onset of dysfunction included post viral infections [about 30% of patients], post concussive syndrome [about 20%], allergic rhinitis [about 15%], idiopathic causes [about 12%] and several other etiologies. Patient abnormalities of sensory function included loss of taste acuity [elevated DT, RT and ME for two or more tastants in 90% of patients], loss of smell acuity [elevated DT, RT and/or ME for two or more odorants in 98% of patients], dysgeusia [distortions of taste function including aliageusia and phantageusia, in 70%] and dysosmia [distortions of smell function including aliosmia and phantosmia, in 70%]. More than 85% of patients had more than one sensory abnormality.

Saliva was collected in the morning hours with subjects abstaining from eating or smoking at least two hours prior to collection. Saliva was collected by placing a modified Lashley cup over Stensen's duct and maximally stimulating flow by lingual placement of reconstituted lemon juice (Borden, Tarrytown, N.Y.) at 10 sec intervals. Saliva was collected continuously over an eight-12 min period until approximately 8 ml were present. Flow rate was calculated by obtaining mean fluid weight per time of collection. Saliva was stored at −20° C. until assayed.

cAMP and cGMP were measured by a spectrophotometric colormetric 96 plate ELISA technique using kits supplied by R&D Systems (Minneapolis, Minn.). Mean variation of kit standards was 5 5%. Protein was measured by obtaining spectrophotometric absorbance at 215-225 nm and use of the extinction coefficient; in this manner protein in very small samples was estimated. cAMP and cGMP were expressed in three ways; per ml saliva, per mg protein and per ml flow rate.

To determine methodological reliability cAMP and cGMP were determined using several parameters. Duplicates of six saliva samples were determined on 20 occasions; the standard deviation of these samples varied from 0.007-0.038 for both cAMP and cGMP; mean coefficients of variation varied from 1-10% for both moieties with an overall mean of 4%. cAMP and cGMP from one subject were determined on 20 separate occasions over a period of two years; the standard deviation for these determinations for cAMP (in pmol/ml) was 0.29 with a mean coefficient of variation of 3%; for cAMP/mg protein standard deviation was 0.13 with a mean coefficient of variation of 4%; for cAMP per/ml flow rate standard deviation was 0.49 with a mean coefficient of variation of 5%; for cGMP (in pmol/ml), standard deviation was 0.02 with a coefficient of variation of 6%; for cGMP (in pmol/mg protein), standard deviation was 0.007 with a coefficient of variation of 7%; for cGMP (in pmol/ml flow rate), standard deviation was 0.05 with a coefficient of variation of 10%.

Mean and SEM for each subject group were calculated. Differences between group means were calculated using Student t tests. Age data are presented only for the patients since there were sufficient gaps in the ages of the normals studied. However, calculation of age changes with the normals included did not affect the results obtained using only the patient data.

Results: Salivary cAMP and cGMP in Normal Subjects

Both cAMP and cGMP are present in parotid saliva in normal subjects in the detection range of the assay used (Table 5). Salivary cAMP is significantly higher than cGMP by all methods of determination and varied from seven-10 times higher (Table 5). Salivary cAMP levels are consistently higher in women than in men and varied from 25-49% higher (Table 5). There were no differences in flow rate, protein or age between men and women (Table 5).

Salivary cAMP and cGMP in Patients with Taste and Smell Dysfunction Compared with Normal Subjects Both cAMP and cGMP are present in parotid saliva obtained from patients with taste and smell dysfunction (Table 6). Patients exhibit lower mean concentrations of both salivary cAMP and cGMP than do normal subjects but only cAMP levels are significantly lower (Table 6). These results are independent of methods of expression. Concentrations of cAMP were eight-nine times higher than cGMP (Table 6). Mean salivary flow rate was significantly lower in patients than in normals (Table 6).

Salivary cAMP was significantly lower than normal in both men and women patients, respectively (Table 7) whereas there were no differences in cGMP (Table 7). Mean salivary flow rates were significantly lower among both men and women patients compared to normals (Table 7).

Salivary cAMP and cGMP with Respect to Age

Figure 14:
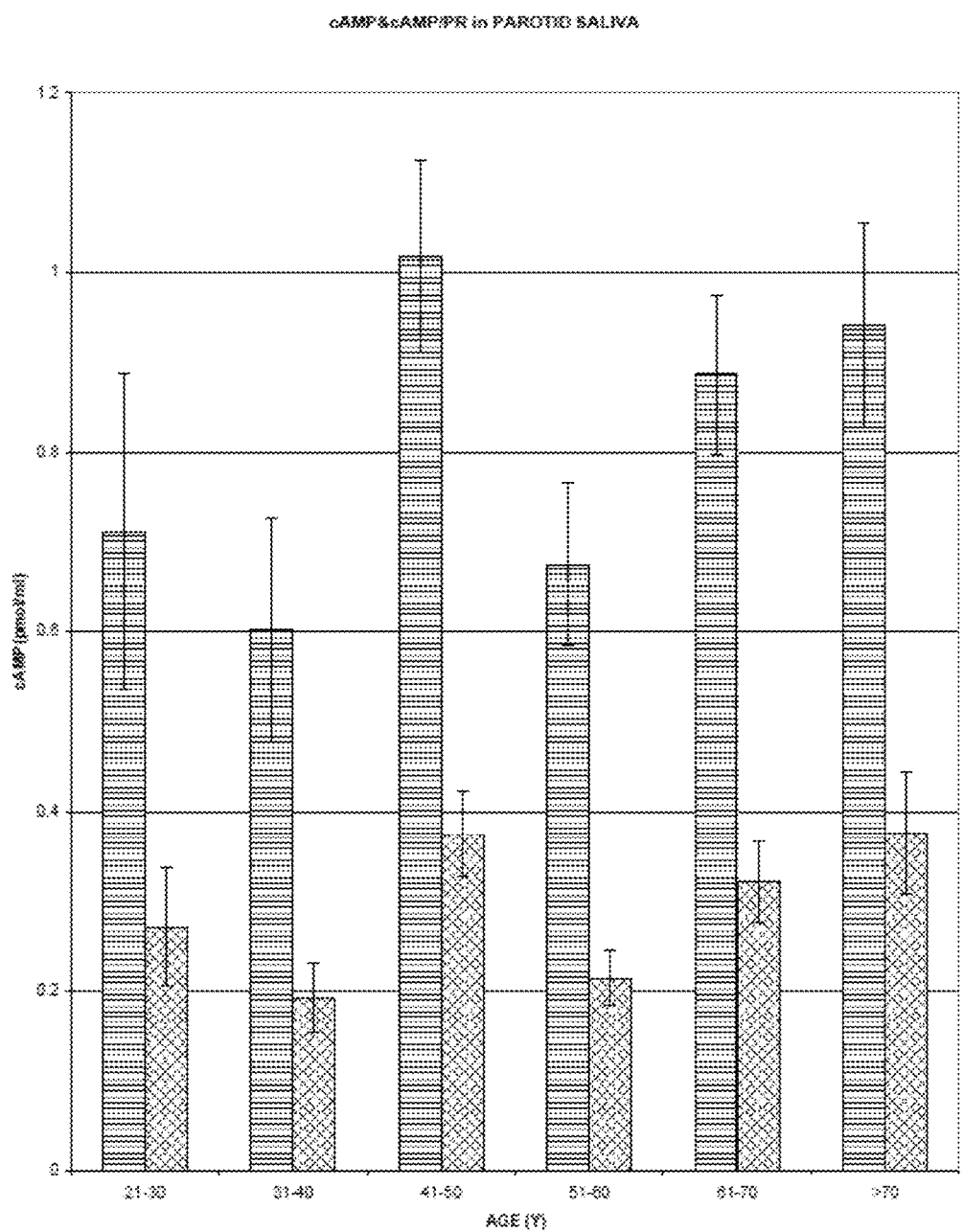
FIG. 14: Parotid saliva cAMP with respect to age. Hatched bars reflect cAMP with lines indicating ±1 SEM. Dotted bars reflect cAMP/protein with lines indicating ±1 SEM. There is a complex shaped function with age with a peak at age 41-50 yr., decreasing thereafter with a final increase at age >70 y.
Figure 15:
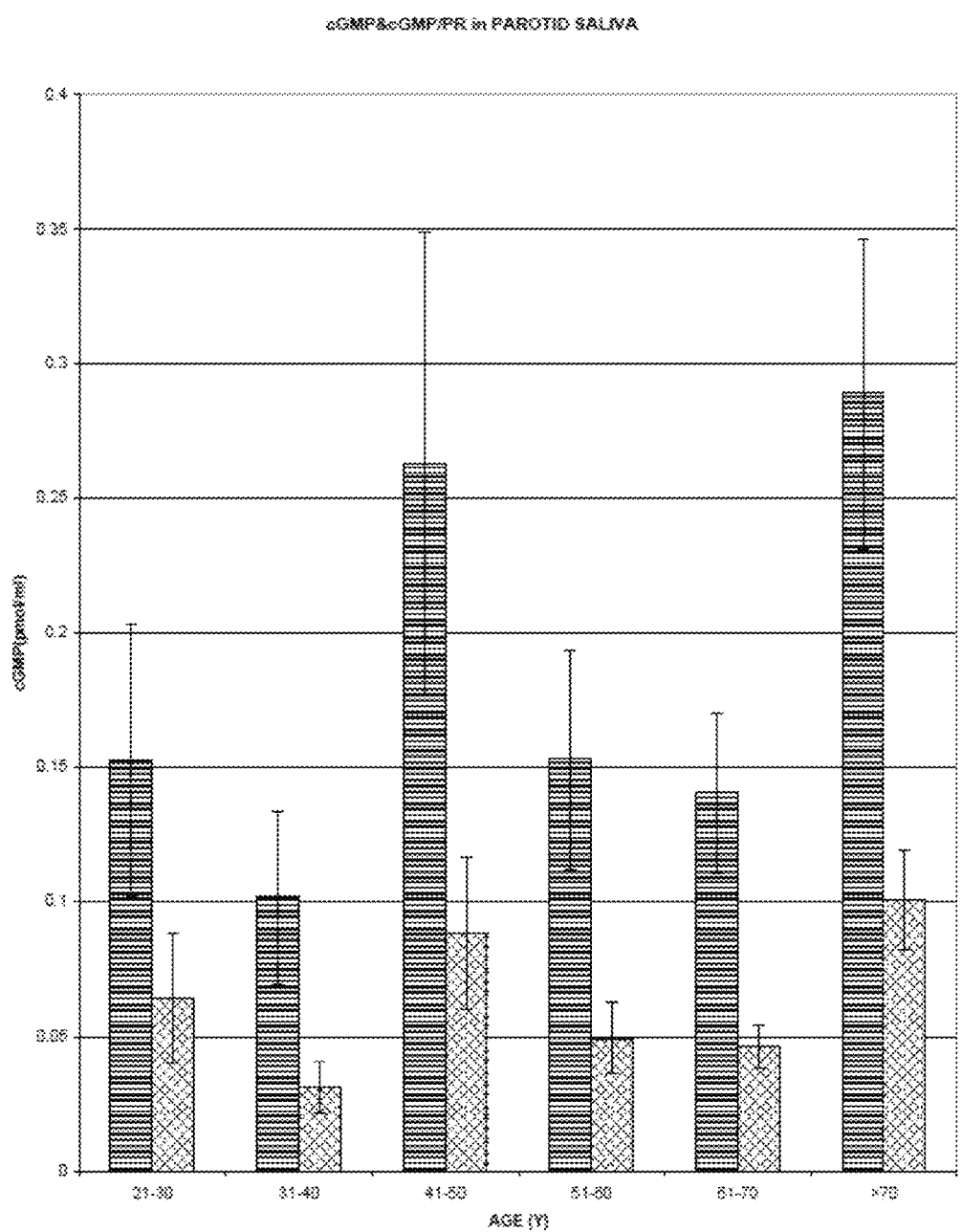
FIG. 15: Parotid saliva cGMP with respect to age. Hatched bars reflect cGMP with lines indicating ±1 SEM. Dotted bars reflect cGMP/protein with lines indicating ±1 SEM. cGMP increases with age with a peak at age 41-50 yr., decreasing thereafter with a final increase at age >70 y.

Salivary cAMP and cGMP concentrations vary with respect to age (FIGS. 14 and 15). While number of subjects is relatively small there is a complex pattern for cAMP over the age range, generally increasing with age reaching a peak at 41-50 y, then decreasing until >70 y when levels 9 increased again (FIG. 14). For cGMP there is a similar pattern with maximum values also reached at 41-50 y, then values decreasing thereafter but, as with cAMP, with a terminal increase at >70 y. For cAMP and cAMP/protein age differences were significantly different comparing ages 31-40 with ages 41-50 ($p<0.02$, and $p<0.05$, respectively, t test) and ages 51-60 with ages 41-50 ($p<0.05$ and $p<0.01$ respectively, t test). For cGMP and cGMP/protein age differences were significantly different comparing ages 31-40 with ages >70 ($p<0.01$ and $p<0.005$, respectively, t test) and ages 61-70 with ages >70 ($p<0.05$, t test). Salivary protein secretion and flow rate did not change significantly throughout the aging process (Table 8).

TABLE 5 cAMP and cGMP IN PAROTID SALIVA IN NORMAL SUBJECTS

| NORMALS | cAMP | | | cGMP | | | PROTEIN mg/dl | FLOW RATE ml/min | AGE y |
|---|---|---|---|---|---|---|---|---|---|
| | pmol/ml | pmol/mg protein | pmol/min flow rate | pmol/ml | pmol/mg protein | pmol/min flow rate | | | |
| Total (61) | 2.00 ± 0.19 | 0.63 ± 0.06 | 2.17 ± 0.19 | 0.21 ± 0.02$^a$ | 0.006 ± 0.009$^a$ | 0.23 ± 0.04$^a$ | 3.17 ± 0.18 | 0.92 ± 0.05 | 50 ± 5 |
| Men (40) | 1.69 ± 0.17 | 0.53 ± 0.04 | 1.86 ± 0.24 | 0.22 ± 0.05$^a$ | 0.069 ± 0.015$^a$ | 0.24 ± 0.08 | 3.17 ± 0.10 | 0.91 ± 0.02 | 51 ± 7 |
| Women (21) | 2.26 ± 0.31 | 0.71 ± 0.10 | 2.43 ± 0.18 | 0.21 ± 0.02$^a$ | 0.066 ± 0.009$^a$ | 0.23 ± 0.02 | 3.18 ± 0.19 | 0.93 ± 0.06 | 49 ± 4 | cAMP and cGMP in parotid saliva in normal subjects.

( ) reflects subject number.

Data are presented as Mean ± SEM for each parameter studied.

P values (determined by Student t test) are considered significant if <0.05

[$^a$p < 0.001, compared to cAMP respectively].

TABLE 6 cAmp and cGMP IN PAROTID SALIVA IN NORMAL
SUBJECTS AND IN PATIENTS WITH SELL LOSS

| | cAMP | | | cGMP | | | | FLOW | |
|---|---|---|---|---|---|---|---|---|---|
| | pmol/ml | pmol/mg protein | pmol/min flow rate | pmol/ml | pmol/mg protein | pmol/min flow rate | PROTEIN mg/dl | RATE ml/min | AGE y |
| Patients (253) | $0.83 \pm 0.04^a$ | $0.27 \pm 0.02^a$ | $1.19 \pm 0.07^a$ | $0.16 \pm 0.02$ | $0.050 \pm 0.007$ | $0.23 \pm 0.02$ | $3.10 \pm 0.06$ | $0.70 \pm 0.02^a$ | $55 \pm 3$ |
| Normals (61) | $2.00 \pm 0.19$ | $0.63 \pm 0.06$ | $2.17 \pm 0.19$ | $0.21 \pm 0.02$ | $0.066 \pm 0.009$ | $0.23 \pm 0.04$ | $3.17 \pm 0.18$ | $0.92 \pm 0.05$ | $50 \pm 5$ | cAMP and cGMP in parotid saliva in patients with taste and smell fysfunction and in normal subjects.
( ) reflects subject number.
Data are presented as Mean ± SEM for each parameter studied.
P values (determined by Student t test) are considered significant if <0.05
[$^a$p < 0.001, with respective to normals].

TABLE 7 cAMP and cGMP IN PAROTID SALIVA IN NORMAL MEN
AND WOMEN AND MEN AND WOMEN WITH SMELL LOSS

| | cAMP | | | cGMP | | | | FLOW | |
|---|---|---|---|---|---|---|---|---|---|
| | pmol/ml | pmol/mg protein | pmol/min flow rate | pmol/ml | pmol/mg protein | pmol/min flow rate | PROTEIN mg/dl | RATE ml/min | AGE y |
| PATIENTS | | | | | | | | | |
| Men (104) | $0.90 \pm 0.06^a$ | $0.28 \pm 0.03^a$ | $1.27 \pm 0.13^c$ | $0.14 \pm 0.20$ | $0.044 \pm 0.005$ | $0.20 \pm 0.03$ | $3.18 \pm 0.09$ | $0.71 \pm 0.03^a$ | $56 \pm 2$ |
| Women (149) | $0.80 \pm 0.07^a$ | $0.26 \pm 0.03^a$ | $1.14 \pm 0.14^a$ | $0.17 \pm 0.02$ | $0.062 \pm 0.009$ | $0.24 \pm 0.05$ | $3.05 \pm 0.09$ | $0.70 \pm 0.03^b$ | $54 \pm 2$ |
| NORMALS | | | | | | | | | |
| MEN (40) | $1.69 \pm 0.17$ | $0.53 \pm 0.04$ | $1.86 \pm 0.24$ | $0.22 \pm 0.05$ | $0.069 \pm 0.015$ | $0.24 \pm 0.09$ | $3.17 \pm 0.10$ | $0.91 \pm 0.02$ | $51 \pm 7$ |
| Women (21) | $2.26 \pm 0.31$ | $0.71 \pm 0.10$ | $2.43 \pm 0.18$ | $0.21 \pm 0.02$ | $0.069 \pm 0.009$ | $0.23 \pm 0.02$ | $3.18 \pm 0.19$ | $0.93 \pm 0.07$ | $49 \pm 4$ | cAMP and cGMP in parotid saliva in men and women patients with taste and smell dysfunction and in normal men and women.
( ) reflects subject number.
Data are presented as Mean ± SEM for each parameter studied.
P values (determined by Student t test) are considered significant if <0.05
[$^a$p < 0.001 with respective to normal men or women;
$^c$p < 0.05 with respect to normal men;
$^b$p < 0.005 with respect to normal women].

TABLE 8

CHANGES IN PAROTID SALIVA PROTEIN
AND FLOW RATE RELATED TO AGE

| AGE | AGE | PROT mg/dl | Flow Rate ml/min |
|---|---|---|---|
| <20 (5) | $16 \pm 2$ | $2.59 \pm 0.41$ | $1.00 \pm 0.30$ |
| 21-30 (15) | $27 \pm 1$ | $2.79 \pm 0.17$ | $0.76 \pm 0.06$ |
| 31-40 (23) | $36 \pm 1$ | $3.27 \pm 0.14$ | $0.63 \pm 0.04$ |
| 41-50 (46) | $45 \pm 1$ | $2.99 \pm 0.15$ | $0.73 \pm 0.05$ |
| 51-60 (46) | $56 \pm 1$ | $3.40 \pm 0.14$ | $0.70 \pm 0.04$ |
| 61-70 (37) | $66 \pm 1$ | $3.08 \pm 0.16$ | $0.69 \pm 0.04$ |
| >70 (30) | $77 \pm 1$ | $2.94 \pm 0.17$ | $0.64 \pm 0.06$ |

Parotid saliva protein and flow rate related to age.
( ) reflects subject matter.
Data are presented as Mean ± SEM.

Example 6: Decreased Parotid Salivary Cyclic
Nucleotides Related to Smell Loss Severity in
Patients with Taste and Smell Dysfunction Methods:

All studies were performed at The Taste and Smell Clinic, Washington, D.C., between February 2001 and July 2005 and constitute studies on consecutive healthy subjects and patients. Studies were approved by the Institutional Review Board of the Georgetown University Medical Center.

Parotid saliva was collected from 61 healthy volunteers, aged 18 to 75 years (mean f SEM, 50±5 years). The volunteers were 40 men, aged 23 to 73 years (51±7 years), and 21 women, aged 19 to 69 years (49±4 years), who were well and healthy, without any acute or chronic disease, and not taking any medication. Smell and taste function in each subject was within normal limits. Parotid saliva was also collected from 253 patients, aged 9 to 83 years (55±3 years), with taste and smell dysfunction. Patients were all those with taste and smell dysfunction who had loss of smell. These included 104 men, aged 9 to 83 years (56±2 years), and 149 women, aged 12 to 79 years (49±4 years).

Saliva was collected in the morning hours with subjects abstaining from eating or smoking at least 2 hours before collection. Saliva was collected by placing a modified Lashley cup over the Stensen duct and maximally stimulating flow by lingual placement of reconstituted lemon juice (Borden, Tarrytown, N.Y.) at 10-second intervals. In patients, saliva was collected immediately after completion of sensory tasting. Saliva was collected continuously over an 8- to 12-minute period until approximately 8 mL was collected. Flow rate was calculated by obtaining mean fluid weight per time of collection. Saliva was stored at −20° C. until assayed.

Cyclic AMP and cGMP were measured by a sensitive spectrophotometric 96-plate enzyme-linked immunosorbent assay technique using kits supplied by R&D Systems (Minneapolis, Minn.). Mean variation of kit standards was less than or equal to 5%. Protein was measured by obtaining spectrophotometric absorbance at 215 to 225 nm with the use of the extinction coefficient; in this manner, protein in very small samples was estimated. Cyclic AMP and cGMP in picomole/concentration were expressed in 3 ways: per milliliter saliva, per milligram protein, and per milliliter flow rate.

To determine methodological reliability, cAMP and cGMP were determined in several ways. Duplicates of 6 saliva samples were determined on 20 occasions; the standard deviation of these samples varied from 0.007 to 0.038 for cAMP and 0.007 to 0.038 for cGMP, respectively; mean coefficients of variation varied from 1% to 10% for each moiety. Cyclic AMP and cGMP from 1 subject were determined on 12 separate occasions over a period of 2 years. The standard deviation for these determinations for cAMP (picomoles per milliliter) was 0.29 with a mean coefficient of variation of 3%; for cAMP (picomoles per milligram protein), 0.13 with a mean coefficient of variation of 4%; for cAMP (picomoles per milliliter flow rate), 0.49 with a mean coefficient of variation of 5%; for cGMP (picomoles per milliliter), 0.02 with a coefficient of variation of 6%; for cGMP (picomoles per milligram protein), 0.007 with a coefficient of variation of 7%; and for cGMP (picomoles per milliliter flow rate), 0.05 with a coefficient of variation of 10%.

Smell loss was measured by psychophysical techniques by use of a forced-choice, 3-stimuli, stepwise staircase technique in a fixed controlled design. Efficacy of these techniques and results therefrom were previously documented in a double-blind clinical trial. Four odors were used: pyridine or "dead-fish" odor, nitrobenzene or bitter-almond odor, thiophene or petroleum-based odor, and amyl acetate or banana oil odor. Detection thresholds (DTs), recognition thresholds (RTs), and magnitude estimation (ME) for each odor were determined in this fixed controlled design.

Odors were presented in the order of thiophene, amyl acetate, nitrobenzene, and pyridine. Odors were stored in 60-mL, wide-mouth, screw-capped amber bottles with 12 mL of test solution in each bottle. For each test, each patient was seated at a right angle to the test administrator and was shielded from any visual contact with the test materials. For each test, the patient was required to sniff the headspace above the solution in each bottle in a sequence of 3 stimuli in succession in a fixed, mixed design. Two of the stimuli were emollient (water or light mineral oil), and one was emollient with odorant. Each of the 3 solutions was opened and closed in sequence with the patients sniffing about 2 to 3 cm above the edge of the open bottle for 2 to 10 seconds. Each sequence of 3 stimuli required 20 to 60 seconds, with a rest period of 5 to 20 seconds between each set of 3 stimuli.

The patient was required to perform 3 tasks after the presentation of each set of 3 stimuli. First, the patient determined which stimulus with odorant was different from the 2 emollients without odorant (to detect a difference among the 3 stimuli); second, the patient described the odorant in the odorant containing stimulus in words, that is, recognizing and describing the character of the odorant; and third, the patient estimated the intensity of the identified odorant using a scale from 1 to 100 (an estimate of magnitude intensity). On this scale, 100 was described as the most intense odorant of the odorant type previously experienced under normal conditions within that odor category. Thus, 1 was the least intense, 100 was the greatest, and any intensity between 1 and 100 was judged accordingly.

Testing always began at what had been previously determined to be the upper limit of normal detection ($10^{-5}$ mol/L for each odorant). If the patient detected and recognized the odorant correctly at this concentration, the odorant concentration was decreased stepwise ($10^{-6}$, $10^{-7}$, $10^{-8}$, and $10^{-9}$ mol/L) until the patient could no longer correctly detect or recognize any difference among the 3 stimuli. If the patient could neither detect nor recognize the odorant correctly at $10^{-5}$ mol/L, the odorant concentration was increased stepwise ($10^{-4}$, $10^{-3}$, $10^{-2}$, $10^{-1}$, and 100 mol/L and absolute) until the patient could detect and recognize the odorant correctly. Using this staircase, turnaround technique, odorant concentrations were either increased or decreased until the patient detected and recognized correctly the odorant as different from emollient 2 out of 3 times at 1 concentration and could not do so at the next lower or higher concentration. Thus, if the patient could neither detect nor recognize correctly $10^{-5}$, $10^{-4}$, and $10^{-3}$ mol/L odorant but could both detect and recognize correctly odorant at $10^{-2}$ mol/L, the next stimulus presented was the next lower concentration, $10^{-3}$ mol/L. If the patient could once again neither detect nor recognize correctly the stimulus at $10^{-3}$ mol/L, the stimulus at $10^{-2}$ mol/L was once again presented. If the patient once again detected and correctly recognized the stimulus at $10^{-2}$ mol/L, this part of the test was completed because the patient gave 2 incorrect responses at 1 stimulus concentration and 2 correct responses at the next higher concentration. The odorant concentration at $10^{-2}$ mol/L was considered the DT and RT.

Magnitude estimation determination began in healthy subjects at what had previously been determined to be the lower limit of normal odor recognition ($10^{-2}$ mol/L), although measurements of odorant stimulus magnitude was always requested along with each statement of odorant detection and recognition. Thus, the actual ME determination was calculated using the intensity and correct recognition response by averaging intensity given from odorant concentrations $10^{-2}$, $10^{-1}$, or 100 mol/L and absolute. The mean of these numbers comprised the ME response.

Because interval presentations for DT and RT were not equal, odor concentrations were transformed to a linear scale (e.g., $10^{-9}$ mol/L=1, $10^{-8}$ mol/L=2, ... absolute=11) so that a scale of equal units and an absolute zero was obtained. Using this scale, DT and RT for each patient were assigned a number, and mean±SEM of responses for each patient group was calculated. Mean±SEM for ME for each patient group was similarly determined (in percentage) using the individual values previously determined.

Based upon results of DT, RT, and ME, smell loss degree was classified as shown in Table 9. This classification indicates that patients with anosmia have the greatest severity of smell loss; those with type I hyposmia, the next greatest; those with type II hyposmia, the next greatest; and those with type III hyposmia, the least severe loss. Related to severity of smell loss, acuity decreased from greatest to least degree of smell loss such that anosmia N type I hyposmia N type II hyposmia N type III hyposmia (Table 9).

Each measurement of saliva cAMP and cGMP was placed into 1 of the 4 categories of smell loss severity. Afterward, mean±SEM for cyclic nucleotides in each group of loss severity was calculated. Differences between group means were calculated using Student t tests. Biochemical determination of each salivary cAMP and cGMP level was also correlated with each of the 4 smell loss categories by use of a Spearman rank correlation technique, and significance of correlation was determined.

All studies of saliva cyclic nucleotides were initially coded. Results of smell loss classification were obtained independent of any saliva cyclic nucleotide results. Only after all patient classifications of smell loss were defined were saliva studies uncoded and correlated.

Results:

Levels of salivary cAMP in all patients with smell loss were significantly lower than those in healthy subjects (Table 10). When categorized by loss severity, there was a consistent decrease in salivary cAMP and cGMP with increased loss severity (Table 10).

Although only 2 patients with anosmia were studied, mean levels of both cAMP and cGMP were lower than normal and lower than in any other smell loss type (Table 10).

Patients with the next most severe type of hyposmia (type I) had significantly lower salivary levels of cAMP than did both patients with the next least severe smell loss type (type II) and healthy subjects. When categorized by flow rate, cAMP was significantly lower than in patients with types II and III hyposmia. When categorized with respect to protein, cAMP in patients with type II hyposmia, although not significantly different from that in patients with type III hyposmia, was 6% lower (Table 10) and, when characterized by flow rate levels, was 7% lower (Table 10).

Levels of cGMP were 2 to 3 times lower than in healthy subjects (Table 10). Although levels were not significantly different, cGMP in patients with type I hyposmia were one half that in patients with type III hyposmia. In patients with type II hyposmia, levels were 46% those with type III hyposmia. Mean salivary cGMP for patients with type III hyposmia (the least severe type of hyposmia), although 27% lower than levels of healthy subjects, were not significantly different from normal levels (Table 10).

Salivary levels of cAMP were higher than those for cGMP in all patient groups except for the 2 patients with anosmia in whom measurements of both cyclic nucleotides were close to zero. However, levels of cAMP in the patients were only 3 to 5 times higher than cGMP, whereas in healthy subjects, this difference ranged from 7 to 10 times higher.

Correlation of salivary cAMP with smell loss type was rs=−0.83 (P b.001); correlation of salivary cGMP with smell loss type was rs=−0.79 (P b.001). These demonstrate that the higher the level of salivary cGMP or cGMP, the less severe the loss of smell acuity among these patients. Saliva flow rate was significantly lower than normal only in patients with type II hyposmia.

Salivary cyclic nucleotides were also determined in patients with smell loss classified by both degree of smell loss and sex (Table 11). There were no significant sex differences in either salivary cAMP or cGMP related to degree of smell loss. However, both men and women with type II hyposmia were significantly older than men and women with type I hyposmia; salivary protein was significantly lower in women with type I hyposmia than in those with type II hyposmia (Table 11).

TABLE 9

| CLASSIFICATION OF SEVERITY OF ODOR LOSS | | | |
|---|---|---|---|
| SEVERITY OF SMELL LOSS | DT | RT | ME |
| Anosmia | 0 | 0 | 0* |
| Hyposmia | | | |
| Type I | − | 0 | 0* |
| Type II | − | −* | ≥0 < normal |
| Type III | + | +* | ≥0 < normal |

Detection threshold, RT, and ME.

0 indicates inability to both detect and recognize correctly any odorant at any concentrations;

0*, the patient is unable to recognize correctly any oderant at any concentration, rendering any intensity measurement invalid or 0;

DT−, inability to detect any oderant at ≤$10^{-5}$ mol/L (responses are ≥$10^{-4}$ mol/L for all odorants);

RT−*, inability to recognize correctly any oderant at ≤$10^{-2}$ mol/L (responses are ≥$10^{-1}$ mol/L for all odorants);

DT+, ability tp detect all oderants at ≤$10^{-5}$ mol/L

RT+*, ability to recognize correctly all odorants at ≤$10^{-2}$ mol/L.

Magnitude estimation, normal (pyridine, <61%; nitobenzene, <46%; thiophene, <63%, amyl acetate, <48%).

TABLE 10

CYCLIC AMP AND CGMP IN PAROTID SALIVA IN PATIENTS WITH TASTE AND SMELL LOSS CLASSIFIED BY SEVERITY OF LOSS

| Smell loss | cAMP | | | cGMP | | | PROTEIN mg/dl | FLOW RATE mL/min | AGE y |
|---|---|---|---|---|---|---|---|---|---|
| | pmol/ml | pmol/mg protein | pmol/min flow rate | pmol/ml | pmol/mg protein | pmol/min flow rate | | | |
| Anosmia (2) | 0.22 | 0.06 | 3.70 | 0.62 | 0.01 | 0.06 | 0.62 | 3.70 | 56 |
| Hyposmia | | | | | | | | | |
| Type I (54) | 0.78 ± 0.09$^A$ | 0.26 ± 0.02$^A$ | 3.01 ± 0.09 | 0.76 ± 0.09$^C$ | 0.047 ± 0.010$^{B,B1}$ | 0.18 ± 0.04 | 0.76 ± 0.09$^C$ | 3.01 ± 0.09 | 47 ± 2 |
| II (189) | 0.87 ± 0.04$^A$ | 0.28 ± 0.02$^B$ | 3.12 ± 0.02 | 0.68 ± 0.07$^E$ | 0.047 ± 0.005$^{A,B1}$ | 0.22 ± 0.05 | 0.68 ± 0.07$^E$ | 3.12 ± 0.02 | 57 ± 1 |
| III (8) | 1.01 ± 0.12$^A$ | 0.33 ± 0.06$^B$ | 3.09 ± 0.14 | 0.62 ± 0.15 | 0.091 ± 0.009 | 0.45 ± 0.09 | 0.62 ± 0.15 | 3.09 ± 0.14 | 51 ± 5 |
| Healthy subjects (61) | 2.00 ± 0.19 | 0.63 ± 0.06 | 3.17 ± 0.18 | 0.92 ± 0.05 | 0.066 ± 0.009 | 0.23 ± 0.04 | 0.92 ± 0.05 | 3.17 ± 0.18 | 50 ± 5 |

Numbers in parentheses indicate number of subjects.
With respect to Type II hyposmia:
$^A$p < .001,
$^B$p < .005,
$^C$p < .02,
$^E$p < .01.
With respect to Type III hyposmia:
$^{B1}$p < .005.
*Mean ± SEM

TABLE 11

CYCLIC AMP AND CGMP CONCENTRATIONS IN PAROTID SALIVA OF MEN AND WOMEN WITH ANOSMIA AND HYPOSMIA

| | cAMP | | | cGMP | | | PROTEIN mg/dL | FLOW RATE mL/min | AGE y |
|---|---|---|---|---|---|---|---|---|---|
| | pmol/mL | pmol/mg protein | pmol/min flow rate | pmol/mL | pmol/mg protein | pmol/min flow rate | | | |
| Men | | | | | | | | | |
| Anosmia (2) | 0.22 | 0.06 | 0.35 | 0.05 | 0.01 | 0.06 | 3.70 | 0.62 | 56 |
| Hyposmia | | | | | | | | | |
| Type I (28) | 0.75 ± 0.11* | 0.24 ± 0.04 | 1.03 ± 0.15 | 0.13 ± 0.03 | 0.03 ± 0.012 | 0.18 ± 0.06 | 3.05 ± 0.09 | 0.74 ± 0.05 | 50 ± 3$^{D1}$ |
| Type II (109) | 0.84 ± 0.07 | 0.27 ± 0.03 | 1.25 ± 0.14 | 0.20 ± 0.04 | 0.64 ± 0.023 | 0.30 ± 0.07 | 3.14 ± 0.09 | 0.67 ± 0.03 | 58 ± 2 |
| Type III (2) | 0.99 | 0.36 | 1.10 | 0.39 | 0.14 | 0.43 | 2.78 | 0.90 | 61 |
| Women | | | | | | | | | |
| Hyposmia | | | | | | | | | |
| Type I (26) | 0.79 ± 0.09$^{C1}$ | 0.27 ± 0.03 | 1.07 ± 0.10$^{A1}$ | 0.16 ± 0.03 | 0.054 ± 0.010 | 0.22 ± 0.05 | 2.97 ± 0.11$^{E1}$ | 0.74 ± 0.05$^{C1}$ | 46 ± 3$^{B1}$ |
| Type II (80) | 0.97 ± 0.05 | 0.30 ± 0.02 | 1.62 ± 0.09$^{C2}$ | 0.15 ± 0.01 | 0.047 ± 0.004 | 0.25 ± 0.02 | 3.25 ± 0.05$^{D2}$ | 0.60 ± 0.02 | 56 ± 1 |
| Type III (6) | 1.07 ± 0.16 | 0.42 ± .015 | 1.98 ± 0.07 | 0.21 ± 0.10 | 0.083 ± 0.040 | 0.38 ± 0.09 | 2.54 ± 0.10 | 0.54 ± 0.10 | 50 ± 16 |

Cyclic AMP and cGMP concentrations in parotid saliva of men and women with anosmia and hyposmia
Numbers in parentheses indicate number of subjects.
With respect to Type II hyposmia:
$^{A1}$p < .001,
$^{B1}$p < .005,
$^{C1}$p < .02,
$^{D1}$p < .05,
$^{E1}$p < .01.
With respect to Type III hyposmia:
$^{C2}$p < .02,
$^{D2}$p < .05.
*Mean ± SEM.

Example 7: Intranasal Administration of Theophylline

Objective:

To determine whether intranasal theophylline methylpropyl paraben can correct hyposmia and hypogeusia.

Design:

We performed an open-label pilot study in patients with hyposmia and hypogeusia under the following 3 conditions: (1) before treatment, (2) after oral theophylline treatment, and (3) after intranasal theophylline treatment. Under each condition, we performed subjective evaluations of taste or smell functions, quantitative measurements of taste (gustometry) and smell (olfactometry), and measurements of serum theophylline level and body weight.

Patients:

Ten patients with hyposmia and hypogeusia clinically related to the effects of viral illness, allergic rhinitis, traumatic brain injury, congenital hyposmia, and other chronic disease processes were selected.

Interventions:

Oral theophylline methylpropyl paraben, 200 to 800 mg/d for 2 to 12 months, was administered to each patient. This treatment was discontinued for 3 weeks to 4 months when intranasal theophylline methylpropyl paraben, 20 pg/d in each naris, was administered for 4 weeks.

Main Outcome Measures:

At termination of each condition, taste or smell function was determined subjectively, by means of gustometry and olfactometry, with measurement of serum theophylline levels and body weight.

Results:

Oral theophylline treatment improved taste or smell acuity in 6 patients after 2 to 12 months of treatment. Intranasal theophylline treatment improved taste or smell acuity in 8 patients after 4 weeks, with improvement greater than after oral administration. No adverse effects accompanied intranasal drug use. Body weight increased with each treatment but was greater after intranasal than after oral administration.

Conclusions:

Intranasal theophylline treatment is safer and more effective in improving hyposmia and hypogeusia than oral theophylline treatment.

Loss of smell (hyposmia) and taste (hypogeusia) are common symptoms that affect many thousands of patients in the United States, as reported by several investigators. Effective treatment for these symptoms has been demonstrated only recently and has not been formally established.

Before effective treatment to correct loss of smell and taste can be established, a biochemical basis for the cause of these symptoms is necessary. To accomplish this, we determined that these symptoms are commonly caused by decreased secretion of several growth factors in the saliva and nasal mucus. The growth factors act on stem cells in taste buds and olfactory epithelial cells to generate the elegant repertoire of cellular components in these sensory organs. Growth factor stimulation of these sensory organs is thought to maintain normal taste or smell function. If these growth factors were diminished by any of several diseases and pathological conditions, then hyposmia and hypogeusia occur. These conditions and diseases can include trace metal deficiencies; vitamin deficiencies; liver disease; diabetes mellitus; other metabolic, otolaryngological, and neurodegenerative disorders, including multiple sclerosis, Parkinson disease, and Alzheimer disease; and other neurological disorders. Effective treatment to increase secretion of these growth factors is therefore necessary to improve hypogeusia and hyposmia and return taste or smell function to normal as demonstrated by several previous studies.

To understand more about these processes, a comprehensive study of many patients with loss of smell and taste determined that levels of the salivary and nasal mucus growth factors cyclic adenosine monophosphate (cAMP) and cyclic guanosine monophosphate (cGMP) were lower than in healthy subjects and were responsible for the onset of hyposmia and hypogeusia in many of these patients. Indeed, as hyposmia increased in severity, levels of these salivary and nasal mucus growth factors decreased in a consistent manner.

To increase salivary and nasal mucus cAMP and cGMP levels and thereby correct hypogeusia and hyposmia, we hypothesized that treatment with a phosphodiesterase inhibitor would be useful. To test this hypothesis, a previous study from our institution administered oral theophylline to 312 patients with hyposmia and hypogeusia in an open-label controlled clinical trial. Results of this study demonstrated that oral theophylline treatment successfully corrected hyposmia in more than 50% of these patients. Subsequent investigators have used other oral phosphodiesterase inhibitors to correct hyposmia. An open-label study also demonstrated that, as nasal mucus cAMP and cGMP levels increased, hyposmia was corrected, whereas in patients in whom these moieties did not increase, hyposmia was not corrected. These results suggested that some patients can be resistant to treatment with oral theophylline.

However, successful treatment with oral theophylline that increased nasal mucus levels of cAMP and cGMP required increased theophylline doses, sometimes prolonged treatment duration, and endurance of adverse effects, including restlessness, gastrointestinal tract discomfort, sleep difficulties, tachycardia, and other unwanted symptoms. Theophylline treatment also required regular determinations of blood theophylline levels to ensure adequate drug absorption and lack of toxic effects. These efforts limited use of this orally administered drug.

Because of these adverse effects, we wished to learn more about the pharmacology of theophylline administration. After treatment with oral theophylline, the drug was found in blood, nasal mucus, and saliva in a dose dependent manner. These results were consistent with improvement in smell function as demonstrated in patients with hyposmia in the prior clinical trial. Results of these studies and efforts to improve therapeutic efficacy and reduce adverse effects of oral theophylline administration resulted in intranasal administration of the drug. In this manner, the drug could affect olfactory receptors more directly without causing the systemic adverse effects associated with oral therapy.

To accomplish this, with assistance of an established medical device company, an intranasal delivery device was developed. With assistance of an established pharmaceutical company, the drug was packaged for sterile, intranasal delivery. Using this device, an open-label, single source, controlled pilot study in 10 patients with hyposmia and hypogeusia and with levels of parotid saliva and nasal mucus cAMP and cGMP below the reference range was performed to determine safety and to compare smell and taste responses after intranasal theophylline treatment, with patient responses before any treatment and after oral theophylline treatment.

Methods

Patients

We selected 10 patients with hyposmia and hypogeusia from the 312 patients who participated in the prior open-label controlled clinical trial for this pilot study. Each patient had undergone previous evaluation before any drug treatment, followed by treatment with oral theophylline. These patients had hyposmia and hypogeusia and exhibited levels of cAMP and cGMP lower than their respective reference ranges in the saliva and nasal mucus before theophylline treatment. These 10 patients were selected from the group undergoing previous evaluation and treatment for the intranasal trial because (1) their response to oral theophylline was subjectively submaximal; (2) they developed adverse effects after attempts to increase the drug dose to obtain a more maximal clinical response, thus limiting the administered drug dose; and (3) they resided in an area in close proximity to The Clinic, which made their frequent return visits to The Clinic more practical for any additional clinical trial.

These 10 patients included 7 men, aged 37 to 77 (mean [SEM] age, 64 [6]) years, and 3 women, aged 47 to 77 (62 [11]) years. Patients had 1 of the following 5 different clinical causes of sensory dysfunction: allergic rhinitis (n=3), post influenza-like hyposmia and hypogeusia (n =3), head injury (n=2), congenital hyposmia49 (n=1), and other disorders (n=11). Patients served as their own control throughout each condition of this study. The conditions included no treatment (before entry into the oral theophylline study), oral theophylline treatment, and intranasal theophylline treatment.

Procedures

Subjective changes in smell and taste function under each study condition were measured by questionnaire before measurements of smell or taste function. Responses were graded on a scale from 0 to 100, with 0 reflecting no subjective response in overall sensory function; 100, return to normal sensory function; and values between 0 and 100 intermediate responses. Overall sensory function was defined as the ability to smell all odors and identify all tastants, although response intensity varied.

Smell and taste functions under each study condition were measured by standardized psychophysical sensory testing techniques. Measurements included determination of detection thresholds (DTs), recognition thresholds (RTs), magnitude estimation (ME), and hedonic response (HR) for 4 odors (i.e., pyridine [dead fish], nitrobenzene [bitter almond], thiophene [petroleum], and amyl acetate [banana oil]) (olfactometry) and for 4 tastants (i.e., sodium chloride [salt], sucrose [sweet], hydrochloride [sour], and urea [bitter]) (gustometry). These techniques have been previously described with olfactometry confirmed in a prior controlled double-blind clinical trial. Each measurement was performed independent of any prior knowledge of response.

Serum theophylline levels were measured by fluorescence polarization at each treatment condition. Body weight was measured with a calibrated clinical scale during each study condition and reported at the final measurement in each study condition.

Study Protocol

The patients each underwent initial clinical evaluation at The Clinic to establish the cause, degree, and character of hyposmia and hypogeusia exhibited. Measurements in blood, urine, erythrocytes, saliva, and nasal mucus determined before their entry into the open trial of oral theophylline established the biochemical cause of their hyposmia and hypogeusia to be related to their levels of saliva and nasal mucus cAMP and cGMP being lower than the reference range. These 10 patients were then selected for this study on the basis of the laboratory and clinical criteria noted previously.

The 10 patients in this intranasal pilot study entered into the previous oral theophylline study according to a protocol approved by the institutional review board of the Georgetown University Medical Center. In this prior trial, oral theophylline was administered daily in 2 divided doses (at breakfast and lunch) of 200, 400, 600, or 800 mg for 2 to 12 months of treatment. Treatment was divided into 2- to 4-month periods, at which time patients returned to The Clinic for measurements of subjective sensory responses, olfactometry, gustometry, serum theophylline level, and body weight. If oral theophylline treatment failed to correct hyposmia at a given dose, the theophylline dose was increased by 200 mg, and the patient underwent reevaluation at 2- to 4-month intervals to a dose of 800 mg. As noted previously, study patients did not obtain a maximal clinical response to oral theophylline or, while taking oral theophylline at a given dose, demonstrated some clinical improvement but experienced significant adverse effects that limited increasing the oral dose as necessary to achieve maximum clinical benefit. In the 10 patients selected for the intranasal pilot study, oral theophylline treatment was discontinued 3 weeks to 4 months before initiation of the intranasal drug trial. At that time, the mean (SEM) serum theophylline level was unmeasurable in any patient (0 [0] mg/L).

A pilot study of intranasal theophylline treatment was then initiated among these 10 patients. This trial was an investigator initiated phase 1, open-label, single-source, controlled pilot study. Intranasal drug therapy reflected a compassionate trial of a potentially more useful therapeutic method to improve hyposmia (and hypogeusia) than oral theophylline. Before the intranasal trial, risks and benefits were explained and the patients signed an informed consent.

The intranasal administration device was a calibrated 1 mL syringe fitted with a nozzle that fit comfortably into the anterior naris (Wolfe Tory Medical, Inc.) and loaded under sterile conditions with 20 µg of theophylline methylpropyl paraben in a 0.4-mL saline solution (Foundation Care). Patients were instructed to direct the spray superiorly into the nasal cavity but not posteriorly into the nasopharynx. This technique was practiced before study initiation with sterile saline. Each patient used the technique easily and as demonstrated before drug administration.

Each patient delivered the theophylline dose in each naris once daily throughout the study. Patients underwent evaluation 1, 2, and 4 weeks during drug use with the same measurements used for the oral study.

Values for the oral trial were taken from the last measurements made before discontinuation of oral drug treatment and before initiation of the intranasal trial. This period varied from 2 to 12 months after oral treatment initiation and reflected the maximal improvement in sensory function each patient experienced. Values for the intranasal pilot study were taken from measurements obtained after completion of 4 weeks of intranasal treatment.

The mean and standard error of the mean for all values obtained at each study condition were compared. Differences were considered significant if P<0.05 by the unpaired t test. Paired comparison tests were also used with differences considered significant if P<0.05 by the t test.

Results

With oral theophylline administration, hypogeusia improved after 2 to 12 months of treatment, but hypogeusia improved further within 1 to 4 weeks of intranasal treatment. Before treatment, DTs for sucrose, hydrochloride, and urea (less sensitive) and RTs for all tastants were elevated (less sensitive) above the reference levels. Magnitude estimations for all tastants were lower (less sensitive) than the reference level. Hedonic responses for sodium chloride, hydrochloride, and urea were lower (less unpleasant) than the reference levels. After oral theophylline treatment, DTs for sucrose and hydrochloride and RTs for sodium chloride, hydrochloride, and urea decreased (more sensitive). Magnitude estimations for all tastants increased (more sensitive) and HR for hydrochloride and urea increased (more unpleasant) as previously reported. After intranasal theophylline treatment, DTs and RTs for all tastants were lower (more sensitive) than before treatment or after oral theophylline treatment. Magnitude estimations for all tastants after intranasal theophylline treatment were higher (more intense) than before any treatment or after oral theophylline treatment. Hedonic responses for sodium chloride, hydrochloride, and urea were more negative (more unpleasant), whereas HRs for sucrose were more positive (more pleasant) than before any treatment or after oral theophylline treatment.

After oral theophylline treatment, hyposmia improved with 2 to 12 months of treatment but improved more with intranasal theophylline after 1 to 4 weeks of treatment. Before treatment, compared with reference levels, DTs and RTs for all odorants were elevated (less sensitive); MEs for all odorants were decreased (less sensitive); HRs for pyridine and thiophene were decreased (less unpleasant); and HRs for nitrobenzene and amyl acetate were decreased (less pleasant). After oral theophylline treatment, DTs and RTs for all odorants were decreased (more sensitive), MEs for all odorants were increased (more sensitive), and HRs for all odorants increased (for pyridine and thiophene, more unpleasant; for nitrobenzene and amyl acetate, more pleasant) as previously reported. After intranasal theophylline treatment, DTs and RTs for each odor were lower (more sensitive) than before treatment or after oral theophylline treatment. Magnitude estimations for each odor were higher (more intense) than before treatment or after oral theophylline treatment. Hedonic responses to thiophene were more negative (more unpleasant) and to nitrobenzene were more positive (more pleasant) than before treatment or after oral theophylline treatment.

Smell and taste acuity were reported to be subjectively improved with oral theophylline treatment, but greater improvement was reported after 4 weeks of intranasal theophylline treatment. After oral theophylline treatment, 6 patients reported overall increased taste or smell function, whereas 4 reported no improvement. After intranasal theophylline treatment, 8 of the 10 patients reported overall improvement in taste or smell functions, whereas 2 reported no improvement. This response frequency is higher than that previously reported among patients with hyposmia and treated with oral theophylline, in which slightly more than 50% reported improvement.

Taste or smell acuity were measured as subjectively improved after oral theophylline treatment, but this improvement was measured as increased after 4 weeks of intranasal theophylline treatment. After intranasal theophylline treatment, a 2-fold improvement was measured for taste or smell functions compared with oral treatment. Paired t test results showed that responses after intranasal theophylline were significantly greater than after oral theophylline treatment (taste, P<0.05; smell, P<0.025).

Body weight increased from pretreatment levels after oral theophylline treatment, but weight increased more after intranasal theophylline treatment. After oral theophylline treatment, mean (SEM) weight increased by 1.5 (0.4) kg from pretreatment values, whereas after intranasal theophylline treatment, weight increased by 2.5 (0.5) kg from pretreatment values. Patients related this change to increased food flavor obtained by improved smell function after intranasal theophylline treatment, which increased appetite and food enjoyment, resulting in subsequent weight gain. These changes were measured in each patient group despite no sensory improvement in 4 patients after oral theophylline treatment and none in 2 after intranasal theophylline treatment.

During oral theophylline treatment, the mean (SEM) serum theophylline level at the time of maximum improvement for these 10 patients was 6.4 (2.0) mg/L (to convert to micromoles per liter, multiply by 5.55). During intranasal theophylline treatment, the mean serum theophylline level was 0.0 (0.0). Discontinuation of intranasal theophylline treatment resulted in loss of smell and taste function within 1 week in 2 patients and after 6 weeks in 2. Four patients reported some persistence of improvement after 10 weeks.

Comment

Results of this open-label, single-source, controlled pilot trial demonstrates that oral theophylline effectively improved hyposmia, as previously reported. The earliest this improvement was measured was after 2 months of treatment, but maximal improvement varied from 4 to 12 months. These results also demonstrate that oral theophylline was effective in improving hypogeusia in the same time frame as improvement in smell acuity.

In addition, intranasal theophylline was shown to be safe and more effective than oral theophylline in correcting hyposmia and hypogeusia. This improvement was measured as early as 1 week after starting treatment, but maximal improvement varied from 1 to 4 weeks.

Mechanisms by which intranasal theophylline was more effective than oral theophylline are not clearly defined. Intranasal drug delivery avoids the first-pass hepatic effect of an oral drug, bypassing initial cytochrome P450 metabolism and decreasing metabolism of the orally administered drug, thereby allowing for lower intranasally administered drug doses to be clinically efficacious. This lowering of the drug dose from a range of 200 to 800 mg orally to 40 pg intranasally was sufficient and specific enough to also avoid production of systemic adverse effects. This delivery mechanism may also avoid development of drug resistance that has occurred with oral theophylline. In addition, because more drug presumably contacts the olfactory epithelium with intranasal than with oral theophylline, direct nasal administration may activate more olfactory receptors than does oral administration.

However, additional actions of intranasal theophylline might enhance its therapeutic efficacy. Theophylline has been shown to inhibit symptoms of allergic rhinitis, which affected 3 patients in the intranasal trial. Many of the diseases and conditions that caused hyposmia and hypogeusia have an associated inflammatory component that can be suppressed by the anti-inflammatory effects of a phosphodiesterase inhibitor. In addition, drugs introduced intranasally can be delivered into the brain (1) directly by absorption through the cribriform plate along the olfactory bulb, (2) indirectly by absorption through blood-brain barrier receptors, or (3) through combinations of both methods. Although studies of theophylline absorption from nasal mucus into the brain have not been performed, studies of insulin, nerve growth factor, several neurotransmitters, and other moieties indicate uptake of these intranasally introduced moieties into the brain.

Whatever its mechanism of action, intranasal theophylline in this pilot study corrected hyposmia and hypogeusia relatively rapidly in 8 of 10 patients with several clinical diagnoses. The 2 patients who did not experience improvement were men, one with allergic rhinitis and the other with the effects of viral illness.

These results are consistent with prior studies in which several intranasal drugs were more effective than oral drugs. Inhaled adrenocorticosteroids were more effective with fewer adverse effects for asthma treatment than oral adrenocorticosteroids, and inhaled adrenocorticosteroids were more efficacious in asthma treatment than oral prednisolone acetate. Intranasal zolmitriptan achieved faster control of migraine headaches with fewer effects than the orally administered drug. Nasal administration of chicken type II collagen suppressed adjuvant arthritis in rats more effectively than oral administration.

However, intranasally administered drugs have also been reported to be only as effective as these same drugs given orally. Intranasal estradiol valerate was as effective as oral administration in alleviating postmenopausal symptoms but produced less frequent mastalgia and uterine bleeding. Intranasal desmopressin acetate was as effective for nocturnal enuresis as the oral drug but at a dose one-tenth that of the oral drug. Intranasal desmopressin is the preferred route for management of central diabetes insipidus.

Example 8. Treatment with Antibody Inhibitors of IL-6

In this example, a subject with hypogeusia or ageusia is treated by administration of an effective amount of an inhibitory antibody against IL-6 or a receptor of IL-6. The inhibitory antibody can be tociluzumab, sarilumab, elsilimomab, siltuximab, sirukumab, BMS-945429, CDP6038, VX30, ARGX-109, or FM101. The administration is by intranasal administration. Treatment efficacy is evaluated by administering the standardized psychophysical sensory testing techniques before and after administration of the antibody. The administration is repeated as necessary according to the efficacy testing data. Recipient's ability to taste or smell improves according to the standardized psychophysical sensory testing.

Example 9. SHH in Hyposmia

Objective:

To determine the presence of SHH in human nasal mucus in normal subjects and in patients with smell loss (hyposmia).

Methods:

SHH was measured in 14 normal subjects and in 44 untreated patients with smell loss (hyposmia) of several causes and in 30 of these patients after treatment with oral theophylline using sensitive spectrophotometric ELISA assay.

Results:

SHH was present in nasal mucus in both normal subjects and in patients with hyposmia. However, SHH levels in hyposmic patients were significantly lower than in normal subjects. After treatment with oral theophylline, SHH levels in nasal mucus increased significantly to over 300 times higher than in the untreated state associated. 60% of patients exhibited improved smell function.

Conclusion:

SHH may act as a cell signaling moiety to stimulate stem cells in olfactory epithelium; its diminution in hyposmic patients compared to normals suggests that SHH serves as a biochemical marker for smell loss and acts as a growth factor to maintain normal olfactory function.

Introduction

Members of the hedgehog signaling pathway belong to a family of extracellular signaling molecules involved in the regulation of multiple physiological processes including invertebrate and vertebrate embryo development. Vertebrate organisms express multiple forms of hedgehog; there are three known hedgehogs in mammals—Sonic hedgehog (SHH), Indian hedgehog (IHH) and Desert hedgehog (DHH). SHH plays an important role in several developmental processes involving induction of dopaminergic neurons and cholinergic neurons.

SHH is synthesized as a 45-kD precursor protein that is cleaved autocatalytically to yield a 20-kD N-terminal fragment with a cholesterol molecule covalently attached to the C-terminal glycine and a 25-kD C-terminal fragment. Its crystal structure has been determined and it is structurally homologous to several zinc-dependent hydrolases. The crystal structure of SHH reveals one zinc atom coordinated by two histidines and a glutamate residue. Removal of zinc from SHH inhibits its activity. Increase in activity of cAMP-dependent protein kinase A antagonizes SHH signaling.

Methods

Subjects:

Forty-four patients, aged 10-88 y, 56±3 y (Mean±SEM) took part in this study. Patients were 24 men, aged 12-88 y, 54±4 y, and 20 women, aged 10-84 y, 51±5 y. All patients exhibited smell loss as measured by subjective statement and olfactometry, as previously described. Olfactometry can include determination of detection (DT) and recognition (RT) thresholds and magnitude estimation (ME) for four odors (pyridine, nitrobenzene, thiophene and amyl acetate). Abnormalities of smell function consisted of increased DT or RT above normal (decreased sensitivity) and/or decreased ME (decreased sensitivity) for one or more of the odors presented. Patients exhibited six etiologies related to their smell loss: post-influenza-like hyposmia [(PIHH) 10 patients], allergic rhinitis [15 patients], congenital loss of smell [nine patients], head injury [eight patients], post general anesthesia [one patient] and dysgeusia and oropyrosis [one patient].

Thirty of the hyposmic patients were treated with oral theophylline with a dose range of 200-800 mg taken over a period of 2-10 months. These patients were 17 men, aged 12-78 y, 62+5 y, six with PIHH, nine with allergic rhinitis, one with congenital smell loss and one post anesthesia, and 13 women, aged 12-67 y, 42±6 y, with four with PIHH, one with allergic rhinitis and eight with congenital smell loss. Improvement in smell function consisted of decreased DT or RT (increased sensitivity) and/or increased ME (increased sensitivity) for one or more of the presumed odors.

Normal Subjects:

Fourteen subjects who presented to The Taste or smell Clinic in Washington, D.C. for evaluation of symptoms unrelated to smell loss and other volunteers were a part of this study. Normal subjects were selected in a consecutive manner and included all subjects who exhibited no sensory abnormalities.

Study protocols were previously approved by the Georgetown University Medical Center Institutional Review Board. Each participants of the study voluntarily agreed and signed an informal consent participation form.

Procedures:

Patients and subjects were instructed to deposit all the nasal mucus they produced spontaneously over a period of 1-4 days into a 50 ml plastic tube. All samples were refrigerated overnight and collection was longer than 24 hrs.

Each sample was transferred to a 12 ml plastic tube and centrifuged in a refrigerated RC2B Spinco centrifuge at 18,400 rpm for 45-55 min. The supernatant was transferred to PCR tubes and stored at −20° C. until analyzed.

Each sample was analyzed by using a specific spectrophotometric ELISA technique obtained from Abcam Inc. (Cambridge, Mass.). Analysis of duplicate samples agreed within 5%.

All analyses were made independent of the knowledge of the status of any subject. Only after all samples were analyzed and results tabulated were samples codified in relationship to clinical diagnosis. Results were analyzed such that Mean±SEM levels in each category were obtained and results compared using Student t tests with $p<0.05$ considered significant.

Results

SHH was measured in the nasal mucus of all participants (Table 12). Levels of SHH in patients were less than 2% of the levels of SHH found in normal subjects (Table 12).

Mean SHH levels in women were 1.5 times higher than in men (Table 13).

Mean SHH levels in patients having a wide range of etiologies for the cause of their smell loss, varied widely (Table 14). Patients with general anesthesia exhibited the lowest levels of any patient group followed in rank order by patients with allergic rhinitis, congenital smell loss, the patient with dysgeusia and oropyrosis, head injury and PIHH. Mean SHH levels of each patient group were significantly lower than in normal subjects.

Treatment with oral theophylline significantly increased SHH levels by over 330 times among patients (Table 14). Theophylline levels increased significantly above normal levels in both men and women with an increase of 320 times in men but only 17 times in women (Table 14). However, prior to theophylline treatment SHH levels in women were significantly higher than in men ($p<0.001$).

Categorized by etiology each patient group studied exhibited a significant increase in nasal mucus SHH (Table 15). Patients with allergic rhinitis increased the greatest amount (by over 719 times the untreated state), next the patient post anesthesia (by 48 times), by patients with PIHH (by 46 times) and least by patients with congenital smell loss (by over 21 times).

Oral theophylline treatment in PIHH patients increased SHH to levels significantly above levels in all patients before theophylline treatment (Table 15). However, levels in treated patients with allergic rhinitis and congenital smell loss and following general anesthesia did not exhibit as much change in SHH levels and were below the mean of all treated patients.

Improvement in smell function after oral theophylline treatment occurred in 19 of 31 patients or an overall improvement in 61%.

Discussion

This study indicates that SHH is present in the nasal mucus in both normal subjects and in untreated patients with hyposmia. However, levels in untreated hyposmic patients were significantly lower than in normal subjects similar to results previously demonstrated for levels of nasal mucus cAMP and cGMP which were also significantly lower than in normal subjects.

Treatment with oral theophylline significantly increased SHH levels in nasal mucus of patients with hyposmia over those measured in the untreated state consistent with results previously demonstrated for levels of nasal mucus cAMP and cGMP. Prior treatment among prior hyposmic patients with oral theophylline resulted in smell improvement in slightly over 50% of patients whereas in this study 60% of patients exhibited improvement in smell function. Among prior theophylline treated hyposmic patients some exhibited resistance to oral theophylline treatment, a result which also may have occurred among patients in this study.

TABLE 12

SONIC HEDGEHOG IN NASAL MUCUS IN NORMAL SUBJECTS AND IN PATIENTS WITH HYPOSMIA

| SUBJECTS | SONIC HEDGEHOG* |
|---|---|
| PATIENTS (44) | 149 ± 2+,a |
| NORMALS (14) | 7538 ± 1105 |

( ) Subject number
*in pg/ml
+Mean ± SEM
With respect to normal subjects
$^a$p < 0.001

TABLE 13

SONIC HEDGEHOG IN NASAL MUCUS IN PATIENTS WITH HYPOSMIA CLASSIFIED BY ETIOLOGY OF SMELL LOSS

| SUBJECTS | SONIC HEDGEHOG* |
|---|---|
| ALL PATIENTS (44) | 149 ± 2+,a |
| PIHH (10) | 1527 ± 159a |
| ALLERGIC RHINITIS (15) | 34 ± 2a |
| CONGENITAL (9) | 180 ± 12a |
| HEAD INJURY (8) | 1396 ± 252a |
| DYSGEUSIA WITH OROPYROSIS (1) | 226 |
| POST GENERAL ANESTHESIA (1) | 1.3 |
| NORMALS (14) | 7538 ± 1105 |

( ) Subject number
*in pg/ml
+Mean ± SEM
With respect to normals
$^a$p < 0.001

TABLE 14

SONIC HEDGEHOG IN PATIENTS WITH HYPOSMIA UNTREATED AND AFTER TREATMENT WITH ORAL THEOPHYLLINE

| | CONDITION | |
|---|---|---|
| SUBJECTS | Untreated | Treatment With Oral Theophylline‡ |
| NORMALS | 7538 ± 1105 (14) | |
| MEN | 150 ± 6$^{a1}$ (24) | 47952 ± 3085$^{a,a1}$ (18) |
| WOMEN | 229 ± 8$^{a1}$ (20) | 38590 ± 3030$^{a,a1}$ (13) |
| ALL PATIENTS | 149 ± 2+,$^{a1}$ (44) | 49191 ± 1710$^{a,a1}$ (31) |

( ) Subject number
+Mean ± SEM of sonic hedgehog concentration (in pg/ml)
‡Oral theophylline (400-800 mg daily for 2-10 months)
With respect to untreated patients
$^a$p < 0.001
With respect to normals
$^{a1}$p < 0.001

TABLE 15

SONIC HEDGEHOG IN NASAL MUCUS IN PATIENTS CLASSIFIED BY ETIOLOGY UNTREATED AND TREATED WITH ORAL THEOPHYLLINE

| | CONDITION* | | SMELL IMPROVEMENT |
|---|---|---|---|
| PATIENTS | Untreated | Treatment With Oral Theophylline | Patient Number (%) |
| ALL PATIENTS | 149 ± 2 (44) | 49191 ± 1710$^a$ (31) | 19 (61) |
| PIHH | 1537 ± 159+,$^{a1}$ (10) | 70735 ± 5751$^a$, (10) | 8 (80) |
| ALLERGIC RHINITIS | 34 ± 2$^{a2}$ (15) | 24460 ± 2610$^{a,}$ $^{a1}$ (11) | 5 (45) |
| CONGENITAL | 180 ± 12$^{a2}$ (9) | 3825 ± 474$^{a,a1}$ (9) | 5 (56) |
| HEAD INJURY | 1396 ± 252$^{a2}$ (8) | | |
| DYSGEUSIA WITH OROPYROSIS | 226 (1) | | |
| POST GENERAL ANESTHESIA | 1.3 (1) | 57 (1) | 1 (100) |
| NORMALS | 7538 ± 1105 (14) | | |

( ) Patient number
*Sonic hedgehog concentration (in pg/ml)
+Mean ± SEM
With respect to untreated patients
$^a$p < 0.001
With respect to treated patients
$^{a1}$p < 0.001
With respect to untreated patients
$^{a2}$p < 0.001

Example 10: Improved Smell Function Associated with Increased Sonic Hedgehog in Nasal Mucus in Patients with Hyposmia after Treatment with Oral Theophylline Purpose:

To demonstrate improvement in smell function in hyposmic patients after treatment with oral theophylline in relationship to increased nasal mucus levels of sonic hedgehog (SHH).

Methods:

Forty-four hyposmic patients were evaluated by olfactometry and by measurement of SHH in nasal mucus. Thirty-one of these patients were treated with oral theophylline at doses of 200-800 mg for periods of 2-10 months, at which time their smell function was evaluated by subjective measurements, by olfactometry and by SHH measurements in nasal mucus by use of a sensitive spectrophotometric ELISA assay.

Results:

There was a consistent and significant improvement in subjective responses in smell function, in olfactometry and in nasal mucus SHH in theophylline treated patients.

Conclusions:

Improvement in smell function and in SHH levels in nasal mucus were positively correlated in a dose-response relationship after treatment with oral theophylline.

These results indicate the role of theophylline in the successful treatment of smell function in hyposmic patients of various etiologies and of SHH as a biochemical marker for smell function.

Without being bound by theory, it is possible that theophylline acts as a stimulator of olfactory epithelial stem cell growth and development.

The purpose of the present study is to evaluate changes both in smell function and SHH levels in nasal mucus before and after oral theophylline treatment in patients with hyposmia of several etiologies.

Methods

Subjects

Normal Subjects.

Fourteen volunteers with normal smell and taste function were studied. These subjects were either patients who were presented to The Taste and Smell Clinic in Washington, D.C. for evaluation of symptoms unrelated to smell loss or who were employees of The Taste and Smell Clinic who volunteered for the study. Subjects were selected in a consecutive manner and included all subjects who volunteered for the study.

Patients.

Forty-four patients, aged 10-88 y, 56±3 y (Mean±SEM) who presented to The Taste and Smell Clinic in Washington, D.C. for evaluation and treatment of smell loss were also subjects of the study. Patients were selected consecutively from patients evaluated at The Clinic from 2012-2013. Patients were 24 men, aged 12-88 y, 54±4 y and 20 women, aged 10-84 y, 51±5 y. All patients exhibited smell loss as measured by subjective statements and by olfactometry. Olfactometry was measured by determination of detection (DT) and recognition (RT) thresholds, magnitude estimation (ME) and hedonic evaluation (H) for four odors (pyridine, nitrobenzene, thiophene and amyl acetate). Abnormalities of smell function consisted of increased DT and/or RT above normal (decreased sensitivity) and/or decreased ME (decreased sensitivity) for one or more of the odors presented or decreased unpleasantness for odors of pyridine and thiophene or increased unpleasantness for odors of nitrobenzene or amyl acetate.

Patients exhibited six etiologies related to their smell loss: post-influenza-like hyposmia [(PIHH) 10 patients], allergic rhinitis [15 patients], congenital loss of smell [nine patients], head injury [eight patients], post general anesthesia [one patient] and dysgeusia and oropyrosis [one patient].

Thirty-one of the hyposmic patients were treated with oral theophylline with a dose range of 200-800 mg taken over a period of 2-10 months. These patients were 18 men, aged 12-78 y, 62+5 y, with six with PIHH, 10 with allergic rhinitis, one with congenital smell loss and one post anesthesia and 13 women, aged 12-67 y, 42±6 y, with four with PIHH, one with allergic rhinitis and eight with congenital smell loss. Improvement in smell function consisted of improvement in both subjective responses to oral theophylline and in olfactometry. Subjective improvement in smell function consisted of measurements of improvement in perception for all external odors based upon a scale of 1-100 with 100 indicating complete recovery of normal smell function with responses from 1-100 scaled appropriately. Improvement in flavor perception was measured by responses of a 1-100 scale with 100 indicating that all flavors of food were considered normal and responses <100 scaled consistently less. Subjective improvement in taste function was also measured with changes in taste for salt, sweet, sour and bitter tastants measured on the same 1-100 scale with 100 indicating return to normal for each of the four tastants considered and responses <100 scaled consistently less. Improvement by olfactometry was indicated by decreased DT or RT (increased sensitivity), increased ME (increased sensitivity) and changes in H consistent with decreased distortions.

Olfactometry improvement reflects specific changes in sensory function. Decreased DTs after theophylline treatment reflect increased olfactory detection function with increased receptor sensitivity. Decreased RTs after this treatment reflect improvement with increased sensitivity in olfactory receptor-brain relationships. Increased MEs reflect increased olfactory receptor number. Changes in H reflect changes in brain function related to decreased perception of olfactory distortions.

Study protocol was consistent with studies previously approved by the Institutional Review Board of the Georgetown University Medical Center. Each patient and subject agreed to participate in the study and signed an informed consent participation form.

Methods

Patients and volunteers collected all nasal mucus they spontaneously produced over a period of 1-4 days into a 50 ml plastic tube. All samples were refrigerated overnight for collections longer than 24 h.

Each sample was transferred to a 12 ml plastic tube and centrifuged in a refrigerated RC5C Plus Sorvall centrifuge at 18,000 rpm for 45-55 min. Supernatant was transferred to PCR tubes and stored at −20° C. until analyzed.

Each sample was analyzed by use of a sensitive spectrophotometric ELISA technique obtained from Abcam Inc. (Cambridge, Mass.). Analysis of duplicate samples agreed within 5%. All analyses were made independent of the knowledge of the status of any subject. Only after all samples were analyzed were results tabulated and samples classified in relationship to subject status.

Results were analyzed such that mean±SEM levels in each category were obtained and results compared using Student t tests with $p<0.05$ considered significant. Comparison of results of SHH levels with respect to oral theophylline doses were also analyzed by use of Pearson product correlation with statistical improvement measured by $p<0.05$.

Results

Smell function in hyposmic patients before and after oral theophylline associated with levels of SHH in nasal mucus is shown in Table 16. Smell function in the untreated hyposmic patients were significantly impaired with respect to normal subjects with respect to DTs and RTs for pyridine, thiophene and amyl acetate and with respect to DT for nitrobenzene. After treatment with oral theophylline there was significant improvement in smell function. There were significant decreases with respect to the untreated state in DTs for pyridine, nitrobenzene, thiophene and amyl acetate and RTs for nitrobenzene. MEs for all odors increased except for thiophene and Hs increased in unpleasantness for pyridine and increased in pleasantness for amyl acetate. These changes were associated with significant increases in SHH in the treated patients.

Subjective changes in smell function following treatment with oral theophylline are shown in Table 17. Of the 31 patients treated 19 (61%) improved with a range of 2-100% with a mean improvement of 34±6%. Of these improved patients 11 were men with a mean improvement of 27±9% and eight were women with a mean improvement of 43±17%.

Flavor perception improved in 19 patients (61%) consistent with their improvement in smell function. Taste function improved in 20 patients (64%).

Changes in smell function and in nasal mucus SHH levels and in nasal mucus SHH levels before and after treatment with oral theophylline before treatment and after treatment with each of the four doses of oral theophylline are shown in Table 18. With each increased dose of oral theophylline there was both a consistent and significant increase in SHH [(r=0.91) (p<0.001)] and a decrease in DT and RT (increased sensitivity) for each odor presented except for the RT of thiophene at 400 mg. There was an increase in ME for all doses of 600 mg and 800 mg of oral theophylline and similar increases in H for the unpleasantness of pyridine and thiophene and increases in pleasantness of nitrobenzene and amyl acetate.

Changes in smell function in relationship to changes in SHH in nasal mucus in untreated men and women are shown in Table 19. Before treatment there were no significant differences in any aspect of smell function between men and women although DT and RT were lower (more sensitive) in women for nitrobenzene, thiophene and amyl acetate. ME values were higher (more sensitive) in untreated women than in untreated men for these same odors. After treatment DTs and RTs for pyridine and nitrobenzene were significantly lower (more sensitive) in men than in women and DTs and RTs were lower (more sensitive) for thiophene and amyl acetate in men than in women but not significantly so. However, after treatment measurements of unpleasantness for pyridine and thiophene (H values) were judged more unpleasant in women than in men and measurements of pleasantness (H values) were judged more pleasant in women than in men although changes were not significant. In the untreated state SHH levels in nasal mucus in women were significantly higher than men whereas after treatment SHH in men were significantly higher than in women.

Discussion

These results indicate that SHH levels in nasal mucus serves not only as an index of loss of smell function in untreated hyposmic patients but also as an index of improvement after treatment with oral theophylline. These results confirm the usefulness and importance of collecting and measuring changes in nasal mucus as an important biological fluid in the evaluation of patients with hyposmia.

These results also suggests that SHH acts as a growth factor to promote receptor function in olfactory epithelial maturation and perpetuation and in taste bud growth and development.

Results of these studies indicate that oral theophylline increases nasal mucus levels of SHH in hyposmic patients and that this treatment improves smell function.

It is useful to note the dose response improvement in smell function to oral theophylline treatment and in increases in nasal mucus SHH. These results are consistent with the relationship between smell improvement and increased SHH concentration in nasal mucus.

There were significant differences discovered between normal subjects and hyposmic patients both with respect to smell function and SHH changes in nasal mucus.

TABLE 16

CHANGES IN SMELL FUNCTION AND IN SONIC HEDGEHOG (Shh) LEVELS IN NASAL MUCUS BEFORE AND AFTER TREATMENT WITH ORAL THEOPHYLLINE

| CONDITION | PYRIDINE | | | | NITROBENZENE | | | |
| --- | --- | --- | --- | --- | --- | --- | --- | --- |
| | DT | RT | ME | H | DT | RT | ME | H |
| PATIENTS | | | | | | | | |
| UNTREATED (44) | $7.8 \pm 0.4^{*,a1}$ | $8.7 \pm 0.4^{a1}$ | $34 \pm 4$ | $-30 \pm 4$ | $8.0 \pm 0.6^{a1}$ | $9.0 \pm 0.3$ | $17 \pm 4$ | $6 \pm 3$ |
| TREATED (31) | $5.7 \pm 0.7^{c,b2}$ | $6.7 \pm 0.8^{d}$ | $40 \pm 6$ | $-32 \pm 6$ | $4.7 \pm 0.9^{b,b2}$ | $5.6 \pm 0.9^{d,e2}$ | $19 \pm 4$ | $2 \pm 3$ |
| NORMALS (14) | $3.0 \pm 0.4$ | $4.1 \pm 0.5$ | $52 \pm 5$ | $-51 \pm 5$ | $1.4 \pm 0.3$ | $2.4 \pm 1.0$ | $52 \pm 5$ | $3 \pm 1$ |

*Mean ± SEM
( ) Patient number
DT, detection threshold (in BU)
RT, recognition threshold (in BU)
ME, magnitude estimation (in %)
H, hedonic value (in %)
Shh (in pg/ml)
Treated with respect to untreated
$^{a}p < 0.001$
$^{b}p < 0.005$
$^{c}p < 0.02$
$^{d}p < 0.05$
Untreated with respect to normals
$^{a1}p < 0.001$
Treated with respect to normals
a2
b2
c2
d2

TABLE 16-continued

CHANGES IN SMELL FUNCTION AND IN SONIC HEDGEHOG (Shh) LEVELS IN NASAL MUCUS BEFORE AND AFTER TREATMENT WITH ORAL THEOPHYLLINE

| CONDITION | THEOPHENE | | | | AMYL ACETATE | | | | SONIC HEDGEHOG |
|---|---|---|---|---|---|---|---|---|---|
| | DT | RT | ME | H | DT | RT | ME | H | |
| PATIENTS | | | | | | | | | |
| UNTREATED (44) | $8.1 \pm 0.6^{*,a1}$ | $9.5 \pm 0.5^{a1}$ | $20 \pm 4^{a1}$ | $-13 \pm 4^{a1}$ | $8.2 \pm 0.6^{a1}$ | $9.2 \pm 0.5^{a1}$ | $16 \pm 3^{a1}$ | $0.4 \pm 3$ | $149 \pm 2^{a1}$ |
| TREATED (31) | $5.1 \pm 0.7^{e,a2}$ | $5.5 \pm 0.8^{e,e2}$ | $18 \pm 4^{a2}$ | $-9 \pm 4^{a2}$ | $1.2 \pm 0.6^{d,a2}$ | $5.5 \pm 0.8^{d}$ | $17 \pm 5^{a2}$ | $3 \pm 4$ | $4919 \pm 3085^{d}$ |
| NORMALS (14) | $2.2 \pm 0.5$ | $3.2 \pm 0.8$ | $53 \pm 5$ | $-58 \pm 4$ | $1.1 \pm 0.1$ | $3.5 \pm 0.7$ | $49 \pm 6$ | $5 \pm 1$ | $7838 \pm 105^{a1}$ |

*Mean ± SEM
( ) Patient number
DT, detection threshold (in BU)
RT, recognition threshold (in BU)
ME, magnitude estimation (in %)
H, hedonic value (in %)
Shh (in pg/ml)
Treated with respect to Untreated
$^{a}$p < 0.001
$^{b}$p < 0.005
$^{c}$p < 0.02
$^{d}$p < 0.05
Untreated with respect to normals
$^{a1}$p < 0.001
Treated with respect to normals
$^{a2}$p < 0.001
$^{d2}$p < 0.05

TABLE 17

SUBJECTIVE RESPONSES TO ORAL THEOPHYLLINE TREATMENT IN HYPOSMIC PATIENTS TREATED WITH ORAL THEOPHYLLINE

| CONDITION | NUMBER STUDIED [%] | RESPONSE RANGE [%] | RESPONSE Mean ± SEM |
|---|---|---|---|
| SMELL FUNCTION (31) | | | |
| IMPROVED | 19 [61] | 2-100 | $34 \pm 6$ |
| MEN | 11 | 3-95 | $27 \pm 9$ |
| WOMEN | 8 | 2-100 | $43 \pm 17$ |
| NOT IMPROVED | 12 [39] | 0 | 0 |
| FLAVOR FUNCTION (31) | | | |
| IMPROVED$^{d}$ | 19 [61] | 1-100 | $43 \pm 8$ |
| NOT IMPROVED | 12 [39] | 0 | 0 |
| TASTE FUNCTION (31) | | | |
| IMPROVED$^{b}$ | 20 [64]$^{d}$ | 3-100 | $47 \pm 8$ |
| NOT IMPROVED | 11 [36] | 0 | 0 |

[ ] % of patients studied
( ) Patient number
With respect to Not Improved
$^{d}$p < 0.05, $X^2$ (2.45)
$^{b}$p < 0.01, $X^2$ (4.00)

TABLE 18

CHANGES IN SMELL FUNCTION AND IN NASAL MUCUS SONIC HEDGEHOG AND AFTER TREATMENT WITH SEVERAL DOSES OF ORAL THEOPHYLLINE

| ORAL THEOPHYLLINE DOSE (in mg) | PYRIDINE | | | | NITROBENZENE | | | |
|---|---|---|---|---|---|---|---|---|
| | DT | RT | ME | H | DT | RT | ME | H |
| 200 (6) | $8.4 \pm 0.8^{*}$ | $9.8 \pm 0.9$ | $35 \pm 15$ | $-34 \pm 13$ | $8.8 \pm 1.9$ | $10.6 \pm 0.8$ | $12 \pm 11$ | $0.8 \pm 0.8$ |
| 400 (6) | $7.0 \pm 1.8$ | $7.8 \pm 2.2$ | $43 \pm 12$ | $-35 \pm 15$ | $5.0 \pm 2.1$ | $7.0 \pm 2.6$ | $28 \pm 14$ | $2 \pm 10$ |
| 600 (14) | $5.2 \pm 0.9^{d}$ | $5.8 \pm 1.1^{d}$ | $50 \pm 8$ | $-10 \pm 8$ | $5.4 \pm 1.5$ | $5.6 \pm 1.5^{e}$ | $22 \pm 7$ | $2 \pm 6$ |

TABLE 18-continued

CHANGES IN SMELL FUNCTION AND IN NASAL MUCUS SONIC HEDGEHOG AND AFTER TREATMENT WITH SEVERAL DOSES OF ORAL THEOPHYLLINE

| 800 (5) | $2.8 \pm 1.2^a$ | $4.0 \pm 1.8^d$ | $36 \pm 15$ | $-20 \pm 13$ | $3.2 \pm 1.3^b$ | $4.0 \pm 1.5^e$ | $28 \pm 18$ | $21 \pm 20$ |
|---|---|---|---|---|---|---|---|---|
| UNTREATED (44) | $7.8 \pm 0.4$ | $8.7 \pm 0.4$ | $34 \pm 4$ | $-30 \pm 4$ | $8.0 \pm 0.6$ | $9.0 \pm 0.5$ | $17 \pm 4$ | $6 \pm 5$ |

*Mean ± SEM
( ) Patient number
DT, detection threshold (in BU)
RT, recognition threshold (in BU)
ME, magnitude estimation (in %)
H, hedonic value (in %)
With respect to Untreated
$^a$p < 0.001
$^b$p < 0.005
$^c$p < 0.02
$^d$p < 0.05

| ORAL THEOPHYLLINE | THIOPHENE | | | | AMYL ACETATE | | | | SONIC HEDGEHOG |
|---|---|---|---|---|---|---|---|---|---|
| DOSE (in mg) | DT | RT | DT | H | DT | RT | ME | H | (in pmol/ml) |
| 200 (6) | $8.2 \pm 1.8^*$ | $8.8 \pm 2.0$ | $10 \pm 15$ | $-14 \pm 11$ | $8.2 \pm 2.1$ | $8.6 \pm 1.9$ | $12 \pm 11$ | $8 \pm 8$ | $910 \pm 57^{a,a3}$ (6) |
| 400 (6) | $6.2 \pm 1.9$ | $9.2 \pm 2.4$ | $0 \pm 0$ | $-6 \pm 1$ | $6.0 \pm 1.0$ | $6.2 \pm 1.7$ | $17 \pm 10$ | $0 \pm 0$ | $4202 \pm 851^a$ (6) |
| 600 (14) | $6.2 \pm 1.1$ | $7.9 \pm 1.0$ | $26 \pm 7$ | $-19 \pm 7$ | $5.0 \pm 1.2^c$ | $5.4 \pm 1.2^b$ | $24 \pm 8$ | $14 \pm 5$ | $4052 \pm 241^{a,a1}$ (14) |
| 800 (5) | $4.0 \pm 1.5^d$ | $5.2 \pm 1.4$ | $29 \pm 16$ | $-15 \pm 16$ | $4.0 \pm 1.3^d$ | $4.5 \pm 1.0^b$ | $17 \pm 11$ | $15 \pm 12$ | $6640 \pm 666^{a,a1}$ (5) |
| UNTREATED (44) | $8.1 \pm 0.6$ | $9.5 \pm 0.8$ | $20 \pm 4$ | $-13 \pm 4$ | $8.2 \pm 0.6$ | $9.2 \pm 0.5$ | $16 \pm 3$ | $0.4 \pm 3$ | $149 \pm 2^{a,a1,a2,a3}$ |

*Mean ± SEM
( ) Patient number
DT, detection threshold (in BU)
RT, recognition threshold (in BU)
ME, magnitude estimation (in %)
H, hedonic value (in %)
With respect to Untreated
$^a$p < 0.001
$^b$p < 0.005
$^c$p < 0.02
$^d$p < 0.05
With respect to 200 mg
$^{a1}$p < 0.001
$^{b1}$
$^{c2}$ With respect to 400 mg
$^{a2}$p < 0.001
With respect to 600 mg
$^{a3}$

TABLE 19

CHANGES IN SMELL FUNCTION AND IN SONIC HEDGEHOG IN NASAL MUCUS IN HYPOSMIC MEN AND WOMEN BEFORE AND AFTER TREATMENT WITH ORAL THEOPHYLLINE

| | PYRIDINE | | | | NITROBENZENE | | | |
|---|---|---|---|---|---|---|---|---|
| CONDITION | DT | RT | ME | H | DT | RT | ME | H |
| UNTREATED | | | | | | | | |
| MEN (24) | $7.9 \pm 0.5^*$ | $8.7 \pm 0.5$ | $34 \pm 5$ | $-27 \pm 5$ | $9.0 \pm 0.7$ | $9.9 \pm 0.6$ | $10 \pm 3$ | $4 \pm 3$ |
| WOMEN (20) | $7.9 \pm 0.7$ | $9.1 \pm 0.8$ | $33 \pm 9$ | $-30 \pm 8$ | $7.3 \pm 1.0$ | $8.1 \pm 1.0$ | $16 \pm 6$ | $-1 \pm 2$ |
| TREATED | | | | | | | | |
| MEN (19) | $4.8 \pm 0.9^a$ | $5.6 \pm 1.0^c$ | $36 \pm 7$ | $-30 \pm 7$ | $4.8 \pm 1.1^b$ | $5.2 \pm 1.2^b$ | $19 \pm 5$ | $6 \pm 5$ |
| WOMEN (12) | $7.1 \pm 0.9$ | $8.0 \pm 1.0$ | $42 \pm 9$ | $-38 \pm 8$ | $6.8 \pm 1.4$ | $7.3 \pm 1.1$ | $25 \pm 8$ | $8 \pm 7$ |

*Mean ± SEM
( ) Patient number
DT, detection threshold (in BU)
RT, recognition threshold (in BU)
ME, magnitude estimation (in %)
H, hedonic value (in %)
With respect to Untreated State
$^a$p < 0.001
$^b$p < 0.005
$^c$p < 0.01

TABLE 19-continued

CHANGES IN SMELL FUNCTION AND IN SONIC HEDGEHOG IN NASAL MUCUS IN HYPOSMIC MEN AND WOMEN BEFORE AND AFTER TREATMENT WITH ORAL THEOPHYLLINE

| CONDITION | THIOPHENE | | | | AMYL ACETATE | | | | SONIC HEDGEHOG |
|---|---|---|---|---|---|---|---|---|---|
| | DT | RT | ME | H | DT | RT | ME | H | |
| UNTREATED | | | | | | | | | |
| MEN (24) | 8.7 ± 0.7* | 9.7 ± 0.6 | 16 ± 4 | −4 ± 4 | 8.7 ± 0.7 | 9.8 ± 0.7 | 11 ± 3 | 2 ± 3 | 150 ± 6 |
| WOMEN (20) | 7.6 ± 1.0 | 9.2 ± 0.8 | 19 ± 7 | −12 ± 6 | 8.1 ± 1.0 | 9.1 ± 0.9 | 13 ± 6 | −5 ± 7 | 229 ± 8$^{a1}$ |
| TREATED | | | | | | | | | |
| MEN (19) | 5.6 ± 0.9$^b$ | 7.6 ± 1.0 | 15 ± 5 | −7 ± 3 | 4.7 ± 0.9$^b$ | 5.3 ± 0.9$^a$ | 17 ± 5 | 3 ± 3 | 4795 ± 3085 |
| WOMEN (12) | 7.1 ± 1.2 | 8.1 ± 1.3 | 30 ± 7 | −19 ± 6 | 7.4 ± 1.1 | 8.7 ± 1.0 | 22 ± 7 | 2 ± 6 | 3859 ± 3030 |

*Mean ± SEM
DT, detection threshold (in BU)
RT, recognition threshold (in BU)
ME, magnitude estimation (in %)
H, hedonic value (in %)
With respect to Untreated State
$^a$p < 0.001
$^b$p < 0.01
$^c$p < 0.02
$^d$p < 0.05

Example 11. Sonic Hedgehog in Human Taste Function

Purpose:

To determine the role of sonic hedgehog (Shh) in human taste function.

Background:

Shh is a 20 kD $NH_2$ terminal protein involved with signaling in multiple cellular systems. We hypothesized that Shh should be found in saliva. Thus, we attempted to measure Shh in saliva in both normal subjects and in patients with taste dysfunction.

Methods:

Shh was measured in parotid saliva of both normal subjects and patients with taste dysfunction of multiple etiologies by use of sensitive spectrophotometric ELISA assay. Taste dysfunction was defined clinically by both subjective inhibition of taste function (including acuity loss) and impaired gustometry.

Results:

Shh was found in parotid saliva in each normal subject. It was also found in each patient with taste dysfunction but at levels significantly lower than in normal subjects.

Patients expressed subjective loss of taste function. Impaired gustometry was also measured.

Methods

Subjects

Normal Subjects.

Twenty-six volunteers, aged 22-84 y, 54±5 y (Mean±SEM) with normal taste function were studied. These volunteers were either patients who were presented to The Taste and Smell Clinic in Washington, D.C. for evaluation of symptoms unrelated to taste loss or who were employees of The Taste and Smell Clinic who volunteered for the study. Subjects were selected in a consecutive manner and included all subjects who volunteered for the study.

Patients.

Sixty-four patients, aged 10-88 y, 56±3 y who presented to The Taste and Smell Clinic in Washington, D.C. for evaluation and treatment of taste and smell loss were also studied. Patients were selected consecutively from patients evaluated at The Clinic from 2012-2013. Patients were 12 men, aged 12-88 y, 54±4 y and 14 women, aged 10-84 y, 51±5 y. Taste dysfunction was caused by seven pathological events including post-influenza-like hypogeusia [(PIHH) 17 patients], allergic rhinitis [26 patients], congenital loss of smell with associated hypogeusia [10 patients], head injury [12 patients], post general anesthesia [two patients], dysgeusia and oropyrosis [one patient] and post systemic radiation [one patient]. All patients exhibited taste dysfunction as measured by subjective statement of acuity loss and by impaired gustometry.

Subjective statements of acuity loss were quantitated by use of a scale from 0-100 with 100 reflecting total loss of taste function, 0 reflecting no loss and a number between 0-100 reflecting appropriate degree of loss. Mean±SEM of loss degree was measured among all patients and each pathology initiating taste dysfunction.

Gustometry measurements included measurements of detection (DT) and recognition (RT) thresholds and magnitude estimation (ME) for four tastants [NaCl (salt), sucrose (sweet), HCl (sour) and urea (bitter)]. Abnormalities of taste function were measured by increased DT or RT above normal (decreased sensitivity) and/or decreased ME (decreased sensitivity) for one or more of the tastants presented.

Study protocol was consistent with studies previously approved by the Institutional Review Board of the Georgetown University Medical Center. Each patient and subject agreed to participate in the study and signed an informed consent participation form.

Methods

Patients and volunteers collected saliva by placement of a Lashley cup over Stensen's duct of one parotid gland with saliva stimulated by lingual placement of concentrated lemon juice. Saliva was collected in plastic tubes in ice for timed periods of 8-10 min, as previously described. Flow rate was measured by mean flow over a four minute time period, as previously described. Samples were stored at −20° C. until analyzed.

Each sample was analyzed by use of a sensitive spectrophotometric ELISA technique obtained from Abcam Inc. (Cambridge, Mass.). Analysis of duplicate samples agreed within 5%. All analyses were made independent of the knowledge of the status of any subject. Only after all samples were analyzed were results tabulated and samples classified in relationship to subject status.

Results were analyzed such that mean±SEM levels in each category were obtained and results compared using Student t tests with p<0.05 considered significant.

Results

Mean Shh was present in saliva in each normal volunteer and patient studied (Table 20). Levels in patients were significantly lower than those measured in normal subjects (Table 20).

Shh in saliva did not differ in men or women patients (Table 21).

Shh in saliva demonstrated a pattern of increasing with age with the highest levels demonstrated in the oldest patients studied (Table 22).

Mean Shh levels in patients with various etiologies related to the cause of their taste dysfunction varied widely (Table 23). The lowest level was demonstrated in the patient with dysgeusia and oropyrosis, the highest levels in patients with PIHH (Table 23). While the mean level in all patients was significantly lower than in normal subjects levels in patients with head injury were significantly lower than patients with PIHH.

Subjective loss of taste acuity was present in each patient with taste dysfunction with a mean loss of 41+3%. Subjective loss of flavor perception was present in each patient with a loss of 28+3%. Impaired gustometry were demonstrated in the patients with measurements of increased DT (decreased sensitivity), increased RT (decreased sensitivity) and decreased ME (decreased sensitivity) compared to similar results in normal subjects (Table 24).

Discussion

Results of this study indicate that Shh is present in saliva in both normal subjects and in patients with taste dysfunction. Its presence in human saliva is herein reported for the first time.

As patients aged there was an increase in saliva Shh with the highest levels demonstrated in the oldest patients.

Shh levels in untreated patients with taste dysfunction were significantly lower than in normal subjects similar to results previously demonstrated for levels of saliva cAMP and which have previously been demonstrated to be significantly lower than in normal subjects.

Salivary Shh levels were lower than normal in patients in all diagnostic categories studied. This result suggests that lower than normal levels of salivary Shh may serve as a general diagnostic value for taste dysfunction in patients with these symptoms.

TABLE 20

SONIC HEDGEHOG IN SALIVA
IN NORMAL SUBJECTS AND IN
PATIENTS WITH TASTE DYSFUNCTION

| SUBJECTS | SONIC HEDGEHOG* |
|---|---|
| NORMALS (26) | 215 ± 7[+] |
| PATIENTS (64) | 63 ± 6[a] |

( ) Subject number
*in pmol/ml
[+]Mean ± SEM
With respect to normals
[a]p < 0.001

TABLE 21

SONIC HEDGEHOG IN SALIVA
IN PATIENTS WITH TASTE DYSFUNCTION
CHARACTERIZED BY GENDER

| PATIENTS | AGE (y) | SONIC HEDGEHOG* |
|---|---|---|
| MEN (37) | 56 ± 3 | 61 ± 7[+] |
| WOMEN (30) | 55 ± 4 | 62 ± 10 |

( ) Subject number
*in pmol/ml
[+]Mean ± SEM

TABLE 22

SONIC HEDGEHOG IN SALIVA IN PATIENTS WITH
TASTE DYSFUNCTION CHARACTERIZED BY AGE

| PATIENTS[‡] | SONIC HEDGEHOG* |
|---|---|
| <30 (11) | 66 ± 8[+] |
| 31-40 (4) | 80 ± 24 |
| 41-50 (7) | 63 ± 14 |
| 51-60 (9) | 62 ± 10 |
| 61-70 (16) | 90 ± 13 |
| 71-80 (14) | 96 ± 13 |
| >81 (6) | 104 ± 35 |

( ) Subject number
*in pmol/ml
[+]Mean ± SEM

TABLE 23

SONIC HEDGEHOG IN SALIVA OF PATIENTS WITH
TASTE DYSFUNCTION

| CONDITION | SONIC HEDGEHOG* |
|---|---|
| PIHH (17) | 104 ± 16[+] |
| ALLERGIC RHINITIS (26) | 76 ± 6 |
| CONGENITAL (10) | 70 ± 11 |
| HEAD INJURY (12) | 54 ± 11 |
| DYSGEUSIA WITH OROPYROSIS (1) | 29 |
| POST GENERAL ANESTHESIA (2) | 77 |
| POST RADIATION (1) | 115 |

( ) Subject number
*in pmol/ml
[+]Mean ± SEM

TABLE 24

TASTE FUNCTION IN PATIENTS COMPARED TO NORMAL SUBJECTS

| | NaCl | | | Sucrose | | | HCl | | | UREA | | |
|---|---|---|---|---|---|---|---|---|---|---|---|---|
| | DT | RT | ME | DT | RT | ME | DT | RT | ME | DT | RT | ME |
| PATIENTS (18) | $3.9 \pm 0.3^a$ | $4.8 \pm 0.6^d$ | $52 \pm 7$ | $3.8 \pm 0.3^a$ | $3.9 \pm 0.2^a$ | $44 \pm 6^b$ | $3.8 \pm 0.3$ | $4.9 \pm 0.7$ | $49 \pm 7^d$ | $4.3 \pm 0.5^e$ | $5.3 \pm 0.7^d$ | $44 \pm 7^c$ |
| NORMALS (55) | $2.3 \pm 0.1$ | $3.1 \pm 0.2$ | $68 \pm 4$ | $2.5 \pm 0.1$ | $3.2 \pm 0.1$ | $69 \pm 4$ | $3.1 \pm 0.2$ | $3.5 \pm 0.1$ | $68 \pm 4$ | $3.2 \pm 0.1$ | $3.4 \pm 0.1$ | $68 \pm 4$ |

RT, Recognition Threshold
DT, Detection Threshold
ME, Magnitude Estimation
( ) Patient number
+Mean ± SEM
With respect to untreated patients
$^a$p < 0.001
$^b$p < 0.005
$^c$p < 0.01
$^d$p < 0.02
$^e$p < 0.05

Additional subjects were examined and the data reanalyzed in view of new data.

Methods:

Shh was measured in parotid saliva of both normal subjects and in patients with taste dysfunction of multiple etiologies by use of a sensitive spectrophotometric ELISA assay. Taste dysfunction was defined clinically by both subjective changes of taste acuity and flavor perception and by impaired gustometry. Patients were treated with oral theophylline 200-800 mg daily for 2-10 months with saliva Shh and taste function measured at intervals of 2-8 months.

Results:

Shh was found in parotid saliva in both normal subjects and in patients with taste dysfunction but levels were significantly lower in patients than in normal subjects. Both subjective loss of taste acuity and flavor perception and impaired gustometry was measured in each patient. Theophylline treatment increased saliva Shh and improved both subjective taste function and gustometry.

Conclusions:

This is the first demonstration of Shh in saliva. Decreased saliva Shh secretion can be considered a marker for taste dysfunction in patients with multiple etiologies.

Theophylline acts to increase Shh in saliva and thereby improve human taste dysfunction as its increase in nasal mucus improved human smell dysfunction.

Methods
Subjects
Normal Subjects.

Twenty-six volunteers, aged 22-84 y, 54±5 y (Mean±SEM) with normal taste function were studied. These volunteers were either patients who presented to The Taste and Smell Clinic in Washington, D.C. for evaluation of symptoms unrelated to taste loss or who were employees of The Taste and Smell Clinic who volunteered for the study. Subjects were selected in a consecutive manner and included all subjects who volunteered for the study.

Patients.

Eighty-one patients, aged 10-88 y, 56±3 y who presented to The Taste and Smell Clinic in Washington, D.C. for evaluation and treatment of taste and smell loss were also studied. Patients were selected consecutively from patients evaluated at The Clinic from 2012-2013. Patients were 58 men, aged 12-88 y, 54±4 y and 56 women, aged 10-84 y, 51±5 y. Taste dysfunction was caused by seven pathological events including post-influenza-like hypogeusia [(PIHH) 20 patients], allergic rhinitis [31 patients], congenital loss of smell with associated hypogeusia [9 patients], head injury [14 patients], post general anesthesia [three patients], dysgeusia with oropyrosis [one patient] and post systemic radiation [one patient]. All patients exhibited taste dysfunction as measured by subjective statement of taste acuity loss and loss of flavor perception and by impaired gustometry.

Subjective statements of taste acuity loss and loss of flavor perception were quantitated by use of a scale from 0-100 with 100 reflecting total loss of taste acuity or flavor perception, 0 reflecting no loss and a number between 0-100 reflecting appropriate degree of loss. Some of these patients also exhibited taste distortions but these results were not the subject matter for this study and are not included in this study. Mean±SEM of loss degree was measured among all patients and each pathology initiating taste dysfunction.

Gustometry measurements included measurements of detection (DT) and recognition (RT) thresholds and magnitude estimation (ME) for four tastants [NaCl (salt), sucrose (sweet), HCl (sour) and urea (bitter)]. Abnormalities of taste function were measured by increased DT or RT above normal (decreased sensitivity) and/or decreased ME (decreased sensitivity) for one or more of the tastants presented.

Treatment with oral theophylline was administered to 79 of these patients, aged 12-86 y, 41 men and 38 women at doses of 200-1000 mg for periods of 2-10 months. Saliva Shh and measurements of taste function by use of subjective responses of acuity and flavor perception and in olfactometry was measured at intervals of 2-6 months in these patients.

Study protocol was consistent with studies previously approved by the Institutional Review Board of the Georgetown University Medical Center. Each patient and subject agreed to participate in the study and signed an informed consent participation form. All subjects under age 18 y entered into the study after a parent gave informed consent.

Methods

Parotid saliva was collected in patients and normal volunteers by placement of a Lashley cup over Stensen's duct of one parotid gland with saliva stimulated by lingual, timed placement of concentrated lemon juice. Saliva was collected in plastic tubes in ice for timed periods of 8-10 min, as previously described. Flow rate was measured by mean flow over a four minute time period, as previously described. Samples were stored at −20° C. until analyzed.

Each sample was analyzed by use of a sensitive spectrophotometric ELISA technique obtained from Abcam Inc. (Cambridge, Mass.). Analysis of duplicate samples agreed within 5%. All analyses were made independent of the knowledge of the status of any subject. Only after all samples were analyzed were results tabulated and samples classified in relationship to subject status.

Results were analyzed such that mean±SEM levels in each category were obtained and results compared using Student t tests with $p<0.0^5$ considered significant.

Results

Shh was present in parotid saliva in each normal volunteer and in each untreated patient with hypogeusia (Table 25). Levels in patients were significantly lower than those measured in normal subjects (Table 25).

Shh in saliva did not differ in untreated men or women patients (Table 26).

Shh in saliva demonstrated a varying pattern with age (Table 27).

Mean Shh levels in patients with various etiologies related to the cause of their taste dysfunction varied widely (Table 28). The lowest level was present in one patient with dysgeusia (distorted taste sensation) and oropyrosis, the highest levels in patients post anesthesia (Table 28). The mean level in each patient category was significantly lower than the mean level in normal subjects.

Subjective loss of taste acuity and flavor perception was present in each patient before treatment with oral theophylline. Impaired gustometry were demonstrated in patients with measurements of increased DT (decreased sensitivity), increased RT (decreased sensitivity) and decreased ME (decreased sensitivity) compared to similar results in normal subjects (Table 29).

After treatment with oral theophylline Shh increased in parotid saliva to levels above those in normal subjects or in untreated patients (Table 30). There was improvement in both subjective taste acuity and flavor perception in about 60% of patients (Table 31). Degree of return of acute acuity and flavor perception was greater in women than in men. Improvement in olfactometry also occurred (data not shown).

Discussion

Results of this study indicate that Shh is present in saliva in both normal subjects and in patients with taste dysfunction. Its presence in human saliva is herein reported for the first time.

Salivary Shh levels were lower than normal in patients in all diagnostic categories studied. This result suggests that lower than normal levels of salivary Shh may serve as a general diagnostic marker for taste dysfunction in patients with these symptoms.

TABLE 25

SONIC HEDGEHOG IN PAROTID SALIVA
IN NORMAL SUBJECTS AND
IN PATIENTS WITH TASTE DYSFUNCTION

| SUBJECTS | SONIC HEDGEHOG* |
|---|---|
| NORMALS (26) | 184 ± 12[+] |
| PATIENTS (81) | 64 ± 6[3] |

( ) Subject number
*in pmol/ml
[+]Mean ± SEM
With respect to normals
[a]p < 0.001

TABLE 26

SONIC HEDGEHOG IN PAROTID SALIVA IN NORMAL
SUBJECTS AND IN UNTREATED PATIENTS WITH TASTE
DYSFUNCTION CHARACTERIZED BY GENDER

| | AGE (y) | SONIC HEDGEHOG* |
|---|---|---|
| NORMAL SUBJECTS | | |
| MEN (10) | 70 ± 6 | 186 ± 16[+] |
| WOMEN (17) | 61 ± 4 | 180 ± 12 |
| PATIENTS | | |
| MEN (41) | 56 ± 3 | 76 ± 7 |
| WOMEN (40) | 55 ± 4 | 66 ± 6 |

( ) Subject number
*in pmol/ml
[+]Mean ± SEM

TABLE 27

SONIC HEDGEHOG IN SALIVA IN PATIENTS
WITH TASTE DYSFUNCTION
CHARACTERIZED BY AGE

| PATIENTS‡ | SONIC HEDGEHOG* |
|---|---|
| <30 (11) | 62 ± 9[+] |
| 31-40 (5) | 76 ± 19 |
| 41-50 (5) | 56 ± 12 |
| 51-60 (11) | 57 ± 9 |
| 61-70 (22) | 76 ± 8 |
| 71-80 (15) | 93 ± 13 |
| >81 (7) | 62 ± 24 |

‡Age (in years)
( ) Patient number
*in pmol/ml
[+]Mean ± SEM

TABLE 28

SONIC HEDGEHOG IN SALIVA OF
UNTREATED PATIENTS WITH
TASTE DYSFUNCTION

| CONDITION | SONIC HEDGEHOG* |
|---|---|
| PIHH (27) | 58 ± 10[+a] |
| ALLERGIC RHINITIS (26) | 70 ± 6[a] |
| CONGENITAL (10) | 76 ± 11[a] |
| HEAD INJURY (14) | 49 ± 10[a] |
| DYSGEUSIA WITH OROPYROSIS (1) | 29 |
| POST GENERAL ANESTHESIA (2) | 82 |
| POST RADIATION (1) | 145 |

( ) Patient number
*in pmol/ml
[+]Mean ± SEM
With respect to normals
[a]p < 0.001

TABLE 29

TASTE FUNCTION IN UNTREATED HYPOGEUSIC PATIENTS COMPARED TO NORMAL SUBJECTS BY USE OF GUSTOMETRY

| | HCL | | | UREA | | | NaCl | | | SUCROSE | | |
|---|---|---|---|---|---|---|---|---|---|---|---|---|
| | DT | RT | ME | DT | RT | ME | DT | RT | ME | DT | RT | ME |
| PATIENTS (64) | 3.8 ± 0.3 | 4.9 ± 0.7 | 49 ± 7$^e$ | 4.3 ± 0.5$^e$ | 5.3 ± 0.7$^d$ | 44 ± 7$^c$ | 3.9 ± 0.3$^a$ | 4.8 ± 0.6$^d$ | 52 ± 7 | 3.8 ± 0.3$^a$ | 3.9 ± 0.2$^b$ | 44 ± 6$^b$ |
| NORMALS (55) | 3.1 ± 0.2 | 3.5 ± 0.1 | 68 ± 4 | 3.2 ± 0.1 | 3.4 ± 0.1 | 68 ± 4 | 2.3 ± 0.1 | 3.1 ± 0.2 | 68 ± 4 | 2.5 ± 0.1 | 3.2 ± 0.1 | 69 ± 4 |

RT, Recognition Threshold
DT, Detection Threshold
ME, Magnitude Estimation
( ) Patient number
$^+$Mean ± SEM
With respect to untreated patients
$^a$p < 0.001
$^b$p < 0.005
$^c$p < 0.01
$^d$p < 0.02
$^e$p < 0.05

TABLE 30

SALIVA SONIC HEDGEHOG IN HYPOGEUSIC PATIENTS BEFORE AND AFTER TREATMENT WITH ORAL THEOPHYLLINE

| PATIENTS | SALIVA SONIC HEDGEHOG* |
|---|---|
| BEFORE TREATMENT (66) | 71 ± 4$^{+,a}$ |
| AFTER TREATMENT (66) | 199 ± 20 |
| MEN (61) | 180 ± 15 |
| WOMEN (58) | 213 ± 33 |

( ) Patient number
*in pmol/ml
$^+$Mean ± SEM
With respect to pretreatment
$^a$p < 0.001

TABLE 31

CHANGES IN TASTE FUNCTION IN PATIENTS AFTER TREATMENT WITH ORAL THEOPHYLLINE

| PATIENTS | PATIENT NUMBER | IMPROVEMENT NUMBER | DEGREE OF IMPROVEMENT (%) |
|---|---|---|---|
| TASTE ACUITY | 79 | 45 (63) | 28 ± 4$^+$ |
| MEN | 38 | 21 (55) | 20 ± 5 |
| WOMEN | 41 | 24 (59) | 35 ± 6 |
| FLAVOR PERCEPTION | 79 | 45 (63) | 24 ± 4 |
| MEN | 38 | 22 (58) | 18 ± 4 |
| WOMEN | 41 | 23 (54) | 36 ± 6 |

( ) Patient number
$^+$Mean ± SEM

Example 12. Sonic Hedgehog in Patients with Taste Dysfunction: Before and after Treatment with Oral Theophylline Methods:

After treatment with oral theophylline, Shh was measured in parotid saliva of patients with taste dysfunction of multiple etiologies by use of sensitive spectrophotometric ELISA assay. Taste dysfunction was defined clinically by impaired gustometry.

Results:

Shh was found in parotid saliva in each subject, but was significantly lower in patients with taste dysfunction. Tables 20, 25, and 32. Patients treated with oral theophylline improved subjectively in taste function.

Methods

Subjects

Normal Subjects.

Forty-three patients were treated with oral theophylline at doses of 200-800 mg for periods of 2-10 months, at which time their smell function was evaluated by olfactometry and by SHH measurements in nasal mucus by use of a sensitive spectrophotometric ELISA assay.

These volunteers were either patients who were presented to The Taste and Smell Clinic in Washington, D.C. for evaluation of symptoms unrelated to taste loss or who were employees of The Taste and Smell Clinic who volunteered for the study. Subjects were selected in a consecutive manner and included all subjects who volunteered for the study.

Patients.

Forty-three patients were presented to The Taste and Smell Clinic in Washington, D.C. for evaluation and treatment of taste and smell loss. Taste dysfunction was caused by seven pathological events including post-influenza-like hypogeusia [(PIHH) 13 patients], allergic rhinitis [15 patients], congenital loss of smell with associated hypogeusia [8 patients], head injury [4 patients], post general anesthesia [two patients], and post systemic radiation [one patient]. All patients exhibited a decreased Shh level.

Gustometry measurements included measurements of detection (DT) and recognition (RT) thresholds and magnitude estimation (ME) for four tastants [NaCl (salt), sucrose (sweet), HCl (sour) and urea (bitter)]. Abnormalities of taste function were measured by increased DT or RT above normal (decreased sensitivity) and/or decreased ME (decreased sensitivity) for one or more of the tastants presented.

Study protocol was consistent with studies previously approved by the Institutional Review Board of the Georgetown University Medical Center. Each patient and subject agreed to participate in the study and signed an informed consent participation form.

Methods

Patients and volunteers collected saliva by placement of a Lashley cup over Stensen's duct of one parotid gland with saliva stimulated by lingual placement of concentrated lemon juice. Saliva was collected in plastic tubes in ice for timed periods of 8-10 min, as previously described. Flow rate was measured by mean flow over a four minute time period, as previously described. Samples were stored at −20° C. until analyzed.

Each sample was analyzed by use of a sensitive spectrophotometric ELISA technique obtained from Abcam Inc. (Cambridge, Mass.). Analysis of duplicate samples agreed within 5%. All analyses were made independent of the knowledge of the status of any subject. Only after all samples were analyzed were results tabulated and samples classified in relationship to subject status.

Results were analyzed such that mean±SEM levels in each category were obtained and results compared using Student t tests with p<0.05 considered significant.

Results

Shh was present in saliva in each patient studied however various etiologies related to the cause of their taste dysfunction varied widely (Table 32). Levels in patients were significantly lower than those measured in normal subjects (Tables 20 and 25).

The lowest level was demonstrated in the patient with congenital, the highest levels in patients with Anesthesia Induced (Table 32).

Impaired gustometry were demonstrated in the patients with measurements of increased DT (decreased sensitivity), increased RT (decreased sensitivity) and decreased ME (decreased sensitivity) compared to similar results in normal subjects (Tables 20, 25, and 33). Surprisingly, treatment with theophylline increased levels of Shh by almost 2 fold while improving gustometric functions (Table 33).

Discussion

Results of this study indicate that Shh is increased in saliva in patients with taste dysfunction as a result of theophylline treatment. Theophylline also improved gustometric functions of treated patients.

TABLE 32

SALIVA SONIC HEDGEHOG IN PATIENTS ATTER ORAL THEOPHYLLINE

| CONDITION | SALIVA SONIC HEDGEHOG (pmol/ml)) |
|---|---|
| ANESTHESIA INDUCED (2) | 151 |
| ALLERGIC RHINITIS (26) | 212 ± 14[+] |
| CONGENITAL (10) | 132 ± 23 |
| HEAD INJURY (14) | 115 ± 15 |
| PIHH (27) | 210 ± 12 |
| POST RADIATION (1) | 145 |

( ) Patient number
[+]Mean ± SEM

TABLE 33

TASTE FUNCTION AND SONIC HEDGEHOG IN SALIVA IN PATIENTS WITH TASTE DYSFUNCTION BEFORE AND AFTER TREATMENT WITH THEOPHYLLINE

| CONDITION | NaCl | | | SUCROSE | | | SCl | | | UREA | | | SALIVA SONIC HEDGEHOG (pmol/ml) |
|---|---|---|---|---|---|---|---|---|---|---|---|---|---|
| | DT | RT | ME | DT | RT | ME | DT | RT | ME | DT | RT | ME | |
| UNTREATED (81) | 3.9 ± 0.3[+] | 4.8 ± 0.6 | 52 ± 7 | 3.8 ± 0.3 | 3.9 ± 0.2 | 44 ± 6 | 3.8 ± 0.3 | 4.9 ± 0.7 | 49 ± 7 | 4.3 ± 0.5 | 5.3 ± 0.7 | 44 ± 7 | 63 ± 6 |
| THEOPHYLLINE TREATED (81) | 3.4 ± 0.2 | 3.6 ± 0.2 | 58 ± 5 | 3.3 ± 0.2 | 3.6 ± 0.2 | 49 ± 5 | 3.6 ± 0.2 | 3.7 ± 0.3 | 54 ± 5 | 3.9 ± 0.3 | 3.9 ± 0.3 | 54 ± 5 | 102 ± 10 |

RT, Recognition Threshold
DT, Detection Threshold
ME, Magnitude Estimation
( ) Patient number
[+]Mean ± SEM Example 13. Diagnosing Patients with Loss and/or Distortion of Taste or Smell Bodily fluids will be used to measure the levels of one or more members of the hedgehog signaling pathway. For example, in one example, a saliva sample or a mucus sample will be extracted from a patient and prepared for analysis as described throughout. Levels of SHH, DHH, and IHH, will then be measured by and an antibody-based method, such as an ELISA assay.

The levels of members of the hedgehog signaling pathway in patients exhibiting loss and/or distortion of taste or smell (e.g., hyposmia, dysosmia, anosmia, phantosmia, hypogeusia, dysgeusia, phantogeusia, and/or ageusia) will be lower than normal controls. For example, in patients suffering from loss and/or distortion of taste or smell, the level of SHH, in some cases, will be or about: 0 pg/mL, greater than 0 pg/mL to less than less than 1 pg/mL, 1 pg/mL to 25 pg/mL, 15 pg/mL to 30 pg/mL, 20 pg/mL to 40 pg/mL; 35 pg/mL to 50 pg/mL; 45 pg/mL to 100 pg/mL; 75 pg/mL to 150 pg/mL, 125 pg/mL to 1000 pg/mL, 900 pg/mL to 2500 pg/mL, 2000 pg/mL to 5000 pg/mL, 4000 pg/mL to 7500 pg/mL, 6000 pg/mL to 10,000 pg/mL; (b) the level of IHH can be or about: 0 pg/mL, greater than 0 pg/mL to 0.1 pg/mL, 0.05 pg/mL to 0.15 pg/mL, 0.125 pg/mL to 0.2 pg/mL, 0.15 pg/mL to 0.30 pg/mL, 0.25 pg/mL to 0.5 pg/mL, 0.4 pg/mL to 0.7 pg/mL, 0.6 pg/mL to 0.75 pg/mL, 0.725 pg/mL to 0.9 pg/mL, 0.8 pg/mL to 1.0 pg/mL, less than 1.0 ng/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL; (c) the level of DHH can be or about: 0 pg/mL, greater than 0 pg/mL to 0.1 pg/mL, 0.05 pg/mL to 0.15 pg/mL, 0.125 pg/mL to 0.2 pg/mL, 0.15 pg/mL to 0.30 pg/mL, 0.25 pg/mL to 0.5 pg/mL, 0.4 pg/mL to 0.7 pg/mL, 0.6 pg/mL to 0.75 pg/mL, 0.725 pg/mL to 0.9 pg/mL, 0.8 pg/mL to 1.0 pg/mL, 0.9 pg/mL to 1.1 pg/mL, 1.0 pg/mL to 1.3 pg/mL, 1.2 pg/mL to 1.5 pg/mL, 1.4 pg/mL to 2.0 pg/mL, 1.9 pg/mL to 2.5 pg/mL, 2.4 pg/mL to 3.0 pg/mL, 2.9 pg/mL to 3.5 pg/mL, 3.4 pg/mL to 3.8 pg/mL, 3.7 pg/mL to 3.9 pg/mL, 3.85 pg/mL to 5.0 pg/mL, less than 5.0 pg/mL, less than 0.05 ng/mL, less than 0.15 ng/mL, less than 0.2 ng/mL, less than 0.3 ng/mL, less than 0.5 ng/mL, less than 0.7 ng/mL, less than 0.75 ng/mL, less than 0.9 ng/mL, less than 1.0 ng/mL, less than 1.1 ng/mL, less than 1.5 ng/mL, less than 1.75 ng/mL, less than 2.0 ng/mL, less than 2.25 ng/mL, less than 5.0 ng/mL, less than 6.0 ng/mL, less than 7.0 ng/mL, less than 10.0 ng/mL, or less than 100.0 ng/mL. However, there can be some inter-patient variability because the levels of the different members of the hedgehog signaling pathway vary based on the person.

In normal controls, the levels of SHH, IHH, and DHH, will be higher, and in some cases can be significantly higher, than the levels of patients with loss and/or distortion of taste or smell. In most cases, the threshold level can be an average level for one or more members of the hedgehog signaling pathway as measured in a control population comprising subjects with normal olfactory and/or gustatory function.

In some cases, the threshold level can be an average level for one or more members of the hedgehog signaling pathway as measured in the same subject before exhibiting loss and/or distortion of taste or smell. For example, with the advent of personalized medicine, a basal level of one or more members of the hedgehog signaling pathway can be known prior to a subject being diagnosed with loss and/or distortion of taste or smell.

In another example, the level of one or more members of the hedgehog signaling pathway is at least one order of magnitude lower than said threshold level. For example, 2 or more orders of magnitude lower than said threshold level.

Other markers will be measured from the biological samples obtained from the patients with loss and/or distortion of taste or smell. For example, pro-inflammatory cytokines (e.g., IL-1a, IL-1β, IL-6, IL-18, TNF-α, or any combination thereof) can be measured as previously described. Additional markers can be measured including but are not limited to anti-inflammatory cytokines (e.g., IL-1ra, IL-10, IFN-γ, IFN-3, or combinations thereof), immunoglobulin E (IgE), eosinophils, cyclic adenosine monophosphate (cAMP), cyclic guanosine monophosphate (cGMP), nitric oxide (NO), IL-1 RII, IL-2R, or any combination thereof. These additional markers can be used to assess if patients have loss and/or distortion of taste or smell.

Additionally, any combination of the markers can be used to assess the severity of a patient's loss and/or distortion of taste or smell. For example, if a patient has little to no measurable levels of one or more markers, the patient can be diagnosed as having a severe case of loss and/or distortion of taste or smell. The threshold level can be an average level for one or more markers as measured in a control population comprising subjects with normal olfactory and/or gustatory function. In some cases, the threshold level can be an average level for one or more markers as measured in the same subject before exhibiting loss and/or distortion of taste or smell. In another example, the level of one or more markers is at least one order of magnitude lower than said threshold level, for example, 2 or more orders of magnitude lower than said threshold level.

For all the patients, the test subject's gustatory and/or olfactory function can be determined by detecting a threshold (DT) score, a recognition threshold (RT) score, a magnitude estimation (ME) score, or any combination thereof with a forced-choice, three-stimuli, stepwise-staircase technique using one or more olfaction testing compounds.

In some cases, the diagnosed result, e.g., loss and/or distortion of taste or smell can be transferred via a communication medium. Exemplary types of communication media can include, but are not limited to written, printed, and electronic types of media.

In other cases, a computer can implement the diagnosis of loss and/or distortion of taste or smell. The computer can be a specialty computer, designed specifically for the task at hand.

Example 14: Treating Patients with Loss and/or Distortion of Taste or Smell

Patients diagnosed with loss and/or distortion of taste or smell will be treated using a variety of methods. For example, patients can be treated with a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof.

To treat loss and/or distortion of taste or smell, some of the patients receiving a non-selective PDE inhibitor, can be given a methylxanthine derivative, including but not limited to caffeine, theophylline, doxophylline, cipamphylline, neuphylline, pentoxiphylline, or diprophylline. Some patients receiving a PDE 1 inhibitor can be given vinpocetine, compound KS505a, bepril, flunarizine, amiodarone, zaprinast, 8-methoxymethyl IPMX, SCH 51866, Nimodipine, or IC224. Some patients receiving a PDE 2 inhibitor can be given EHNA. Some patients receiving a PDE 3 inhibitor can be given enoximone, milrinone (Primacor), amrinone, cilostamide, cilostazol (Pletal), trequinsin, inamrinone, anagrelide, pimobendan, lixazinone, or dihydro-pyridazinone. Some patients receiving a PDE 4 inhibitor can be given mesembrine, rolipram, ibudilast, roflumilast (Daxas), cilomilast (Airflo), piclamilast, luteolin, drotaverine, or denbufylline. Some patients receiving a PDE 5 inhibitor can be given sildenafil, tadalafil, vardenafil, udenafil and avanafil, dipyridamole, icariin, 4-Methylpiperazine, Pyrazolo Pyrimidin-7-1, cilomilast, or zaprinast. Some patients receiving a PDE 6 inhibitor can be given zaprinast, dipyridamole, vardenafil, or tadalafil. Some patients receiving a PDE 7 inhibitor can be given quinazoline type PDE7 inhibitor, dipyridamole, or thiadiazole. Some patients receiving a PDE 8 inhibitor can be given dipyridamole. Some patients receiving a PDE 9 inhibitor can be given zaprinast. Some patients receiving a PDE 10 inhibitor can be given papaverine, OMS824 (from Omeros Corporation), and/or PF-2545920 (from Pfizer). Some patients receiving a PDE 11 inhibitor can be given tadalafil, zaprinast, or dipyridamole.

In some cases, patients can be given forskolin to treat loss and/or distortion of taste or smell. In other cases, patients can be given theophylline to treat loss and/or distortion of taste or smell. Because different patients react differently to forskolin and/or theophylline, patients can be given an optimal amount of the respective drugs. For example, forskolin can be given and/or present in an amount of less than 500 mg to greater than 0 mg, or any amount in between. In other cases, theophylline can be given and/or present in an amount of less than 45 mg or about 20 µg, or any amount in between.

In some cases, patients can be given riociguat. In many case, low levels of riociguat can be given to patients. For example, riociguat can be given and/or present in an amount of greater than 0.0 µg to less than 250 µg, or any amount in between.

Patients can be also given a variety of other therapeutic agents. For examples, cytochrome p450 inhibitors can be given to patients.

Patients can be also given β-adrenergic agonists, including but not limited to pi-adrenergic agonist, β2-adrenergic agonist, and uncharacterized β-adrenergic agonists. For example, patients can be given a $β_1$-adrenergic agonist selected from a group consisting of dobutamine, isoproterenol, xamoterol, and epinephrine; a β2-adrenergic agonist selected from a group consisting of albuterol, levalbuterol, fenoterol, formoterol, isoproterenol ($β_1$ and $β_2$), metaproterenol, salmeterol, terbutaline, clenbuterol, isoetarine, pirbuterol, procaterol, ritodrine, and epinephrine; and/or a uncharacterized β-adrenergic agonists selected from a group consisting of arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol.

Patients can be also given anti-inflammatory cytokines, including but not limited to IL-1ra, IL-10, IFN-γ, IFN-β, or any combination thereof.

Patients can be also given antibody, antibody fragment, or antibody mimetic that can inhibit one of the one or more pro-inflammatory cytokines. For example, the antibody fragments that can be given to a patient can be FAB fragments, FAB2 fragments, Fv fragments, ScFv fragments, antibody light chains, or antibody heavy chains. Antibody mimetics given to patients can include an affibody molecule, an affilin, an affitin, an anticalins, an avimers, a DARPins, a fynomer, a Kunitz domain peptide, or a monobody.

In many cases, the therapeutic agents given to the patients can be steroid-free.

Some patients can be treated for loss and/or distortion of taste or smell, e.g., hyposmia, dysosmia, anosmia, phantosmia, hypogeusia, dysgeusia, phantogeusia, and/or ageusia by altering the levels of members of the hedgehog signaling pathway. For example, patients can be given an effective amount of one or more members of the hedgehog signaling pathway. In some cases, patients can be given an effective amount of the one or more exogenous members of the hedgehog signaling pathway. These members (e.g., RNA or protein) can be made in vitro or in vivo by known methods.

Alternatively, patients can be treated for loss and/or distortion of taste or smell by activating the expression of an effective amount of one or more members of the hedgehog signaling pathway. In some cases, genetic manipulation responsible for the expression of one or more members of the hedgehog signaling pathway can be performed in vitro or in vivo. For example, promoter regions can be activated to increase the expression of one or more members of the hedgehog signaling pathway. This can include, but not limited to methods such as gene therapy. In other cases, activated expression can be effectuated through a therapeutic agent. Additionally, the treatment can directly or indirectly affect levels of one or more members of the hedgehog signaling pathway.

In many cases, the patients can be given any combination treatment. Any of the previously mentioned therapeutic agents and/or methods can be given in combinations of two or more. This in some cases will produce synergistic effects.

Example 15: Treating Disease with cGMP Activators and/or cAMP Activators

To ameliorate loss and/or distortion of taste or smell in patients in need thereof, patients can be given one or more cGMP activators, one or more cAMP activators, or any combination thereof.

The patients can be given a cGMP activators selected from a group consisting of 3-(5'-hydroxymethyl-2'-furyl)-1-benzylindazole (YC-1), YC-1 derivatives, anthranilic acids derivatives, ataciguat (HMR1766), benzydamine analogs, CFM1517, A-350619, nitrovasodilators, molsidomine, nitroxyl (HNO), BAY 41-2272, BAY 41-8543, BAY 58-2667, cinaciguat (BAY 58-2667), and riociguat (BAY 63-2521).

Sometimes the patients can be given a cAMP activators selected from a group consisting of 3-(5'-hydroxymethyl-2'-furyl)-1-benzylindazole (YC-1), glucagon, PDE inhibitors, prostaglandin E1 (PGE1; pharmaceutically known as alprostadil), forskolin, and β-adrenergic agonists.

In many cases, giving a patient one or more cAMP activator and/or one or more cAMP activators will ameliorate loss and/or distortion of taste or smell in patients so diagnosed.

In many cases, the patients can be given any combination treatment. Any of the previously mentioned therapeutic agents and/or methods can be given in combinations of two or more. This in some cases produces synergistic effects.

Example 16: Alternative Formulations

The previously described therapeutic agents, individually or in combination, can be formulated so that they can be suitable for administration by a method selected from a group consisting of: oral administration, transmucosal administration, buccal administration, inhalation administration, intranasal administration, parental administration, intravenous administration, subcutaneous administration, intramuscular administration, sublingual administration, transdermal administration, and rectal administration. In this case, for ease of delivery to the target site, the therapeutic agents can be formulated as suitable for intranasal and oral administration.

Different excipients can be used for the different formulations. For example, sweeter excipients can be used to mask bitterness with while binders can be used to form tablets.

Patients can be given a liquid form of the therapeutic agent, suitable for intranasal and oral administration. The pH of the liquid therapeutic agent can be adjusted because the pH can play a role in efficacy. The pH can be, for example, about: 6.0 to about 8.0, or any amount in between.

Example 17: Treating Disease with Low Levels of Ricociguat

Patients who exhibit pulmonary hypertension, e.g., thromboembolic pulmonary hypertension and pulmonary arterial hypertension, can be treated with an intranasal formulation of riociguat. Patients with other diseases such as bone related disorders, loss and/or distortion of taste or smell can be also treated with intranasal formulations of riociguat.

The intranasal formulation contains lower and sometimes significantly lower amounts of riociguat. For example, patients can be given an intranasal formulation of riociguat, wherein riociguat can be present in an amount of greater than 0.0 µg to less than about 250 µg, or any amount in between. Other patients can be given an intranasal formulation of riociguat wherein riociguat can be present in an amount of about less than 250 µg to greater than 0, or any amount in between.

Some patients can be also treated with non-intranasal inhalational and/or intravenous formulations of riociguat because the effective dosage of riociguat for inhalational and/or intravenous formulations require significantly lower amounts of riociguat.

In many cases, the patients can be given any combination treatment. Any of the previously mentioned therapeutic agents and/or methods can be given in combinations of two or more. This in some cases can produce synergistic effects.

Example 18: Sonic Hedgehog Levels During Cilostazol and Roflumilast Treatment

Patients were given oral doses of roflumilast alone and the patients' nasal mucus was isolated and measured for sonic hedgehog levels. For example, Patient ID No. 11, was given 500 micrograms of daliresp (roflumilast) orally once per day for 4 months. Sonic hedgehog levels were presented at 6665 ng/mol, which is within the levels measured with theophylline treatment alone.

Patients were also given oral doses of cilostazol alone and then measured for nasal mucosal sonic hedgehog levels. For example, Patient ID No. 7, was given 100 mg of cilostazol one per day orally for 4 months. Sonic hedgehog levels were present at a mean of 769 ng/mol, which is also within levels previously measured for theophylline treatment alone.

Treatment with both oral theophylline and cilostazol levels reveal a sonic hedgehog level of a mean of 520 ng/mol. Similar values were measured with oral theophylline and roflumilast. As with oral theophylline values varied a great deal but they were all significantly higher than before the drugs were administered.

Table 34 provides the raw data from these studies. Regarding the terms in the following data, "AR" can refer to allergic rhinitis. "PIHH" can refer to post-influenza-like hyposmia and hypogeusia. "C" can refer to congenital. "HI" can refer to head injury. "A" can refer to anesthesia-induced. "I" can mean idiopathic. Patient names were blocked out for privacy.

TABLE 34

| ID | Date of Visit | Gender | Date of Birth | Age | Diagnosis | ShhN (pg/mol) Nasal Mucus | Theo Dose (mg) | Date 1° Theo | Cilostazol Dose (mg) | Date 1° Cilostazol | Daliresp Dose (mcg) | Date 1° Daliresp | Other Med | Date 1° Other | Hx Dexa |
|---|---|---|---|---|---|---|---|---|---|---|---|---|---|---|---|
| | | | | | | | DALIRESP ONLY | | | | | | | | |
| 11 | Apr. 24, 2014 | 1 | Sep. 20, 1927 | 87 | AR | 6564.912 | — | — | — | — | 500 qd | Apr. 27, 2012 | — | — | Oct. 10, 2002, Jul. 13, 2016, Sep. 7, 2006 |
| 7 | Jan. 2, 2014 | 0 | Aug. 11, 1931 | 82 | PIHH | 520.278 | — | Apr. 18, 2002-Dec. 1, 2006 | — | — | 250 qd | Nov. 7, 2013 | — | — | — |
| | | | | | | | CILOSTAZOL + DALIRESP ONLY | | | | | | | | |
| 1 | Mar. 6, 2014 | 0 | Apr. 12, 1944 | 70 | AR | 176.644 | — | — | 200 | Mar. 14, 2013 | 500 qd | Nov. 7, 2013 | — | — | — |
| | | | | | | THEOPHYLLINE + DALIRESP ONLY | | | | | | | | | |
| 4 | Apr. 26, 2012 | 0 | Sep. 25, 1931 | 81 | PIHH | 1604.655 | 800 | Apr. 22, 2010 | — | — | 250 qod | Mar. 29, 2012 | Zinc | May 3, 2001 | Nov. 1, 2008 |
| 5 | Nov. 29, 2012 | 1 | Nov. 7, 1965 | 47 | Congenital | 97.581 | 600 | Mar. 21, 1996 | — | — | 250 qd | Mar. 1, 2012 | — | — | — |
| 9 | Jun. 8, 2013 | 0 | Mar. 8, 1957 | 56 | AR | 60.592 | 300 | Apr. 14, 2011 | — | — | 500 qd | May 20, 2011 | Zinc | Jun. 24, 2011 | May 19, 2011, Jun. 6, 2013 |
| | | | Average | n = 4 | Average | n = 4 | 600 | May 19, 2011 | | | | | | | |
| | | | Std. Error | 63 | Std. Error | 484.87 | | | | | | | | | |
| | | | | 7 | | 374.05 | | | | | | | | | |
| | | | | | | THEOPHYLLINE + CILOSTAZOL + DALIRESP | | | | | | | | | |
| 3 | Jul. 9, 2012 | 0 | Sep/ 26, 1971 | 41 | AR | 57.044 | 400 | Mar. 2, 2006 | 100 | Jun. 19, 2009 | 250 qd | Mar. 15, 2012 | — | — | Jan. 26, 2005 |
| 8 | Jan. 9, 2014 | 0 | Aug. 15, 1938 | 75 | PIHH | 665.448 | 800 | Aug. 26, 2004 | 100 | Jun. 2, 2005 | 500 qd | May 17, 2012 | — | — | — |
| 12 | Aug. 23, 2012 | 0 | Nov. 1, 1939 | 73 | AR | 48.084 | 800 | Dec. 7, 2006 | 100 | Dec. 6, 2007 | 250 qd | Jun. 8, 2012 | — | — | Apr. 5, 2007, Sep. 10, 2009 |
| 2 | Mar. 1, 2013 | 0 | Oct. 11, 1945 | 67 | AR | 58.179 | 800 | Jan. 18, 2007 | 200 | Sep. 10, 2009 | 250 qd | Mar. 8, 2012 | Singulair 10 mg | Aug. 30, 2010 | Feb. 27, 2007, Nov. 9, 2007, Mar. 19, 2009, Jun. 16, 2011 |
| 6 | Mar. 27, 2014 | 1 | Oct. 26, 1972 | 41 | AR | 811.333 | 800 | Jan. 14, 2010 | 200 | Feb. 2, 2011 | 500 qd | Jan. 11, 2013 | — | — | — |
| 10 | Mar. 28, 2013 | 1 | Nov. 10, 1956 | 56 | HI | 55.868 | 800 | Feb. 22, 2007 | 200 | Jun. 16, 2011 | 500 qd | Mar. 28, 2013 | — | — | — |
| | | | Average | n = 6 | Average | n = 6 | | | | | | | | | |
| | | | Std. Error | 59 | Std. Error | 282.66 | | | | | | | | | |
| | | | | 6 | | 145.35 | | | | | | | | | |
| | | | | | | CILOSTAZOL ONLY | | | | | | | | | |
| 31 | Nov. 7, 2013 | 0 | Aug. 11, 1931 | 82 | PIHH | 768.949 | — | — | 200 | Mar. 14, 2013 | — | Nov. 7, 2013 | — | — | — |
| | | | | | | THEOPHYLLINE + CILOSTAZOL | | | | | | | | | |
| 17 | May 10, 2012 | 0 | Jun. 7, 1933 | 79 | Anesthesia Induced | 52.872 | 800 | Oct. 26, 2007 | 200 | Feb. 10, 2011 | — | — | Thioridizine 20 mg, TCMS Singulair 10 mg | Jan. 8, 2009, Apr. 23, 2007 | — |
| 14 | Feb. 3, 2012 | 0 | Oct. 11, 1945 | 66 | AR | 72.95 | 800 | Jan. 18, 2007 | 200 | Sep. 10, 2019 | — | Mar. 18, 2012 | Singulair 10 mg | Aug. 30, 2010 | Apr. 5, 2007, Sep. 10, 2009 |
| 16 | Feb. 16, 2012 | 0 | Sep. 26, 1971 | 40 | AR | 346.327 | 400 | Mar. 2, 2006 | 100 | Jun. 19, 2009 | — | Mar. 15, 2012 | — | — | — |
| 18 | Feb. 6, 2014 | 0 | Dec. 3, 1944 | 69 | AR | 288.166 | 800 | Jan. 19, 2012 | 100 | Sep. 12, 2013 | — | — | — | — | — |
| 19 | Feb. 20, 2014 | 0 | Jan. 17, 1933 | 81 | AR | 254.448 | 800 | Oct. 25, 2012 | 200 | Feb. 20, 2014 | — | — | — | — | — |
| 20 | Mar. 27, 2014 | 0 | Mar. 16, 1985 | 29 | AR | 595.648 | 1000 | Jun. 10, 2010 | 100 | Sep. 1, 2011 | — | — | — | — | — |

TABLE 34-continued

| ID | Date of Visit | Gender | Date of Birth | Age | Diagnosis | ShhN (pg/mol) Nasal Mucus | Theo Dose (mg) | Date 1° Theo | Cilostazol Dose (mg) | Date 1° Cilostazol | Daliresp Dose (mcg) | Date 1° Daliresp | Other Med | Date 1° Other | Hx Dexa |
|---|---|---|---|---|---|---|---|---|---|---|---|---|---|---|---|
| 24 | Apr. 17, 2014 | 0 | Jun. 22, 1957 | 57 | AR | | 800 | May 31, 2012 | 100 | Nov. 21, 2013 | — | — | — | — | — |
| 29 | Oct. 25, 2012 | 1 | Dec. 26, 1972 | 40 | AR | 75.482 | 800 | Jan. 14, 2010 | 200 | Feb. 2, 2011 | — | Jan. 11, 2013 | — | — | Sep. 16, 2010 |
| 34 | Mar. 7, 2014 | 0 | Mar. 25, 1933 | 81 | AR | 2921.864 | 600 | Mar. 20, 2008 | 50 | Mar. 7, 2014 | — | — | — | — | — |
| 35 | Sep. 8, 2006 | 1 | Sep. 20, 1927 | 79 | AR | 311.893 | 200 | Apr. 18, 2002–Dec. 1, 2006 | 200 | Jul. 16, 2004–Dec. 1, 2006 | — | Apr. 27, 2012 | — | — | Oct. 10, 2002, Jul. 13, 2006, Sep. 7, 2006 |
| 36 | Feb. 23, 2012 | 0 | Nov. 1, 1939 | 72 | AR | 143.319 | 800 | Dec. 7, 2006 | 200 | Dec. 6, 2007 | — | Jun. 8, 2012 | — | — | — |
| 25 | Mar. 4, 2010 | 0 | Aug. 23, 1957 | 53 | AR, PIHH | 80.761 | 800 | Jan. 8, 2007 | 100 | Apr. 25, 2009 | — | — | Zinc | Mar. 10, 1983 | — |
| 13 | Aug. 30, 2012 | 0 | May 24, 1949 | 63 | HI | 100.518 | 400 | May 30, 1996 | 100 | Apr. 28, 2011 | — | Mar. 38, 2013 | — | — | — |
| 33 | Mar. 20, 2009 | 1 | Nov. 10, 1956 | 52 | HI | 57.003 | 800 | Feb. 22, 2007 | 200 | Jun. 16, 2011 | — | — | — | — | Feb. 27, 2007, Nov. 9, 2007, Mar. 19, 2009, Jun. 16, 2011 |
| 22 | May 22, 2014 | 0 | Apr. 17, 1945 | 69 | Idiopathic | 283.519 | 200 | Nov. 29, 2007 | 50 | Jan. 8, 2009 | — | — | — | — | — |
| 26 | Mar. 27, 2014 | 1 | Nov. 25, 1950 | 63 | Idiopathic | 3125.654 | 600 | Jun. 7, 2010 | 200 | Mar. 21, 2013 | — | — | — | — | — |
| 28 | May 17, 2012 | 1 | Jan. 12, 1940 | 72 | Idiopathic | 197.55 | 200 | Dec. 14, 2000 | 150 | Aug. 19, 2005 | — | May 17, 2012 | Zinc | Nov. 8, 2001 | Nov. 1, 2008 |
| 21 | Jun. 5, 2014 | 0 | Sep. 25, 1931 | 83 | PIHH | 4100.101 | 600 | Mar. 21, 1996 | 200 | Jul. 25, 2013 | — | Mar. 29, 2012, DC | Zinc | May 3, 2001 | — |
| 23 | Feb. 24, 2011 | 1 | Feb. 24, 1951 | 60 | PIHH | 59.375 | 800 | Mar. 19, 2009 | 200 | Feb. 1, 2010 | — | — | — | — | — |
| 27 | May 5, 2011 | 0 | Jul. 3, 1953 | 58 | PIHH | 169.563 | 400 | Dec. 11, 2008 | 200 | Jun. 11, 2009 | — | — | — | — | — |
| 32 | Jan. 5, 2012 | 0 | Aug. 15, 1938 | 73 | PIHH | | 800 | Aug. 26, 2004 | 100 | Jun. 2, 2005 | — | May 17, 2012 | Thioridazine 10 mg Singulair 10 mg, Thioridazine 10 mg | May 26, 2011 | Jan. 26, 2005 |
| 15 | Jun. 5, 2014 | 0 | Nov. 1, 1946 | 68 | PIHH, AR | | 800 | Feb. 19, 2009 | 100 | Jun. 4, 2011 | — | — | — | Mar. 3, 2011, Sep. 10, 2009 | — |
| 30 | Jun. 5, 2009 | 0 | Jun. 11, 1954 | 55 | PIHH, AR | 775.176 | 400 | Oct. 17, 2002 | 100 | Jun. 6, 2009 | — | — | — | — | Aug. 19, 2010, Jun. 4, 2009, Nov. 11, 2005, Dec. 16, 2005, Dec. 18, 2003, Mar. 27, 2003 |
| | | | Average Std. Error | n = 23 64 3 | | Average Std. Error | n = 23 808.03 282.38 | | | | | | | | |

Example 19: Treating Appetite Loss

Patients exhibiting appetite loss are treated with one or more therapeutic agents. For example, PDE inhibitors are used to treat appetite loss. The one or more PDE inhibitors can be a non-selective PDE inhibitor, a PDE-1 selective inhibitor, a PDE-2 selective inhibitor, a PDE-3 selective inhibitor, a PDE-4 selective inhibitor, a PDE-5 selective inhibitor, a PDE-10 selective inhibitor, or any combination thereof. In particular, patients are treated with a non-selective PDE inhibitor, e.g., theophylline.

The subjects chosen for this study are subjects that are experiencing appetite loss associated with having Addison's disease, amyloidosis, asthma, cancer, cat scratch disease, acute lymphoblastic leukemia, coxsackie virus, dementia, depression, encopresis, gastroespophageal reflux disease, acid reflux, infectious mononucleosis, kidney failure, legionnaires' disease, leigh's disease, peptic ulcer, postpartum depression, psychotic disorders, rheumatoid arthritis, rocky mountain spotted fever, stress, anthrax, anorexia nervosa, pernicious anemia, alcohol withdrawal, migraine headaches, vitamin B12 deficiency, acute mountain sickness, stroke, thyroid diseases, yellow fever, liver disease, chronic obstructive pulmonary disease, heart failure, hepatitis, HIV, pregnancy, bowel disease, disease of the gastrointestinal tract (e.g., gallbladder disease, crohn's disease, irritable bowel syndrome, appendicitis), brain damage (e.g., from trauma), hormone (endocrine) disease, inflammation (e.g., from chronic infectious or chronic inflammatory diseases, or loss of taste. Other subjects that are part of the treatment group are subjects that are experiencing appetite loss associated with taking medication or drugs (e.g., including but not limited to digoxin, cocaine, codeine, demerol, morphine, antibiotics, amphetamines, methamphetamine, chemotherapy agents, common cold medicines, and cough & stuffy nose decongestants). Other subjects included in this study are those subjects that are experiencing appetite loss associated with infections such as flu, mumps, syphilis, vasculitis, giardiasis, listeriosis, AIDS/HIV, pneumonia, chickenpox, strep throat, yellow fever, typhoid fever, leishmaniasis, gastroenteritis, mononucleosis, schistosomiasis, cat scratch fever, coxsackie disease, hookworm disease, Rocky Mountain spotted fever, and food poisoning—*E. coli* enteritis.

Treatment varies based on the disease and the severity of the conditions of the subject in need thereof. A physician will determine the appropriate dose of PDE inhibitor or other drugs that can be effective in treating appetite loss.

After treatment, body weight will increase from pretreatment levels after treatment with one or more therapeutic agents, e.g., PDE inhibitor treatment, such as with theophylline treatment.

While preferred embodiments of the present invention have been shown and described herein, it will be obvious to those skilled in the art that such embodiments can be provided by way of example only. Numerous variations, changes, and substitutions will now occur to those skilled in the art without departing from the invention. It should be understood that various alternatives to the embodiments of the invention described herein can be employed in practicing the invention.

What is claimed is:

1. A method of diagnosing and treating a taste or smell disorder, the method comprising:
    a) obtaining a biological sample from a human subject, wherein the biological sample comprises nasal mucus, saliva, or a combination thereof;
    b) measuring a level of sonic hedgehog (SHH) in the biological sample;
    c) detecting a level of SHH in the biological sample that is lower than a threshold level; and
    d) administering an effective amount of a PDE inhibitor, or a salt thereof, to the human subject.

2. The method of claim 1, wherein the biological sample comprises the nasal mucus.

3. The method of claim 2, wherein the taste or smell disorder comprises hyposmia, dysosmia, anosmia, phantosmia, or a combination thereof.

4. The method of claim 1, wherein the biological sample comprises the saliva.

5. The method of claim 4, wherein the taste or smell disorder comprises hypogeusia, dysgeusia, phantogeusia, ageusia, or a combination thereof.

6. The method of claim 1, wherein the PDE inhibitor, or a salt thereof, is a non-selective PDE inhibitor, or a salt thereof.

7. The method of claim 1, wherein the PDE inhibitor, or a salt thereof, is a selective PDE inhibitor, or a salt thereof.

8. The method of claim 7, wherein the selective PDE inhibitor, or a salt thereof, is a phosphodiesterase-1 selective inhibitor, or a salt thereof; a phosphodiesterase-2 selective inhibitor, or a salt thereof; a phosphodiesterase-3 selective inhibitor, or a salt thereof; a phosphodiesterase-4 selective inhibitor, a phosphodiesterase-5 selective inhibitor, or a salt thereof, a phosphodiesterase-10 selective inhibitor, or a salt thereof; or any combination thereof.

9. The method of claim 1, wherein the PDE inhibitor, or a salt thereof, is roflumilast, or a salt thereof; cilostazol, or a salt thereof; or any combination thereof.

10. The method of claim 1, wherein the PDE inhibitor, or a salt thereof, is theophylline, or a salt thereof.

11. The method of claim 1, wherein the PDE inhibitor, or a salt thereof, is administered intranasally.

12. The method of claim 1, further comprising diagnosing the subject with a taste and smell disorder based on the detecting of the lower level of SHH in the biological sample compared to the threshold level.

* * * * *